United States Patent
Choi et al.

(10) Patent No.: US 10,294,207 B2
(45) Date of Patent: May 21, 2019

(54) PYRAZOLE DERIVATIVES AS TNIK, IKKε AND TBK1 INHIBITOR AND PHARMACEUTICAL COMPOSITION COMPRISING SAME

(71) Applicant: GREEN CROSS CORPORATION, Yongin-si, Gyeonggi-do (KR)

(72) Inventors: Soongyu Choi, Yongin-si (KR); Kisoo Park, Yongin-si (KR); Hee Jeong Seo, Yongin-si (KR); Eun-Jung Park, Yongin-si (KR); Younggyu Kong, Yongin-si (KR); Ickhwan Son, Yongin-si (KR); Sang-ho Ma, Yongin-si (KR); Kwang-Seop Song, Yongin-si (KR); Min Ju Kim, Yongin-si (KR); So Ok Park, Yongin-si (KR); Man-Young Cha, Yongin-si (KR); Mi-Soon Kim, Yongin-si (KR); Sang Mi Kang, Yongin-si (KR); Dong Hyuk Jang, Yongin-si (KR); Jangwon Hong, Yongin-si (KR)

(73) Assignee: GREEN CROSS CORPORATION, Yongin (KR)

( * ) Notice: Subject to any disclaimer, the term of this patent is extended or adjusted under 35 U.S.C. 154(b) by 0 days.

(21) Appl. No.: 15/083,503

(22) Filed: Mar. 29, 2016

(65) Prior Publication Data
US 2016/0289196 A1 Oct. 6, 2016

(30) Foreign Application Priority Data

Mar. 30, 2015 (KR) .................. 10-2015-0044628

(51) Int. Cl.
| | | |
|---|---|---|
| *C07D 231/56* | (2006.01) |
| *C07D 401/12* | (2006.01) |
| *C07D 403/12* | (2006.01) |
| *C07D 405/12* | (2006.01) |
| *C07D 409/12* | (2006.01) |
| *C07D 409/14* | (2006.01) |
| *C07D 413/12* | (2006.01) |
| *C07D 413/14* | (2006.01) |
| *C07D 495/04* | (2006.01) |
| *C07D 409/04* | (2006.01) |
| *C07D 417/12* | (2006.01) |

(52) U.S. Cl.
CPC ......... *C07D 231/56* (2013.01); *C07D 401/12* (2013.01); *C07D 403/12* (2013.01); *C07D 405/12* (2013.01); *C07D 409/04* (2013.01); *C07D 409/12* (2013.01); *C07D 409/14* (2013.01); *C07D 413/12* (2013.01); *C07D 413/14* (2013.01); *C07D 417/12* (2013.01); *C07D 495/04* (2013.01)

(58) Field of Classification Search
CPC .. C07D 231/56; C07D 401/12; C07D 403/12; C07D 405/12; C07D 409/12; C07D 409/14; C07D 413/12; C07D 413/14
See application file for complete search history.

(56) References Cited

U.S. PATENT DOCUMENTS

| 7,429,609 B2* | 9/2008 | Ohi ...................... A61K 31/407 514/406 |
| 7,632,854 B2* | 12/2009 | Martina ............... C07D 231/56 514/403 |
| 8,569,512 B2* | 10/2013 | Burgey .................. A61K 31/16 548/360.1 |

OTHER PUBLICATIONS

Voskoglou-Nomikos et al., Clinical Cancer Research, vol. 9, 4227-4239.*
ptcl.chem.ox.ac.uk/MSDS structure activity relationship; Jaworska, 1-8, 2004.*
Cancer and Metastasis Reviews (1998), 17(1), 91-106.*
Science (1999), vol. 286, 531-537.*
Registry No. 1176561-07-1, File Registry on STN, Aug. 27, 2009.*
Krishnamurty et al., Bioorganic & Medicinal Chemistry Letters 21 (2011) 550-554.*
Registry No. 485840-23-1, File Registry on STN, Feb. 5, 2003.*

* cited by examiner

*Primary Examiner* — Rebecca L Anderson
(74) *Attorney, Agent, or Firm* — Sughrue Mion, PLLC

(57) ABSTRACT

Provided is pyrazole derivatives as a TNIK (Traf2- and NCK-interacting kinase), IKKε (I-kappa-B kinase epsilon) and TBK1 (TANK-binding kinase 1) inhibitor; the pyrazole derivative according to the present invention effectively inhibits TNIK, IKKε and TBK1, and thus is useful not only as an anticancer agent for the treatment of various cancers including colorectal cancer, breast cancer, CNS cancer, colon cancer, non-small cell lung cancer, kidney cancer, prostate cancer, ovarian cancer, uterus cancer, stomach cancer, liver cancer, skin cancer, lung cancer, brain cancer, bladder cancer, esophageal cancer, pancreatic cancer, thyroid cancer, head and neck cancer, squamous cell carcinoma, osteosarcoma, B-cell or T-cell lymphoma, acute or chronic leukemia and multiple myeloma, but as a therapeutic agent for chronic inflammation.

1 Claim, No Drawings

PYRAZOLE DERIVATIVES AS TNIK, IKKε AND TBK1 INHIBITOR AND PHARMACEUTICAL COMPOSITION COMPRISING SAME

CROSS REFERENCE TO RELATED APPLICATIONS

This application claims priority based on Korean Patent Application No. 10-2015-0044628, filed Mar. 30, 2015, the contents of all of which are incorporated herein by reference in their entirety.

FIELD OF THE INVENTION

The present invention relates to novel pyrazole derivatives as a TNIK (Traf2- and NCK-interacting kinase), IKKε (I-kappa-B kinase epsilon) and TBK1 (TANK-binding kinase 1) inhibitor and a pharmaceutical composition comprising same for the prevention or treatment of cancer.

BACKGROUND OF THE INVENTION

Cancer, a genetic disorder caused by mutations of genes such as oncogene and tumor suppressor gene, is a serious life-threatening disease which is considered as $1^{st}$ or $2^{nd}$ ranked cause of death in humans. Although various techniques have been developed for the treatment of cancer including surgical treatment, radiation therapy, immunotherapy, etc., problems related with inhibition and recurrence of malignant tumor still remain unresolved.

Protein kinase is a family of enzymes which plays an important role in signal transduction for various cellular activities including cellular proliferation, carcinogenesis, apoptosis, and cytodifferentiation, and it has been known that inhibitors thereof are useful in the treatment and prevention of proliferative diseases such as cancer (see Plowman, G. D, et al., *Drug Discovery Today*, 334-339 (1994)). In this regard, attempts have been made to treat proliferative diseases such as cancer by inhibiting protein kinase which is closely related with various signal transductions and disease mechanisms in cells.

IKKε and TBK1 are homologous Ser/Thr kinases which play an essential role in the innate immune responses derived by induction of Type I interferon and other cytokines, and are activated by viral and bacterial infection. The immune responses triggered by viral and bacterial infection include binding between Toll-like receptor and an antigen, e.g., lipopolysaccharide (LPS) or viral double-stranded RNA (dsRNA), followed by the activation of IKKε and/or TBK1 pathway. The activation of IKKε and TBK1 leads to phosphorylation of IFN regulatory factor 3 (IRF3) and/or IFN regulatory factor 7 (IRF7), which triggers dimerization and nuclear translocalization of interferon regulatory transcription factors, inducing signaling cascade that ultimately leads to the production of interferon (see Y.-H. Ou et al., *Molecular Cell* 41, 458-470, 2011 and D. A. Barbie et al., *Nature*, 1-5, 2009).

Recently, a study revealed that, TNIK, IKKε and TBK1 are over-activated in patients with colon cancer, breast cancer, brain tumor, gastric cancer, hepatic cancer, ovarian cancer, and the like (see J. S. Boehm et al., *Cell* 129, 1065-1079, 2007). Medications exhibiting inhibitory actions on TNIK, IKKε and TBK1 block signal transduction pathways of TNIK, IKKε and TBK1 by inhibiting phosphorylation of IRF3 and/or IRF7, which leads to the inhibition of angiogenesis, proliferation and survival of cancer, etc. Thus, it is expected that such medications can be effectively used as therapeutic agents for the treatment of cancer (see WO2010-100431 and WO2009-030890).

Additionally, it is known that TNIK, IKKε and TBK1 play an important role not only in basic processes of memory and learning via cellular signaling pathways, but also in the regulation of learning ability and judgment (see Takaoka et al., *Drug Delivery Rev* 60, 847-857, 2008). It is also expected that TNIK, IKKε and TBK1 inhibitors can be useful in the treatment and prevention of a wide range of diseases including inflammatory diseases as well as cancer.

Conventionally, a number of TNIK, IKKε and TBK1 inhibitors have been developed, but such inhibitors have not yet been commercialized due to their poor effectiveness and deviations in therapeutic effects depending on the type of cancer. Thus, there is an increasing need for developing various compounds which are more effective in the treatment of cancer.

SUMMARY OF THE INVENTION

Therefore, it is an object of the present invention to provide pyrazole derivatives as a TNIK (Traf2- and NCK-interacting kinase), IKKε (I-kappa-B kinase epsilon) and TBK1 (TANK-binding kinase 1) inhibitor.

Also, it is another object of the present invention to provide a pharmaceutical composition comprising the compound for the prevention or treatment of cancer.

In accordance with one object, the present invention provides a compound selected from the group consisting of a pyrazole derivative of formula (I) and a pharmaceutically acceptable salt, a hydrate, and a solvate thereof:

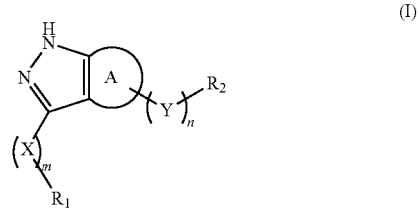

(I)

wherein:

A is benzene or thiophene ring;

X is —NH—C(=O) or —NH—S(=O)$_2$—;

m is 0 or 1;

R$_1$ is substituted or unsubstituted C$_{5-14}$ aryl or substituted or unsubstituted 5- to 13-membered heteroaryl;

said aryl is optionally substituted with one or more substituents selected from the group consisting of hydroxy; halogen; C$_{1-7}$ alkyl; C$_{1-7}$ alkoxy; C$_{1-7}$ alkylthio; 5- to 10-membered heterocycloalkyl which is optionally substituted with one or more substituents selected from hydroxy, C$_{1-7}$ alkyl, C$_{1-7}$ alkoxy, t-butyloxycarbonyl or C$_{1-7}$ alkyl-carbonyl; nitro; amino; 5- to 13-membered heteroaryl; (diC$_{1-7}$ alkyl)amino; —NH—(CH$_2$)$_p$—R$_3$; —O—(CH$_2$)$_p$—R$_3$; and —NH—C(=O)—R$_3$; R$_3$ being H, hydroxy, C$_{1-7}$ alkoxy, 5- to 10-membered heterocycloalkyl which is unsubstituted or substituted with at least one alkyl, (diC$_{1-7}$ alkyl)amino, C$_{1-7}$ alkylamino, C$_{1-7}$ alkyl, saturated or unsaturated C$_{3-10}$ cycloalkyl, (trifluoromethyl) (saturated or unsaturated C$_{3-10}$ cycloalkyl), 5- to 13-membered heteroaryl or oxo-C$_{3-10}$ cycloalkyl; and p being an integer from 0 to 7;

Y is

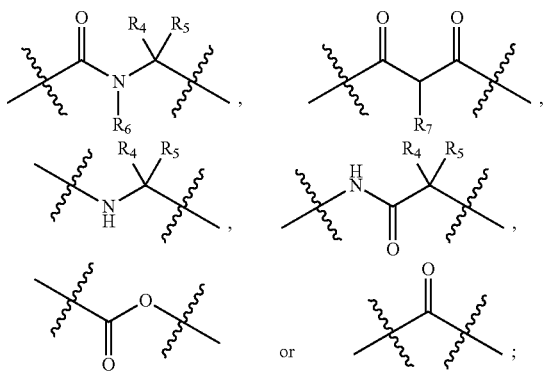

$R_4$ and $R_5$ being each independently hydrogen, $C_{1-7}$ alkyl, $C_{3-10}$ cycloalkyl, hydroxy-$C_{1-7}$ alkyl or —$CF_3$; $R_6$ being hydrogen or $C_{1-7}$ alkyl; $R_7$ being 5- to 13-membered heteroaryl; and $R_4$ and $R_5$ being optionally bonded to each other to form $C_{3-10}$ cycloalkyl;

n is 0 or 1; and $R_2$ is hydroxy, $C_{1-7}$ alkyl, cyano, hydroxy-$C_{1-7}$ alkyl, substituted or unsubstituted $C_{3-10}$ cycloalkyl, substituted or unsubstituted $C_{5-14}$ aryl, substituted or unsubstituted 5- to 13-membered heteroaryl or substituted or unsubstituted 5- to 10-membered heterocycloalkyl; said cycloalkyl, aryl, heteroaryl or heterocycloalkyl being optionally substituted with one or more substituents selected from the group consisting of halogen, $C_{1-7}$ alkyl and —$(CH_2)_q$-(5- to 10-membered heterocycloalkyl); and q being an integer from 0 to 2.

In accordance with another object, the present invention provides a pharmaceutical composition for the prevention or treatment of cancer, comprising the aforementioned compound and one or more pharmaceutically acceptable additives.

A pyrazole derivative in accordance with the present invention effectively inhibits TNIK, IKKε and TBK1, and thus is useful not only as an anticancer agent for the treatment of various cancers including colorectal cancer, breast cancer, CNS cancer, colon cancer, non-small cell lung cancer, kidney cancer, prostate cancer, ovarian cancer, uterus cancer, stomach cancer, liver cancer, skin cancer, lung cancer, brain cancer, bladder cancer, esophageal cancer, pancreatic cancer, thyroid cancer, head and neck cancer, squamous cell carcinoma, osteosarcoma, B-cell or T-cell lymphoma, acute or chronic leukemia and multiple myeloma, but as a therapeutic agent for chronic inflammation.

DETAILED DESCRIPTION OF THE INVENTION

The term "halogen" as used herein, refers to fluorine, chlorine, bromine or iodine, unless otherwise specified.

The term "alkyl" as used herein, refers to linear or branched hydrocarbon chain radicals having 1 to 7 carbon atoms. Particular examples thereof may include, but not limited to, methyl, ethyl, N-propyl, i-propyl, N-butyl, i-butyl, t-butyl, N-pentyl, N-hexyl and the like.

Also, the term "cycloalkyl" refers to a saturated carbocyclic group having 3 to 10 carbon atoms which has a single ring (e.g., cyclohexyl) or a plurality of fused rings (e.g., norbornyl and adamantyl). Particular examples thereof may include, but not limited to, cyclopropyl, cyclopentyl, cyclohexyl, norbornyl, adamantyl, and the like.

Also, the term "aryl" refers to an organic radical derived from aromatic hydrocarbon by removing one hydrogen atom therefrom, which includes a substituted or unsubstituted single ring or a plurality of fused rings, wherein each ring has 5 to 20, preferably 5 to 14 atoms; it also includes a plurality of aryls which are connected via single bonds. Particular examples thereof may include, but not limited to, phenyl, naphthyl, biphenyl, terphenyl, indenyl, and the like. Preferably, the aryl group may be selected from phenyl, naphthyl, and the like.

Also, the term "heteroaryl" refers to a 5- to 13-membered aromatic radical having at least one, preferably, 1 to 4, hetero atom selected from O, N and S; the heteroaryl includes monocyclic heteroaryl with 5- to 6-membered ring and polycyclic heteroaryl group condensed with at least one benzene ring; and the heteroaryl may be partially saturated. Also, in the present invention, the heteroaryl also includes a plurality of heteroaryls which are connected via single bonds. The heteroaryl group includes heteroaryl in which the hetero atom in the ring is oxidized or forms a quaternary salt. Particular examples may include, but not limited to, monocyclic heteroaryl such as furyl, thiophenyl, pyrrolyl, imidazolyl, pyrazolyl, thiazolyl, thiadiazolyl, isothiazolyl, isoxazolyl, oxazolyl, oxadizolyl, triazinyl, tetrazinyl, oxotriazolyl, tetrazolyl, furazanyl, pyridyl, pyrazinyl, pyrimidinyl, pyridazinyl, and the like; polycyclic heteroaryl such as benzofuranyl, benzothiophenyl, dibenzofuranyl, dibenzothiophenyl, isobenzofuranyl, benzoimidazolyl, benzothiazolyl, benzoisothiazolyl, benzoisoxazolyl, benzoxazolyl, benzodioxolyl, benzothiadiazolyl, dihydrobenzofuranyl, dihydrobenzoxazinyl, benzodioxinyl, dihydrobenzodioxinyl, thioxothiazolidinyl, isoindolyl, indolyl, indazolyl, quinolyl, isoquinolyl, cinnolinyl, quinazolinyl, quinoxalinyl, carbazolyl, phenanthridinyl, acridinyl, phenanthrolinyl, phenazinyl, phenothiazinyl, phenoxazinyl, and the like; N-oxides thereof (for example, pyridyl N-oxide and quinolyl N-oxide); and quaternary salts thereof. Preferably, the heteroaryl is thiophenyl, imidazolyl, pyrazolyl, thiazolyl, oxotriazolyl, tetrazolyl, pyridyl, pyrimidinyl, pyridazinyl, benzothiophenyl, benzoimidazolyl, benzothiazolyl, benzothiadiazolyl, indolyl, indazolyl, quinolyl, isoquinolyl, benzodioxolyl, dihydrobenzofuranyl, dihydrobenzoxazinyl, benzodioxinyl, dihydrobenzodioxinyl, thioxothiazolidinyl, and the like.

Also, the term "heterocycloalkyl" refers to 5- to 10-membered mono- or polycyclic ring, excluding aromatic ring, having at least one, preferably, 1 to 4, hetero atom selected from O, N and S. Particular examples may include pyrrolidine, imidazoline, imidazolidine, pyrazoline, pyrazolidine, piperidine, morpholine, piperazine, tetrahydropyridinyl and the like.

The present invention provides a compound selected from the group consisting of a pyrazole derivative of formula (I) and a pharmaceutically acceptable salt, a hydrate, and a solvate thereof:

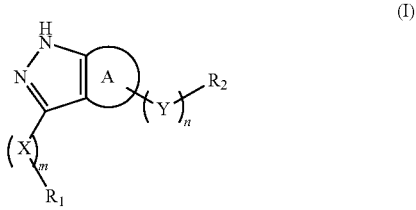

wherein:
A is benzene or thiophene ring;
X is —NH—C(=O) or —NH—S(=O)$_2$—;
m is 0 or 1;
$R_1$ is substituted or unsubstituted $C_{5-14}$ aryl or substituted or unsubstituted 5- to 13-membered heteroaryl;
   said aryl is optionally substituted with one or more substituents selected from the group consisting of hydroxy; halogen; $C_{1-7}$ alkyl; $C_{1-7}$ alkoxy; $C_{1-7}$ alkylthio; 5- to 10-membered heterocycloalkyl which is optionally substituted with one or more substituents selected from hydroxy, $C_{1-7}$ alkyl, $C_{1-7}$ alkoxy, t-butyloxycarbonyl or $C_{1-7}$ alkyl-carbonyl; nitro; amino; 5- to 13-membered heteroaryl; (di$C_{1-7}$ alkyl)amino; —NH—(CH$_2$)$_p$—$R_3$; —O—(CH$_2$)$_p$—$R_3$; and —NH—C(=O)—$R_3$; $R_3$ being H, hydroxy, $C_{1-7}$ alkoxy, 5- to 10-membered heterocycloalkyl which is unsubstituted or substituted with at least one alkyl, (di$C_{1-7}$ alkyl)amino, $C_{1-7}$ alkylamino, $C_{1-7}$ alkyl, saturated or unsaturated $C_{3-10}$ cycloalkyl, (trifluoromethyl) (saturated or unsaturated $C_{3-10}$ cycloalkyl), 5- to 13-membered heteroaryl or oxo-$C_{3-10}$ cycloalkyl; and p being an integer from 0 to 7;
Y is

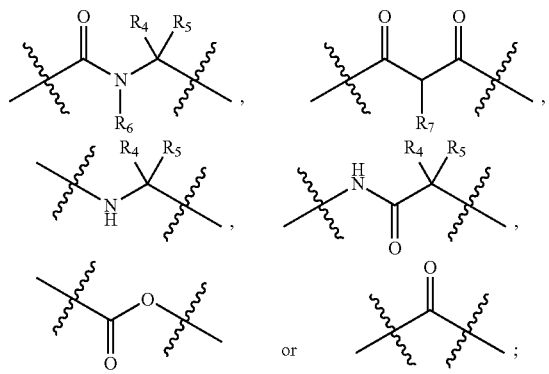

$R_4$ and $R_5$ being each independently hydrogen, $C_{1-7}$ alkyl, $C_{3-10}$ cycloalkyl, hydroxy-$C_{1-7}$ alkyl or —CF$_3$; $R_6$ being hydrogen or $C_{1-7}$ alkyl; $R_7$ being 5- to 13-membered heteroaryl; and $R_4$ and $R_5$ being optionally bonded to each other to form $C_{3-10}$ cycloalkyl;
   n is 0 or 1; and
   $R_2$ is hydroxy, $C_{1-7}$ alkyl, cyano, hydroxy-$C_{1-7}$ alkyl, substituted or unsubstituted $C_{3-10}$ cycloalkyl, substituted or unsubstituted $C_{5-14}$ aryl, substituted or unsubstituted 5- to 13-membered heteroaryl or substituted or unsubstituted 5- to 10-membered heterocycloalkyl; said cycloalkyl, aryl, heteroaryl or heterocycloalkyl being optionally substituted with one or more substituents selected from the group consisting of halogen, $C_{1-7}$ alkyl and —(CH$_2$)$_q$-(5- to 10-membered heterocycloalkyl); and q being an integer from 0 to 2.
According to one embodiment of the present invention, $R_1$ is substituted or unsubstituted phenyl, pyrazole or pyridine.
Preferably, $R_1$ is phenyl which is substituted with at least one substituent selected from the group consisting of fluoro, methoxy, methylthio, methyl, tert-butyl, methylpiperazinyl, piperazinyl, morpholino, dimethylpiperazinyl, dimethylmorpholino, hydroxypiperidinyl, ethylpiperazinyl, methoxypiperidinyl, methoxyethylamino, methoxypropylamino, pyrrolidinylethylamino, morpholinoethylamino, dimethylaminopropylamino, methyl(methylaminoethylamino), tetrahydrofuranylmethylamino, dimethylamino ethylamino, isopentylamino, tetrahydropyranyl ethylamino, hexylamino, cyclohexylamino, cyclopentylamino, cycloheptylamino, cyclooctylamino, cyclohexylmethylamino, cyclohexenylethylamino, pyrrolylethylamino, tert-butyloxycarbonyl tetrahydropyridinyl, tetrahydropyridinyl, hydroxy, morpholinoethoxy, nitro, amino, cyclobutanecarboxamido, (trifluoromethyl)cyclopropanecarboxamido, oxocyclobutanecarboxamido, acetylpiperazinyl, tert-butyloxycarbonylpyrrolidinecarboxamido, acetamido, imidazolyl, methylpiperidinylamino, dimethylamino, piperidinylethylamino and hydroxyethylamino.
Preferably, $R_1$ is methylpyrazole or methoxypyridine.
According to one embodiment of the present invention, Y is

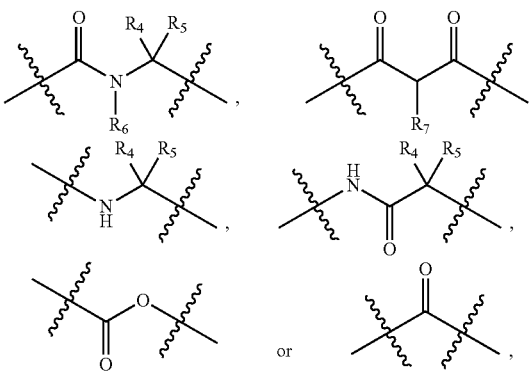

wherein $R_4$ and $R_5$ being each independently hydrogen, methyl, ethyl, propyl, cyclopropyl, isobutyl, hydroxymethyl or —CF$_3$.
According to another embodiment of the present invention, $R_4$ and $R_5$ are bonded to each other to form cyclopropyl or cyclohexyl.
According to one embodiment of the present invention, $R_7$ is thiophenyl.
According to one embodiment of the present invention, $R_2$ is phenyl, furanyl, thiophenyl, 4,5,6,7-tetrahydrothieno[2,3-c]pyridine, morpholinomethylthiophenyl, cyano, methylthiophenyl, chlorothiophenyl, trifluoromethylphenyl, cyclohexyl, cyclopropyl, propyl, isobutyl, oxadiazolyl, thiazolyl, pyridinyl, furanyl, methylpyridinyl, trifluoromethylpyridinyl, hydroxy, cyclopentyl, hydroxyethyl, triazolyl, cyclobutyl, oxazolyl, piperazinyl, isoxazolyl, fluorophenyl, methyloxazolyl, methylthiazolyl, methyl, morpholinomethyl, ethyloxazolyl, pyrrolidinyl or ethylthiazolyl.
According to preferred embodiments of the present invention, the compound of the present invention is selected from the group consisting of:
(1) N-benzyl-3-(4-fluorobenzamido)-1H-indazole-5-carboxamide;
(2) N-(furan-2-yl-methyl)-3-(4-methoxybenzamido)-1H-indazole-5-carboxamide;
(3) 3-(4-methoxybenzamido)-N-(thiophen-2-ylmethyl)-1H-indazole-5-carboxamide;
(4) 3-(4-methoxybenzamido)-N-methyl-N-(thiophen-2-yl-methyl)-1H-indazole-5-carboxamide;
(5) 4-methoxy-N-(5-(4,5,6,7-tetrahydrothieno[2,3-c]pyridine-6-carbonyl)-1H-indazol-3-yl)benzamide
(6) 3-(4-(methylthio)benzamido)-N-(thiophen-2-ylmethyl)-1H-indazole-5-carboxamide;

(7) 3-(1-methyl-1H-pyrazole-4-carboxamido)-N-(thiophen-2-ylmethyl)-1H-indazole-5-carboxamide;
(8) 3-(5-methoxypicolinamido)-N-(thiophen-2-ylmethyl)-1H-indazole-5-carboxamide hydrochloride;
(9) 3-(2-methoxynicotinamido)-N-(thiophen-2-ylmethyl)-1H-indazole-5-carboxamide;
(10) 3-(4-tert-butylbenzamido)-N-(thiophen-2-ylmethyl)-1H-indazole-5-carboxamide;
(11) 4-methoxy-N-(5-((thiophen-2-ylmethyl)amino)-1H-indazol-3-yl)benzamide;
(12) 4-methoxy-N-(5-(5-(morpholinomethyl)thiophen-2-yl)-1H-indazol-3-yl)benzamide;
(13) 3-benzamido-N-(thiophen-2-ylmethyl)-1H-indazole-5-carboxamide;
(14) 3-(4-fluorobenzamido)-N-(1-(thiophen-2-yl)ethyl)-1H-indazole-5-carboxamide;
(15) 3-(4-fluorobenzamido)-N-(1-(thiophen-2-yl)cyclopropyl)-1H-indazole-5-carboxamide;
(16) N-(1-cyanocyclopropyl)-3-(4-fluorobenzamido)-1H-indazole-5-carboxamide;
(17) 3-(4-fluorobenzamido)-N-(1-(thiophen-2-yl)propyl)-1H-indazole-5-carboxamide;
(18) 3-(4-fluorobenzamido)-N-(1-(thiophen-2-yl)butyl)-1H-indazole-5-carboxamide;
(19) 3-(4-fluorobenzamido)-N-((5-methylthiophen-2-yl)methyl)-1H-indazole-5-carboxamide;
(20) 3-(4-fluorobenzamido)-N-(2-phenylpropan-2-yl)-1H-indazole-5-carboxamide;
(21) 3-(4-fluorobenzamido)-N-(4-(trifluoromethyl)benzyl)-1H-indazole-5-carboxamide;
(22) N-(cyclohexylmethyl)-3-(4-fluorobenzamido)-1H-indazole-5-carboxamide;
(23) N-(cyclopropylmethyl)-3-(4-fluorobenzamido)-1H-indazole-5-carboxamide;
(24) N-butyl-3-(4-fluorobenzamido)-1H-indazole-5-carboxamide;
(25) 3-(4-fluorobenzamido)-N-isopentyl-1H-indazole-5-carboxamide;
(26) N-((1,2,4-oxadiazol-3-yl)methyl)-3-(4-fluorobenzamido)-1H-indazole-5-carboxamide;
(27) 3-(4-fluorobenzamido)-N-(thiazol-5-ylmethyl)-1H-indazole-5-carboxamide 2,2,2-trifluoroacetate;
(28) 3-(4-fluorobenzamido)-N-(pyridin-2-ylmethyl)-1H-indazole-5-carboxamide 2,2,2-trifluoroacetate;
(29) 3-(4-fluorobenzamido)-N-(pyridin-4-ylmethyl)-1H-indazole-5-carboxamide;
(30) N-(cyclopropyl(thiophen-2-yl)methyl)-3-(4-fluorobenzamido)-1H-indazole-5-carboxamide;
(31) 4-fluoro-N-(5-(((thiophen-2-ylmethyl)amino)methyl)-1H-indazol-3-yl)benzamide hydrochloride;
(32) 4-fluoro-N-(5-(((1-(thiophen-2-yl)propyl)amino)methyl)-1H-indazol-3-yl)benzamide;
(33) 3-(4-fluorobenzamido)-N-(3-methyl-1-(thiophen-2-yl)butyl)-1H-indazole-5-carboxamide;
(34) 3-(4-fluorobenzamido)-N-(2-(thiophen-2-yl)butan-2-yl)-1H-indazole-5-carboxamide;
(35) 3-(2,4-difluorobenzamido)-N-(thiophen-2-ylmethyl)-1H-indazole-5-carboxamide;
(36) 3-(4-fluorobenzamido)-N-(thiophen-2-ylmethyl)-1H-indazole-5-carboxamide;
(37) 3-(4-fluorobenzamido)-N-(1-phenylethyl)-1H-indazole-5-carboxamide;
(38) 3-(4-fluorobenzamido)-N-(1-phenylpropyl)-1H-indazole-5-carboxamide;
(39) 3-(phenyl sulfonamido)-N-(thiophen-2-ylmethyl)-1H-indazole-5-carboxamide;
(40) N-benzyl-3-(4-(4-methylpiperazin-1-yl)benzamido)-1H-indazole-5-carboxamide;
(41) N-(1-phenylpropyl)-3-(4-(piperazin-1-yl)benzamido)-1H-indazole-5-carboxamide;
(42) N-methyl-3-(4-morpholinobenzamido)-N-(thiophen-2-ylmethyl)-1H-indazole-5-carboxamide;
(43) 3-(4-morpholinobenzamido)-N-(1-(thiophen-2-yl)ethyl)-1H-indazole-5-carboxamide;
(44) 3-(4-(4-methylpiperazin-1-yl)benzamido)-N-(1-(thiophen-2-yl)ethyl)-1H-indazole-5-carboxamide;
(45) N-(2-hydroxy-1-(thiophen-2-yl)ethyl)-3-(4-(4-methylpiperazin-1-yl)benzamido)-1H-indazole-5-carboxamide;
(46) 3-(4-morpholinobenzamido)-N-(thiophen-3-ylmethyl)-1H-indazole-5-carboxamide;
(47) 3-(4-(4-methylpiperazin-1-yl)benzamido)-N-(thiophen-3-ylmethyl)-1H-indazole-5-carboxamide;
(48) 3-(4-morpholinobenzamido)-N-(1-(thiophen-2-yl)cyclopropyl)-1H-indazole-5-carboxamide;
(49) 3-(4-(4-methylpiperazin-1-yl)benzamido)-N-(1-(thiophen-2-yl)cyclopropyl)-1H-indazole-5-carboxamide;
(50) N-(furan-2-ylmethyl)-3-(4-morpholinobenzamido)-1H-indazole-5-carboxamide;
(51) N-(furan-2-ylmethyl)-3-(4-(4-methylpiperazin-1-yl)benzamido)-1H-indazole-5-carboxamide;
(52) 3-(4-morpholinobenzamido)-N-(1-(pyridin-3-yl)ethyl)-1H-indazole-5-carboxamide;
(53) 3-(4-(4-methylpiperazin-1-yl)benzamido)-N-(1-(pyridin-3-yl)ethyl)-1H-indazole-5-carboxamide;
(54) 3-(4-morpholinobenzamido)-N-(1-(thiophen-2-yl)propyl)-1H-indazole-5-carboxamide;
(55) 3-(4-(4-methylpiperazin-1-yl)benzamido)-N-(1-(thiophen-2-yl)propyl)-1H-indazole-5-carboxamide;
(56) 3-(4-morpholinobenzamido)-N-(pyridin-3-ylmethyl)-1H-indazole-5-carboxamide 2,2,2-trifluoroacetate;
(57) 3-(4-(4-methylpiperazin-1-yl)benzamido)-N-(pyridin-3-ylmethyl)-1H-indazole-5-carboxamide bis(2,2,2-trifluoroacetate);
(58) 3-(4-morpholinobenzamido)-N-(1-(thiophen-2-yl)butyl)-1H-indazole-5-carboxamide;
(59) 3-(4-(4-methylpiperazin-1-yl)benzamido)-N-(1-(thiophen-2-yl)butyl)-1H-indazole-5-carboxamide;
(60) N-((5-methylthiophen-2-yl)methyl)-3-(4-morpholinobenzamido)-1H-indazole-5-carboxamide;
(61) 3-(4-(4-methylpiperazin-1-yl)benzamido)-N-((5-methylthiophen-2-yl)methyl)-1H-indazole-5-carboxamide;
(62) 3-(4-morpholinobenzamido)-N-(2-phenylpropan-2-yl)-1H-indazole-5-carboxamide;
(63) 3-(4-(4-methylpiperazin-1-yl)benzamido)-N-(2-phenylpropan-2-yl)-1H-indazole-5-carboxamide;
(64) 3-(4-(4-methylpiperazin-1-yl)benzamido)-N-(2-phenylpropan-2-yl)-1H-indazole-5-carboxamide hydrochloride;
(65) 3-(4-morpholinobenzamido)-N-(4-(trifluoromethyl)benzyl)-1H-indazole-5-carboxamide;
(66) 3-(4-(4-methylpiperazin-1-yl)benzamido)-N-(4-(trifluoromethyl)benzyl)-1H-indazole-5-carboxamide;
(67) 3-(4-morpholinobenzamido)-N-(1-phenylcyclopropyl)-1H-indazole-5-carboxamide;
(68) 3-(4-(4-methylpiperazin-1-yl)benzamido)-N-(1-phenylcyclopropyl)-1H-indazole-5-carboxamide;
(69) N-((2-methylpyridin-4-yl)methyl)-3-(4-morpholinobenzamido)-1H-indazole-5-carboxamide;
(70) 3-(4-(4-methylpiperazin-1-yl)benzamido)-N-((2-methylpyridin-4-yl)methyl)-1H-indazole-5-carboxamide;
(71) 3-(4-morpholinobenzamido)-N-((6-(trifluoromethyl)pyridin-3-yl)methyl)-1H-indazole-5-carboxamide;

(72) 3-(4-(4-methylpiperazin-1-yl)benzamido)-N-((6-(trifluoromethyl)pyridin-3-yl)methyl)-1H-indazole-5-carboxamide;
(73) 3-(2-methyl-4-morpholinobenzamido)-N-(thiophen-2-ylmethyl)-1H-indazole-5-carboxamide;
(74) 3-(2-methyl-4-(4-methylpiperazin-1-yl)benzamido)-N-(thiophen-2-ylmethyl)-1H-indazole-5-carboxamide;
(75) 3-(3-(4-(4-methylpiperazin-1-yl)benzamido)-1H-indazol-5-yl)-3-oxo-2-(thiophen-2-yl)propanoic acid;
(76) (S)-3-(4-(3-methylpiperazin-1-yl)benzamido)-N-(1-phenylcyclopropyl)-1H-indazole-5-carboxamide;
(77) (R)-3-(4-(3-methylpiperazin-1-yl)benzamido)-N-(1-phenylcyclopropyl)-1H-indazole-5-carboxamide;
(78) 3-(3-methyl-4-morpholinobenzamido)-N-(thiophen-2-ylmethyl)-1H-indazole-5-carboxamide;
(79) 3-(3-methyl-4-(4-methylpiperazin-1-yl)benzamido)-N-(thiophen-2-ylmethyl)-1H-indazole-5-carboxamide;
(80) 3-(4-(4-methylpiperazin-1-yl)benzamido)-N-(1-(thiophen-3-yl)ethyl)-1H-indazole-5-carboxamide;
(81) N-(1-(furan-2-yl)ethyl)-3-(4-(4-methylpiperazin-1-yl)benzamido)-1H-indazole-5-carboxamide;
(82) 3-(4-(4-methylpiperazin-1-yl)benzamido)-N-(1-(thiazol-2-yl)ethyl)-1H-indazole-5-carboxamide;
(83) 3-(4-(4-methylpiperazin-1-yl)benzamido)-N-(1-(thiazol-5-yl)ethyl)-1H-indazole-5-carboxamide;
(84) 3-(4-(4-methylpiperazin-1-yl)benzamido)-N-(1-(thiazol-2-yl)propyl)-1H-indazole-5-carboxamide;
(85) 3-(4-(4-methylpiperazin-1-yl)benzamido)-N-(pyridin-2-ylmethyl)-1H-indazole-5-carboxamide bis(2,2,2-trifluoroacetate);
(86) 3-(4-morpholinobenzamido)-N-(pyridin-2-ylmethyl)-1H-indazole-5-carboxamide;
(87) N-(cyclohexylmethyl)-3-(4-(4-methylpiperazin-1-yl)benzamido)-1H-indazole-5-carboxamide;
(88) N-(cyclohexylmethyl)-3-(4-morpholinobenzamido)-1H-indazole-5-carboxamide;
(89) 3-(4-(3,5-dimethylpiperazin-1-yl)benzamido)-N-(thiophen-2-ylmethyl)-1H-indazole-5-carboxamide 2,2,2-trifluoroacetate;
(90) N-(cyclopentylmethyl)-3-(4-(4-methylpiperazin-1-yl)benzamido)-1H-indazole-5-carboxamide 2,2,2-trifluoroacetate;
(91) N-(cyclopentylmethyl)-3-(4-morpholinobenzamido)-1H-indazole-5-carboxamide 2,2,2-trifluoroacetate;
(92) 3-(4-(2,6-dimethylmorpholino)benzamido)-N-(thiophen-2-ylmethyl)-1H-indazole-5-carboxamide 2,2,2-trifluoroacetate;
(93) N-(4-hydroxybutan-2-yl)-3-(4-(4-methylpiperazin-1-yl)benzamido)-1H-indazole-5-carboxamide;
(94) N-((1H-1,2,3-triazol-4-yl)methyl)-3-(4-(4-methylpiperazin-1-yl)benzamido)-1H-indazole-5-carboxamide;
(95) 3-(4-(3,5-dimethylpiperazin-1-yl)benzamido)-N-(1-(thiophen-2-yl)propyl)-1H-indazole-5-carboxamide 2,2,2-trifluoroacetate;
(96) 3-(4-(2,6-dimethylmorpholino)benzamido)-N-(1-(thiophen-2-yl)propyl)-1H-indazole-5-carboxamide 2,2,2-trifluoroacetate;
(97) 3-(4-((S)-3-methylpiperazin-1-yl)benzamido)-N-(1-(thiophen-2-yl)propyl)-1H-indazole-5-carboxamide 2,2,2-trifluoroacetate;
(98) 3-(4-((R)-3-methylpiperazin-1-yl)benzamido)-N-(1-(thiophen-2-yl)propyl)-1H-indazole-5-carboxamide 2,2,2-trifluoroacetate;
(99) 3-(4-((3R,5S)-3,5-dimethylpiperazin-1-yl)benzamido)-N-(1-(thiophen-2-yl)propyl)-1H-indazole-5-carboxamide 2,2,2-trifluoroacetate;
(100) N-((3-methyl-1,2,4-oxadiazol-5-yl)methyl)-3-(4-morpholinobenzamido)-1H-indazole-5-carboxamide 2,2,2-trifluoroacetate;
(101) N-((3-methyl-1,2,4-oxadiazol-5-yl)methyl)-3-(4-(4-methylpiperazin-1-yl)benzamido)-1H-indazole-5-carboxamide 2,2,2-trifluoroacetate;
(102) 3-(4-(piperazin-1-yl)benzamido)-N-(1-(thiophen-2-yl)propyl)-1H-indazole-5-carboxamide;
(103) 3-(4-(4-methylpiperazin-1-yl)benzamido)-N-(thiazol-2-ylmethyl)-1H-indazole-5-carboxamide 2,2,2-trifluoroacetate;
(104) 3-(4-morpholinobenzamido)-N-(thiazol-2-ylmethyl)-1H-indazole-5-carboxamide 2,2,2-trifluoroacetate;
(105) N-((1,2,4-oxadiazol-3-yl)methyl)-3-(4-morpholinobenzamido)-1H-indazole-5-carboxamide 2,2,2-trifluoroacetate;
(106) N-(cyclobutylmethyl)-3-(4-(4-methylpiperazin-1-yl)benzamido)-1H-indazole-5-carboxamide;
(107) 3-(4-(3,3-dimethylpiperazin-1-yl)benzamido)-N-(thiophen-2-ylmethyl)-1H-indazole-5-carboxamide 2,2,2-trifluoroacetate;
(108) 3-(4-(4-hydroxypiperidin-1-yl)benzamido)-N-(1-(thiophen-2-yl)propyl)-1H-indazole-5-carboxamide;
(109) 3-(4-(4-ethylpiperazin-1-yl)benzamido)-N-(1-(thiophen-2-yl)propyl)-1H-indazole-5-carboxamide;
(110) 3-(4-(4-methoxypiperidin-1-yl)benzamido)-N-(1-(thiophen-2-yl)propyl)-1H-indazole-5-carboxamide;
(111) (S)-3-(4-(4-methylpiperazin-1-yl)benzamido)-N-(1-(thiophen-2-yl)propyl)-1H-indazole-5-carboxamide;
(112) (R)-3-(4-(4-methylpiperazin-1-yl)benzamido)-N-(1-(thiophen-2-yl)propyl)-1H-indazole-5-carboxamide;
(113) N-butyl-3-(4-(4-methylpiperazin-1-yl)benzamido)-1H-indazole-5-carboxamide 2,2,2-trifluoroacetate;
(114) N-isopentyl-3-(4-(4-methylpiperazin-1-yl)benzamido)-1H-indazole-5-carboxamide 2,2,2-trifluoroacetate;
(115) N-butyl-3-(4-morpholinobenzamido)-1H-indazole-5-carboxamide 2,2,2-trifluoroacetate;
(116) N-isopentyl-3-(4-morpholinobenzamido)-1H-indazole-5-carboxamide 2,2,2-trifluoroacetate;
(117) (S)-3-(4-(3-methylpiperazin-1-yl)benzamido)-N-(thiophen-2-ylmethyl)-1H-indazole-5-carboxamide 2,2,2-trifluoroacetate;
(118) N-((1,2,4-oxadiazol-3-yl)methyl)-3-(4-(4-methylpiperazin-1-yl)benzamido)-1H-indazole-5-carboxamide 2,2,2-trifluoroacetate;
(119) N-((1H-1,2,3-triazol-4-yl)methyl)-3-(4-morpholinobenzamido)-1H-indazole-5-carboxamide 2,2,2-trifluoroacetate;
(120) 3-(4-morpholinobenzamido)-N-(pyridin-4-ylmethyl)-1H-indazole-5-carboxamide;
(121) 3-(4-(4-methylpiperazin-1-yl)benzamido)-N-(pyridin-4-ylmethyl)-1H-indazole-5-carboxamide;
(122) N-(cyclopropyl(thiophen-2-yl)methyl)-3-(4-morpholinobenzamido)-1H-indazole-5-carboxamide;
(123) 4-morpholino-N-(5-(((thiophen-2-ylmethyl)amino)methyl)-1H-indazol-3-yl)benzamide;
(124) 4-(4-methylpiperazin-1-yl)-N-(5-(((1-(thiophen-2-yl)propyl)amino)methyl)-1H-indazol-3-yl)benzamide;
(125) N-(cyclopropyl(thiophen-2-yl)methyl)-3-(4-(4-methylpiperazin-1-yl)benzamido)-1H-indazole-5-carboxamide;
(126) N-(cyclopropyl(thiophen-2-yl)methyl)-3-(4-(piperazin-1-yl)benzamido)-1H-indazole-5-carboxamide;
(127) 3-(4-morpholinobenzamido)-N-(1-(pyridin-2-yl)ethyl)-1H-indazole-5-carboxamide;

(128) 3-(4-(4-methylpiperazin-1-yl)benzamido)-N-(1-(pyridin-2-yl)ethyl)-1H-indazole-5-carboxamide;
(129) N-(3-methyl-1-(thiophen-2-yl)butyl)-3-(4-(4-methylpiperazin-1-yl)benzamido)-1H-indazole-5-carboxamide;
(130) N-(3-methyl-1-(thiophen-2-yl)butyl)-3-(4-morpholinobenzamido)-1H-indazole-5-carboxamide;
(131) 3-(4-(4-methylpiperazin-1-yl)benzamido)-N-(2-(thiophen-2-yl)butan-2-yl)-1H-indazole-5-carboxamide;
(132) 3-(4-morpholinobenzamido)-N-(1-(pyridin-4-yl)ethyl)-1H-indazole-5-carboxamide;
(133) 3-(4-(4-methylpiperazin-1-yl)benzamido)-N-(1-(pyridin-4-yl)ethyl)-1H-indazole-5-carboxamide;
(134) 3-(4-morpholinobenzamido)-N-(2-(thiophen-2-yl)propan-2-yl)-1H-indazole-5-carboxamide;
(135) 3-(4-(4-methylpiperazin-1-yl)benzamido)-N-(2,2,2-trifluoro-1-(thiophen-2-yl)ethyl)-1H-indazole-5-carboxamide;
(136) 3-(4-(4-methylpiperazin-1-yl)benzamido)-N-(2-(thiophen-2-yl)propan-2-yl)-1H-indazole-5-carboxamide;
(137) (S)-3-(4-(3-methylpiperazin-1-yl)benzamido)-N-(2-(thiophen-2-yl)propan-2-yl)-1H-indazole-5-carboxamide;
(138) 3-(4-morpholinobenzamido)-N-(2,2,2-trifluoro-1-(thiophen-2-yl)ethyl)-1H-indazole-5-carboxamide;
(139) N-(cyclopropyl(pyridin-2-yl)methyl)-3-(4-morpholinobenzamido)-1H-indazole-5-carboxamide;
(140) N-(cyclopropyl(pyridin-2-yl)methyl)-3-(4-(4-methylpiperazin-1-yl)benzamido)-1H-indazole-5-carboxamide;
(141) 4-(4-methylpiperazin-1-yl)-N-(5-(2-(thiophen-2-yl)acetamido)-1H-indazol-3-yl)benzamide;
(142) N-(cyclopropyl(pyridin-3-yl)methyl)-3-(4-morpholinobenzamido)-1H-indazole-5-carboxamide;
(143) N-(cyclopropyl(pyridin-3-yl)methyl)-3-(4-(4-methylpiperazin-1-yl)benzamido)-1H-indazole-5-carboxamide;
(144) 4-morpholino-N-(5-(2-(thiophen-2-yl)acetamido)-1H-indazol-3-yl)benzamide;
(145) 3-(4-(4-methylpiperazin-1-yl)benzamido)-N-(2-(thiophen-3-yl)propan-2-yl)-1H-indazole-5-carboxamide;
(146) N-((5-chlorothiophen-2-yl)methyl)-3-(4-(4-methylpiperazin-1-yl)benzamido)-1H-indazole-5-carboxamide;
(147) 3-(4-(4-methylpiperazin-1-yl)benzamido)-N-(1-(thiophen-2-yl)cyclohexyl)-1H-indazole-5-carboxamide;
(148) 3-(4-morpholinobenzamido)-N-(thiophen-2-ylmethyl)-1H-indazole-5-carboxamide;
(149) 3-(4-(4-methylpiperazin-1-yl)benzamido)-N-(thiophen-2-ylmethyl)-1H-indazole-5-carboxamide;
(150) 3-(4-((2-methoxyethyl)amino)benzamido)-N-(thiophen-2-ylmethyl)-1H-indazole-5-carboxamide;
(151) 3-(4-((3-methoxypropyl)amino)benzamido)-N-(thiophen-2-ylmethyl)-1H-indazole-5-carboxamide;
(152) 3-(4-((2-(pyrrolidin-1-yl)ethyl)amino)benzamido)-N-(thiophen-2-ylmethyl)-1H-indazole-5-carboxamide;
(153) 3-(4-((2-morpholinoethyl)amino)benzamido)-N-(thiophen-2-ylmethyl)-1H-indazole-5-carboxamide;
(154) 3-(4-((3-(dimethylamino)propyl)amino)benzamido)-N-(thiophen-2-ylmethyl)-1H-indazole-5-carboxamide;
(155) 3-(4-(methyl(2-(methylamino)ethyl)amino)benzamido)-N-(thiophen-2-ylmethyl)-1H-indazole-5-carboxamide;
(156) 3-(3-morpholinobenzamido)-N-(thiophen-2-ylmethyl)-1H-indazole-5-carboxamide;
(157) 3-(4-((((tetrahydrofuran-2-yl)methyl)amino)benzamido)-N-(thiophen-2-ylmethyl)-1H-indazole-5-carboxamide;
(158) 3-(4-((2-(dimethylamino)ethyl)amino)benzamido)-N-(thiophen-2-ylmethyl)-1H-indazole-5-carboxamide;
(159) 3-(4-(isopentylamino)benzamido)-N-(thiophen-2-ylmethyl)-1H-indazole-5-carboxamide;
(160) 3-(4-((2-(tetrahydro-2H-pyran-4-yl)ethyl)amino)benzamido)-N-(thiophen-2-ylmethyl)-1H-indazole-5-carboxamide;
(161) 3-(4-(hexylamino)benzamido)-N-(thiophen-2-ylmethyl)-1H-indazole-5-carboxamide;
(162) 3-(4-(cyclohexylamino)benzamido)-N-(thiophen-2-ylmethyl)-1H-indazole-5-carboxamide;
(163) 3-(4-(cyclopentylamino)benzamido)-N-(thiophen-2-ylmethyl)-1H-indazole-5-carboxamide;
(164) 3-(4-(cycloheptylamino)benzamido)-N-(thiophen-2-ylmethyl)-1H-indazole-5-carboxamide;
(165) 3-(4-(cyclooctylamino)benzamido)-N-(thiophen-2-ylmethyl)-1H-indazole-5-carboxamide;
(166) 3-(4-((cyclohexylmethyl)amino)benzamido)-N-(thiophen-2-ylmethyl)-1H-indazole-5-carboxamide;
(167) 3-(4-((2-(cyclohex-1-en-1-yl)ethyl)amino)benzamido)-N-(thiophen-2-ylmethyl)-1H-indazole-5-carboxamide;
(168) 3-(2,4-dimorpholinobenzamido)-N-(thiophen-2-ylmethyl)-1H-indazole-5-carboxamide;
(169) 3-(4-((2-(1H-pyrrol-1-yl)ethyl)amino)benzamido)-N-(thiophen-2-ylmethyl)-1H-indazole-5-carboxamide;
(170) 3-(2-fluoro-4-(4-methylpiperazin-1-yl)benzamido)-N-(thiophen-2-ylmethyl)-1H-indazole-5-carboxamide;
(171) 3-(4-(piperazin-1-yl)benzamido)-N-(thiophen-2-ylmethyl)-1H-indazole-5-carboxamide;
(172) 3-(4-(4-methylpiperazin-1-yl)benzamido)-N-(oxazol-5-ylmethyl)-1H-indazole-5-carboxamide;
(173) N-(is oxazol-3-ylmethyl)-3-(4-(4-methylpiperazin-1-yl)benzamido)-1H-indazole-5-carboxamide;
(174) 3-(4-(4-methylpiperazin-1-yl)benzamido)-N-(thiazol-4-ylmethyl)-1H-indazole-5-carboxamide;
(175) (R)-3-(4-(4-methylpiperazin-1-yl)benzamido)-N-(1-phenylethyl)-1H-indazole-5-carboxamide;
(176) (S)-3-(4-(4-methylpiperazin-1-yl)benzamido)-N-(1-phenylethyl)-1H-indazole-5-carboxamide;
(177) N-benzyl-3-(4-morpholinobenzamido)-1H-indazole-5-carboxamide;
(178) N-(is oxazol-5-ylmethyl)-3-(4-(4-methylpiperazin-1-yl)benzamido)-1H-indazole-5-carboxamide;
(179) 3-(4-(4-methylpiperazin-1-yl)benzamido)-N-(1-phenylethyl)-1H-indazole-5-carboxamide;
(180) 3-(4-morpholinobenzamido)-N-(1-phenylethyl)-1H-indazole-5-carboxamide;
(181) N-(1-phenylethyl)-3-(4-(piperazin-1-yl)benzamido)-1H-indazole-5-carboxamide 2,2,2-trifluoroacetate;
(182) 3-(4-(3,5-dimethylpiperazin-1-yl)benzamido)-N-(1-phenylethyl)-1H-indazole-5-carboxamide;
(183) 3-(4-(2,6-dimethylmorpholino)benzamido)-N-(1-phenylethyl)-1H-indazole-5-carboxamide;
(184) 3-(4-((S)-3-methylpiperazin-1-yl)benzamido)-N-(1-phenylethyl)-1H-indazole-5-carboxamide 2,2,2-trifluoroacetate;
(185) 3-(4-((R)-3-methylpiperazin-1-yl)benzamido)-N-(1-phenylethyl)-1H-indazole-5-carboxamide 2,2,2-trifluoroacetate;
(186) 3-(4-((3R,5S)-3,5-dimethylpiperazin-1-yl)benzamido)-N-(1-phenylethyl)-1H-indazole-5-carboxamide;
(187) 3-(4-(4-methylpiperazin-1-yl)benzamido)-N-(1-phenylpropyl)-1H-indazole-5-carboxamide;
(188) 3-(4-morpholinobenzamido)-N-(1-phenylpropyl)-1H-indazole-5-carboxamide;
(189) N-(4-fluorobenzyl)-3-(4-(4-methylpiperazin-1-yl)benzamido)-1H-indazole-5-carboxamide;

(190) (S)-3-(4-(4-methylpiperazin-1-yl)benzamido)-N-(1-phenylpropyl)-1H-indazole-5-carboxamide;
(191) (R)-3-(4-(4-methylpiperazin-1-yl)benzamido)-N-(1-phenylpropyl)-1H-indazole-5-carboxamide;
(192) (R)-3-(4-(4-methylpiperazin-1-yl)benzamido)-N-(1-phenylpropyl)-1H-indazole-5-carboxamide hydrochloride;
(193) (S)-3-(4-(4-methylpiperazin-1-yl)benzamido)-N-(1-phenylbutyl)-1H-indazole-5-carboxamide;
(194) (R)-3-(4-(4-methylpiperazin-1-yl)benzamido)-N-(1-phenylbutyl)-1H-indazole-5-carboxamide;
(195) N-(3-fluorobenzyl)-3-(4-(4-methylpiperazin-1-yl)benzamido)-1H-indazole-5-carboxamide;
(196) N-(2-fluorobenzyl)-3-(4-(4-methylpiperazin-1-yl)benzamido)-1H-indazole-5-carboxamide;
(197) N-(cyclopropyl(phenyl)methyl)-3-(4-(4-methylpiperazin-1-yl)benzamido)-1H-indazole-5-carboxamide;
(198) tert-butyl 4-(4-((5-((thiophen-2-ylmethyl)carbamoyl)-1H-indazol-3-yl)carbamoyl)phenyl)-3,6-tetrahydropyridine-1 (2H)-carboxylate;
(199) 3-(4-(1,2,3,6-tetrahydropyridin-4-yl)benzamido)-N-(thiophen-2-ylmethyl)-1H-indazole-5-carboxamide;
(200) 3-(4-hydroxybenzamido)-N-(thiophen-2-ylmethyl)-1H-indazole-5-carboxamide;
(201) 3-(4-(2-morpholinoethoxy)benzamido)-N-(thiophen-2-ylmethyl)-1H-indazole-5-carboxamide;
(202) tert-butyl 3-(4-nitrobenzamido)-5-((thiophen-2-ylmethyl)carbamoyl)-1H-indazole-1-carboxylate;
(203) 3-(4-nitrobenzamido)-N-(thiophen-2-ylmethyl)-1H-indazole-5-carboxamide;
(204) 3-(3-nitrobenzamido)-N-(thiophen-2-ylmethyl)-1H-indazole-5-carboxamide;
(205) 3-(4-aminobenzamido)-N-(thiophen-2-ylmethyl)-1H-indazole-5-carboxamide;
(206) 3-(4-(cyclobutanecarboxamido)benzamido)-N-(thiophen-2-ylmethyl)-1H-indazole-5-carboxamide;
(207) N-(thiophen-2-ylmethyl)-3-(4-(1-(trifluoromethyl)cyclopropanecarboxamido)benzamido)-1H-indazole-5-carboxamide;
(208) 3-(4-(3-oxocyclobutanecarboxamido)benzamido)-N-(thiophen-2-ylmethyl)-1H-indazole-5-carboxamide;
(209) 3-(4-(4-acetylpiperazin-1-yl)benzamido)-N-(1-(thiophen-3-yl)propyl)-1H-indazole-5-carboxamide;
(210) tert-butyl (S)-2-((4-((5-((thiophen-2-ylmethyl)carbamoyl)-1H-indazol-3-yl)carbamoyl)phenyl)carbamoyl)pyrrolidine-1-carboxylate;
(211) 3-(4-acetamidobenzamido)-N-(thiophen-2-ylmethyl)-1H-indazole-5-carboxamide;
(212) 3-(4-(1H-imidazol-1-yl)benzamido)-N-(thiophen-2-ylmethyl)-1H-indazole-5-carboxamide;
(213) 3-(4-((l-methylpiperidin-4-yl)amino)benzamido)-N-(thiophen-2-ylmethyl)-1H-indazole-5-carboxamide;
(214) 3-(4-fluorobenzamido)-N-(1-(pyridin-4-yl)ethyl)-1H-indazole-5-carboxamide;
(215) 3-(4-fluorobenzamido)-N-(2-(thiophen-2-yl)propan-2-yl)-1H-indazole-5-carboxamide;
(216) 3-(4-fluorobenzamido)-N-(1-(pyridin-2-yl)cyclopropyl)-1H-indazole-5-carboxamide;
(217) 3-(4-fluorobenzamido)-N-(1-(pyridin-3-yl)cyclopropyl)-1H-indazole-5-carboxamide;
(218) N-(5-(5-methyloxazol-2-yl)-1H-thieno[3,2-c]pyrazol-3-yl)-4-morpholinobenzamide;
(219) N-(5-(5-methylthiazol-2-yl)-1H-thieno[3,2-c]pyrazol-3-yl)-4-morpholinobenzamide;
(220) N-(5-(5-methyloxazol-2-yl)-1H-thieno[3,2-c]pyrazol-3-yl)benzamide;
(221) 4-fluoro-N-(5-(5-methyloxazol-2-yl)-1H-thieno[3,2-c]pyrazol-3-yl)benzamide;
(222) 4-methoxy-N-(5-(5-methyloxazol-2-yl)-1H-thieno[3,2-c]pyrazol-3-yl)benzamide;
(223) 4-(dimethylamino)-N-(5-(5-methyloxazol-2-yl)-1H-thieno[3,2-c]pyrazol-3-yl)benzamide;
(224) N-(5-(5-methyloxazol-2-yl)-1H-thieno[3,2-c]pyrazol-3-yl)-4-((2-(piperidin-1-yl)ethyl)amino)benzamide;
(225) N-(5-(5-methyloxazol-2-yl)-1H-thieno[3,2-c]pyrazol-3-yl)-4-(4-methylpiperazin-1-yl)benzamide;
(226) N-(5-(5-methyloxazol-2-yl)-1H-thieno[3,2-c]pyrazol-3-yl)-4-((2-(pyrrolidin-1-yl)ethyl)amino)benzamide;
(227) N-(5-(5-methyloxazol-2-yl)-1H-thieno[3,2-c]pyrazol-3-yl)-4-((2-morpholinoethyl)amino)benzamide;
(228) 4-((2-hydroxyethyl)amino)-N-(5-(5-methyloxazol-2-yl)-1H-thieno[3,2-c]pyrazol-3-yl)benzamide;
(229) 4-((2-methoxyethyl)amino)-N-(5-(5-methyloxazol-2-yl)-1H-thieno[3,2-c]pyrazol-3-yl)benzamide;
(230) 3-fluoro-N-(5-(5-methyloxazol-2-yl)-1H-thieno[3,2-c]pyrazol-3-yl)benzamide;
(231) methyl 3-(4-methoxyphenyl)-1H-thieno[3,2-c]pyrazole-5-carboxylate;
(232) N-ethyl-3-(4-methoxyphenyl)-1H-thieno[3,2-c]pyrazole-5-carboxamide;
(233) N-isopropyl-3-(4-methoxyphenyl)-1H-thieno[3,2-c]pyrazole-5-carboxamide;
(234) methyl 3-(4-(dimethylamino)phenyl)-1H-thieno[3,2-c]pyrazole-5-carboxylate;
(235) 2-(3-(4-methoxyphenyl)-1H-thieno[3,2-c]pyrazol-5-yl)-5-methyloxazole;
(236) methyl 3-phenyl-1H-thieno[3,2-c]pyrazole-5-carboxylate;
(237) 3-(4-(dimethylamino)phenyl)-N-ethyl-1H-thieno[3,2-c]pyrazole-5-carboxamide;
(238) N-ethyl-3-phenyl-1H-thieno[3,2-c]pyrazole-5-carboxamide;
(239) methyl 3-(4-fluorophenyl)-1H-thieno[3,2-c]pyrazole-5-carboxylate;
(240) N-ethyl-3-(4-fluorophenyl)-1H-thieno[3,2-c]pyrazole-5-carboxamide;
(241) N-ethyl-3-(4-morpholinophenyl)-1H-thieno[3,2-c]pyrazole-5-carboxamide;
(242) 3-(4-fluorophenyl)-N-(2-morpholinoethyl)-1H-thieno[3,2-c]pyrazole-5-carboxamide;
(243) 4-(4-(5-(5-methyloxazol-2-yl)-1H-thieno[3,2-c]pyrazol-3-yl)phenyl)morpholine;
(244) 4-(4-(5-(5-ethyloxazol-2-yl)-1H-thieno[3,2-c]pyrazol-3-yl)phenyl)morpholine;
(245) methyl 3-(4-acetamidophenyl)-1H-thieno[3,2-c]pyrazole-5-carboxylate;
(246) 2-(3-(4-fluorophenyl)-1H-thieno[3,2-c]pyrazol-5-yl)-5-methyloxazole;
(247) 3-(4-fluorophenyl)-5-(5-methylthiazol-2-yl)-1H-thieno[3,2-c]pyrazole;
(248) (3-(4-morpholinophenyl)-1H-thieno[3,2-c]pyrazol-5-yl)(pyrrolidin-1-yl)methanone;
(249) methyl 3-(4-(2-morpholinoethoxy)phenyl)-1H-thieno[3,2-c]pyrazole-5-carboxylate;
(250) 4-(2-(4-(5-(5-methyloxazol-2-yl)-1H-thieno[3,2-c]pyrazol-3-yl)phenoxy)ethyl)morpholine;
(251) 4-(dimethylamino)-N-(5-(5-methylthiazol-2-yl)-1H-thieno[3,2-c]pyrazol-3-yl)benzamide;
(252) N-(5-(5-ethylthiazol-2-yl)-1H-thieno[3,2-c]pyrazol-3-yl)-4-morpholinobenzamide;
(253) N-(5-(5-methylthiazol-2-yl)-1H-thieno[3,2-c]pyrazol-3-yl)-4-((2-(piperidin-1-yl)ethyl)amino)benzamide; and (254) methyl 3-(4-morpholinophenyl)-1H-thieno[3,2-c]pyrazole-5-carboxylate.

The pyrazole derivative according to the present invention may exist as a pharmaceutically acceptable salt. Preferably, the pharmaceutically acceptable salt of the inventive compound is a salt formed with an inorganic or organic acid. Examples of the inorganic acid include hydrochloric acid, sulfuric acid, nitric acid, phosphoric acid, perchloric acid, bromic acid, and the like. Examples of the organic acid include acetic acid, methanesulfonic acid, ethanesulfonic acid, p-toluenesulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, and the like. Examples of organic bases which can be used for preparing an organic base addition salt include tris(hydroxymethyl)methylamine, dicyclohexylamine, and the like. Examples of amino acids which can be used for preparing an amino acid addition salt include natural amino acids such as alanine, glycine, and the like.

Said salts may be prepared by conventional methods known in the art, e.g., dissolving the compound of formula (I) in a water-miscible solvent such as methanol, ethanol, acetone, 1,4-dioxane, adding a free acid or free base thereto, and subjecting the mixture to crystallization.

Also, the compounds of the present invention may have asymmetric carbon centers and, thus, may exist as R- or S-isomer, racemic mixtures, individual enantiomers or mixtures thereof, and individual diastereomers or mixtures thereof. Such stereoisomers and mixtures thereof are all included within the scope of the present invention.

Additionally, solvates and hydrates of the pyrazole derivative of formula (I) are also included within the scope of the present invention. Such solvates and hydrates may be prepared by conventional methods known in the art. Preferably, the solvates and hydrates are non-toxic and water-soluble, and form 1 to 5 bonds with water or alcohol-based solvent (particularly, ethanol and the like).

Meanwhile, the present invention provides a pharmaceutical composition for the prevention or treatment of cancer, comprising a compound selected from the group consisting of the pyrazole derivative of formula (I), and a pharmaceutically acceptable salt, a hydrate and a solvate thereof.

Examples of said cancer include colorectal cancer, breast cancer, CNS cancer, colon cancer, non-small cell lung cancer, kidney cancer, prostate cancer, ovarian cancer, uterus cancer, stomach cancer, liver cancer, skin cancer, lung cancer, brain cancer, bladder cancer, esophageal cancer, pancreatic cancer, thyroid cancer, head and neck cancer, squamous cell carcinoma, osteosarcoma, B-cell or T-cell lymphoma, acute or chronic leukemia and multiple myeloma.

In addition, since the inventive compound of formula (I) can inhibit TNIK, IKKε and TBK1 activities, it can also be used for the prevention or treatment of diseases associated with IKKε and TBK1 protein activation, e.g., chronic inflammatory, and the like.

A pharmaceutical composition of the present invention may comprise one or more conventional non-toxic pharmaceutically acceptable additives as effective components, in addition to the pyrazole derivative of formula (I) or a pharmaceutically acceptable salt, a hydrate or a solvate thereof.

Examples of acceptable additives for the pharmaceutical composition of the present invention include sweeteners, binders, solubilizing agents, dissolution aids, wetting agents, emulsifiers, isotonic agents, adsorbents, disintegrants, antioxidants, preservatives, lubricants, fillers, fragrances, and the like, e.g., lactose, dextrose, sucrose, mannitol, sorbitol, cellulose, glycine, silica, talc, stearic acid, stearin, magnesium stearate, magnesium aluminum silicate, starch, gelatin, tragacanth gum, alginic acid, sodium alginate, methylcellulose, sodium carboxymethyl cellulose, agar, water, ethanol, polyethylene glycol, polyvinyl pyrrolidone, sodium chloride, calcium chloride, orange essence, strawberry essence, vanilla flavor, etc.

A pharmaceutical composition of the present invention may be prepared as an oral dosage form such as a tablet, a pill, powders, a capsule, a syrup or an emulsion or a parenteral dosage form for intramuscular, intravenous or subcutaneous administration. Preferably, the pharmaceutical composition is prepared in an oral dosage form.

In the case where the pharmaceutical composition of the present invention is prepared as an oral dosage form, the inventive pharmaceutical composition may comprise additives such as cellulose, calcium silicate, corn starch, lactose, sucrose, dextrose, calcium phosphate, stearic acid, magnesium stearate, calcium stearate, gelatin, talc, a surfactant, a suspension agent, an emulsifier, a diluent, etc.

Also, in the case where the pharmaceutical composition of the present invention is prepared as an injectable dosage form, the inventive pharmaceutical composition may comprise additives such as water, brine, a glucose aqueous solution, an analog glucose aqueous solution, alcohol, glycol, ether, oil, a fatty acid, a fatty acid ester, a glyceride, a surfactant, a suspension agent, an emulsifier, etc.

Preferably, a proposed daily dose of the compound in accordance with the present invention for an adult patient (of approximately 70 kg body weight) may be in the range of 0.1 to 2,000 mg/day. The compound in accordance with the present invention may be administered in a single dose or in divided doses per day. It is understood that the daily dose should be determined in light of various relevant factors including health status, age, weight and sex of a subject to be treated, administration route and disease severity. Thus, the amount of proposed daily dose is not limited to the above-described range.

Hereinafter, the present invention is described in detail with reference to the following examples. However, these examples are merely presented to exemplify the present invention, and the scope of the present invention is not limited thereto.

The symbols and conventions used for describing the processes, schemes and examples of the present invention are consistent with those used in contemporary scientific literatures, for example, the *Journal of the American Chemical Society* or the *Journal of Biological Chemistry*. Unless otherwise noted, all starting materials were obtained from commercial suppliers and used without further purification.

The following are definitions of abbreviations that are used in the examples.

Hz (Hertz)
TLC (thin layer chromatography)
$T_r$ (retention time)
RP (reverse phase)
MeOH (methanol)
i-PrOH (isopropanol)
TFA (trifluoroacetic acid)
TEA (triethylamine)
EtOH (ethanol)
THF (tetrahydrofuran)
DMSO (dimethylsulfoxide)
EtOAc (ethyl acetate)
DCM (dichloromethane)

HOAc (acetic acid)
DMF (N,N-dimethylformamide)
Ac (acetyl)
HOBt (1-hydroxybenzotriazole)
Bn (benzyl)
Boc (tert-butyloxycarbonyl)
mCPBA (meta-chloroperbenzoic acid)
FMOC (9-fluorenylmethoxycarbonyl)
DCC (dicyclohexylcarbodiimide)
Cbz (benzyloxycarbonyl)
NMM (N-methyl morpholine)
HOAt (1-hydroxy-7-azabenzotriazole)
TBAF (tetra-n-butylammonium fluoride)
THP (tetrahydro-2H-pyran-2-yl)
DMAP (4-dimethylaminopyridine)
HPLC (high pressure liquid chromatography)
BOP (bis(2-oxo-3-oxazolidinyl)phosphinic chloride);
EDCI (1-ethyl-3-[3-dimethylaminopropyl]carbodiimide hydrochloride)
HBTU (O-Benzotriazole-1-yl-N,N,N',N'-tetramethyluronium hexafluorophosphate)
AIBN (2,2'-azobis(2-methylpropionitrile))
MeI (iodomethane)
DIPEA (diisopropylethylamine)
NaSMe (sodium thiomethoxide)
DAST (diethylaminosulfur trifluoride)
DMAc (Dimethylacetamide)

All references to ether are to diethyl ether; brine refers to a saturated aqueous solution of NaCl. Unless otherwise indicated, all temperatures are expressed in ° C. (degrees Centigrade). All reactions were conducted under an inert atmosphere at room temperature unless otherwise noted, and all solvents are of the highest available purity unless otherwise indicated.

Microwave reaction was conducted with a Biotage Initiator™ microwave synthesizer.

$^1$H NMR spectra were recorded on Bruker Ultrashield 400 plus spectrometer. Chemical shifts were expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet) or br (broad).

Mass spectra were obtained with either Quattro LC Triple Quadruple Tandem Mass Spectrometer (ESI; Micromass) or 1200LC/MSD (ESI; Agilent).

For preparative HPLC, ca 100 mg of a product was injected into 1 mL of DMSO onto a SunFire™ Prep C18 OBD 5 μm 19×100 mm Column with a 10 min gradient from 10% CH$_3$CN to 90% CH$_3$CN in H$_2$O (purification systems from Gilson, Inc). Flash chromatography was carried out using Merck silica gel 60 (230-400 mesh). Biotage SP1™ FLASH Purification System and Biotage Isolera™ FLASH Purification System were used for normal phase column chromatography with ethyl acetate and hexane. Most of the reactions were monitored by thin-layer chromatography on 0.25 mm E. Merck silica gel plates (60F-254), visualized with UV light using a 5% ethanolic phosphomolybdic acid or p-anisaldehyde solution.

The following synthetic schemes are merely illustrative of the methods by which the compounds of the invention may be prepared and are not intended to limit the scope of the invention as defined in the appended claims.

Preparation Example 1: Preparation of 3-(4-fluorobenzamido)-1H-indazole-5-carboxylic Acid

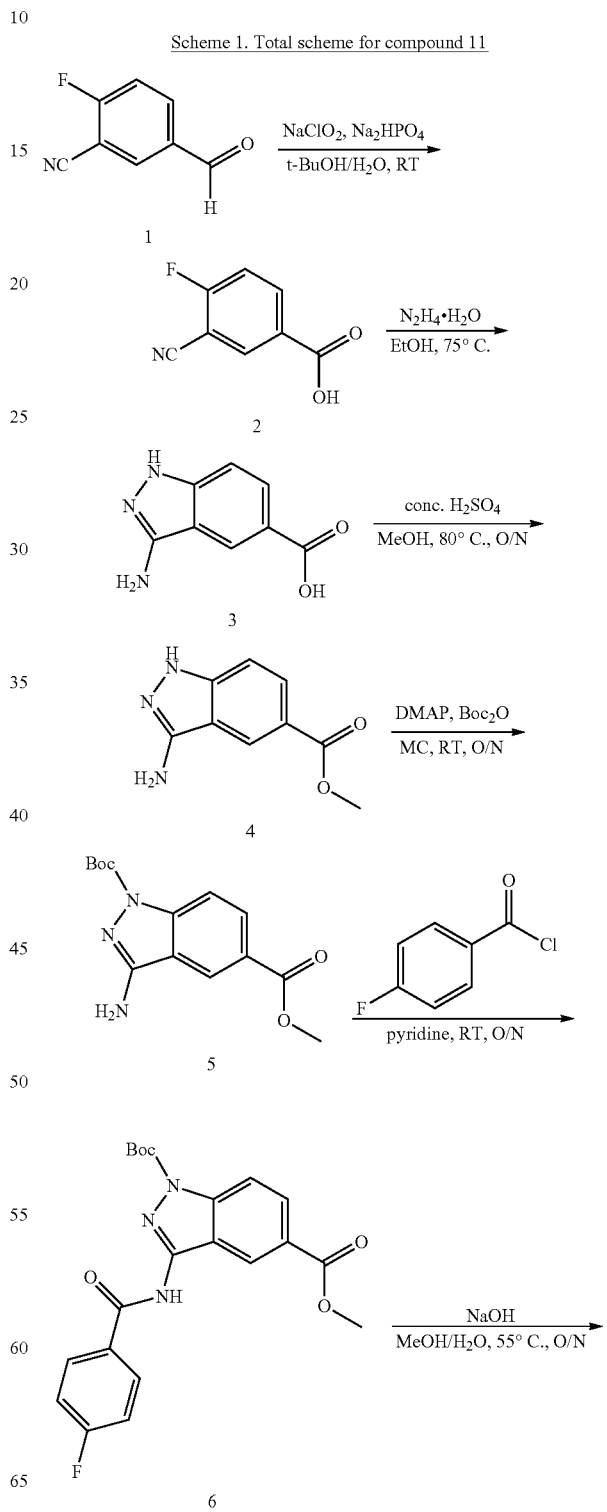

Scheme 1. Total scheme for compound 11

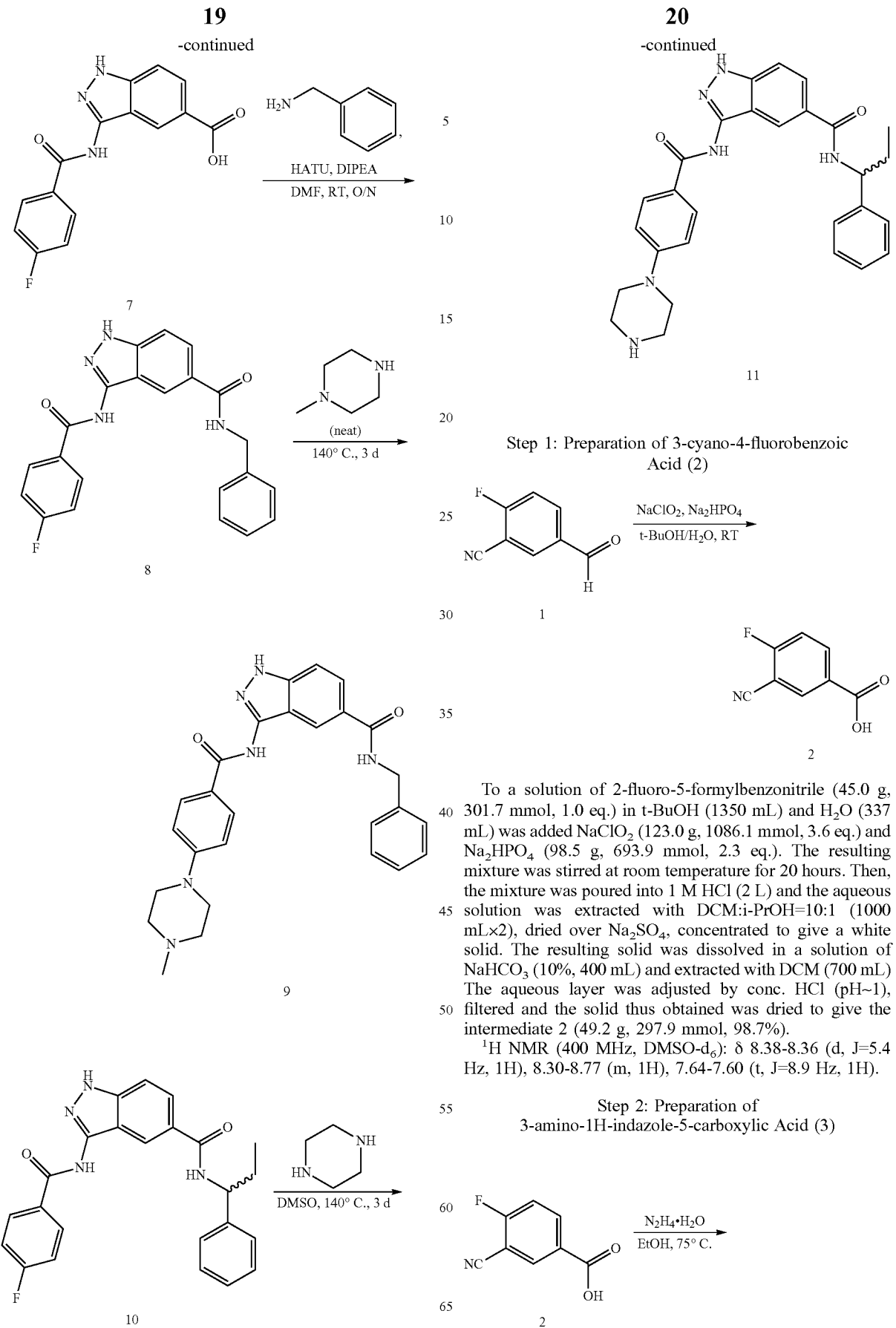

Step 1: Preparation of 3-cyano-4-fluorobenzoic Acid (2)

To a solution of 2-fluoro-5-formylbenzonitrile (45.0 g, 301.7 mmol, 1.0 eq.) in t-BuOH (1350 mL) and H₂O (337 mL) was added NaClO₂ (123.0 g, 1086.1 mmol, 3.6 eq.) and Na₂HPO₄ (98.5 g, 693.9 mmol, 2.3 eq.). The resulting mixture was stirred at room temperature for 20 hours. Then, the mixture was poured into 1 M HCl (2 L) and the aqueous solution was extracted with DCM:i-PrOH=10:1 (1000 mL×2), dried over Na₂SO₄, concentrated to give a white solid. The resulting solid was dissolved in a solution of NaHCO₃ (10%, 400 mL) and extracted with DCM (700 mL) The aqueous layer was adjusted by conc. HCl (pH~1), filtered and the solid thus obtained was dried to give the intermediate 2 (49.2 g, 297.9 mmol, 98.7%).

$^1$H NMR (400 MHz, DMSO-d$_6$): δ 8.38-8.36 (d, J=5.4 Hz, 1H), 8.30-8.77 (m, 1H), 7.64-7.60 (t, J=8.9 Hz, 1H).

Step 2: Preparation of 3-amino-1H-indazole-5-carboxylic Acid (3)

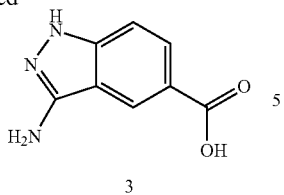

3

To a solution of intermediate 2 (49.2 g, 297.9 mmol, 1.0 eq.) in EtOH (500 mL) was added $N_2H_4 \cdot H_2O$ (56 mL, 893.9 mmol, 3.0 eq.). The mixture was stirred at 75° C. for 20 hours. The mixture was filtered and the filtrate thus obtained was concentrated to give a solid. The resulting solid was washed with MeOH (30 mL) and dried to give the intermediate 3 (50.9 g, 287.3 mmol, 96.4%).

$^1$H NMR (400 MHz, DMSO-$d_6$): δ 8.54 (s, 1H), 7.85-7.82 (d, J=8.7 Hz, 1H), 7.14-7.12 (d, J=8.6 Hz, 1H), 5.50 (s, 2H).

Step 3: Preparation of Methyl 3-amino-1H-indazole-5-carboxylate (4)

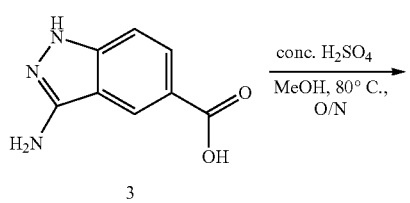

To a solution of intermediate 3 (10.0 g, 0.056 mol) in MeOH (224 mL) was added conc. $H_2SO_4$ (16.5 g, 0.168 mol). The mixture was heated to 80° C. overnight until the reaction was completed (monitored by UPLC), cooled to room temperature, concentrated, poured into water (300 mL), sonicated and stirred. The precipitate was collected by filtration, washed with water (150 mL) and dried to give the intermediate 4 (10.2 g, 96%) as a light brown solid.

$^1$H NMR (400 MHz, DMSO-$d_6$) δ 8.60 (t, J=0.7 Hz, 1H), 7.90 (dd, J=8.9, 1.5 Hz, 1H), 7.36 (dd, J=8.8, 0.6 Hz, 1H), 3.85 (s, 3H); [M+H]$^+$ 192.

Step 4: Preparation of 1-tert-butyl 5-methyl 3-amino-1H-indazole-1,5-dicarboxylate (5)

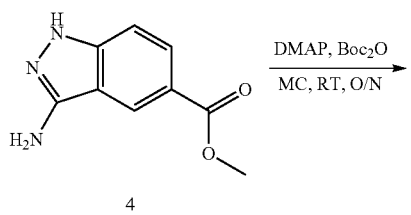

A solution of intermediate 4 (13.9 g, 0.073 mol) and DMAP (9.8 g, 0.08 mol) in MC (364 mL) was stirred for 1 hour. The mixture was added with Boc$_2$O (19.0 g, 0.087 mol) in one portion. The reaction mixture was stirred overnight at room temperature until the reaction was completed (monitored by UPLC), concentrated, poured into water (500 mL), sonicated and stirred. The precipitate was collected by filtration, washed with water (200 mL) and dried to give the intermediate 5 (18.3 g, 86%) as a yellow solid.

$^1$H NMR (400 MHz, DMSO-$d_6$) δ 8.62 (dd, J=1.4, 0.8 Hz, 1H), 8.09 (dd, J=8.8, 1.6 Hz, 1H), 8.03 (d, J=8.8 Hz, 1H), 6.58 (s, 2H), 3.89 (d, J=5.2 Hz, 3H), 1.59 (s, 9H); [M+H]$^+$ 292.

Step 5: Preparation of 1-tert-butyl 5-methyl 3-(4-fluorobenzamido)-1H-indazole-1,5-dicarboxylate (6)

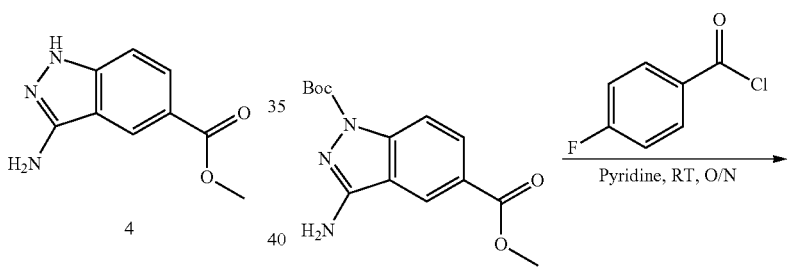

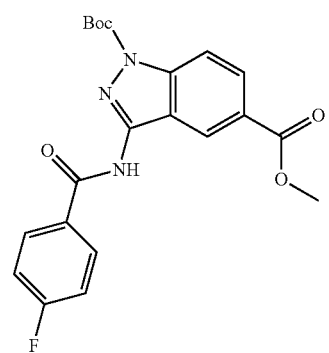

A solution of the intermediate 5 (4.6 g, 0.016 mol) in pyridine (52.3 mL) was stirred for 10 minutes and added with 4-fluorobenzoyl chloride (2.8 mL, 0.024 mol). The reaction mixture was stirred overnight at room temperature until the reaction was completed (monitored by UPLC) and poured into a mixture of water (150 mL) and MC (150 mL) The aqueous layer was extracted with MC (2×200 mL) The combined organic layer was dried over MgSO$_4$, filtered and concentrated to give the crude intermediate 6.

¹H NMR (400 MHz, DMSO-d₆) δ 11.57 (s, 1H), 8.57 (s, 1H), 8.27-8.22 (m, 1H), 8.22-8.16 (m, 3H), 7.45-7.38 (m, 2H), 3.89 (s, 3H), 1.66 (s, 9H); [M+H]⁺ 414.

Step 6: Preparation of 3-(4-fluorobenzamido)-1H-indazole-5-carboxylic Acid (7)

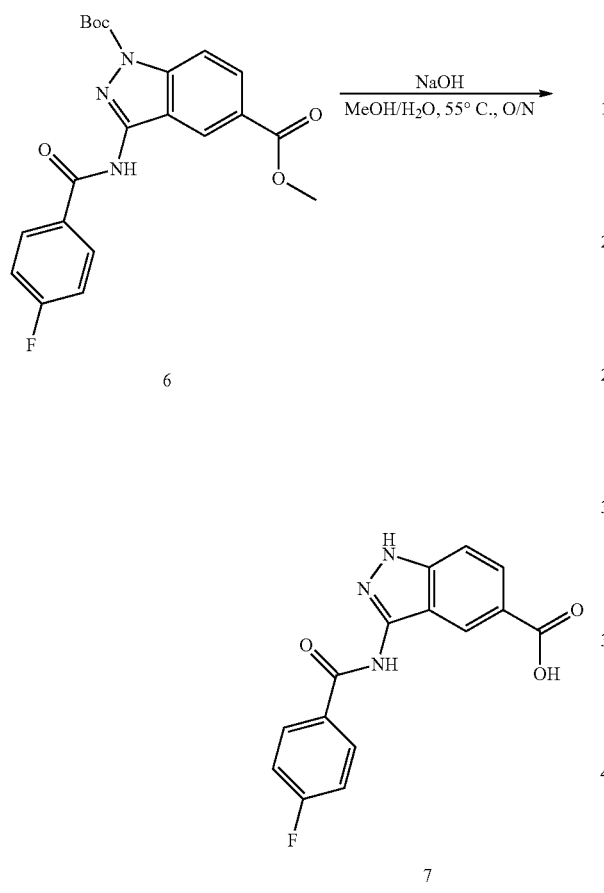

To a solution of the crude intermediate 6 (≈11.8 mmol) in MeOH (59 mL) was added NaOH (4.72 g, 118 mmol) in H₂O (59 mL) The reaction mixture was stirred from room temperature to 55° C. overnight until the reaction was completed (monitored by UPLC). The resulting reaction mixture was acidified to pH 2 with 1N HCl (200 mL), sonicated and stirred. The precipitate was collected by filtration, and then washed with water (2×200 mL) and MC (200 mL) The filtered solid was dried to give the intermediate 7 (2.7 g, 77% for 2 steps) as a light pink solid.

¹H NMR (400 MHz, DMSO-d₆) δ 13.12 (br s, 1H), 11.02 (s, 1H), 8.49 (dd, J=1.5, 0.7 Hz, 1H), 8.17 (td, J=6.1, 2.6 Hz, 2H), 7.92 (dd, J=8.8, 1.5 Hz, 1H), 7.54 (dd, J=8.8, 0.7 Hz, 1H), 7.39 (td, J=7.8, 2.0 Hz, 2H); [M+H]⁺ 300.

Example 1: N-Benzyl-3-(4-fluorobenzamido)-1H-indazole-5-carboxamide

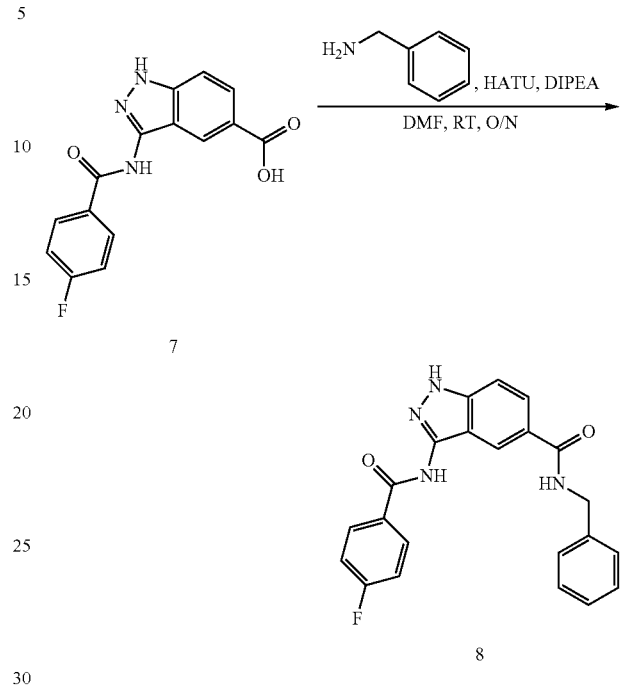

To a solution of the intermediate 7 (200 mg, 0.67 mmol) and HATU (281.4 mg, 0.74 mmol) in DMF (6.7 mL) was added benzylamine (87.4 mL, 0.80 mmol) and DIPEA (502 mL, 2.88 mmol). The reaction mixture was stirred overnight at room temperature until the reaction was completed (monitored by UPLC) and then poured into water (20 mL) The precipitate was collected by filtration and washed with water (2×20 mL) The filtered solid was dried to give the intermediate 8 (195.7 mg, 75%) as a pale gray solid.

¹H NMR (400 MHz, DMSO-d₆) δ 13.04 (s, 1H), 10.90 (s, 1H), 9.03 (t, J=6.1 Hz, 1H), 8.34 (d, J=1.4 Hz, 1H), 8.17 (dd, J=8.6, 5.5 Hz, 2H), 7.92 (dd, J=8.9, 1.6 Hz, 1H), 7.54 (d, J=8.7 Hz, 1H), 7.39 (t, J=8.8 Hz, 2H), 7.31 (d, J=4.4 Hz, 4H), 7.23 (q, J=4.4 Hz, 1H), 4.48 (d, J=5.9 Hz, 2H); [M+H]⁺ 389.

Example 2: N-(Furan-2-yl-methyl)-3-(4-methoxybenzamido)-1H-indazole-5-carboxamide

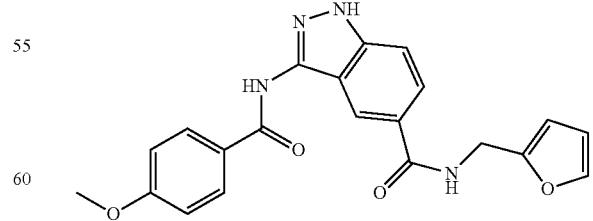

¹H NMR (400 MHz, DMSO-d₆) δ 8.35 (s, 1H), 8.04 (d, J=8.8 Hz, 2H), 7.89 (d, J=8.8 Hz, 1H), 7.53 (d, J=8.8 Hz, 1H), 7.42 (s, 1H), 7.07 (d, J=8.8 Hz, 2H), 6.34 (s, 1H), 6.30 (s, 1H), 4.56 (s, 2H), 3.90 (s, 3H); [M+H]⁺ 391.

Example 3: 3-(4-Methoxybenzamido)-N-(thiophen-2-ylmethyl)-1H-indazole-5-carboxamide

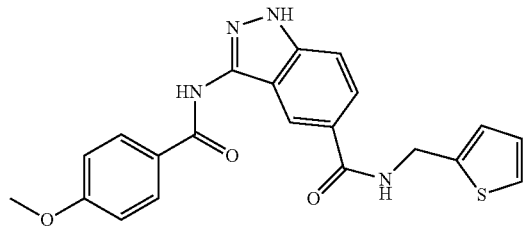 [SMILES: COc1ccc(C(=O)Nc2n[nH]c3ccc(C(=O)NCc4ccco4)cc23)cc1]

1H NMR (400 MHz, DMSO-d6) δ 8.36 (s, 1H), 8.03 (d, J=8.4 Hz, 2H), 7.89 (d, J=8.4 Hz, 1H), 7.52 (d, J=8.4 Hz, 1H), 7.26 (d, J=4.8 Hz, 1H), 7.06 (d, J=8.4 Hz, 2H), 7.04 (m, 1H), 6.94-6.92 (m, 1H), 4.74 (s, 2H), 3.89 (s, 3H); [M+H]$^+$ 391.

Example 4: 3-(4-Methoxybenzamido)-N-methyl-N-(thiophen-2-ylmethyl)-1H-indazole-5-carboxamide

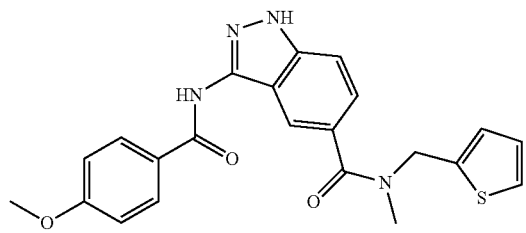 [SMILES: COc1ccc(C(=O)Nc2n[nH]c3ccc(C(=O)N(C)Cc4cccs4)cc23)cc1]

$^1$H NMR (400 MHz, DMSO-$d_6$) δ 13.00 (br s, 1H), 10.78 (br s, 1H), 8.08 (d, J=8.8 Hz, 2H), 7.90 (s, 1H), 7.55 (d, J=8.8 Hz, 1H), 7.45-7.43 (m, 2H), 7.08 (d, J=8.8 Hz, 2H), 6.99 (m, 1H), 4.78 (s, 2H), 3.87 (s, 3H), 2.94 (s, 3H); [M+H]$^+$ 421.

Example 5: 4-Methoxy-N-(5-(4,5,6,7-tetrahydrothieno[2,3-c]pyridine-6-carbonyl)-1H-indazol-3-yl)benzamide

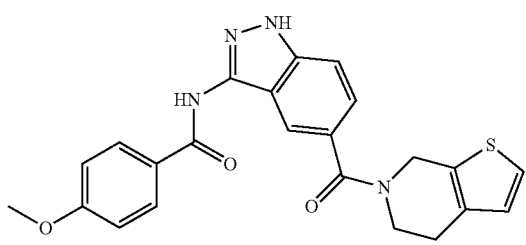 [SMILES: COc1ccc(C(=O)Nc2n[nH]c3ccc(C(=O)N4CCc5ccsc5C4)cc23)cc1]

$^1$H NMR (400 MHz, DMSO-$d_6$) δ 13.00 (br s, 1H), 10.80 (s, 1H), 8.08 (d, J=8.8 Hz, 2H), 7.93-7.91 (m, 1H), 7.56 (d, J=8.4 Hz, 1H), 7.47-7.45 (m, 1H), 7.40-7.38 (m, 1H), 7.08 (d, J=8.8 Hz, 2H), 7.11-7.06 (m, 1H), 6.88 (d, J=4.8 Hz, 1H), 4.79 (br s, 2H), 3.86 (s, 3H), 3.47-3.40 (m, 4H), 2.75; [M+H]$^+$ 433.

Example 6: 3-(4-(Methylthio)benzamido)-N-(thiophen-2-ylmethyl)-1H-indazole-5-carboxamide

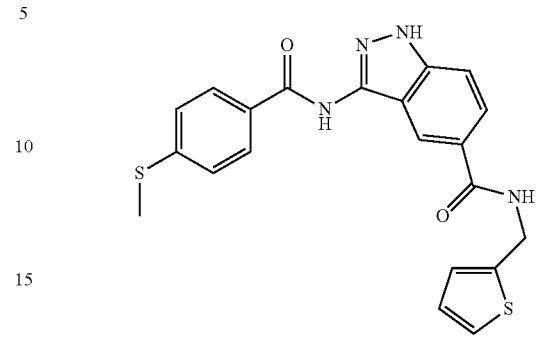

$^1$H NMR (400 MHz, DMSO-$d_6$) δ 13.02 (s, 1H), 10.81 (s, 1H), 9.11 (s, 1H), 8.32 (s, 1H), 8.04 (d, J=8.4 Hz, 2H), 7.89 (dd, J=8.8, 1.2 Hz, 1H), 7.53 (d, J=9.2 Hz, 1H), 7.40 (d, J=8.4 Hz, 2H), 7.00 (d, J=2.8 Hz, 1H), 6.96-6.94 (m, 1H), 4.62 (d, J=5.6 Hz, 2H), 2.56 (s, 3H); [M+H]$^+$ 423.

Example 7: 3-(1-Methyl-1H-pyrazole-4-carboxamido)-N-(thiophen-2-ylmethyl)-1H-indazole-5-carboxamide

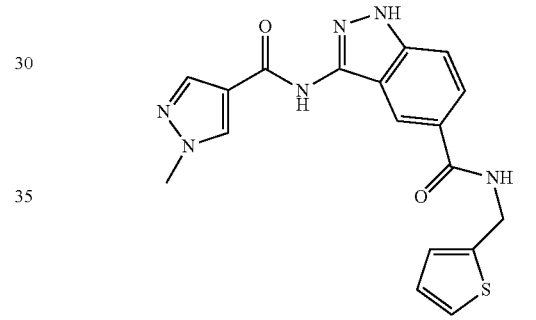

$^1$H NMR (400 MHz, MeOD) δ 8.36 (s, 1H), 8.25 (s, 1H), 8.08 (s, 1H), 7.89 (dd, J=8.8, 1.6 Hz, 1H), 7.52 (d, J=8.8 Hz, 1H), 7.27 (d, J=4.8 Hz, 1H), 7.04 (d, J=2.8 Hz, 1H), 6.94 (dd, J=5.2, 3.6 Hz, 1H), 4.74 (s, 2H), 3.97 (s, 3H); [M+H]$^+$ 381.

Example 8: 3-(5-Methoxypicolinamido)-N-(thiophen-2-ylmethyl)-1H-indazole-5-carboxamide Hydrochloride

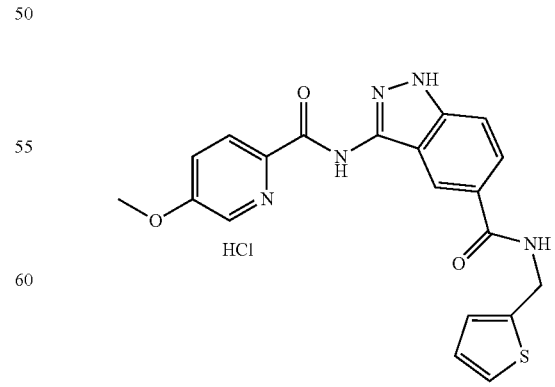

$^1$H NMR (400 MHz, DMSO-$d_6$) δ 10.66 (s, 1H), 8.44-8.43 (m, 2H), 8.18 (d, J=8.8 Hz, 2H), 7.89 (dd, J=8.8, 1.2

Hz, 1H), 7.64 (dd, J=8.8, 2.8 Hz, 1H), 7.53 (d, J=8.8 Hz, 1H), 7.37 (dd, J=5.2, 1.2 Hz, 1H), 7.02-7.01 (m, 1H), 6.96-6.94 (m, 1H), 4.63 (d, J=5.6 Hz, 2H), 3.96 (s, 3H); [M+H]+ 408.

Example 9: 3-(2-Methoxynicotinamido)-N-(thiophen-2-ylmethyl)-1H-indazole-5-carboxamide

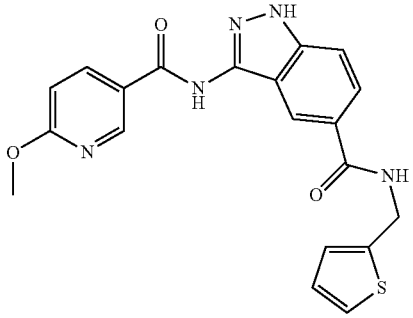 [SMILES: COc1ccc(C(=O)Nc2n[nH]c3ccc(C(=O)NCc4cccs4)cc23)cn1]

$^1$H NMR (400 MHz, MeOD) δ 8.87 (d, J=2.4 Hz, 1H), 8.37 (s, 1H), 8.29 (dd, J=9.0, 2.2 Hz, 1H), 7.90 (dd, J=8.8, 1.6 Hz, 1H), 7.54 (d, J=9.2 Hz, 1H), 7.27 (dd, J=4.8, 1.2 Hz, 1H), 7.04 (d, J=3.6 Hz, 1H), 6.95-6.92 (m, 2H), 4.74 (s, 2H), 4.02 (s, 3H); [M+H]+ 408.

Example 10: 3-(4-tert-Butylbenzamido)-N-(thiophen-2-ylmethyl)-1H-indazole-5-carboxamide

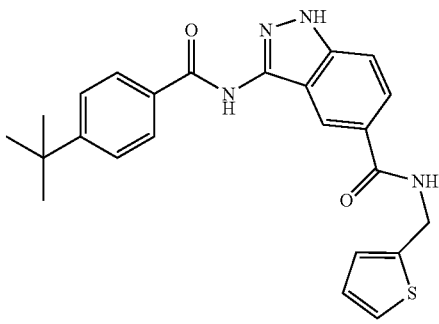 [SMILES: CC(C)(C)c1ccc(C(=O)Nc2n[nH]c3ccc(C(=O)NCc4cccs4)cc23)cc1]

$^1$H NMR (400 MHz, DMSO-d$_6$) δ 10.79 (s, 1H), 9.11 (t, J=5.6 Hz, 1H), 8.31 (s, 1H), 8.04 (d, J=8.4 Hz, 2H), 7.90 (dd, J=9.0, 1.4 Hz, 1H), 7.57 (d, J=8.4 Hz, 2H), 8.53 (d, J=8.8 Hz, 1H), 7.00 (d, J=2.8 Hz, 1H), 6.94 (dd, J=5.2, 3.6 Hz, 1H), 4.62 (d, J=5.6 Hz, 2H); [M+H]+ 434.

Example 11: 4-Methoxy-N-(5-((thiophen-2-ylmethyl)amino)-1H-indazol-3-yl)benzamide

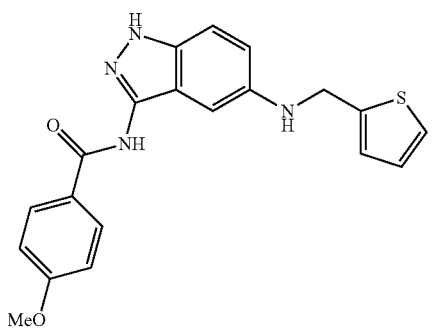 [SMILES: COc1ccc(C(=O)Nc2n[nH]c3ccc(NCc4cccs4)cc23)cc1]

$^1$H NMR (400 MHz, DMSO-d$_6$) δ 12.48 (d, J=20.5 Hz, 1H), 10.41 (d, J=4.6 Hz, 1H), 8.03 (dd, J=8.8, 4.1 Hz, 2H), 7.39-7.30 (m, 3H), 7.05 (dd, J=8.9, 1.8 Hz, 3H), 6.99-6.89 (m, 4H), 4.59 (s, 3H), 3.84 (s, 2H); [M+H]+ 379.

Example 12: 4-Methoxy-N-(5-(5-(morpholinomethyl)thiophen-2-yl)-1H-indazol-3-yl)benzamide

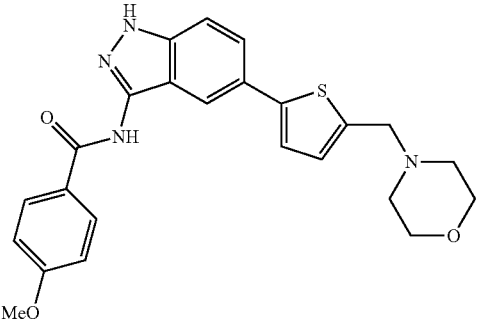 [SMILES: COc1ccc(C(=O)Nc2n[nH]c3ccc(-c4ccc(CN5CCOCC5)s4)cc23)cc1]

$^1$H NMR (400 MHz, DMSO-d$_6$) δ 10.69 (s, 1H), 8.12-8.05 (m, 2H), 7.90 (s, 1H), 7.66 (dd, J=8.8, 1.7 Hz, 1H), 7.51 (d, J=8.7 Hz, 1H), 7.26 (d, J=3.6 Hz, 1H), 7.12-7.04 (m, 2H), 6.94 (d, J=3.6 Hz, 1H), 3.86 (s, 3H), 3.65 (s, 2H), 3.58 (t, J=4.6 Hz, 4H), 2.41 (s, 4H); [M+H]+ 449.

Example 13: 3-Benzamido-N-(thiophen-2-ylmethyl)-1H-indazole-5-carboxamide

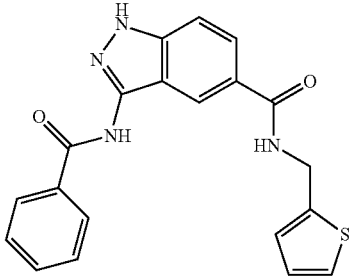 [SMILES: O=C(NCc1cccs1)c1ccc2[nH]nc(NC(=O)c3ccccc3)c2c1]

$^1$H NMR (400 MHz, Methanol-d$_4$) δ 9.07 (s, 1H), 8.38 (s, 1H), 8.10-8.02 (m, 2H), 7.91 (dd, J=8.9, 1.6 Hz, 1H), 7.64 (t, J=7.3 Hz, 1H), 7.56 (dd, J=8.3, 6.8 Hz, 3H), 7.27 (dd, J=5.1, 1.2 Hz, 1H), 7.04 (d, J=3.5 Hz, 1H), 6.94 (dd, J=5.1, 3.5 Hz, 1H), 4.75 (d, J=5.3 Hz, 2H); [M+H]+ 377.

Example 14: 3-(4-Fluorobenzamido)-N-(1-(thiophen-2-yl)ethyl)-1H-indazole-5-carboxamide

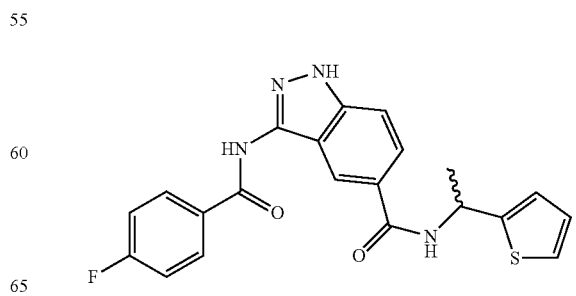

[M+H]+ 409.

Example 15: 3-(4-Fluorobenzamido)-N-(1-(thiophen-2-yl)cyclopropyl)-1H-indazole-5-carboxamide

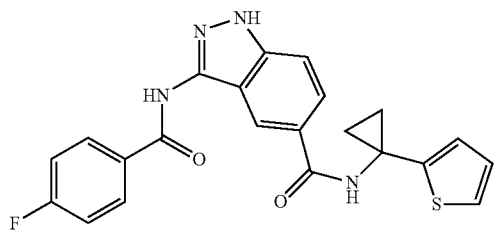 [SMILES: O=C(Nc1n[nH]c2ccc(C(=O)NC3(c4cccs4)CC3)cc12)c1ccc(F)cc1]

[M+H]+ 421.

Example 16: N-(1-Cyanocyclopropyl)-3-(4-fluorobenzamido)-1H-indazole-5-carboxamide

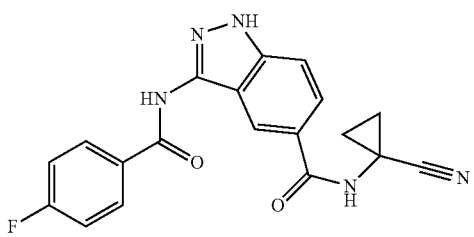 [SMILES: N#CC1(NC(=O)c2ccc3[nH]nc(NC(=O)c4ccc(F)cc4)c3c2)CC1]

$^1$H NMR (400 MHz, DMSO-$d_6$) δ 13.12 (br s, 1H), 10.94 (s, 1H), 9.31 (s, 1H), 8.31 (s, 1H), 8.19-8.16 (m, 2H), 7.86 (dd, J=9.0, 1.4 Hz, 1H), 7.55 (d, J=8.8 Hz, 1H), 7.40 (t, J=8.8 Hz, 2H), 1.56-1.53 (m, 2H), 1.29-1.25 (m, 2H); [M+H]+ 364.

Example 17: 3-(4-Fluorobenzamido)-N-(1-(thiophen-2-yl)propyl)-1H-indazole-5-carboxamide

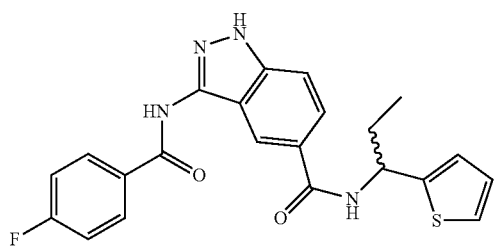 [SMILES: CCC(NC(=O)c1ccc2[nH]nc(NC(=O)c3ccc(F)cc3)c2c1)c1cccs1]

[M+H]+ 423.

Example 18: 3-(4-Fluorobenzamido)-N-(1-(thiophen-2-yl)butyl)-1H-indazole-5-carboxamide

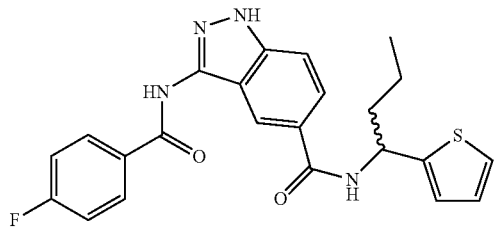 [SMILES: CCCC(NC(=O)c1ccc2[nH]nc(NC(=O)c3ccc(F)cc3)c2c1)c1cccs1]

[M+H]+ 437.

Example 19: 3-(4-Fluorobenzamido)-N-((5-methylthiophen-2-yl)methyl)-1H-indazole-5-carboxamide

$^1$H NMR (400 MHz, DMSO-$d_6$) δ 13.06 (s, 1H), 10.92 (s, 1H), 9.06 (m, 1H), 8.32 (s, 1H), 8.20-8.17 (m, 2H), 7.90 (dd, J=9.2, 2.0 Hz, 1H), 7.54 (d, J=9.2 Hz, 1H), 7.43-7.38 (m, 2H), 6.78 (d, J=3.6 Hz, 1H), 6.62-6.61 (m, 1H), 4.53 (d, J=6.0 Hz, 1H), 2.38 (s, 3H); [M+H]+ 409.

Example 20: 3-(4-Fluorobenzamido)-N-(2-phenylpropan-2-yl)-1H-indazole-5-carboxamide

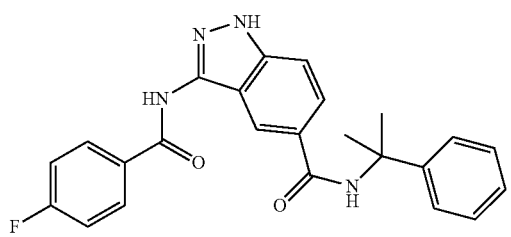 [SMILES: CC(C)(NC(=O)c1ccc2[nH]nc(NC(=O)c3ccc(F)cc3)c2c1)c1ccccc1]

[M+H]+ 417.

Example 21: 3-(4-Fluorobenzamido)-N-(4-(trifluoromethyl)benzyl)-1H-indazole-5-carboxamide

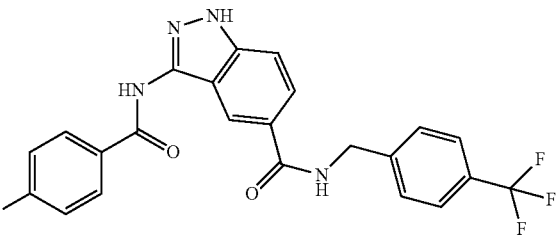

[M+H]+ 457.

Example 22: N-(Cyclohexylmethyl)-3-(4-fluorobenzamido)-1H-indazole-5-carboxamide

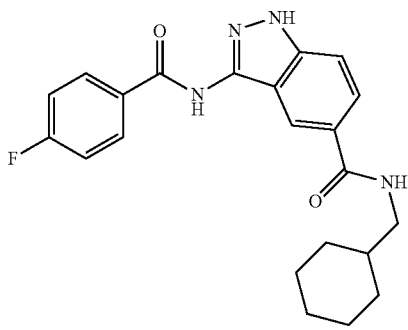 [SMILES: O=C(NCC1CCCCC1)c1ccc2[nH]nc(NC(=O)c3ccc(F)cc3)c2c1]

$^1$H NMR (400 MHz, DMSO-d$_6$) δ 13.02 (s, 1H), 10.90 (s, 1H), 8.41 (t, J=5.6 Hz, 1H), 8.26 (s, 1H), 8.19-8.15 (m, 2H), 7.87 (dd, J=8.8, 1.6 Hz, 1H), 7.51 (d, J=8.8 Hz, 1H), 7.40 (t, J=9.0 Hz, 1H), 3.11 (t, J=6.2 Hz, 2H), 1.71-1.66 (m, 4H), 1.16-1.13 (m, 3H), 0.94-0.92 (m, 4H); [M+11]$^+$ 395.

Example 23: N-(Cyclopropylmethyl)-3-(4-fluorobenzamido)-1H-indazole-5-carboxamide

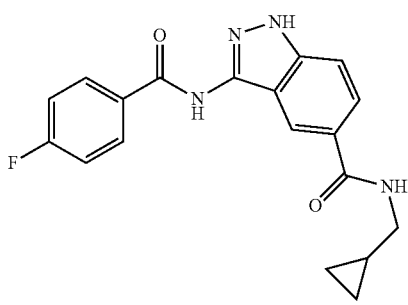 [SMILES: O=C(NCC1CC1)c1ccc2[nH]nc(NC(=O)c3ccc(F)cc3)c2c1]

$^1$H NMR (400 MHz, MeOD) δ 8.36 (s, 1H), 8.13 (dd, J=8.6, 5.4 Hz, 2H), 7.89 (d, J=10.0 Hz, 1H), 7.54 (d, J=8.4 Hz, 1H), 7.31-7.27 (m, 2H), 3.25 (d, J=7.2 Hz, 2H), 1.13-1.10 (m, 1H), 0.52 (q, J=6.0 Hz, 2H), 0.28 (q, J=6.0 Hz, 2H); [M+H]$^+$ 353.

Example 24: N-Butyl-3-(4-fluorobenzamido)-1H-indazole-5-carboxamide

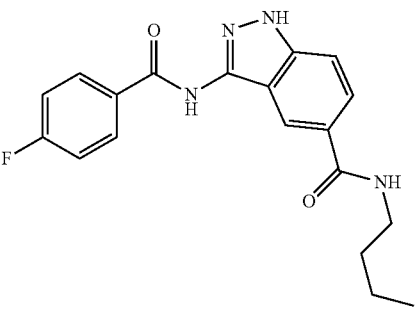 [SMILES: CCCCNC(=O)c1ccc2[nH]nc(NC(=O)c3ccc(F)cc3)c2c1]

$^1$H NMR (400 MHz, DMSO-d$_6$) δ 13.02 (s, 1H), 10.90 (s, 1H), 8.41 (t, J=5.0 Hz, 1H), 8.26 (s, 1H), 8.17 (dd, J=8.2, 5.8 Hz, 2H), 7.86 (d, J=9.6 Hz, 1H), 7.51 (d, J=8.8 Hz, 1H), 7.40 (t, J=8.8 Hz, 2H), 3.25 (q, J=6.6 Hz, 2H), 1.54-1.46 (m, 2H), 1.36-1.27 (m, 2H), 0.89 (t, J=6.8 Hz, 3H); [M+H]$^+$ 355.

Example 25: 3-(4-Fluorobenzamido)-N-isopentyl-1H-indazole-5-carboxamide

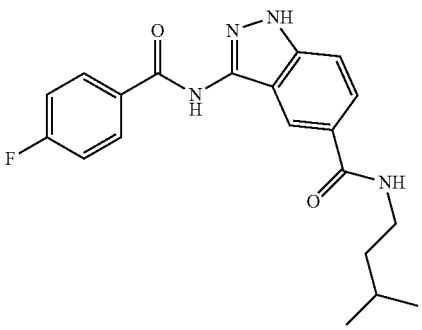 [SMILES: CC(C)CCNC(=O)c1ccc2[nH]nc(NC(=O)c3ccc(F)cc3)c2c1]

$^1$H NMR (400 MHz, DMSO-d$_6$) δ 13.02 (s, 1H), 10.90 (s, 1H), 8.39 (t, J=5.8 Hz, 1H), 8.25 (s, 1H), 8.17 (dd, J=8.6, 5.8 Hz, 2H), 7.86 (d, J=8.8 Hz, 1H), 7.51 (d, J=8.8 Hz, 1H), 7.40 (t, J=8.8 Hz, 2H), 3.28 (q, J=6.6 Hz, 2H), 1.62-1.57 (m, 1H), 1.44-1.39 (m, 2H), 0.91 (s, MA 0.89 (s, 3H); [M+H]$^+$ 369.

Example 26: N-((1,2,4-Oxadiazol-3-yl)methyl)-3-(4-fluorobenzamido)-1H-indazole-5-carboxamide

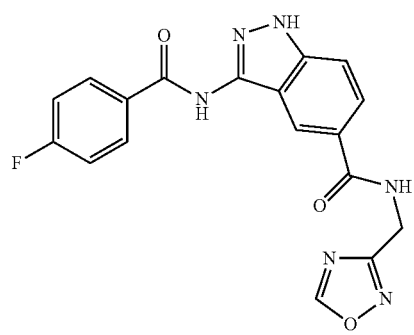 [SMILES: O=C(NCc1ncon1)c1ccc2[nH]nc(NC(=O)c3ccc(F)cc3)c2c1]

$^1$H NMR (400 MHz, DMSO-d$_6$) δ 13.00 (s, 1H), 10.60 (s, 1H), 9.54 (s, 1H), 9.14 (t, J=5.8 Hz, 1H), 8.32 (s, 1H), 8.01 (d, J=8.8 Hz, 2H), 7.88 (dd, J=8.8, 1.6 Hz, 1H), 7.52 (d, J=8.4 Hz, 1H), 7.36 (dd, J=5.2, 1.2 Hz, 1H), 7.14 (d, J=9.2 Hz, 2H), 7.01 (d, J=3.6 Hz, 1H), 4.62 (d, J=5.6 Hz, 2H); [M+H]$^+$ 381.

Example 27: 3-(4-Fluorobenzamido)-N-(thiazol-5-ylmethyl)-1H-indazole-5-carboxamide 2,2,2-trifluoroacetate

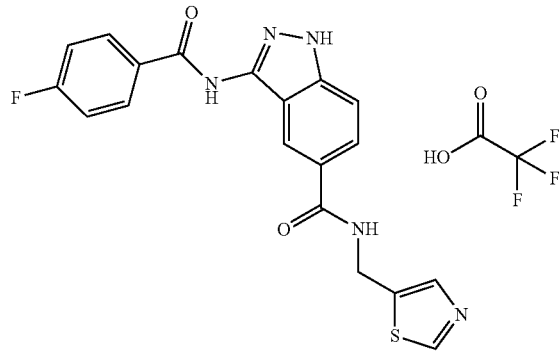 [SMILES: O=C(NCc1cncs1)c1ccc2[nH]nc(NC(=O)c3ccc(F)cc3)c2c1 ; O=C(O)C(F)(F)F]

[M+11]$^+$ 396.

Example 28: 3-(4-Fluorobenzamido)-N-(pyridin-2-ylmethyl)-1H-indazole-5-carboxamide 2,2,2-trifluoroacetate

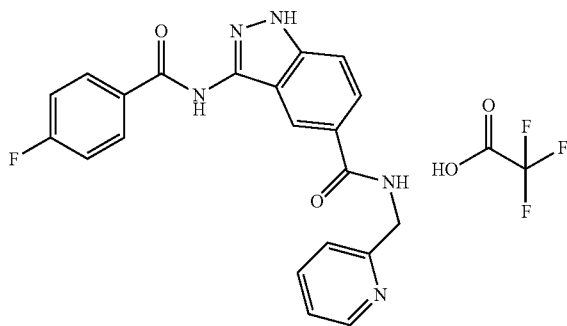 [SMILES: O=C(NCc1ccccn1)c1ccc2[nH]nc(NC(=O)c3ccc(F)cc3)c2c1 ; O=C(O)C(F)(F)F]

$^1$H NMR (400 MHz, DMSO-d$_6$) δ 10.94 (s, 1H), 9.19 (t, J=5.4 Hz, 1H), 8.62 (d, J=4.4 Hz, 1H), 8.38 (s, 1H), 8.19-8.15 (m, 2H), 8.01 (d, J=7.6 Hz, 1H), 7.94 (dd, J=8.8, 1.6 Hz, 1H), 7.58-7.48 (m, 3H), 7.40 (t, J=8.8 Hz, 2H), 4.65 (d, J=6.0 Hz, 2H); [M+H]+ 390.

Example 29: 3-(4-Fluorobenzamido)-N-(pyridin-4-ylmethyl)-1H-indazole-5-carboxamide

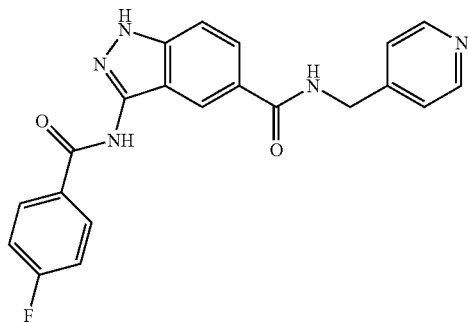 [SMILES: O=C(NCc1ccncc1)c1ccc2[nH]nc(NC(=O)c3ccc(F)cc3)c2c1]

$^1$H NMR (400 MHz, DMSO-d$_6$) δ 13.06 (s, 1H), 10.92 (s, 1H), 9.11 (t, J=6.0 Hz, 1H), 8.55-8.46 (m, 2H), 8.36 (s, 1H), 8.21-8.13 (m, 2H), 7.93 (dd, J=8.8, 1.6 Hz, 1H), 7.56 (d, J=8.7 Hz, 1H), 7.39 (t, J=8.8 Hz, 2H), 7.33-7.26 (m, 2H), 4.50 (d, J=5.9 Hz, 2H); [M+H]+ 390.

Example 30: N-(Cyclopropyl(thiophen-2-yl)methyl)-3-(4-fluorobenzamido)-1H-indazole-5-carboxamide

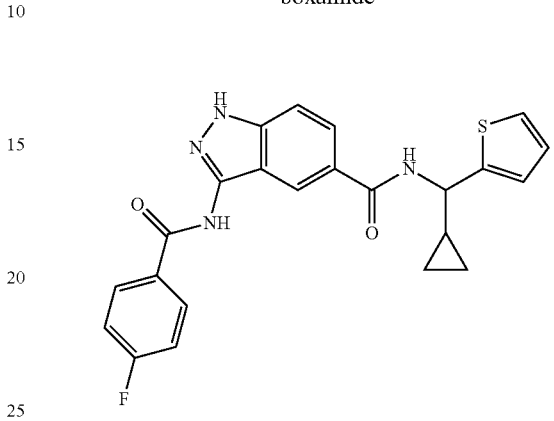

$^1$H NMR (400 MHz, DMSO-d$_6$) δ 13.04 (s, 1H), 10.89 (s, 1H), 9.08 (d, J=8.5 Hz, 1H), 8.35 (s, 1H), 8.21-8.13 (m, 2H), 7.94 (dd, J=8.8, 1.6 Hz, 1H), 7.54 (d, J=8.8 Hz, 1H), 7.45-7.34 (m, 3H), 7.10-7.03 (m, 1H), 6.97 (dd, J=5.1, 3.5 Hz, 1H), 4.66 (t, J=8.9 Hz, 1H), 1.54-1.40 (m, 1H), 0.68 (dt, J=9.3, 5.2 Hz, 1H), 0.54 (s, 1H), 0.44 (tq, J=8.7, 4.3 Hz, 2H); [M+H]$^+$ 435.

Example 31: 4-Fluoro-N-(5-(((thiophen-2-ylmethyl)amino)methyl)-1H-indazol-3-yl)benzamide Hydrochloride

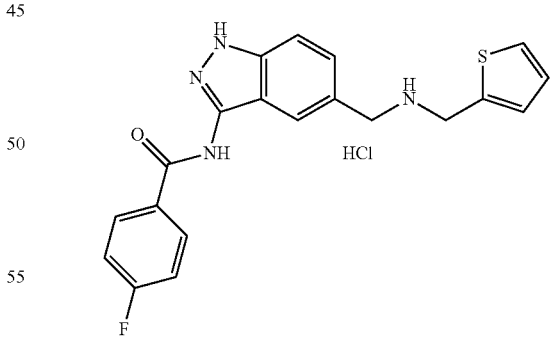

$^1$H NMR (400 MHz, DMSO-d$_6$) δ 13.00 (s, 1H), 10.93 (s, 1H), 9.37 (s, 2H), 8.21-8.12 (m, 2H), 7.88 (s, 1H), 7.63 (dd, J=5.1, 1.3 Hz, 1H), 7.56 (d, J=8.7 Hz, 1H), 7.49 (dd, J=8.7, 1.6 Hz, 1H), 7.40 (t, J=8.8 Hz, 2H), 7.33-7.27 (m, 1H), 7.09 (dd, J=5.1, 3.5 Hz, 1H), 4.40 (s, 2H), 4.25 (s, 2H); [M+H]$^+$ 381.

Example 32: 4-Fluoro-N-(5-((1-(thiophen-2-yl)propyl)amino)methyl)-1H-indazol-3-yl)benzamide

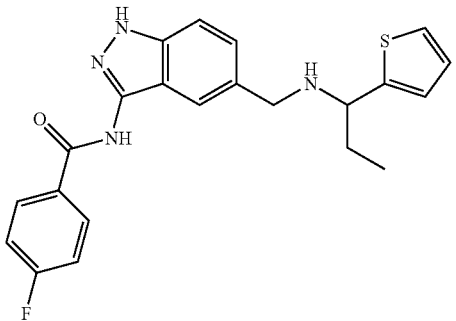 [SMILES: CCC(NCc1ccc2[nH]nc(NC(=O)c3ccc(F)cc3)c2c1)c1cccs1]

$^{1}$H NMR (400 MHz, DMSO-d$_{6}$) δ 13.01 (s, 1H), 10.92 (s, 1H), 8.16 (dd, J=8.6, 5.5 Hz, 2H), 7.78 (s, 1H), 7.69 (d, J=5.0 Hz, 1H), 7.54 (d, J=8.8 Hz, 1H), 7.49-7.35 (m, 4H), 7.19-7.08 (m, 1H), 4.48 (s, 1H), 4.14 (s, 1H), 3.89 (s, 1H), 2.23 (s, 1H), 1.91 (s, 1H), 0.74 (t, J=7.3 Hz, 3H); [M+H]$^{+}$ 409.

Example 33: 3-(4-Fluorobenzamido)-N-(3-methyl-1-(thiophen-2-yl)butyl)-1H-indazole-5-carboxamide

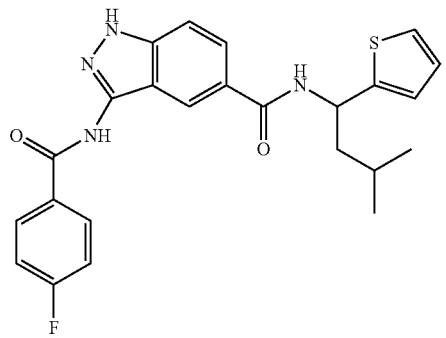 [SMILES: CC(C)CC(NC(=O)c1ccc2[nH]nc(NC(=O)c3ccc(F)cc3)c2c1)c1cccs1]

$^{1}$H NMR (400 MHz, DMSO-d$_{6}$) δ 13.04 (s, 1H), 10.90 (s, 1H), 8.81 (d, J=8.6 Hz, 1H), 8.31 (s, 1H), 8.21-8.13 (m, 2H), 7.91 (d, J=9.1 Hz, 1H), 7.53 (d, J=8.8 Hz, 1H), 7.40 (t, J=8.8 Hz, 2H), 7.35 (dd, J=5.0, 1.2 Hz, 1H), 7.01 (d, J=3.4 Hz, 1H), 6.95 (dd, J=5.0, 3.5 Hz, 1H), 5.80-4.97 (m, 1H), 2.05-1.84 (m, 1H), 1.68 (s, 2H), 0.96-0.88 (m, 6H); [M+H]$^{+}$ 451.

Example 34: 3-(4-Fluorobenzamido)-N-(2-(thiophen-2-yl)butan-2-yl)-1H-indazole-5-carboxamide

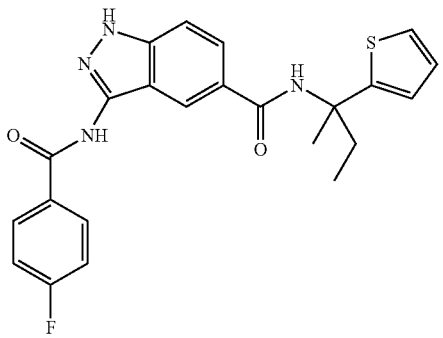 [SMILES: CCC(C)(NC(=O)c1ccc2[nH]nc(NC(=O)c3ccc(F)cc3)c2c1)c1cccs1]

$^{1}$H NMR (400 MHz, DMSO-d$_{6}$) δ 13.02 (s, 1H), 10.90 (s, 1H), 8.31-8.22 (m, 2H), 8.21-8.12 (m, 2H), 7.83 (dd, J=8.8, 1.6 Hz, 1H), 7.51 (d, J=8.8 Hz, 1H), 7.39 (t, J=8.8 Hz, 2H), 7.27 (dd, J=4.1, 2.3 Hz, 1H), 6.93-6.86 (m, 2H), 2.39 (dq, J=14.5, 7.3 Hz, 1H), 1.88 (dp, J=14.3, 7.2, 6.4 Hz, 1H), 1.69 (s, 3H), 0.83 (t, J=7.3 Hz, 3H); [M+H]$^{+}$ 437.

Example 35: 3-(2,4-Difluorobenzamido)-N-(thiophen-2-ylmethyl)-1H-indazole-5-carboxamide

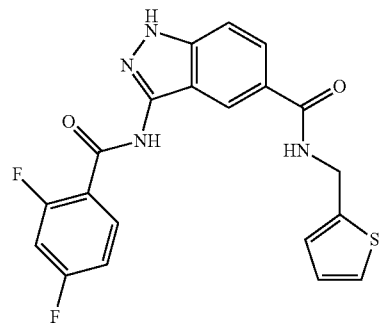 [SMILES: O=C(NCc1cccs1)c1ccc2[nH]nc(NC(=O)c3ccc(F)cc3F)c2c1]

$^{1}$H NMR (400 MHz, DMSO-d$_{6}$) δ 13.05 (s, 1H), 10.89 (s, 1H), 9.13 (t, J=5.9 Hz, 1H), 8.39 (s, 1H), 7.93-7.83 (m, 2H), 7.53 (d, J=8.8 Hz, 1H), 7.45 (t, J=10.1 Hz, 1H), 7.37 (dd, J=5.0, 1.3 Hz, 1H), 7.26 (s, 1H), 7.01 (d, J=2.6 Hz, 1H), 6.95 (dd, J=5.1, 3.4 Hz, 1H), 4.63 (d, J=5.8 Hz, 2H); [M+H]$^{+}$ 413.

Example 36: 3-(4-Fluorobenzamido)-N-(thiophen-2-ylmethyl)-1H-indazole-5-carboxamide

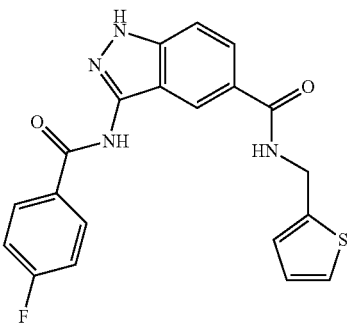 [SMILES: O=C(NCc1cccs1)c1ccc2[nH]nc(NC(=O)c3ccc(F)cc3)c2c1]

$^{1}$H NMR (400 MHz, Methanol-d$_{4}$) δ 8.37 (s, 1H), 8.17-8.08 (m, 2H), 7.90 (dd, J=8.9, 1.7 Hz, 1H), 7.54 (d, J=8.8 Hz, 1H), 7.33-7.23 (m, 3H), 7.04 (d, J=2.7 Hz, 1H), 6.94 (dd, J=5.1, 3.4 Hz, 1H), 4.75 (s, 2H); [M+H]$^{+}$ 395.

Example 37: 3-(4-Fluorobenzamido)-N-(1-phenyl-ethyl)-1H-indazole-5-carboxamide

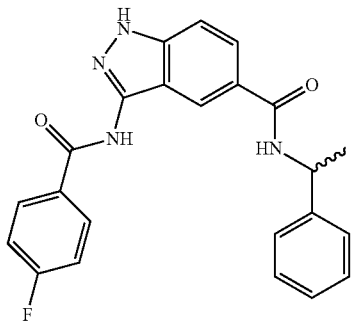 [SMILES: CC(NC(=O)c1ccc2[nH]nc(NC(=O)c3ccc(F)cc3)c2c1)c1ccccc1]

$^1$H NMR (400 MHz, DMSO-d$_6$) δ 13.03 (s, 1H), 10.90 (s, 1H), 8.79 (d, J=8.1 Hz, 1H), 8.32 (s, 1H), 8.21-8.13 (m, 2H), 7.91 (dd, J=8.8, 1.6 Hz, 1H), 7.53 (dd, J=8.8, 0.8 Hz, 1H), 7.44-7.36 (m, 4H), 7.35-7.27 (m, 2H), 7.21 (t, J=6.6 Hz, 1H), 5.19 (p, J=7.3 Hz, 1H), 1.48 (d, J=7.1 Hz, 3H); [M+H]$^+$ 403.

Example 38: 3-(4-Fluorobenzamido)-N-(1-phenyl-propyl)-1H-indazole-5-carboxamide

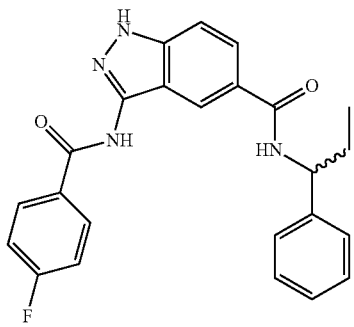

$^1$H NMR (400 MHz, DMSO-d$_6$) δ 13.03 (s, 1H), 10.90 (s, 1H), 8.72 (d, J=8.4 Hz, 1H), 8.31 (s, 1H), 8.21-8.12 (m, 2H), 7.90 (dd, J=8.9, 1.6 Hz, 1H), 7.53 (dd, J=8.8, 0.8 Hz, 1H), 7.43-7.36 (m, 4H), 7.35-7.27 (m, 2H), 7.25-7.16 (m, 1H), 4.93 (td, J=8.7, 6.3 Hz, 1H), 1.93-1.73 (m, 2H), 0.90 (t, J=7.3 Hz, 3H); [M+H]$^+$ 417.

Example 39: 3-(Phenylsulfonamido)-N-(thiophen-2-ylmethyl)-1H-indazole-5-carboxamide

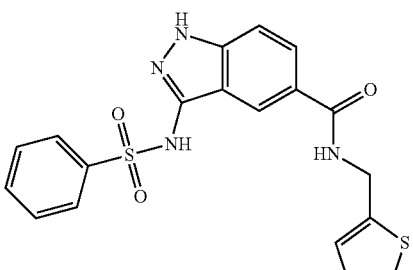

$^1$H NMR (400 MHz, Methanol-d$_4$) δ 8.18 (dd, J=1.7, 0.8 Hz, 1H), 8.11 (dd, J=8.8, 0.8 Hz, 1H), 8.00 (dd, J=8.8, 1.7 Hz, 1H), 7.85-7.76 (m, 2H), 7.57 (t, J=6.9 Hz, 1H), 7.43 (t, J=7.8 Hz, 2H), 7.29 (dd, J=5.1, 1.2 Hz, 1H), 7.05 (dd, J=3.4, 0.8 Hz, 1H), 6.95 (dd, J=5.1, 3.5 Hz, 1H), 4.74 (d, J=0.9 Hz, 2H); [M+H]$^+$ 413.

Example 40: N-Benzyl-3-(4-(4-methylpiperazin-1-yl)benzamido)-1H-indazole-5-carboxamide

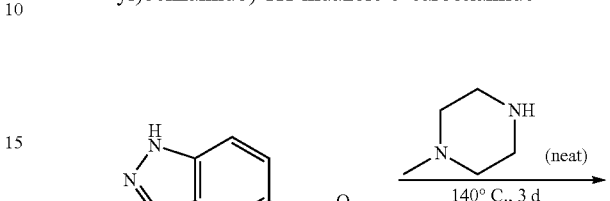

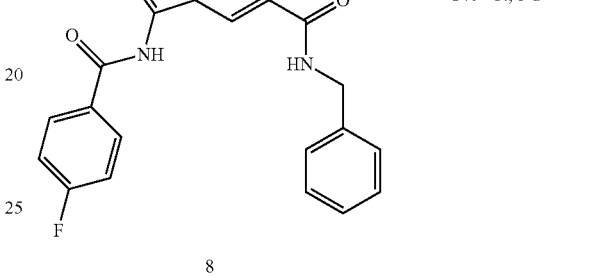

8

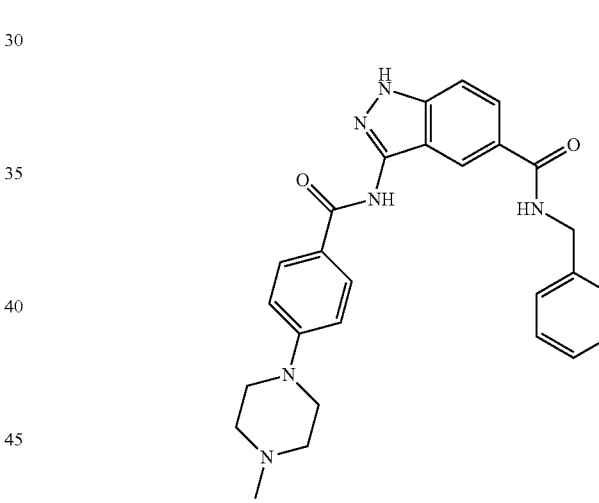

9

A mixture of the compound 8 (195.7 mg, 0.50 mmol) and 1-methylpiperazine (1.7 mL) was heated at 140° C. until the reaction was completed (monitored by UPLC), and then poured into water (10 mL) The precipitate thus obtained was collected by filtration and washed with water (2×10 mL) The filtered solid was dried to give the compound 9 (185 mg, 78%) as a brown solid.

$^1$H NMR (400 MHz, DMSO-d$_6$) δ 12.96 (s, 1H), 10.54 (s, 1H), 9.02 (s, 1H), 8.33 (s, 1H), 7.98 (d, J=8.6 Hz, 2H), 7.91 (d, J=8.7 Hz, 1H), 7.51 (d, J=8.7 Hz, 1H), 7.31 (d, J=4.4 Hz, 4H), 7.23 (d, J=4.6 Hz, 2H), 7.02 (d, J=8.6 Hz, 2H), 4.48 (d, J=5.9 Hz, 2H), 3.30 (s, 4H), 2.45 (s, 4H), 2.23 (s, 3H); [M+H]$^+$ 469.

Example 41: N-(1-Phenylpropyl)-3-(4-(piperazin-1-yl)benzamido)-1H-indazole-5-carboxamide

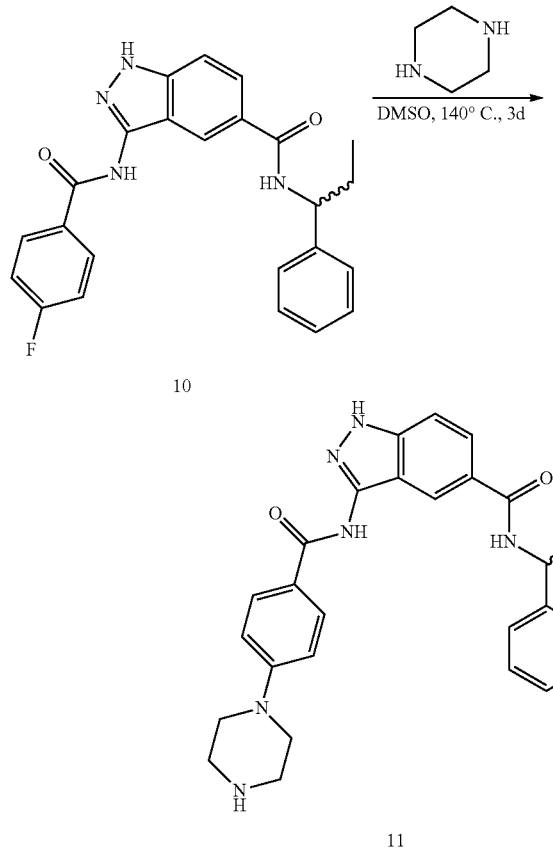

A solution of the compound 8 (60 mg, 0.14 mmol), piperazine (241 mg, 2.8 mmol) in DMSO (1 mL) was heated at 140° C. until the reaction was completed (monitored by UPLC) and then poured into a mixture of water (5 mL) and MC (5 mL) The aqueous layer was extracted with MC (2×5 mL) The combined organic layer was dried over $MgSO_4$, filtered, and concentrated to give the crude product, which was purified by HPLC (used for neutral $H_2O$, ACN) to afford the compound 11 (42.6 mg, 64%) as a brown solid.

$^1$H NMR (400 MHz, Methanol-$d_4$) δ 8.38 (s, 1H), 8.00 (d, J=8.6 Hz, 2H), 7.88 (dd, J=8.8, 1.7 Hz, 1H), 7.52 (d, J=8.8 Hz, 1H), 7.39 (d, J=7.1 Hz, 2H), 7.30 (t, J=7.6 Hz, 2H), 7.26-7.16 (m, 1H), 7.13-7.06 (m, 2H), 4.98 (dd, J=8.5, 6.7 Hz, 1H), 3.57 (dd, J=6.6, 3.9 Hz, 4H), 3.36 (dd, J=6.4, 4.1 Hz, 4H), 1.91 (tt, J=14.2, 6.6 Hz, 2H), 0.97 (t, J=7.3 Hz, 3H); [M+H]$^+$ 483.

Example 42: N-Methyl-3-(4-morpholinobenzamido)-N-(thiophen-2-ylmethyl)-1H-indazole-5-carboxamide

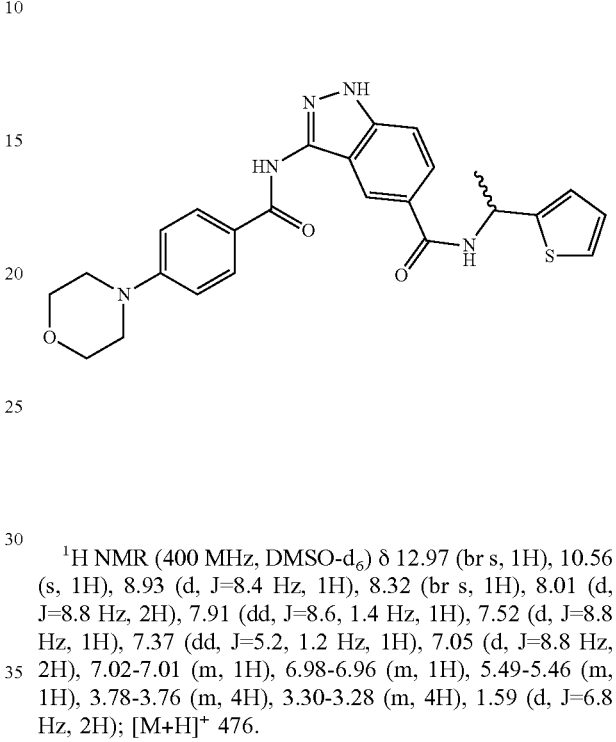

$^1$H NMR (400 MHz, DMSO-$d_6$) δ 11.89 (br s, 1H), 8.62 (s, 1H), 8.52 (s, 1H), 8.07-7.95 (m, 4H), 7.64 (s, 1H), 6.31 (s, 1H), 6.21 (d, J=6.8 Hz, 1H), 4.03 (br s, 2H), 3.99-3.92 (m, 1H), 3.57-3.54 (m, 2H), 3.34-3.25 (m, 3H), 1.86-1.74 (m, 2H), 1.70-1.56 (m, 5H), 1.54-1.36 (m, 5H), 0.95 (t, J=7.4 Hz, 3H); [M+H]$^+$ 476.

Example 43: 3-(4-Morpholinobenzamido)-N-(1-(thiophen-2-yl)ethyl)-1H-indazole-5-carboxamide

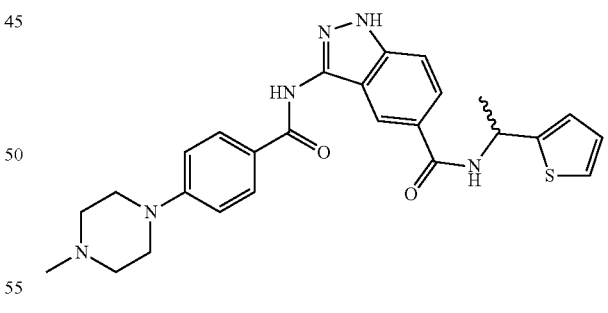

$^1$H NMR (400 MHz, DMSO-$d_6$) δ 12.97 (br s, 1H), 10.56 (s, 1H), 8.93 (d, J=8.4 Hz, 1H), 8.32 (br s, 1H), 8.01 (d, J=8.8 Hz, 2H), 7.91 (dd, J=8.6, 1.4 Hz, 1H), 7.52 (d, J=8.8 Hz, 1H), 7.37 (dd, J=5.2, 1.2 Hz, 1H), 7.05 (d, J=8.8 Hz, 2H), 7.02-7.01 (m, 1H), 6.98-6.96 (m, 1H), 5.49-5.46 (m, 1H), 3.78-3.76 (m, 4H), 3.30-3.28 (m, 4H), 1.59 (d, J=6.8 Hz, 2H); [M+H]$^+$ 476.

Example 44: 3-(4-(4-Methylpiperazin-1-yl)benzamido)-N-(1-(thiophen-2-yl)ethyl)-1H-indazole-5-carboxamide $^1$H NMR (400 MHz, DMSO-$d_6$) δ 11.89 (br s, 1H), 8.62 (s, 1H), 8.52 (s, 1H), 8.07-7.95 (m, 4H), 7.64 (s, 1H), 6.31 (s, 1H), 6.21 (d, J=6.8 Hz, 1H), 4.03 (br s, 2H), 3.99-3.92 (m, 1H), 3.57-3.54 (m, 2H), 3.34-3.25 (m, 3H), 1.86-1.74 (m, 2H), 1.70-1.56 (m, 5H), 1.54-1.36 (m, 5H), 0.95 (t, J=7.4 Hz, 3H); [M+H]$^+$ 489.

Example 45: N-(2-Hydroxy-1-(thiophen-2-yl)ethyl)-3-(4-(4-methylpiperazin-1-yl)benzamido)-1H-indazole-5-carboxamide

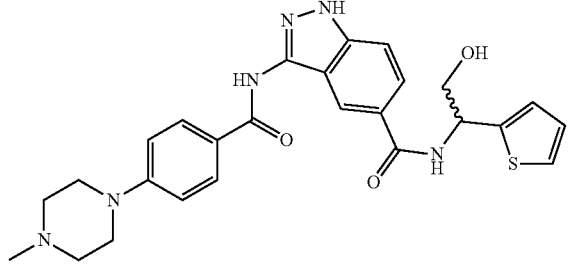 [SMILES: CN1CCN(c2ccc(C(=O)Nc3n[nH]c4ccc(C(=O)NC(CO)c5cccs5)cc34)cc2)CC1]

$^1$H NMR (400 MHz, DMSO-d$_6$) δ 11.89 (br s, 1H), 8.62 (s, 1H), 8.52 (s, 1H), 8.07-7.95 (m, 4H), 7.64 (s, 1H), 6.31 (s, 1H), 6.21 (d, J=6.8 Hz, 1H), 4.03 (br s, 2H), 3.99-3.92 (m, 1H), 3.57-3.54 (m, 2H), 3.34-3.25 (m, 3H), 1.86-1.74 (m, 2H), 1.70-1.56 (m, 5H), 1.54-1.36 (m, 5H), 0.95 (t, J=7.4 Hz, 3H); [M+H]$^+$ 505.

Example 46: 3-(4-Morpholinobenzamido)-N-(thiophen-3-ylmethyl)-1H-indazole-5-carboxamide

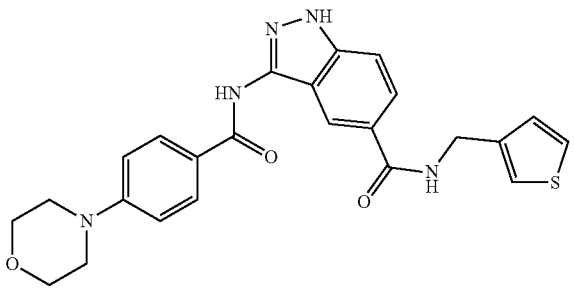 [SMILES: O=C(NCc1ccsc1)c1ccc2[nH]nc(NC(=O)c3ccc(N4CCOCC4)cc3)c2c1]

$^1$H NMR (400 MHz, DMSO-d$_6$) δ 12.99 (br s, 1H), 10.58 (br s, 1H), 8.98 (t, J=6.0 Hz, 1H), 8.33 (m, 1H), 8.02 (d, J=8.8 Hz, 2H), 7.91 (dd, J=8.8, 1.6 Hz, 1H), 7.52 (d, J=8.4 Hz, 1H), 7.49-7.47 (m, 1H), 7.32-7.31 (m, 1H), 7.10 (dd, J=5.0, 1.4 Hz, 1H), 7.06 (d, J=9.2 Hz, 2H), 4.48 (d, J=5.6 Hz, 2H), 3.78-3.76 (m, 4H), 3.31-3.28 (m, 4H); [M+H]$^+$ 475.

Example 47: 3-(4-(4-Methylpiperazin-1-yl)benzamido)-N-(thiophen-3-ylmethyl)-1H-indazole-5-carboxamide

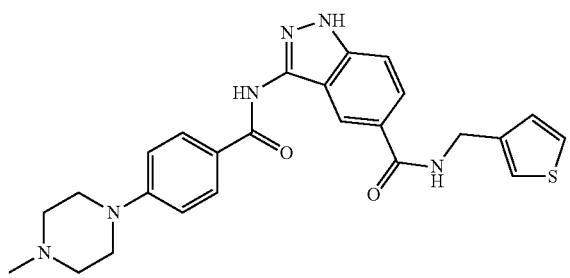 [SMILES: CN1CCN(c2ccc(C(=O)Nc3n[nH]c4ccc(C(=O)NCc5ccsc5)cc34)cc2)CC1]

$^1$H NMR (400 MHz, DMSO-d$_6$) δ 12.99 (br s, 1H), 10.55 (br s, 1H), 8.98 (t, J=6.0 Hz, 1H), 8.32 (m, 1H), 8.00 (d, J=8.8 Hz, 2H), 7.90 (dd, J=8.8, 1.6 Hz, 1H), 7.52 (d, J=8.8 Hz, 1H), 7.49-7.48 (m, 1H), 7.32-7.30 (m, 1H), 7.00 (dd, J=5.0, 1.4 Hz, 1H), 7.04 (d, J=9.2 Hz, 2H), 4.47 (d, J=5.6 Hz, 2H), 3.33-3.31 (m, 4H), 2.48-2.45 (m, 4H), 2.25 (s, 3H); [M+H]$^+$ 475.

Example 48: 3-(4-Morpholinobenzamido)-N-(1-(thiophen-2-yl)cyclopropyl)-1H-indazole-5-carboxamide

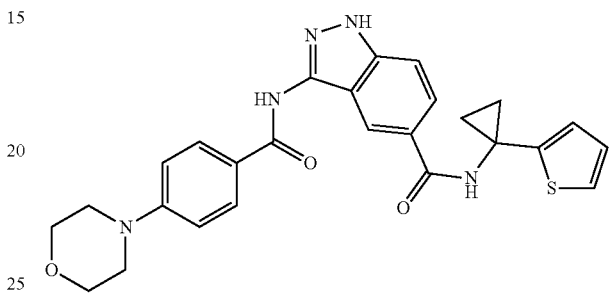

$^1$H NMR (400 MHz, DMSO-d$_6$) δ 12.97 (s, 1H), 10.56 (s, 1H), 9.32 (s, 1H), 8.31 (s, 1H), 8.01 (d, J=8.8 Hz, 2H), 7.88 (dd, J=8.8, 1.6 Hz, 1H), 7.51 (d, J=8.4 Hz, 1H), 7.25 (dd, J=5.2, 1.2 Hz, 1H), 7.06 (d, J=8.8 Hz, 2H), 6.90-6.88 (m, 1H), 6.83 (dd, J=3.6, 1.2 Hz, 1H), 3.78-3.76 (m, 4H), 3.30-3.28 (m, 4H), 1.33-1.30 (m, 2H), 1.27-1.23 (m, 2H); [M+H]$^+$ 488.

Example 49: 3-(4-(4-Methylpiperazin-1-yl)benzamido)-N-(1-(thiophen-2-yl)cyclopropyl)-1H-indazole-5-carboxamide

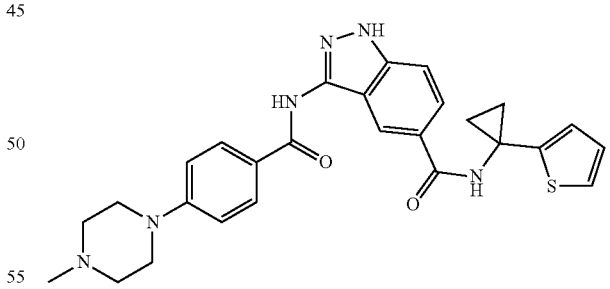

$^1$H NMR (400 MHz, DMSO-d$_6$) δ 12.97 (s, 1H), 10.53 (s, 1H), 9.32 (s, 1H), 8.30 (m, 1H), 7.99 (d, J=8.8 Hz, 2H), 7.88 (dd, J=8.8, 1.6 Hz, 1H), 7.51 (d, J=8.8 Hz, 1H), 7.25 (dd, J=5.2, 1.2 Hz, 1H), 7.04 (d, J=8.8 Hz, 2H), 6.90-6.88 (m, 1H), 6.83 (dd, J=3.4, 1.4 Hz, 1H), 3.34-3.31 (m, 4H), 2.48-2.45 (m, 4H), 2.24 (s, MA 1.31-1.30 (m, 2H), 1.27-1.25 (m, 2H); [M+H]$^+$ 501.

Example 50: N-(Furan-2-ylmethyl)-3-(4-morpholinobenzamido)-1H-indazole-5-carboxamide

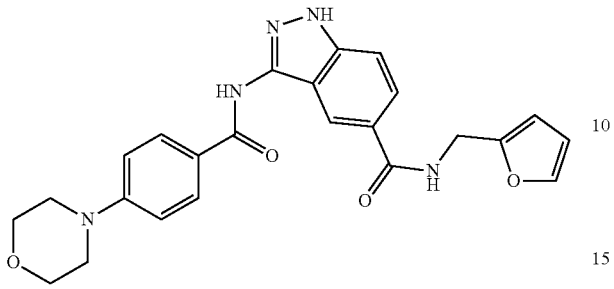

$^1$H NMR (400 MHz, DMSO-d$_6$) δ 12.97 (s, 1H), 10.58 (s, 1H), 8.97-8.94 (m, 1H), 8.32 (m, 1H), 8.01 (d, J=8.8 Hz, 2H), 7.88 (dd, J=9.0, 1.4 Hz, 1H), 7.57 (d, J=1.2 Hz, 1H), 7.51 (d, J=8.8 Hz, 1H), 7.06 (d, J=8.8 Hz, 2H), 6.40-6.39 (m, 1H), 6.26 (d, J=3.2 Hz, 1H), 4.47 (d, J=5.6 Hz, 2H), 3.78-3.76 (m, 4H), 3.30-3.28 (m, 4H); [M+H]$^+$ 446.

Example 51: N-(Furan-2-ylmethyl)-3-(4-(4-methylpiperazin-1-yl)benzamido)-1H-indazole-5-carboxamide

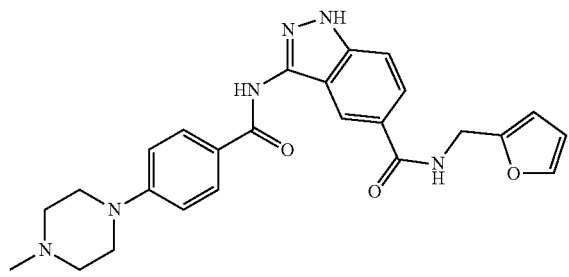 [SMILES: CN1CCN(c2ccc(C(=O)Nc3n[nH]c4ccc(C(=O)NCc5ccco5)cc34)cc2)CC1]

$^1$H NMR (400 MHz, DMSO-d$_6$) δ 13.0 (br s, 1H), 10.56 (s, 1H), 8.96 (m, 1H), 8.32 (m, 1H), 7.99 (d, J=8.8 Hz, 2H), 7.89 (d, J=12.4 Hz, 1H), 7.57 (m, 1H), 7.51 (d, J=9.2 Hz, 1H), 7.04 (d, J=8.8 Hz, 2H), 6.40-6.39 (m, 1H), 6.26 (d, J=2.8 Hz, 1H), 4.47 (d, J=5.2 Hz, 2H), 3.34-3.30 (m, 4H), 2.48-2.45 (m, 4H), 2.26 (s, 3H); [M+H]$^+$ 459.

Example 52: 3-(4-Morpholinobenzamido)-N-(1-(pyridin-3-yl)ethyl)-1H-indazole-5-carboxamide

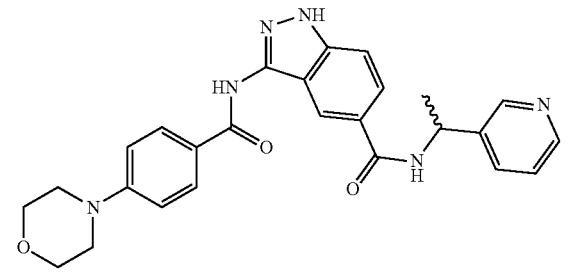 [SMILES: CC(NC(=O)c1ccc2[nH]nc(NC(=O)c3ccc(N4CCOCC4)cc3)c2c1)c1cccnc1]

$^1$H NMR (400 MHz, DMSO-d$_6$) δ 12.98 (s, 1H), 10.58 (s, 1H), 8.88 (d, J=4.0 Hz, 1H), 8.62 (d, J=2.0 Hz, 1H), 8.44 (dd, J=4.6, 1.4 Hz, 1H), 8.31 (m, 1H), 8.01 (d, J=8.8 Hz, 2H), 7.90 (dd, J=8.8, 1.6 Hz, 1H), 7.81-7.79 (m, 1H), 7.52 (d, J=9.2 Hz, 1H), 7.38-7.34 (m, 1H), 7.06 (d, J=8.8 Hz, 2H), 5.25-5.19 (m, 1H), 3.78-3.76 (m, 4H), 3.30-3.28 (m, 4H), 1.52 (d, J=7.2 Hz, 3H); [M+H]$^+$ 457.

Example 53: 3-(4-(4-Methylpiperazin-1-yl)benzamido)-N-(1-(pyridin-3-yl)ethyl)-1H-indazole-5-carboxamide

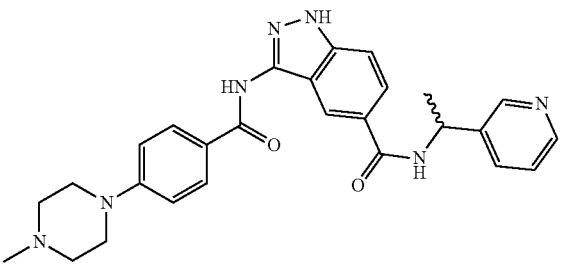 [SMILES: CC(NC(=O)c1ccc2[nH]nc(NC(=O)c3ccc(N4CCN(C)CC4)cc3)c2c1)c1cccnc1]

$^1$H NMR (400 MHz, DMSO-d$_6$) δ 13.01 (s, 1H), 10.56 (s, 1H), 8.89 (d, J=7.2 Hz, 1H), 8.62 (d, J=2.0 Hz, 1H), 8.44 (dd, J=4.8, 1.6 Hz, 1H), 8.31 (m, 1H), 7.99 (d, J=8.8 Hz, 2H), 7.90 (d, J=9.2 Hz, 1H), 7.81-7.79 (m, 1H), 7.52 (d, J=8.8 Hz, 1H), 7.38-7.34 (m, 1H), 7.04 (d, J=8.8 Hz, 2H), 5.25-5.21 (m, 1H), 3.34-3.30 (m, 4H), 2.48-2.45 (m, 4H), 2.24 (s, 3H), 1.52 (d, J=6.8 Hz, 3H); [M+H]$^+$ 484.

Example 54: 3-(4-Morpholinobenzamido)-N-(1-(thiophen-2-yl)propyl)-1H-indazole-5-carboxamide

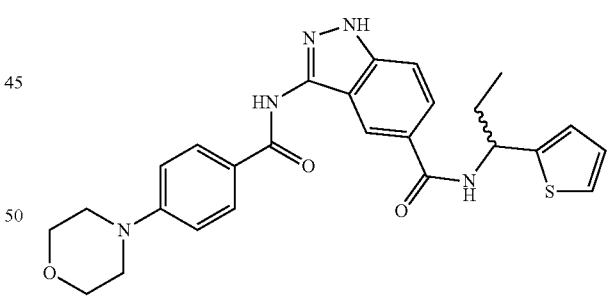

$^1$H NMR (400 MHz, DMSO-d$_6$) δ 12.95 (s, 1H), 10.53 (s, 1H), 8.80 (d, J=8.4 Hz, 1H), 8.30 (s, 1H), 7.98 (d, J=9.2 Hz, 1H), 7.89 (dd, J=8.8 Hz, 1.2 Hz, 1H), 7.51 (d, J=8.8 Hz, 1H), 7.35 (dd, J=5.2 Hz, 1.2 Hz, 1H), 7.03 (d, J=9.2 Hz, 2H), 7.01 (d, J=4.8 Hz, 1H), 6.96 (dd, J=5.0 Hz, 3.4 Hz, 1H), 5.22 (ABq, J ab=8.4 Hz, 1H), 3.30 (m, 4H), 2.48 (m, 4H), 2.24 (s, 3H), 1.98-1.91 (m, 2H), 0.93 (t, J=7.2 Hz, 3H); [M+H]$^+$ 490.

Example 55: 3-(4-(4-Methylpiperazin-1-yl)benzamido)-N-(1-(thiophen-2-yl)propyl)-1H-indazole-5-carboxamide

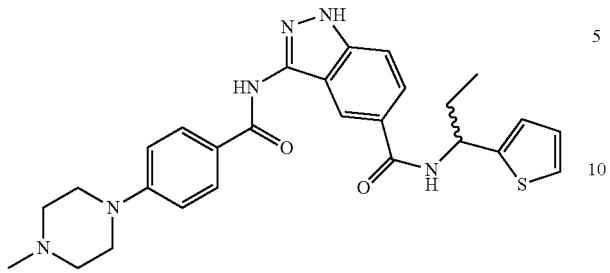

$^1$H NMR (400 MHz, DMSO-d$_6$) δ 12.95 (s, 1H), 10.53 (s, 1H), 8.80 (d, J=8.4 Hz, 1H), 8.30 (s, 1H), 7.98 (d, J=9.2 Hz, 1H), 7.89 (dd, J=8.8, 1.2 Hz, 1H), 7.51 (d, J=8.8 Hz, 1H), 7.35 (dd, J=5.2, 1.2 Hz, 1H), 7.03 (d, J=9.2 Hz, 2H), 7.01 (d, J=4.8 Hz, 1H), 6.96 (dd, J=5.0 Hz, 3.4 Hz, 1H), 5.22 (ABq, J ab=8.4 Hz, 1H), 3.30 (m, 4H), 2.48 (m, 4H), 2.24 (s, 3H), 1.98-1.91 (m, 2H), 0.93 (t, J=7.2 Hz, 3H); [M+H]$^+$ 503.

Example 56: 3-(4-Morpholinobenzamido)-N-(pyridin-3-ylmethyl)-1H-indazole-5-carboxamide 2,2,2-trifluoroacetate

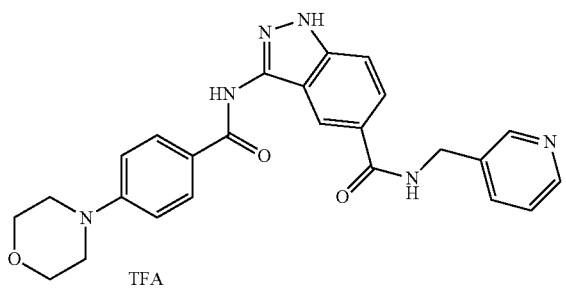 [SMILES: O=C(NCc1cccnc1)c1ccc2[nH]nc(NC(=O)c3ccc(N4CCOCC4)cc3)c2c1]

$^1$H NMR (400 MHz, DMSO-d$_6$) δ 12.98 (br s, 1H), 10.60 (s, 1H), 9.16 (t, J=5.8 Hz, 1H), 8.76 (m, 1H), 8.68 (d, J=4.0 Hz, 1H), 8.33 (m, 1H), 8.21 (d, J=8.0 Hz, 1H), 8.00 (d, J=9.2 Hz, 2H), 7.89 (dd, J=8.8, 1.6 Hz, 1H), 7.78 (dd, J=7.8, 5.4 Hz, 1H), 7.53 (d, J=9.2 Hz, 1H), 7.04 (d, J=8.8 Hz, 2H), 4.59 (d, J=5.6 Hz, 2H), 3.77-3.74 (m, 4H), 3.29-3.26 (m, 4H); [M+H]$^+$ 457.

Example 57: 3-(4-(4-Methylpiperazin-1-yl)benzamido)-N-(pyridin-3-ylmethyl)-1H-indazole-5-carboxamide bis(2,2,2-trifluoroacetate)

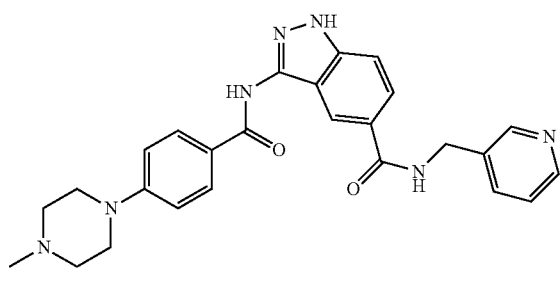

$^1$H NMR (400 MHz, DMSO-d$_6$) δ 13.02 (br s, 1H), 10.65 (s, 1H), 9.83 (br s, 1H), 9.14 (t, J=6.0 Hz, 1H), 8.69 (m, 1H), 8.60 (d, J=5.2 Hz, 1H), 8.33 (m, 1H), 8.04 (d, J=8.8 Hz, 3H), 7.90 (dd, J=8.8, 1.6 Hz, 1H), 7.65-7.62 (m, 1H), 7.54 (d, J=8.8 Hz, 3H), 7.12 (d, J=9.2 Hz, 2H), 4.56 (d, J=5.6 Hz, 2H), 4.09-4.04 (m, 2H), 3.53 (m, 2H), 3.17-3.09 (m, 4H), 2.88 (s, 3H); [M+H]$^+$ 470.

Example 58: 3-(4-Morpholinobenzamido)-N-(1-(thiophen-2-yl)butyl)-1H-indazole-5-carboxamide

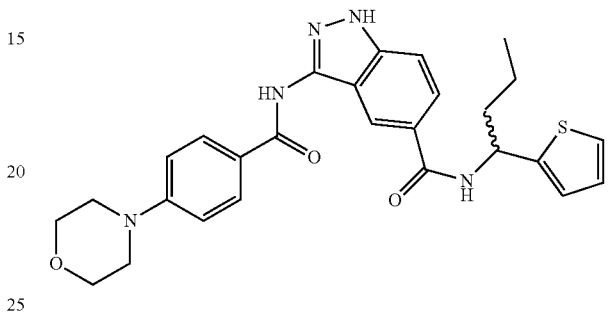

$^1$H NMR (400 MHz, DMSO-d$_6$) δ 12.97 (s, 1H), 10.57 (s, 1H), 8.82 (d, J=8.4 Hz, 1H), 8.31 (s, 1H), 8.02 (d, J=8.8 Hz, 2H), 7.91 (d, J=8.8 Hz, 1H), 7.52 (d, J=8.8 Hz, 1H), 7.37 (d, J=4.4 Hz, 1H), 7.06 (d, J=8.8 Hz, 2H), 7.03-7.02 (m, 1H), 6.98-6.96 (m, 1H), 3.78-3.76 (m, 4H), 3.30-3.28 (m, 4H), 2.01-1.85 (m, 2H), 1.45-1.30 (m, 2H), 0.93 (t, J=7.4 Hz, 3H); [M+H]$^+$ 517.

Example 59: 3-(4-(4-Methylpiperazin-1-yl)benzamido)-N-(1-(thiophen-2-yl)butyl)-1H-indazole-5-carboxamide

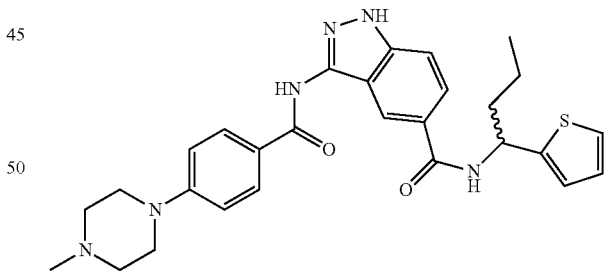

$^1$H NMR (400 MHz, DMSO-d$_6$) δ 12.95 (s, 1H), 10.53 (s, 1H), 8.81 (d, J=8.4 Hz, 1H), 8.29 (s, 1H), 7.98 (d, J=8.8 Hz, 2H), 7.89 (d, J=8.8 Hz, 1H), 7.51 (d, J=8.8 Hz, 1H), 7.35 (d, J=4.4 Hz, 1H), 7.03 (d, J=9.2 Hz, 2H), 7.01 (d, J=5.2 Hz, 1H), 6.97-6.94 (m, 1H), 3.31 (m, 4H), 2.47-2.46 (m, 4H), 2.24 (s, 3H), 2.00-1.83 (m, 2H), 1.43-1.30 (m, 2H), 0.91 (t, J=7.4 Hz, 3H); [M+H]$^+$ 517.

Example 60: N-((5-Methylthiophen-2-yl)methyl)-3-(4-morpholinobenzamido)-1H-indazole-5-carboxamide

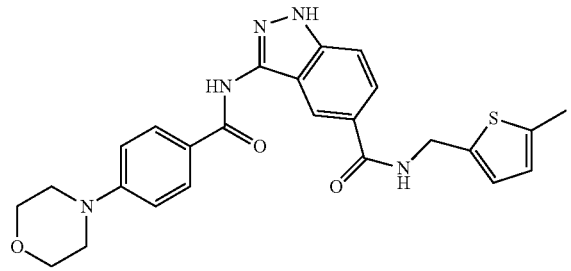 [SMILES: Cc1ccc(CNC(=O)c2ccc3[nH]nc(NC(=O)c4ccc(N5CCOCC5)cc4)c3c2)s1]

$^1$H NMR (400 MHz, DMSO-$d_6$) δ 12.97 (s, 1H), 10.58 (s, 1H), 9.07-9.04 (m, 1H), 8.30 (s, 1H), 8.02 (d, J=9.2 Hz, 2H), 7.89 (dd, J=8.8, 1.6 Hz, 1H), 7.52 (d, J=8.8 Hz, 1H), 7.06 (d, J=9.2 Hz, 2H), 6.77 (d, J=3.2 Hz, 1H), 6.62-6.61 (m, 1H), 4.53 (d, J=5.2 Hz, 2H), 3.78-3.76 (m, 4H), 3.30-3.28 (m, 4H), 2.38 (s, 3H); [M+H]$^+$ 476.

Example 61: 3-(4-(4-Methylpiperazin-1-yl)benzamido)-N-((5-methylthiophen-2-yl)methyl)-1H-indazole-5-carboxamide

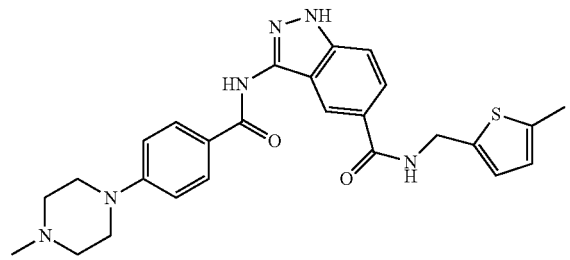

$^1$H NMR (400 MHz, DMSO-$d_6$) δ 12.97 (s, 1H), 10.55 (s, 1H), 9.07-9.04 (m, 1H), 8.30 (m, 1H), 7.99 (d, J=9.2 Hz, 2H), 7.89 (dd, J=8.6, 1.4 Hz, 1H), 7.52 (d, J=8.4 Hz, 1H), 7.04 (d, J=9.2 Hz, 2H), 6.77 (d, J=3.2 Hz, 1H), 6.62-6.61 (m, 1H), 4.53 (d, J=5.6 Hz, 2H), 3.34-3.30 (m, 4H), 2.51-2.47 (m, 4H), 2.38 (s, 3H); [M+H]$^+$ 489.

Example 62: 3-(4-Morpholinobenzamido)-N-(2-phenylpropan-2-yl)-1H-indazole-5-carboxamide

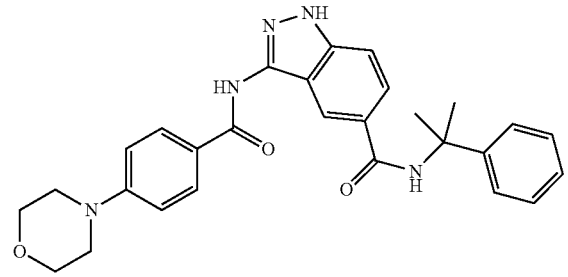 [SMILES: CC(C)(NC(=O)c1ccc2[nH]nc(NC(=O)c3ccc(N4CCOCC4)cc3)c2c1)c1ccccc1]

$^1$H NMR (400 MHz, DMSO-$d_6$) δ 12.94 (s, 1H), 10.57 (s, 1H), 8.44 (s, 1H), 8.27 (s, 1H), 8.01 (d, J=9.2 Hz, 2H), 7.86 (dd, J=8.8, 1.2 Hz, 1H), 7.50 (d, J=8.8 Hz, 1H), 7.38 (d, J=7.6 Hz, 2H), 7.30-7.27 (m, 2H), 7.18-7.15 (m, 1H), 7.05 (d, J=9.2 Hz, 2H), 3.78-3.76 (m, 4H), 3.30-3.27 (m, 4H), 1.68 (s, 6H); [M+H]$^+$ 484.

Example 63: 3-(4-(4-Methylpiperazin-1-yl)benzamido)-N-(2-phenylpropan-2-yl)-1H-indazole-5-carboxamide

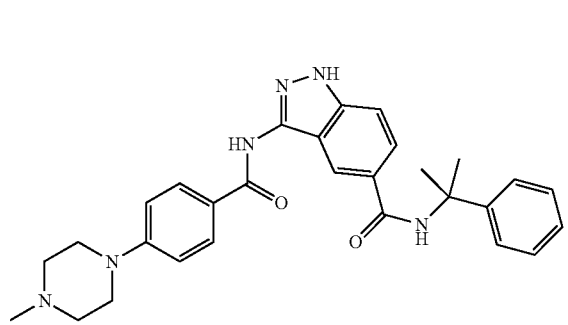 [SMILES: CN1CCN(c2ccc(C(=O)Nc3n[nH]c4ccc(C(=O)NC(C)(C)c5ccccc5)cc34)cc2)CC1]

$^1$H NMR (400 MHz, DMSO-$d_6$) δ 12.93 (s, 1H), 10.54 (s, 1H), 8.44 (s, 1H), 8.26 (s, 1H), 7.99 (d, J=9.2 Hz, 2H), 7.86 (dd, J=8.8, 1.6 Hz, 1H), 7.50 (d, J=8.8 Hz, 1H), 7.38 (d, J=7.6 Hz, 2H), 7.30-7.27 (m, 2H), 7.18-7.15 (m, 1H), 7.04 (d, J=9.2 Hz, 2H), 3.33-3.31 (m, 4H), 2.48-2.45 (m, 4H), 2.24 (s, 3H), 1.68 (s, 6H); [M+H]$^+$ 497.

Example 64: 3-(4-(4-Methylpiperazin-1-yl)benzamido)-N-(2-phenylpropan-2-yl)-1H-indazole-5-carboxamide hydrochloride

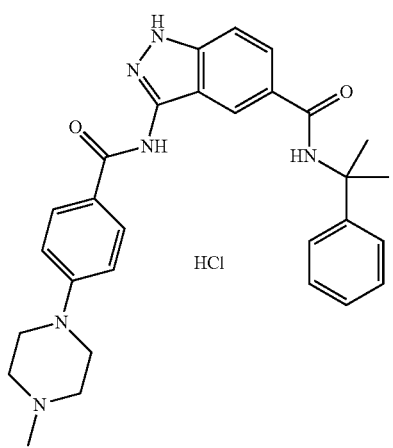 [SMILES: CN1CCN(c2ccc(C(=O)Nc3n[nH]c4ccc(C(=O)NC(C)(C)c5ccccc5)cc34)cc2)CC1 ; Cl]

$^1$H NMR (400 MHz, DMSO-$d_6$) δ 10.96 (s, 1H), 10.62 (s, 1H), 8.44 (s, 1H), 8.24 (s, 1H), 8.03 (d, J=8.3 Hz, 2H), 7.86 (d, J=9.0 Hz, 1H), 7.49 (d, J=8.7 Hz, 1H), 7.37 (d, J=7.8 Hz, 2H), 7.27 (t, J=7.6 Hz, 2H), 7.14 (dd, J=17.0, 8.0 Hz, 3H), 3.56 (t, J=1.7 Hz, 3H), 3.49 (d, J=11.9 Hz, 3H), 3.29-3.09 (m, 5H), 2.81 (s, 3H), 1.66 (s, 5H), 1.27 (dt, J=15.9, 7.5 Hz, 2H); [M+H]$^+$ 497.

Example 65: 3-(4-Morpholinobenzamido)-N-(4-(trifluoromethyl)benzyl)-1H-indazole-5-carboxamide

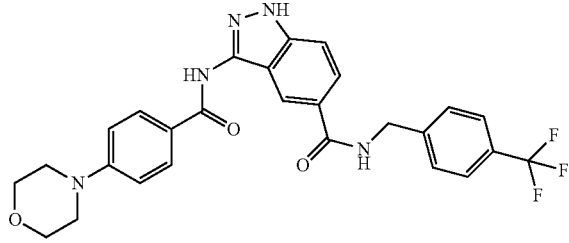 [SMILES: O=C(NCc1ccc(C(F)(F)F)cc1)c1ccc2[nH]nc(NC(=O)c3ccc(N4CCOCC4)cc3)c2c1]

¹H NMR (400 MHz, DMSO-d₆) δ 13.00 (s, 1H), 10.57 (s, 1H), 9.16-9.13 (m, 1H), 8.35 (m, 1H), 7.99 (d, J=8.8 Hz, 2H), 7.92 (dd, J=8.8, 1.6 Hz, 1H), 7.70 (d, J=8.0 Hz, 2H), 7.54 (d, J=8.0 Hz, 3H), 7.04 (d, J=8.8 Hz, 2H), 4.57 (d, J=5.2 Hz, 2H); [M+H]⁺ 524.

Example 66: 3-(4-(4-Methylpiperazin-1-yl)benzamido)-N-(4-(trifluoromethyl)benzyl)-1H-indazole-5-carboxamide

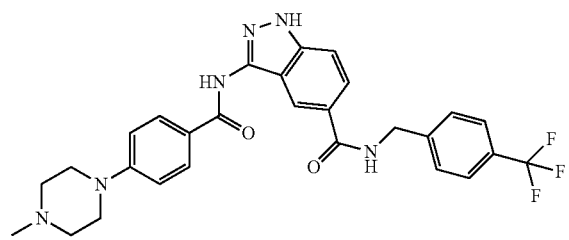 [SMILES: CN1CCN(c2ccc(C(=O)Nc3n[nH]c4ccc(C(=O)NCc5ccc(C(F)(F)F)cc5)cc34)cc2)CC1]

¹H NMR (400 MHz, DMSO-d₆) δ 13.01 (br s, 1H), 10.59 (br s, 1H), 9.14 (m, 1H), 8.35 (s, 1H), 8.02 (d, J=8.8 Hz, 2H), 7.92 (d, J=9.2 Hz, 1H), 7.70 (d, J=7.6 Hz, 2H), 7.54 (d, J=8.0 Hz, 3H), 7.05 (d, J=8.8 Hz, 2H), 4.57 (d, J=4.8 Hz, H), 3.78-3.76 (m, 4H), 3.30-3.27 (m, 4H), 2.24 (s, 3H); [M+H]⁺ 537.

Example 67: 3-(4-Morpholinobenzamido)-N-(1-phenylcyclopropyl)-1H-indazole-5-carboxamide

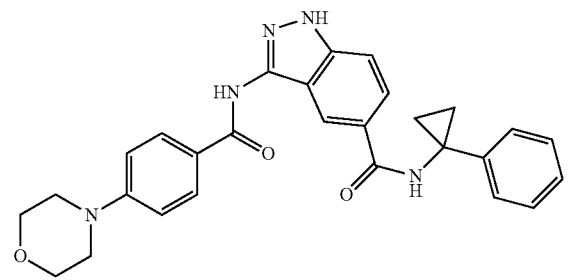 [SMILES: O=C(Nc1n[nH]c2ccc(C(=O)NC3(c4ccccc4)CC3)cc12)c1ccc(N2CCOCC2)cc1]

¹H NMR (400 MHz, DMSO-d₆) δ 12.97 (br s, 1H), 10.55 (s, 1H), 9.17 (s, 1H), 8.33 (s, 1H), 8.00 (d, J=8.8 Hz, 2H), 7.90 (dd, J=8.8, 1.6 Hz, 1H), 7.50 (d, J=8.8 Hz, 2H), 7.26 (t, J=7.6 Hz, 2H), 7.18 (d, J=7.2 Hz, 2H), 7.14 (t, J=7.2 Hz, 1H), 7.04 (d, J=9.2 Hz, 2H), 3.76-3.74 (m, 4H), 3.28-3.25 (m, 4H), 1.26-1.24 (m, 4H); [M+H]⁺ 482.

Example 68: 3-(4-(4-Methylpiperazin-1-yl)benzamido)-N-(1-phenylcyclopropyl)-1H-indazole-5-carboxamide

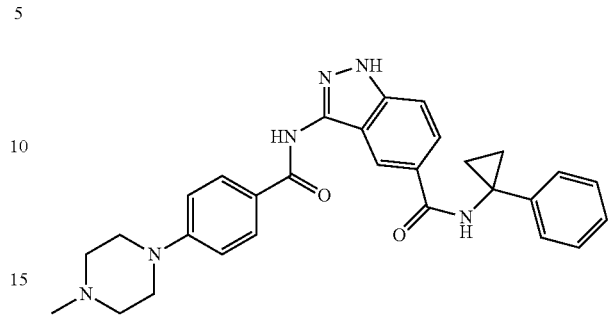

¹H NMR (400 MHz, DMSO-d₆) δ 12.96 (br s, 1H), 10.53 (br s, 1H), 9.17 (s, 1H), 8.32 (s, 1H), 7.98 (d, J=8.8 Hz, 2H), 7.89 (d, J=8.8 Hz, 1H), 7.50 (d, J=8.8 Hz, 1H), 7.26 (t, J=7.6 Hz, 2H), 7.18 (d, J=7.2 Hz, 2H), 7.13 (t, J=6.6 Hz, 1H), 7.02 (d, J=8.8 Hz, 2H), 3.31-3.29 (m, 4H), 2.46-2.43 (m, 4H), 2.22 (s, 3H), 1.26-1.24 (m, 4H); [M+H]⁺ 495.

Example 69: N-((2-Methylpyridin-4-yl)methyl)-3-(4-morpholinobenzamido)-1H-indazole-5-carboxamide

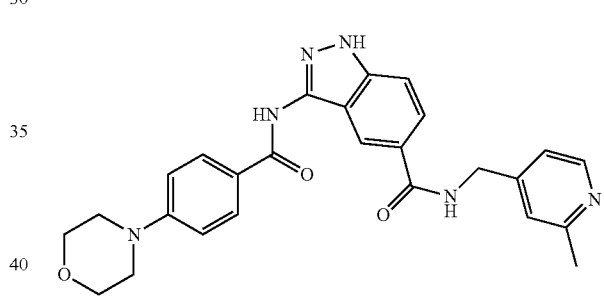

¹H NMR (400 MHz, DMSO-d₆) δ 13.02 (br s, 1H), 10.60 (s, 1H), 9.10-9.09 (m, 1H), 8.37 (s, 1H), 8.36 (s, 1H), 8.02 (d, J=8.8 Hz, 2H), 7.92 (dd, J=9.0, 1.4 Hz, 1H), 7.55 (d, J=8.8 Hz, 1H), 7.16 (s, 1H), 7.11-7.10 (m, 1H), 7.05 (d, J=8.8 Hz, 2H), 4.46 (d, J=5.2 Hz, 2H), 3.78-3.76 (m, 4H), 3.30-3.27 (m, 4H), 2.44 (s, 3H); [M+H]⁺ 471.

Example 70: 3-(4-(4-Methylpiperazin-1-yl)benzamido)-N-((2-methylpyridin-4-yl)methyl)-1H-indazole-5-carboxamide

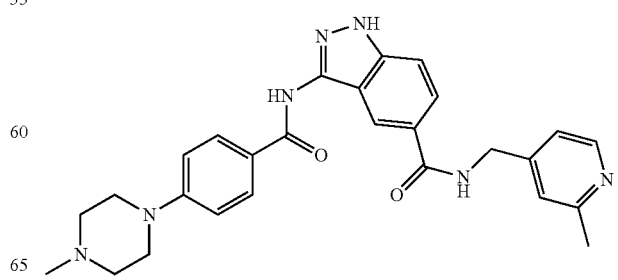

¹H NMR (400 MHz, DMSO-d₆) δ 12.99 (s, 1H), 10.56 (s, 1H), 9.07 (t, J=6.0 Hz, 1H), 8.35 (s, 1H), 8.34 (s, 1H), 7.98 (d, J=8.8 Hz, 2H), 7.53 (dd, J=8.8, 1.6 Hz, 1H), 7.14 (s, 1H), 7.09 (d, J=4.8 Hz, 2H), 7.02 (d, J=9.2 Hz, 2H), 4.45 (d, J=6.0 Hz, 2H), 3.32-3.29 (m, 4H), 2.46-2.44 (m, 4H), 2.23 (s, 1H); [M+H]⁺ 484.

Example 71: 3-(4-Morpholinobenzamido)-N-((6-(trifluoromethyl)pyridin-3-yl)methyl)-1H-indazole-5-carboxamide

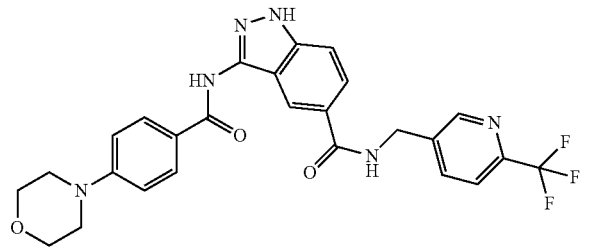 [SMILES: O=C(NCc1ccc(C(F)(F)F)nc1)c1ccc2[nH]nc(NC(=O)c3ccc(N4CCOCC4)cc3)c2c1]

¹H NMR (400 MHz, DMSO-d₆) δ 12.99 (s, 1H), 10.59 (s, 1H), 9.16 (t, J=5.6 Hz, 1H), 8.73 (s, 1H), 8.33 (s, 1H), 7.99 (d, J=8.8 Hz, 3H), 7.88 (t, J=8.0 Hz, 2H), 7.53 (d, J=8.4 Hz, 1H), 7.04 (d, J=9.2 Hz, 2H), 4.58 (d, J=5.6 Hz, 2H), 3.77-3.72 (m, 4H), 3.28-3.26 (m, 4H); [M+H]⁺ 525.

Example 72: 3-(4-(4-Methylpiperazin-1-yl)benzamido)-N-((6-(trifluoromethyl)pyridin-3-yl)methyl)-1H-indazole-5-carboxamide

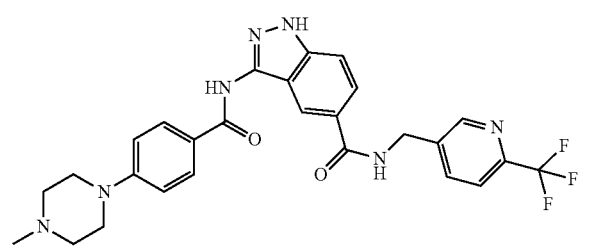 [SMILES: CN1CCN(c2ccc(C(=O)Nc3n[nH]c4ccc(C(=O)NCc5ccc(C(F)(F)F)nc5)cc34)cc2)CC1]

¹H NMR (400 MHz, DMSO-d₆) δ 12.98 (s, 1H), 10.56 (s, 1H), 9.16 (t, J=5.8 Hz, 1H), 8.73 (s, 1H), 8.33 (s, 1H), 7.98 (d, J=8.8 Hz, 3H), 7.88 (t, J=8.0 Hz, 2H), 7.52 (d, J=8.8 Hz, 1H), 7.02 (d, J=9.2 Hz, 1H), 4.58 (d, J=5.6 Hz, 2H), 3.32-3.29 (m, 4H), 2.46-2.44 (m, 4H), 2.23 (s, 3H); [M+H]⁺ 538.

Example 73: 3-(2-Methyl-4-morpholinobenzamido)-N-(thiophen-2-ylmethyl)-1H-indazole-5-carboxamide

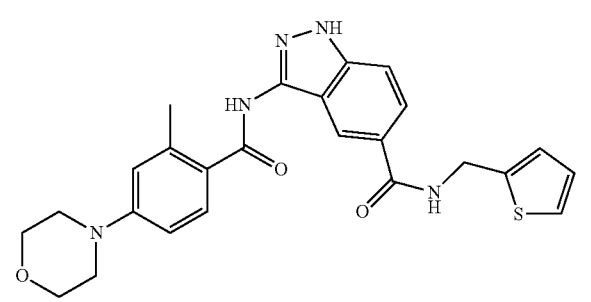 [SMILES: Cc1cc(N2CCOCC2)ccc1C(=O)Nc1n[nH]c2ccc(C(=O)NCc3cccs3)cc12]

¹H NMR (400 MHz, DMSO-d₆) δ 12.93 (br s, 1H), 10.47 (br s, 1H), 9.15-9.12 (m, 1H), 8.36 (s, 1H), 7.88 (dd, J=9.0, 1.4 Hz, 1H), 7.59 (d, J=8.4 Hz, 1H), 7.52 (d, J=8.8 Hz, 1H), 7.38 (dd, J=5.2, 1.2 Hz, 1H), 7.03-7.02 (m, 1H), 6.98-6.96 (m, 1H), 6.86 (d, J=8.8 Hz, 2H), 4.65 (d, J=5.2 Hz, 2H), 3.78-3.75 (m, 4H), 3.24-3.21 (m, 4H), 2.48 (s, 3H); [M+H]⁺ 476.

Example 74: 3-(2-Methyl-4-(4-methylpiperazin-1-yl)benzamido)-N-(thiophen-2-ylmethyl)-1H-indazole-5-carboxamide

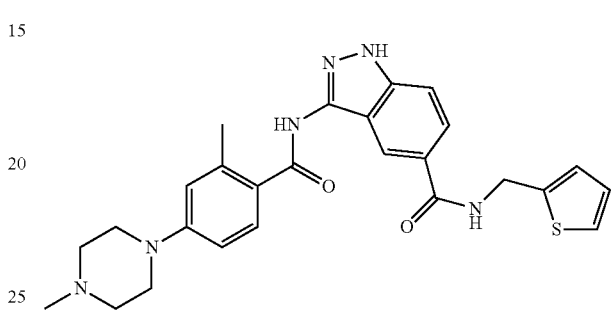

¹H NMR (400 MHz, DMSO-d₆) δ 12.98 (s, 1H), 10.52 (s, 1H), 9.16-9.13 (m, 1H), 8.36 (s, 1H), 7.89 (dd, J=8.8, 1.2 Hz, 1H), 7.61 (d, J=8.4 Hz, 1H), 7.53 (d, J=8.8 Hz, 1H), 7.38 (dd, J=5.2, 1.2 Hz, 1H), 7.03-7.02 (m, 1H), 6.98-6.96 (m, 1H), 6.92 (d, J=8.8 Hz, 2H), 4.65 (d, J=5.2 Hz, 2H), 3.60-3.55 (m, 2H), 3.30-3.25 (m, 2H), 3.19-3.15 (m, 4H), 2.77 (s, 3H), 2.49 (s, 3H); [M+H]⁺ 489.

Example 75: 3-(3-(4-(4-Methylpiperazin-1-yl)benzamido)-1H-indazol-5-yl)-3-oxo-2-(thiophen-2-yl)propanoic Acid

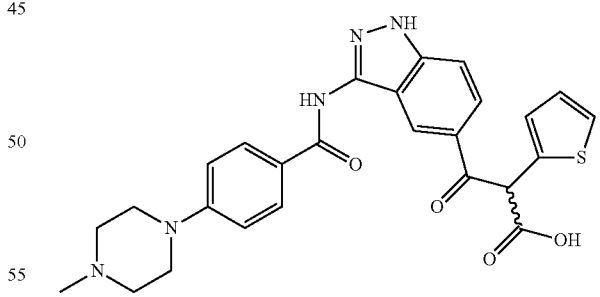

¹H NMR (400 MHz, DMSO-d₆) δ 12.99 (br s, 1H), 10.57 (s, 1H), 9.22 (d, J=7.6 Hz, 1H), 8.37 (s, 1H), 8.00 (d, J=8.8 Hz, 2H), 7.92 (dd, J=8.8, 1.6 Hz, 1H), 7.51 (d, J=8.8 Hz, 1H), 7.48 (dd, J=5.0, 1.4 Hz, 1H), 7.17 (dt, J=2.8, 1.1 Hz, 1H), 7.04 (d, J=9.2 Hz, 2H), 7.00 (m, 1H), 3.77-3.74 (m, 4H), 3.28-3.26 (m, 4H), 2.24 (s, 3H), 1.98-1.91 (m, 2H), 0.93 (t, J=7.2 Hz, 3H); [M+H]⁺ 504.

Example 76: (S)-3-(4-(3-Methylpiperazin-1-yl)benzamido)-N-(1-phenylcyclopropyl)-1H-indazole-5-carboxamide

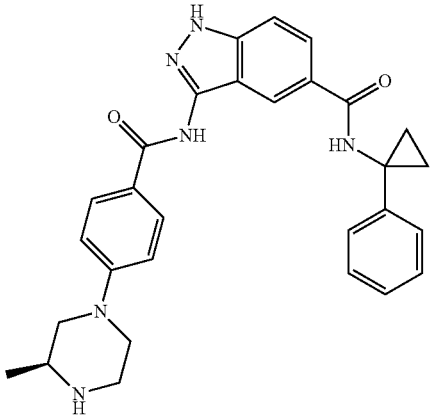 [SMILES: C[C@H]1CN(c2ccc(C(=O)Nc3n[nH]c4ccc(C(=O)NC5(c6ccccc6)CC5)cc34)cc2)CCN1]

¹H NMR (400 MHz, DMSO-d₆) δ 12.95 (s, 1H), 10.51 (s, 1H), 9.18 (s, 1H), 8.33 (s, 1H), 7.97 (d, J=8.8 Hz, 2H), 7.89 (dd, J=9.0, 1.8 Hz, 1H), 7.50 (d, J=8.8 Hz, 2H), 7.28-7.24 (m, 2H), 7.20-7.12 (m, 3H), 7.00 (d, J=8.8 Hz, 1H), 3.75-3.70 (m, 2H), 2.98-2.95 (m, 1H), 2.80-2.73 (m, 2H), 2.69-2.62 (m, 1H), 2.33-2.28 (m, 1H), 1.26-1.24 (m, 4H), 1.05-1.03 (d, J=6.4 Hz, 3H); [M+H]⁺ 493.

Example 77: (R)-3-(4-(3-Methylpiperazin-1-yl)benzamido)-N-(1-phenylcyclopropyl)-1H-indazole-5-carboxamide

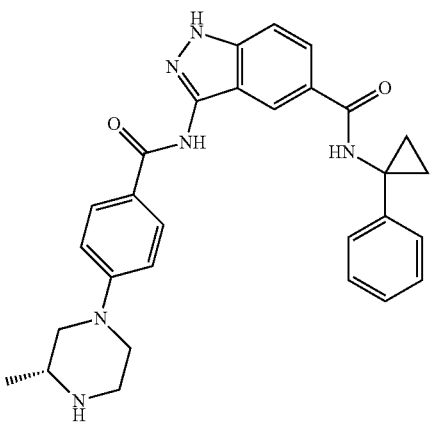 [SMILES: C[C@@H]1CN(c2ccc(C(=O)Nc3n[nH]c4ccc(C(=O)NC5(c6ccccc6)CC5)cc34)cc2)CCN1]

¹H NMR (400 MHz, DMSO-d₆) δ 12.95 (br s, 1H), 10.51 (s, 1H), 9.17 (s, 1H), 8.33 (s, 1H), 7.97 (d, J=8.8 Hz, 2H), 7.89 (dd, J=9.0, 1.8 Hz, 1H), 7.50 (d, J=8.8 Hz, 1H), 7.28-7.24 (m, 2H), 7.20-7.12 (m, 3H), 7.00 (d, J=8.8 Hz, 2H), 3.75-3.70 (m, 2H), 2.98-2.95 (m, 1H), 2.79-2.72 (m, 2H), 2.69-2.62 (m, 1H), 2.33-2.28 (m, 1H), 1.26-1.24 (m, 4H), 1.05-1.03 (d, J=6.4 Hz, 3H); [M+H]⁺ 493.

Example 78: 3-(3-Methyl-4-morpholinobenzamido)-N-(thiophen-2-ylmethyl)-1H-indazole-5-carboxamide

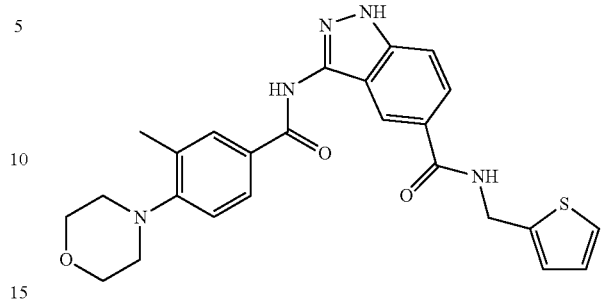

¹H NMR (400 MHz, DMSO-d₆) δ 13.02 (br s, 1H), 10.70 (br s, 1H), 9.12-9.09 (m, 1H), 8.31 (s, 1H), 7.94 (s, 1H), 7.94-7.92 (m, 1H), 7.88 (dd, J=8.8, 1.6 Hz, 1H), 7.52 (d, J=8.8 Hz, 1H), 7.36 (dd, J=5.0, 1.4 Hz, 1H), 7.12 (d, J=8.4 Hz, 1H), 7.00 (m, 1H), 6.96-6.93 (m, 1H), 4.61 (d, J=5.6 Hz, 2H), 3.78-3.76 (m, 4H), 2.94-2.92 (m, 4H), 2.34 (s, 3H); [M+H]⁺ 476.

Example 79: 3-(3-Methyl-4-(4-methylpiperazin-1-yl)benzamido)-N-(thiophen-2-ylmethyl)-1H-indazole-5-carboxamide

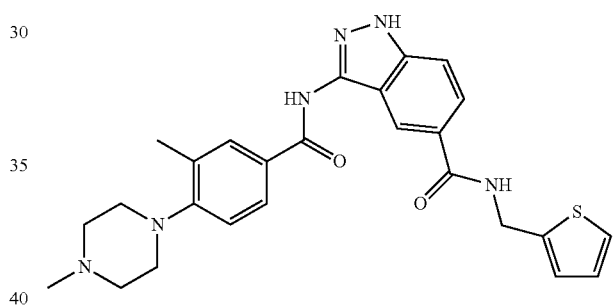

¹H NMR (400 MHz, DMSO-d₆) δ 13.03 (br s, 1H), 10.73 (s, 1H), 9.86 (m, 1H), 9.11 (m, 1H), 8.30 (s, 1H), 7.97 (s, 1H), 7.97-7.94 (m, 1H), 7.88 (dd, J=9.0, 1.4 Hz, 1H), 7.52 (d, J=8.4 Hz, 1H), 7.36 (dd, J=5.0, 1.0 Hz, 1H), 7.18 (d, J=8.0 Hz, 1H), 7.00 (m, 1H), 6.96-6.94 (m, 1H), 4.62 (d, J=5.6 Hz, 2H), 3.55-3.53 (m, 4H), 3.37-3.33 (m, 4H), 2.90 (s, 3H), 2.35 (s, 3H); [M+H]⁺ 489.

Example 80: 3-(4-(4-Methylpiperazin-1-yl)benzamido)-N-(1-(thiophen-3-yl)ethyl)-1H-indazole-5-carboxamide

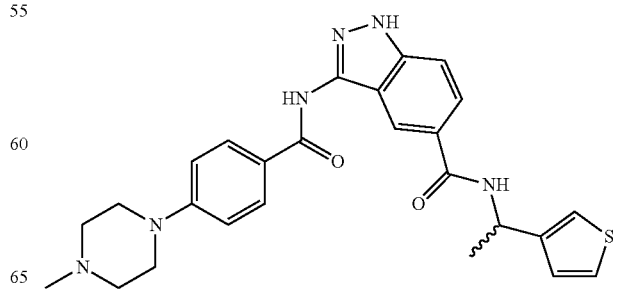

¹H NMR (400 MHz, DMSO-d₆) δ 12.94 (br s, 1H), 10.53 (s, 1H), 8.74 (d, J=8.4 Hz, 1H), 8.29 (s, 1H), 7.97 (d, J=8.8 Hz, 2H), 7.89 (dd, J=8.8, 1.6 Hz, 1H), 7.49 (d, J=8.8 Hz, 1H), 7.47-7.45 (m, 1H), 7.31-7.30 (m, 1H), 7.13 (dd, J=5.2, 1.2 Hz, 1H), 7.02 (d, J=8.8 Hz, 2H), 5.32-5.28 (m, 1H), 3.32-3.29 (m, 4H), 2.47-2.45 (m, 4H), 2.23 (s, 3H), 1.49 (d, J=6.8 Hz, 3H); [M+H]⁺ 489.

Example 81: N-(1-(Furan-2-yl)ethyl)-3-(4-(4-methylpiperazin-1-yl)benzamido)-1H-indazole-5-carboxamide

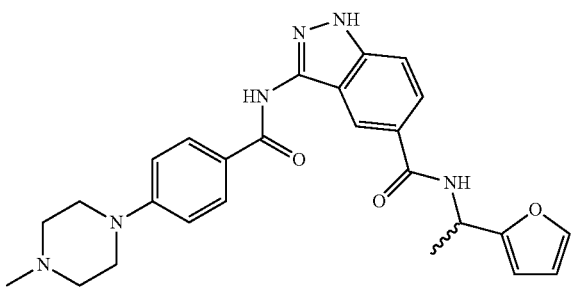 [SMILES: CC(NC(=O)c1ccc2[nH]nc(NC(=O)c3ccc(N4CCN(C)CC4)cc3)c2c1)c1ccco1]

¹H NMR (400 MHz, DMSO-d₆) δ 12.96 (br s, 1H), 10.53 (br s, 1H), 8.76 (d, J=8.4 Hz, 1H), 8.29 (s, 1H), 7.97 (d, J=8.8 Hz, 2H), 7.89 (dd, J=8.8, 1.6 Hz, 1H), 7.56 (m, 1H), 7.49 (d, J=8.8 Hz, 1H), 7.02 (d, J=9.2 Hz, 2H), 6.39-6.38 (m, 1H), 6.24 (d, J=3.2 Hz, 1H), 5.31-5.27 (m, 1H), 3.32-3.29 (m, 4H), 2.46-2.44 (m, 4H), 2.23 (s, 3H), 1.47 (d, J=6.8 Hz, 3H); [M+H]⁺ 473.

Example 82: 3-(4-(4-Methylpiperazin-1-yl)benzamido)-N-(1-(thiazol-2-yl)ethyl)-1H-indazole-5-carboxamide

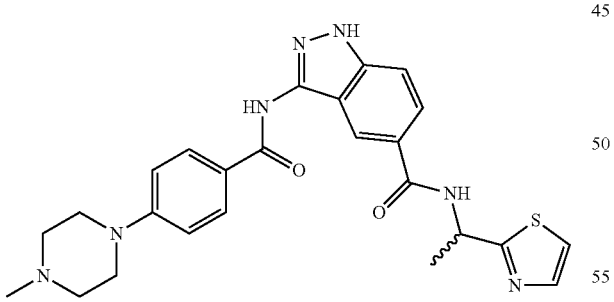

¹H NMR (400 MHz, DMSO-d₆) δ 13.04 (br s, 1H), 10.54 (s, 1H), 9.14 (d, J=8.0 Hz, 1H), 8.35 (s, 1H), 7.98 (d, J=8.8 Hz, 2H), 7.92 (dd, J=8.8, 1.6 Hz, 1H), 7.72 (d, J=3.2 Hz, 1H), 7.59 (d, J=3.2 Hz, 1H), 7.53 (d, J=8.8 Hz, 1H), 7.02 (d, J=8.8 Hz, 2H), 5.50-5.43 (m, 1H), 3.31-3.29 (m, 4H), 2.46-2.44 (m, 4H), 2.23 (s, 3H), 1.62 (d, J=7.2 Hz, 3H); [M+H]⁺ 490.

Example 83: 3-(4-(4-Methylpiperazin-1-yl)benzamido)-N-(1-(thiazol-5-yl)ethyl)-1H-indazole-5-carboxamide

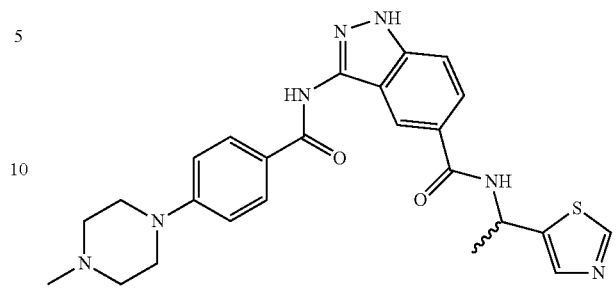

¹H NMR (400 MHz, DMSO-d₆) δ 12.95 (s, 1H), 10.53 (s, 1H), 9.04 (d, J=2.0 Hz, 1H), 8.80 (d, J=8.0 Hz, 1H), 8.32 (s, 1H), 7.98 (d, J=8.8 Hz, 2H), 7.92 (dd, J=8.8, 1.6 Hz, 1H), 7.50 (d, J=8.8 Hz, 1H), 7.43 (m, 1H), 7.03 (d, J=8.8 Hz, 2H) 5.40-5.36 (m, 1H), 3.33 (m, 4H), 2.50 (m, 4H), 2.28 (s, 3H), 1.53 (d, J=7.2 Hz, 3H); [M+H]⁺ 490.

Example 84: 3-(4-(4-Methylpiperazin-1-yl)benzamido)-N-(1-(thiazol-2-yl)propyl)-1H-indazole-5-carboxamide

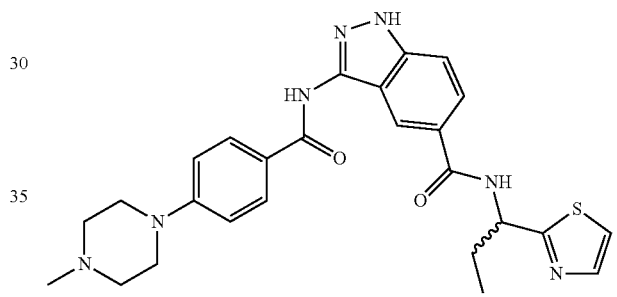

¹H NMR (400 MHz, DMSO-d₆) δ 13.00 (br s, 1H), 10.55 (s, 1H), 9.05 (d, J=8.0 Hz, 1H), 8.35 (s, 1H), 7.98 (d, J=8.8 Hz, 2H), 7.92 (dd, J=8.8, 1.6 Hz, 1H), 7.73 (d, J=7.2 Hz, 1H), 7.59 (d, J=3.6 Hz, 1H), 7.53 (d, J=8.8 Hz, 1H), 7.02 (d, J=8.8 Hz, 2H), 5.29-5.23 (m, 1H), 3.32-3.29 (m, 4H), 2.46-2.44 (m, 4H), 2.23 (s, MA 2.17-2.19 (m, 1H), 1.99-1.91 (m, 1H), 0.98 (t, J=7.4 Hz, 3H); [M+H]⁺ 504.

Example 85: 3-(4-(4-Methylpiperazin-1-yl)benzamido)-N-(pyridin-2-ylmethyl)-1H-indazole-5-carboxamide bis(2,2,2-trifluoroacetate)

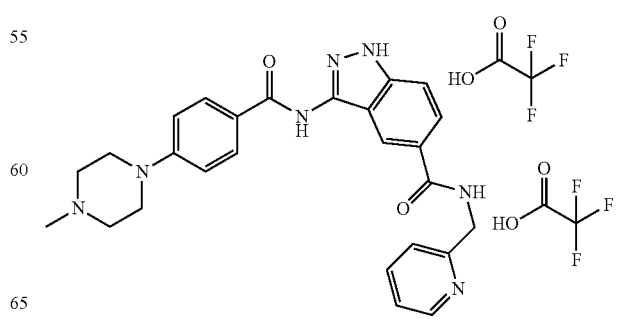

$^1$H NMR (400 MHz, DMSO-d$_6$) δ 10.64 (s, 1H), 9.13 (t, J=6.0 Hz, 1H), 8.55 (d, J=4.4 Hz, 1H), 8.36 (s, 1H), 8.04 (d, J=8.8 Hz, 2H), 7.93 (d, J=6.8 Hz, 1H), 7.85 (s, 1H), 7.54 (d, J=8.8 Hz, 1H), 7.39 (d, J=7.6 Hz, 1H), 7.34 (s, 1H), 7.12 (d, J=8.8 Hz, 2H), 4.60 (d, J=6.4 Hz, 2H), 2.88 (s, 3H), 2.81 (s, 8H); [M+H]$^+$ 470.

Example 86: 3-(4-Morpholinobenzamido)-N-(pyridin-2-ylmethyl)-1H-indazole-5-carboxamide

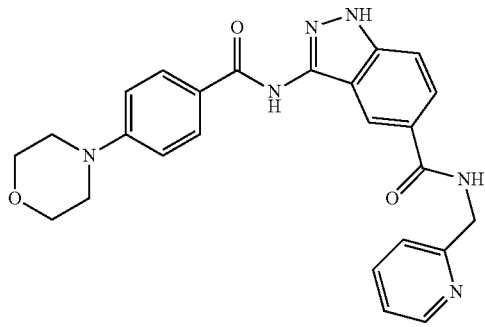 [SMILES: O=C(NCc1ccccn1)c1ccc2[nH]nc(NC(=O)c3ccc(N4CCOCC4)cc3)c2c1]

$^1$H NMR (400 MHz, DMSO-d$_6$) δ 10.59 (s, 1H), 9.19 (t, J=6.2 Hz, 1H), 8.65 (s, 1H), 8.37 (s, 1H), 8.01 (d, J=8.8 Hz, 2H), 7.9 (d, J=8.8 Hz, 1H), 7.54 (d, J=8.8 Hz, 2H), 7.04 (d, J=9.2 Hz, 2H), 4.66 (d, J=6.0 Hz, 2H), 3.75 (t, J=8.4 Hz, 4H), 3.27 (t, J=4.6 Hz, 4H); [M+H]$^+$ 457.

Example 87: N-(Cyclohexylmethyl)-3-(4-(4-methylpiperazin-1-yl)benzamido)-1H-indazole-5-carboxamide

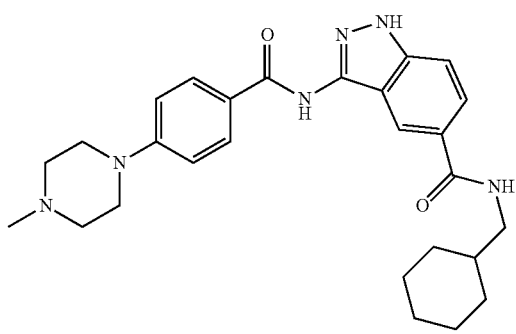 [SMILES: CN1CCN(c2ccc(C(=O)Nc3n[nH]c4ccc(C(=O)NCC5CCCCC5)cc34)cc2)CC1]

$^1$H NMR (400 MHz, DMSO-d$_6$) δ 12.96 (brs, 1H), 10.62 (s, 1H), 9.88 (brs, 1H), 8.41 (t, J=5.4 Hz, 1H), 8.25 (s, 1H), 8.04 (d, J=8.8 Hz, 2H), 7.85 (dd, J=8.8, 1.6 Hz, 1H), 7.50 (d, J=8.8 Hz, 1H), 7.13 (d, J=8.8 Hz, 2H), 4.01 (d, J=12.8 Hz, 2H), 3.55 (d, J=10.4 Hz, 2H), 3.15-3.08 (m, 6H), 2.88 (s, 3H), 1.72-1.66 (m, 5H), 1.59-1.52 (m, 2H), 1.19-1.11 (m, 3H), 0.95-0.86 (m, 2H); [M+H]$^+$ 475.

Example 88: N-(Cyclohexylmethyl)-3-(4-morpholinobenzamido)-1H-indazole-5-carboxamide

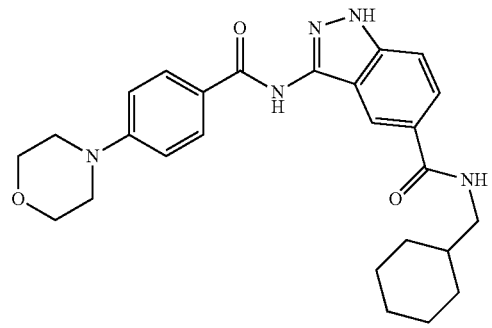 [SMILES: O=C(NCC1CCCCC1)c1ccc2[nH]nc(NC(=O)c3ccc(N4CCOCC4)cc3)c2c1]

$^1$H NMR (400 MHz, DMSO-d$_6$) δ 10.56 (s, 1H), 8.41 (t, J=5.8 Hz, 1H), 8.25 (s, 1H), 8.01 (d, J=8.8 Hz, 2H), 7.85 (dd, 8.6, 1.4 Hz, 1H), 7.49 (d, J=8.8 Hz, 1H), 7.05 (d, J=9.2 Hz, 2H), 3.76 (t, J=4.8 Hz, 4H), 3.28 (t, J=4.8 Hz, 4H), 3.10 (brs, 2H), 1.71-1.66 (m, 4H), 1.61-1.52 (m, 2H), 1.19-1.13 (m, 3H), 0.92-0.89 (m, 2H); [M+H]$^+$ 462.

Example 89: 3-(4-(3,5-Dimethylpiperazin-1-yl)benzamido)-N-(thiophen-2-ylmethyl)-1H-indazole-5-carboxamide 2,2,2-trifluoroacetate

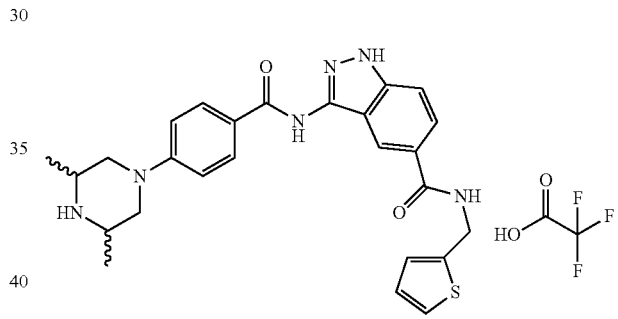

$^1$H NMR (400 MHz, MeOD) δ 8.36 (s, 1H), 8.01 (d, J=8.8 Hz, 2H), 7.89 (dd, J=8.6, 1.4 Hz, 1H), 7.54 (d, J=8.8 Hz, 1H), 7.27 (dd, J=5.0, 1.0 Hz, 1H), 7.15 (d, J=8.8 Hz, 2H), 7.04 (d, J=3.2 Hz, 1H), 6.95-6.93 (m, 1H), 4.74 (s, 2H), 4.13-4.10 (m, 2H), 3.53-3.48 (m, 2H), 2.85-2.79 (m, 2H), 1.42 (s, 3H), 1.40 (s, 3H); [M+H]$^+$ 488.

Example 90: N-(Cyclopentylmethyl)-3-(4-(4-methylpiperazin-1-yl)benzamido)-1H-indazole-5-carboxamide 2,2,2-trifluoroacetate

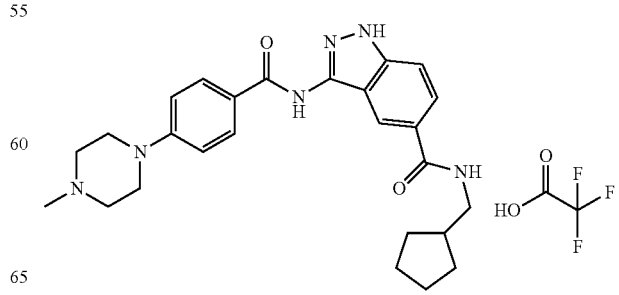

¹H NMR (400 MHz, DMSO-d₆) δ 12.97 (s, 1H), 10.63 (s, 1H), 9.68 (brs, 1H), 8.46 (brs, 1H), 8.24 (s, 1H), 8.04 (d, J=8.8 Hz, 2H), 7.85 (d, J=8.0 Hz, 1H), 7.50 (d, J=8.8 Hz, 1H), 7.13 (d, J=8.8 Hz, 2H), 4.09 (d, J=12.8 Hz, 2H), 3.20-3.08 (m, 5H), 2.88 (s, 3H), 2.19-2.11 (m, 2H), 1.69-1.49 (m, 6H), 1.29-1.24 (m, 3H); [M+H]⁺ 461.

Example 91: N-(Cyclopentylmethyl)-3-(4-morpholinobenzamido)-1H-indazole-5-carboxamide 2,2,2-trifluoroacetate

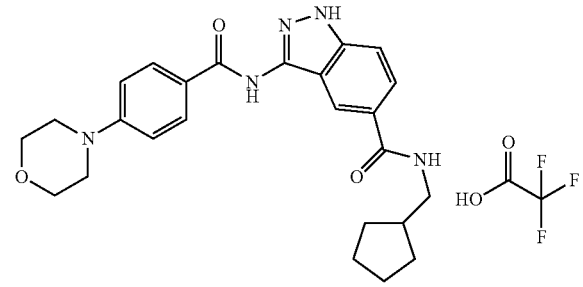

¹H NMR (400 MHz, DMSO-d₆) δ 12.94 (s, 1H), 10.56 (s, 1H), 8.46 (t, J=5.6 Hz, 1H), 8.24 (s, 1H), 8.01 (d, J=8.4 Hz, 2H), 7.85 (d, J=8.0 Hz, 1H), 7.49 (d, J=8.8 Hz, 1H), 7.05 (d, J=8.8 Hz, 2H), 3.76 (t, J=4.6 Hz, 4H), 3.28 (t, J=4.6 Hz, 4H), 3.18 (t, J=6.4 Hz, 2H), 2.19-2.16 (m, 1H), 1.66-1.48 (m, 6H), 1.27-1.24 (m, 2H); [M+H]⁺ 478.

Example 92: 3-(4-(2,6-Dimethylmorpholino)benzamido)-N-(thiophen-2-ylmethyl)-1H-indazole-5-carboxamide 2,2,2-trifluoroacetate

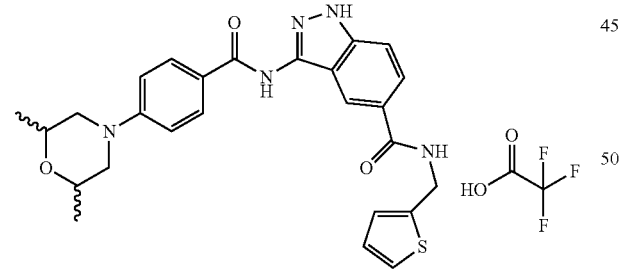

¹H NMR (400 MHz, DMSO-d₆) δ 12.97 (brs, 1H), 10.56 (s, 1H), 9.13 (brs, 1H), 8.03 (s, 1H), 8.00 (d, J=8.8 Hz, 2H), 7.88 (d, J=8.8 Hz, 1H), 7.51 (d, J=8.8 Hz, 1H), 7.37 (d, J=5.2 Hz, 1H), 7.05 (d, J=8.8 Hz, 2H), 7.00 (s, 1H), 6.96-6.94 (m, 1H), 4.62 (d, J=5.6 Hz, 2H), 3.80 (d, J=12.0 Hz, 2H), 3.71-3.67 (m, 2H), 2.37 (t, J=11.6 Hz, 2H), 1.19 (s, 3H), 1.17 (s, 3H); [M+H]⁺ 490.

Example 93: N-(4-Hydroxybutan-2-yl)-3-(4-(4-methylpiperazin-1-yl)benzamido)-1H-indazole-5-carboxamide

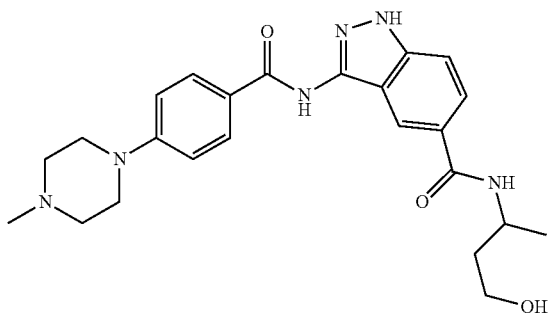 [SMILES: CC(CCO)NC(=O)c1ccc2[nH]nc(NC(=O)c3ccc(N4CCN(C)CC4)cc3)c2c1]

¹H NMR (400 MHz, DMSO-d₆) δ 12.93 (s, 1H), 10.53 (s, 1H), 8.23 (s, 1H), 8.18 (d, J=8.4 Hz, 1H), 7.99 (d, J=8.8 Hz, 2H), 7.84 (dd, J=8.8, 1.6 Hz, 1H), 7.49 (d, J=9.2 Hz, 1H), 7.04 (d, J=9.2 Hz, 2H), 4.42 (t, J=5.2 Hz, 1H), 4.15-4.10 (m, 2H), 3.46-3.41 (m, 2H), 3.31 (s, MA 2.28 (brs, 4H), 1.73-1.59 (m, 4H), 1.15 (d, J=6.8 Hz, 3H); [M+H]⁺ 451.

Example 94: N-((1H-1,2,3-Triazol-4-yl)methyl)-3-(4-(4-methylpiperazin-1-yl)benzamido)-1H-indazole-5-carboxamide

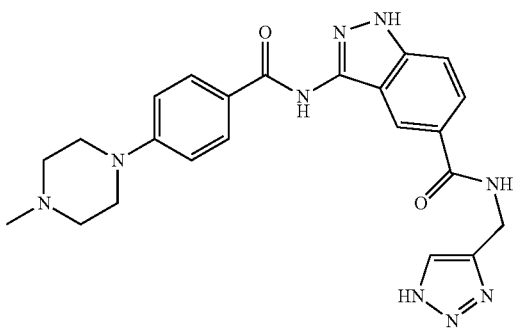 [SMILES: CN1CCN(c2ccc(C(=O)Nc3n[nH]c4ccc(C(=O)NCc5c[nH]nn5)cc34)cc2)CC1]

¹H NMR (400 MHz, DMSO-d₆) δ 12.95 (s, 1H), 10.55 (s, 1H), 8.99 (t, J=5.8 Hz, 1H), 8.30 (s, 1H), 7.98 (d, J=8.8 Hz, 2H), 7.88 (d, J=8.8 Hz, 1H), 7.50 (d, J=8.8 Hz, 1H), 7.0 (d, J=9.2 Hz, 2H), 4.53 (d, J=5.6 Hz, 2H), 3.31 (brs, 7H), 2.26 (brs, 4H); [M+H]⁺ 460.

Example 95: 3-(4-(3,5-dimethylpiperazin-1-yl)benzamido)-N-(1-(thiophen-2-yl)propyl)-1H-indazole-5-carboxamide 2,2,2-trifluoroacetate

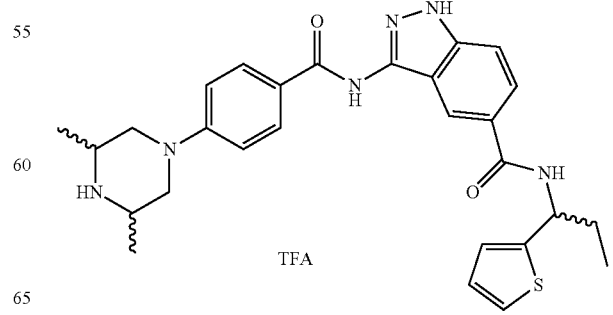

¹H NMR (400 MHz, DMSO-d₆) δ 12.98 (brs, 1H), 10.61 (s, 1H), 9.02-9.00 (m, 1H), 8.78 (d, J=8.4 Hz, 1H), 8.45-8.43 (m, 1H), 8.29 (s, 1H), 8.03 (d, J=8.8 Hz, 2H), 7.90 (dd, J=8.8, 1.6 Hz, 1H), 7.53 (d, J=9.2 Hz, 1H), 7.08 (d, J=8.8 Hz, 2H), 6.96 (dd, J=5.0, 3.2 Hz, 1H), 5.22 (q, J=7.8 Hz, 2H), 4.12 (d, J=11.6 Hz, 2H), 3.41 (brs, 2H), 2.74 (t, J=12.6 Hz, 2H), 1.30 (s, 3H), 1.28 (s, 3H), 0.94 (t, J=7.8 Hz, 3H); [M+H]⁺ 517.

Example 96: 3-(4-(2,6-Dimethylmorpholino)benzamido)-N-(1-(thiophen-2-yl)propyl)-1H-indazole-5-carboxamide 2,2,2-trifluoroacetate

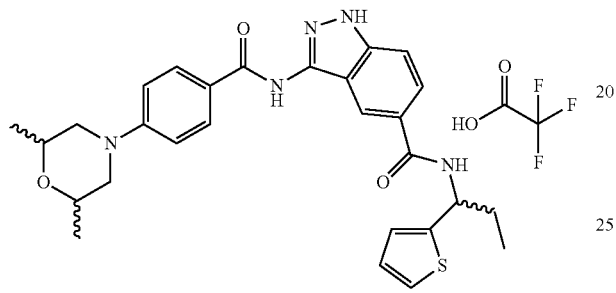

¹H NMR (400 MHz, DMSO-d₆) δ 12.95 (brs, 1H), 10.54 (s, 1H), 8.80 (d, J=8.4 Hz, 1H), 8.30 (s, 1H), 8.00 (d, J=8.8 Hz, 2H), 7.89 (dd, J=8.8, 1.2 Hz, 1H), 7.51 (d, J=8.8 Hz, 1H), 7.36 (dd, J=4.8, 1.2 Hz, 1H), 7.05 (d, J=8.8 Hz, 2H), 7.01 (d, J=3.2 Hz, 1H), 6.96 (dd, J=5.0, 3.2 Hz, 1H), 5.22 (q, J=7.7 Hz, 1H), 3.80 (d, J=11.0 Hz, 2H), 3.71-3.67 (m, 2H), 2.40-2.34 (m, 2H), 1.98-1.93 (m, 2H), 1.19 (s, 3H), 1.17 (s, 3H), 0.93 (t, J=7.7 Hz, 3H); [M+H]⁺ 518.

Example 97: 3-(4-((S)-3-Methylpiperazin-1-yl)benzamido)-N-(1-(thiophen-2-yl)propyl)-1H-indazole-5-carboxamide 2,2,2-trifluoroacetate

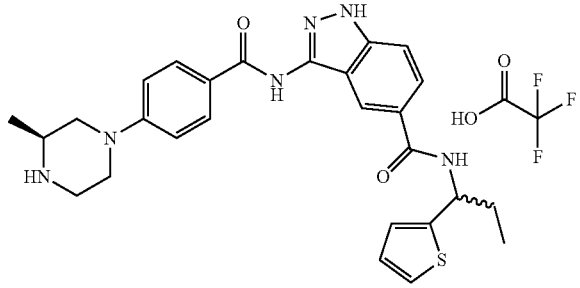

¹H NMR (400 MHz, DMSO-d₆) δ 13.00 (brs, 1H), 10.61 (s, 1H), 8.99 (d, J=9.2 Hz, 1H), 8.80 (d, J=8.4 Hz, 1H), 8.66 (d, J=10.4 Hz, 1H), 8.29 (s, 1H), 8.03 (d, J=9.2 Hz, 2H), 7.90 (dd, J=8.8, 1.6 Hz, 1H), 7.52 (d, J=8.8 Hz, 1H), 7.36 (dd, J=5.5, 1.2 Hz, 1H), 7.13 (d, J=9.2 Hz, 2H), 7.01 (d, J=3.6 Hz, 1H), 6.97-6.95 (m, 1H), 5.22 (q, J=7.7 Hz, 1H), 4.06-3.96 (m, 2H), 3.44-3.41 (m, 2H), 3.19-3.03 (m, 2H), 2.88-2.82 (m, 1H), 1.97-1.93 (m, 2H), 1.29 (d, J=6.4 Hz, 3H), 0.94 (t, J=7.4 Hz, 3H); [M+H]⁺ 503.

Example 98: 3-(4-((R)-3-Methylpiperazin-1-yl)benzamido)-N-(1-(thiophen-2-yl)propyl)-1H-indazole-5-carboxamide 2,2,2-trifluoroacetate

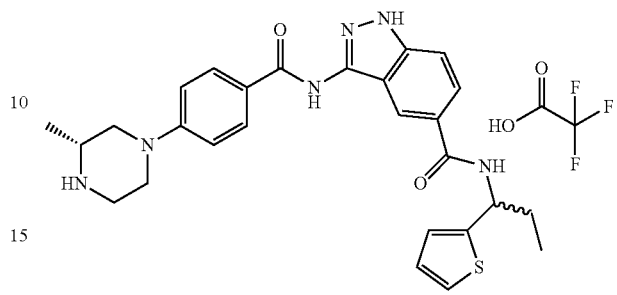

¹H NMR (400 MHz, DMSO-d₆) δ 13.00 (brs, 1H), 10.61 (s, 1H), 9.01 (m, 1H), 8.80 (d, J=8.4 Hz, 1H), 8.70 (brs, 1H), 8.29 (s, 1H), 8.03 (d, J=8.8 Hz, 2H), 7.90 (dd, J=8.8, 1.4 Hz, 1H), 7.52 (d, J=9.2 Hz, 1H), 7.36 (dd, J=5.2, 1.2 Hz, 1H), 7.13 (d, J=9.2 Hz, 2H), 7.01 (d, J=3.2 Hz, 1H), 6.98-6.95 (m, 1H), 5.22 (q, J=7.7 Hz, 1H), 4.06-3.96 (m, 2H), 3.44-3.38 (m, 2H), 3.17-3.04 (m, 2H), 2.88-2.82 (m, 1H), 1.97-1.93 (m, 2H), 1.29 (d, J=6.4 Hz, 3H), 0.94 (t, J=7.4 Hz, 3H); [M+H]⁺ 503.

Example 99: 3-(4-((3R,5S)-3,5-Dimethylpiperazin-1-yl)benzamido)-N-(1-(thiophen-2-yl)propyl)-1H-indazole-5-carboxamide 2,2,2-trifluoroacetate

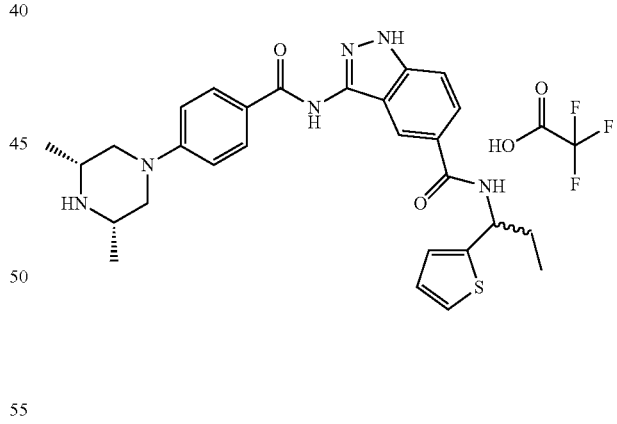

¹H NMR (400 MHz, DMSO-d₆) δ 13.00 (brs, 1H), 10.61 (s, 1H), 9.08 (d, J=7.2 Hz, 1H), 8.80 (d, J=8.4 Hz, 1H), 8.50 (d, J=10.4 Hz, 1H), 8.70 (brs, 1H), 8.30 (s, 1H), 8.04 (d, J=8.8 Hz, 2H), 7.90 (dd, J=8.8, 1.6 Hz, 1H), 7.52 (d, J=8.8 Hz, 1H), 7.36 (dd, J=5.2, 1.2 Hz, 1H), 7.14 (d, J=9.2 Hz, 2H), 7.01 (d, J=3.2 Hz, 1H), 6.98-6.95 (m, 1H), 5.22 (q, J=7.7 Hz, 1H), 4.12 (d, J=12.4 Hz, 2H), 3.39 (brs, 2H), 2.76 (t, J=5.8 Hz, 2H), 1.99-1.93 (m, 2H), 1.30 (s, 3H), 1.28 (s, 3H), 0.94 (t, J=7.7 Hz, 3H); [M+H]⁺ 517.

Example 100: N-((3-Methyl-1,2,4-oxadiazol-5-yl)methyl)-3-(4-morpholinobenzamido)-1H-indazole-5-carboxamide 2,2,2-trifluoroacetate

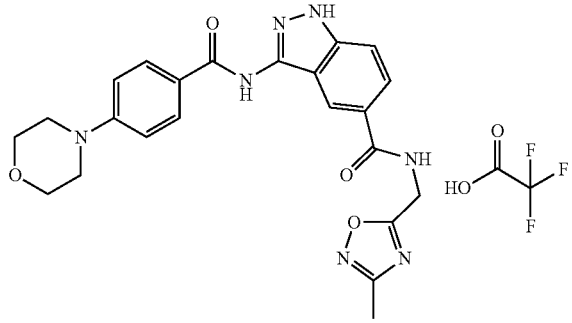

¹H NMR (400 MHz, MeOD) δ 8.44 (s, 1H), 8.01 (d, J=8.8 Hz, 2H), 7.93 (d, J=8.8 Hz, 1H), 7.56 (d, J=8.8 Hz, 1H), 7.09 (d, J=8.8 Hz, 2H), 3.86 (t, J=4.8 Hz, 4H), 3.36-3.33 (m, 4H), 2.34 (s, 3H); [M+H]⁺ 462.

Example 101: N-((3-Methyl-1,2,4-oxadiazol-5-yl)methyl)-3-(4-(4-methylpiperazin-1-yl)benzamido)-1H-indazole-5-carboxamide 2,2,2-trifluoroacetate

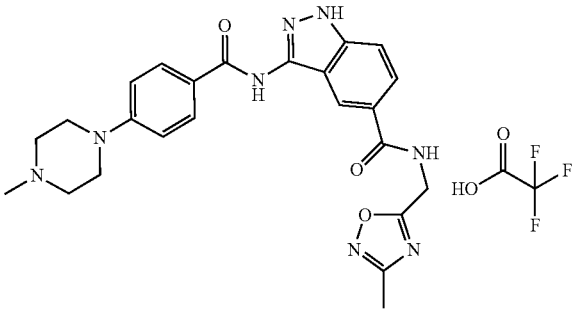

¹H NMR (400 MHz, MeOD) δ 8.43 (s, 1H), 8.04 (d, J=9.2 Hz, 2H), 7.92 (dd, J=8.8, 1.6 Hz, 1H), 7.56 (d, J=8.8 Hz, 1H), 7.15 (d, J=9.2 Hz, 2H), 4.78 (s, 2H), 4.13-4.09 (m, 2H), 3.66-3.63 (m, 2H), 3.29-3.26 (m, 2H), 3.21-3.13 (m, 2H), 3.0 (s, 3H), 2.34 (s, 3H); [M+11]⁺ 475.

Example 102: 3-(4-(Piperazin-1-yl)benzamido)-N-(1-(thiophen-2-yl)propyl)-1H-indazole-5-carboxamide

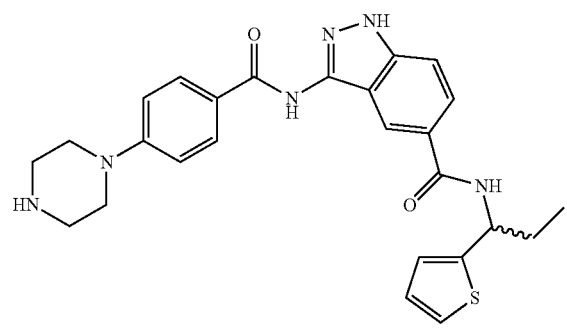 [SMILES: CCC(NC(=O)c1ccc2[nH]nc(NC(=O)c3ccc(N4CCNCC4)cc3)c2c1)c1cccs1]

¹H NMR (400 MHz, DMSO-d₆) δ 12.95 (s, 1H), 10.52 (s, 1H), 8.80 (d, J=8.4 Hz, 1H), 8.30 (s, 1H), 7.97 (d, J=8.8 Hz, 2H), 7.89 (dd, J=8.8, 1.6 Hz, 1H), 7.51 (d, J=8.8 Hz, 1H), 7.35 (dd, J=4.8, 1.2 Hz, 1H), 7.04-6.99 (m, 2H), 6.97-6.95 (m, 1H), 5.22 (q, J=7.7 Hz, 1H), 3.22 (t, J=4.8 Hz, 3H), 2.84 (t, J=5.0 Hz, 3H), 1.97-1.92 (m, 2H), 0.93 (t, J=7.4 Hz, 3H); [M+H]⁺ 489.

Example 103: 3-(4-(4-Methylpiperazin-1-yl)benzamido)-N-(thiazol-2-ylmethyl)-1H-indazole-5-carboxamide 2,2,2-trifluoroacetate

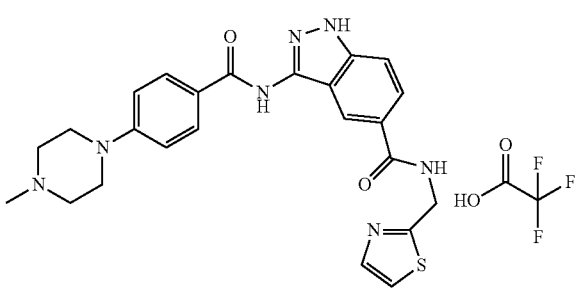

¹H NMR (400 MHz, DMSO-d₆) δ 10.65 (s, 1H), 9.37 (t, J=5.8 Hz, 1H), 8.35 (s, 1H), 8.05 (d, J=9.2 Hz, 2H), 7.91 (dd, J=9.0, 1.4 Hz, 1H), 7.72 (d, J=3.2 Hz, 1H), 7.61 (d, J=3.2 Hz, 1H), 7.55 (d, J=9.2 Hz, 1H), 7.13 (d, J=9.2 Hz, 2H), 4.76 (d, J=6.0 Hz, 2H), 4.10-4.07 (m, 2H), 3.56-3.53 (m, 2H), 3.17-3.08 (m, 4H), 2.88 (d, J=3.6 Hz, 3H); [M+H]⁺ 476.

Example 104: 3-(4-Morpholinobenzamido)-N-(thiazol-2-ylmethyl)-1H-indazole-5-carboxamide 2,2,2-trifluoroacetate

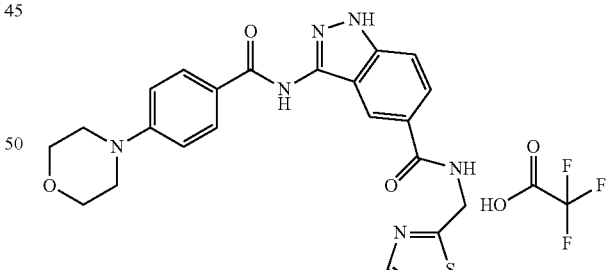

¹H NMR (400 MHz, DMSO-d₆) δ 10.60 (s, 1H), 9.38 (t, J=5.8 Hz, 1H), 8.36 (s, 1H), 8.01 (d, J=9.2 Hz, 2H), 7.91 (d, J=8.8 Hz, 1H), 7.72 (d, J=3.2 Hz, 1H), 7.61 (d, J=3.2 Hz, 1H), 7.54 (d, J=9.2 Hz, 1H), 7.05 (d, J=8.8 Hz, 2H), 4.74 (d, J=6.0 Hz, 2H), 3.76 (t, J=3.6 Hz, 4H), 3.27 (t, J=3.6 Hz, 4H) 3.56-3.53 (m, 2H); [M+H]⁺ 463.

Example 105: N-((1,2,4-Oxadiazol-3-yl)methyl)-3-(4-morpholinobenzamido)-1H-indazole-5-carboxamide 2,2,2-trifluoroacetate

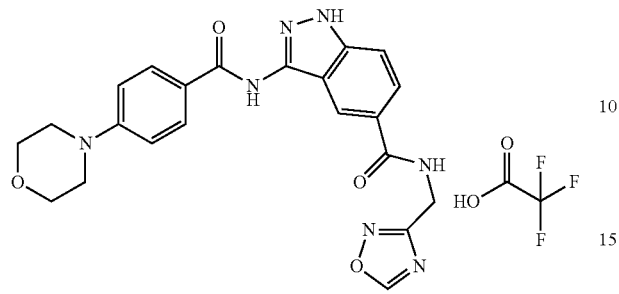

$^1$H NMR (400 MHz, DMSO-d$_6$) δ 10.58 (s, 1H), 9.54 (s, 1H), 9.15 (t, J=5.9 Hz, 1H), 8.32 (s, 1H), 8.01 (d, J=8.8 Hz, 2H), 7.88 Hz, (dd, J=8.8, 1.6 Hz, 1H), 7.53 (d, J=8.4 Hz, 1H), 7.07 (d, J=10.4 Hz, 2H), 4.61 (d, J=5.6 Hz, 2H), 3.76 (t, J=4.8 Hz, 4H), 3.29-3.28 (m, 4H); [M+H]$^+$ 448.

Example 106: N-(Cyclobutylmethyl)-3-(4-(4-methylpiperazin-1-yl)benzamido)-1H-indazole-5-carboxamide

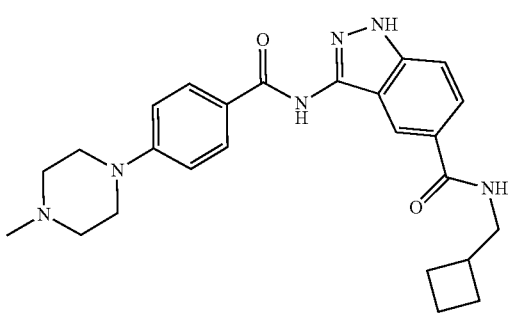 [SMILES: CN1CCN(c2ccc(C(=O)Nc3n[nH]c4ccc(C(=O)NCC5CCC5)cc34)cc2)CC1]

$^1$H NMR (400 MHz, DMSO-d$_6$) δ 12.94 (s, 1H), 10.55 (s, 1H), 8.42 (t, J=5.4 Hz, 1H), 8.24 (s, 1H), 8.00 (d, J=8.8 Hz, 2H), 7.84 (d, J=10.0 Hz, 1H), 7.49 (d, J=8.8 Hz, 1H), 7.06 (d, J=8.8 Hz, 2H), 3.38 (brs, 3H), 3.01-3.29 (m, 4H), 2.67 (brs, 4H), 2.41 (brs, 2H), 1.99-1.93 (m, 2H), 1.83-1.78 (m, 2H), 1.74-1.68 (m, 2H); [M+H]$^+$ 477.

Example 107: 3-(4-(3,3-Dimethylpiperazin-1-yl)benzamido)-N-(thiophen-2-ylmethyl)-1H-indazole-5-carboxamide 2,2,2-trifluoroacetate

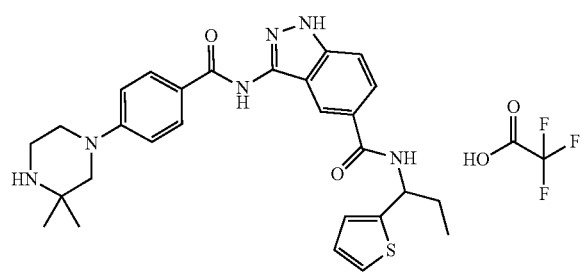 [SMILES: CCC(NC(=O)c1ccc2[nH]nc(NC(=O)c3ccc(N4CCNC(C)(C)C4)cc3)c2c1)c1cccs1 ; O=C(O)C(F)(F)F]

$^1$H NMR (400 MHz, DMSO-d$_6$) δ 12.99 (s, 1H), 10.60 (s, 1H), 9.10 (brs, 1H), 8.80 (d, J=8.4 Hz, 1H), 8.29 (s, 1H), 8.02 (d, J=8.8 Hz, 2H), 7.90 (dd, J=8.8, 1.6 Hz, 1H), 7.52 (d, J=9.2 Hz, 1H), 7.36 (dd, J=4.8, 1.2 Hz, 1H), 7.10 (d, J=8.8 Hz, 2H), 7.01 (d, J=3.2 Hz, 1H), 6.96 (dd, J=5.2, 3.6 Hz, 1H), 5.22 (q, J=7.7 Hz, 1H), 3.77 (brs, 2H), 3.52 (brs, 3H), 3.42 (s, 4H), 3.28 (brs, MA 3.10 (s, 1H), 1.99-1.91 (m, 2H), 0.93 (t, J=7.2 Hz, 3H); [M+H]$^+$ 489.

Example 108: 3-(4-(4-Hydroxypiperidin-1-yl)benzamido)-N-(1-(thiophen-2-yl)propyl)-1H-indazole-5-carboxamide

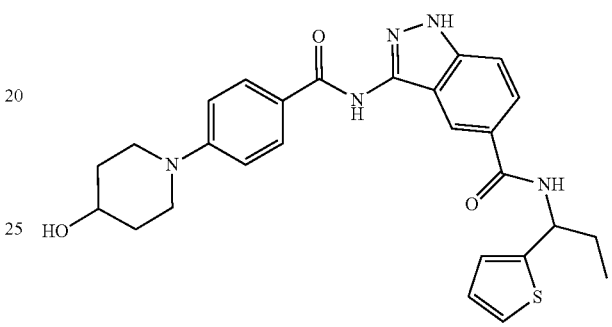

$^1$H NMR (400 MHz, DMSO-d$_6$) δ 12.94 (s, 1H), 10.50 (s, 1H), 8.80 (d, J=8.8 Hz, 1H), 8.30 (s, 1H), 7.96 (d, J=9.2 Hz, 2H), 7.89 (dd, J=8.8, 1.6 Hz, 1H147.51 (d, J=8.8 Hz, 1H), 7.35 (dd, J=4.8, 1.2 Hz, 1H), 7.02-7.00 (m, MA 6.97-6.95 (m, 1H), 5.22 (q, J=7.2 Hz, 1H), 4.72 (d, J=4.0 Hz, 1H), 3.75-3.68 (m, 2H), 3.06-3.00 (m, 2H), 1.98-1.92 (m, 2H), 1.83-1.80 (m, 2H), 1.48-1.42 (m, 2H), 0.93 (t, J=7.2 Hz, 3H); [M+H]$^+$ 504.

Example 109: 3-(4-(4-Ethylpiperazin-1-yl)benzamido)-N-(1-(thiophen-2-yl)propyl)-1H-indazole-5-carboxamide

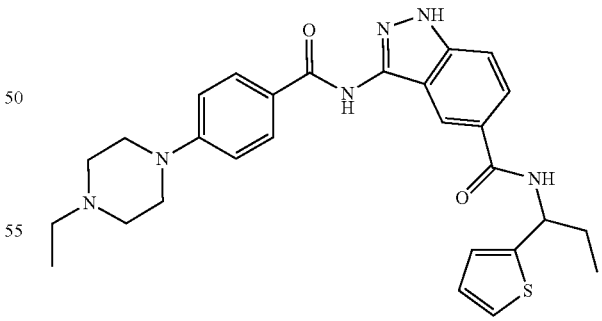

$^1$H NMR (400 MHz, DMSO-d$_6$) δ 12.96 (s, 1H), 10.50 (s, 1H), 8.80 (d, J=8.4 Hz, 1H), 8.30 (s, 1H), 7.98 (d, J=9.2 Hz, 2H), 7.89 (d, J=9.6 Hz, 1H), 7.51 (d, J=8.4 Hz, 1H), 7.35 (dd, J=4.8, 1.2 Hz, 1H), 7.04-7.01 (m, 3H), 6.97-6.95 (m, 1H), 5.24 (q, J=7.2 Hz, 1H), 3.31-3.29 (m, 8H), 2.38 (q, J=7.2 Hz, 2H), 1.97-1.92 (m, 2H), 1.04 (t, J=7.2 Hz, 3H), 0.93 (t, J=7.2 Hz, 3H); [M+H]$^+$ 517.

Example 110: 3-(4-(4-methoxypiperidin-1-yl)benzamido)-N-(1-(thiophen-2-yl)propyl)-1H-indazole-5-carboxamide

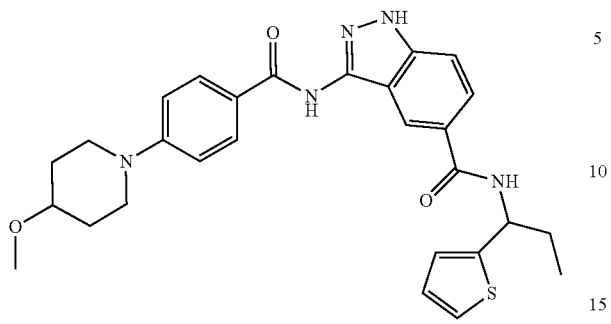

¹H NMR (400 MHz, DMSO-d₆) δ 12.94 (s, 1H), 10.50 (s, 1H), 8.79 (d, J=8.4 Hz, 1H), 8.30 (s, 1H), 7.97 (d, J=8.4 Hz, 2H), 7.89 (d, J=10.0 Hz, 1H), 7.51 (d, J=9.2 Hz, 1H), 7.35 (dd, J=5.2, 1.2 Hz, 1H), 7.04-7.01 (m, 3H), 6.97-3.95 (m, 1H), 5.22 (q, J=7.8 Hz, 1H), 4.10 (t, J=5.2 Hz, 2H), 3.70-3.66 (m, 2H), 3.44-3.39 (m, 1H), 3.28 (s, MA 3.11-3.06 (m, 2H), 1.96-1.93 (m, 2H), 1.54-1.45 (m, 2H), 0.93 (t, J=7.2 Hz, 3H); [M+H]⁺ 518.

Example 111: (S)-3-(4-(4-Methylpiperazin-1-yl)benzamido)-N-(1-(thiophen-2-yl)propyl)-1H-indazole-5-carboxamide

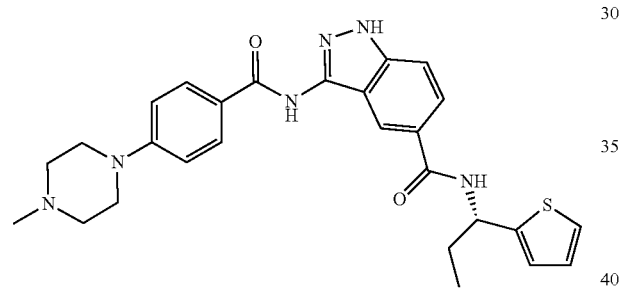

¹H NMR (400 MHz, DMSO-d₆) δ 12.99 (s, 1H), 10.62 (s, 1H), 8.80 (d, J=8.4 Hz, 1H), 8.29 (s, 1H), 8.04 (d, J=8.8 Hz, 2H), 7.90 (dd, J=8.8, 1.6 Hz, 1H), 7.52 (d, J=8.8 Hz, 1H), 7.36 (dd, J=5.2, 1.2 Hz, 1H), 7.13 (d, J=9.2 Hz, 2H), 7.01 (d, J=3.6 Hz, 1), 6.97-6.95 (m, 1H), 5.22 (q, J=7.6 Hz, 1H), 4.08 (brs, 2H), 3.53 (brs, 2H), 3.18-3.09 (m, 4H), 2.86 (s, 3H), 1.99-1.95 (m, 2H), 0.94 (t, J=7.4 Hz, 3H); [M+H]⁺ 503.

Example 112: (R)-3-(4-(4-Methylpiperazin-1-yl)benzamido)-N-(1-(thiophen-2-yl)propyl)-1H-indazole-5-carboxamide

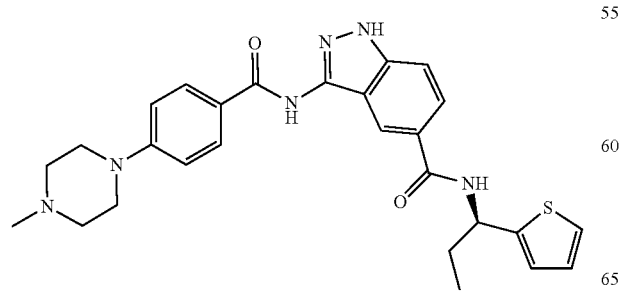

¹H NMR (400 MHz, DMSO-d₆) δ 12.99 (s, 1H), 10.60 (s, 1H), 8.80 (d, J=8.4 Hz, 1H), 8.30 (s, 1H), 8.03 (d, J=8.8 Hz, 2H), 8.90 (dd, J=8.8, 1.6 Hz, 1H), 7.52 (d, J=8.8 Hz, 1H), 7.36 (dd, J=5.0, 1.4 HZ, 1H), 7.13 (d, J=9.2 Hz, 2H), 7.04-7.01 (m, 1H), 6.97-6.95 (m, 1H), 5.23-5.19 (m, 1H), 3.88-3.82 (m, 2H), 3.66-3.61 (m, 2H), 3.60-3.46 (m, 2H), 2.481 (brs, 5H), 1.97-1.93 (m, 2H), 0.93 (t, J=5.3 Hz, 3H); [M+H]⁺ 503.

Example 113: N-Butyl-3-(4-(4-methylpiperazin-1-yl)benzamido)-1H-indazole-5-carboxamide 2,2,2-trifluoroacetate

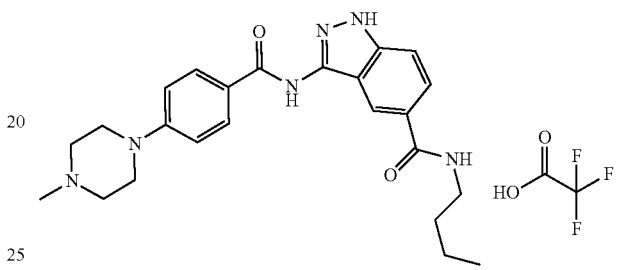

¹H NMR (400 MHz, DMSO-d₆) δ 12.93 (s, 1H), 10.56 (s, 1H), 8.42 (t, J=2.0 Hz, 1H), 8.24 (s, 1H), 8.01 (d, J=9.2 Hz, 2H), 7.84 (dd, J=8.8, 1.6 Hz, 1H), 7.49 (d, J=8.8 Hz, 1H), 7.05 (d, J=8.8 Hz, 2H), 3.76 (t, J=4.6 HZ, 4H), 3.29-3.24 (m, 7H), 3.12-3.08 (m, 2H), 1.53-1.46 (m, 2H), 1.36-1.27 (m, 2H), 0.89 (t, J=7.2 Hz, 3H); [M+H]⁺ 449.

Example 114: N-Isopentyl-3-(4-(4-methylpiperazin-1-yl)benzamido)-1H-indazole-5-carboxamide 2,2,2-trifluoroacetate

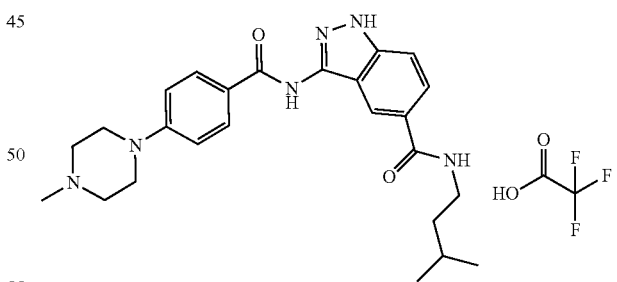

¹H NMR (400 MHz, DMSO-d₆) δ 12.93 (s, 1H), 10.56 (s, 1H), 8.39 (t, J=2.0 Hz, 1H), 8.24 (s, 1H), 8.01 (d, J=8.8 Hz, 2H), 7.84 (dd, J=9.0, 1.8 Hz, 1H), 7.49 (d, J=8.8 Hz, 1H), 7.05 (d, J=8.8 Hz, 2H), 3.76 (t, J=4.8 HZ, 4H), 3.29-3.27 (m, 8H), 1.64-1.57 (m, 2H), 1.44-1.39 (m, 2H), 0.90 (d, J=6.4 Hz, 6H); [M+H]⁺ 449.

Example 115: N-Butyl-3-(4-morpholinobenzamido)-1H-indazole-5-carboxamide 2,2,2-trifluoroacetate

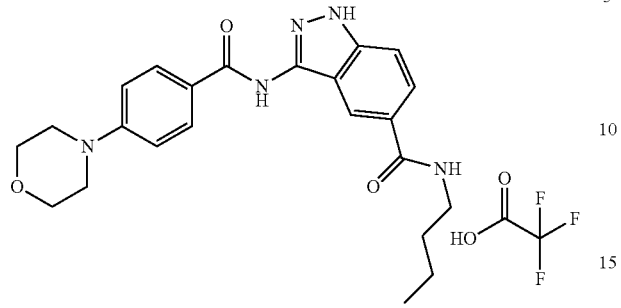

¹H NMR (400 MHz, DMSO-d₆) δ 10.54 (s, 1H), 8.42 (t, J=6.0 Hz, 1H), 8.24 (s, 1H), 7.99 (d, J=9.2 Hz, 2H), 7.84 (dd, J=9.0, 1.8 Hz, 1H), 7.49 (d, J=8.8 Hz, 1H), 7.03 (d, J=9.2 Hz, 2H), 3.36-3.30 (m, 6H), 3.27-3.22 (m, 2H), 2.29-1.19 (m, 4H), 1.52-1.46 (m, 2H), 1.34-1.29 (m, 2H), 0.89 (t, J=7.2 HZ, 3H); [M+H]⁺ 422.

Example 116: N-Isopentyl-3-(4-morpholinobenzamido)-1H-indazole-5-carboxamide 2,2,2-trifluoroacetate

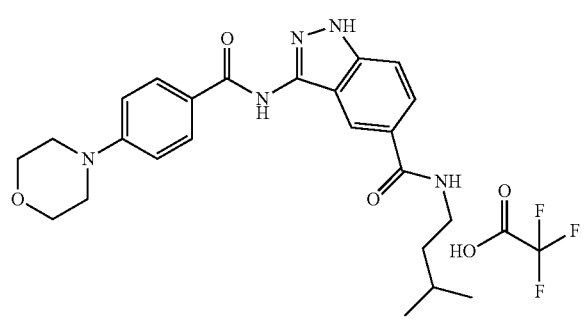

¹H NMR (400 MHz, DMSO-d₆) δ 12.97 (s, 1H), 10.62 (s, 1H), 8.40 (t, J=6.0 Hz, 1H), 8.23 (s, 1H), 8.04 (d, J=8.8 Hz, 2H), 7.84 (d, J=8.8 Hz, 1H), 7.50 (d, J=8.8 Hz, 1H), 7.13 (d, J=8.8 Hz, 2H), 3.30-3.25 (m, 8H), 2.89-2.87 (m, 4H), 1.64-1.57 (m, 2H), 1.44-1.39 (m, 2H), 0.90 (d, J=6.4 Hz, 6H); [M+H]⁺ 436.

Example 117: (S)-3-(4-(3-Methylpiperazin-1-yl)benzamido)-N-(thiophen-2-ylmethyl)-1H-indazole-5-carboxamide 2,2,2-trifluoroacetate

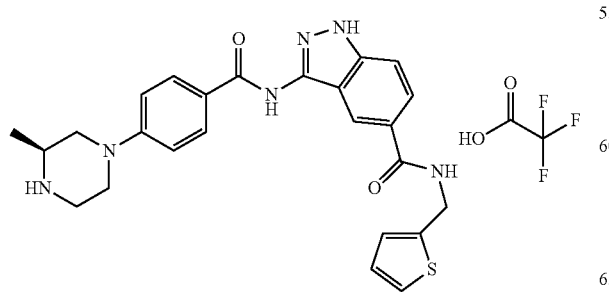

¹H NMR (400 MHz, DMSO-d₆) δ 13.00 (brs, 1H), 10.61 (s, 1H), 8.99 (d, J=9.2 Hz, 1H), 8.80 (d, J=8.4 Hz, 1H), 8.66 (d, J=10.4 Hz, 1H), 8.29 (s, 1H), 8.03 (d, J=9.2 Hz, 2H), 7.90 (dd, J=8.8, 1.6 Hz, 1H), 7.52 (d, J=8.8 Hz, 1H), 7.36 (dd, J=5.5, 1.2 Hz, 1H), 7.13 (d, J=9.2 Hz, 2H), 7.01 (d, J=3.6 Hz, 1H), 6.97-6.95 (m, 1H), 4.61 (d, J=5.6 Hz, 2H), 4.06-3.96 (m, 2H), 3.44-3.41 (m, 2H), 3.19-3.03 (m, 2H); [M+H]⁺ 475.

Example 118: N-(1,2,4-Oxadiazol-3-yl)methyl)-3-(4-(4-methylpiperazin-1-yl)benzamido)-1H-indazole-5-carboxamide 2,2,2-trifluoroacetate

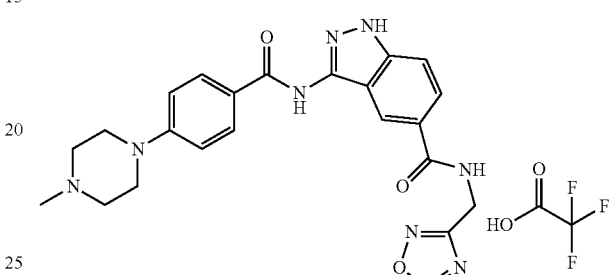

¹H NMR (400 MHz, DMSO-d₆) δ 10.60 (s, 1H), 9.38 (t, J=5.8 Hz, 1H), 8.36 (s, 1H), 8.01 (d, J=9.2 Hz, 2H), 7.91 (d, J=8.8 Hz, 1H), 7.72 (d, J=3.2 Hz, 1H), 7.61 (d, J=3.2 Hz, 1H), 7.54 (d, J=9.2 Hz, 1H), 7.05 (d, J=8.8 Hz, 2H), 4.74 (d, J=6.0 Hz, 2H), 3.76 (t, J=3.6 Hz, 4H), 3.29-3.27 (m, J=3.6 Hz, 7H) 3.56-3.53 (m, 2H); [M+11]⁺ 461.

Example 119: N-(1H-1,2,3-triazol-4-yl)methyl)-3-(4-morpholinobenzamido)-1H-indazole-5-carboxamide 2,2,2-trifluoroacetate

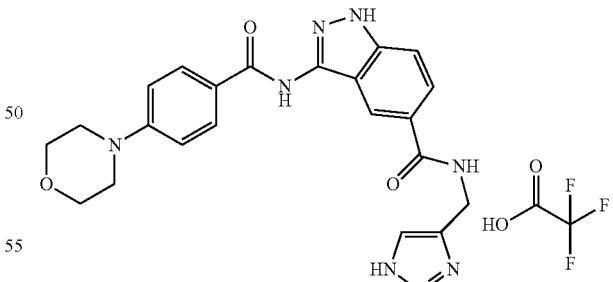

¹H NMR (400 MHz, DMSO-d₆) δ 12.95 (s, 1H), 10.55 (s, 1H), 8.99 (t, J=5.8 Hz, 1H), 8.30 (s, 1H), 7.98 (d, J=8.8 Hz, 2H), 7.88 (d, J=8.8 Hz, 1H), 7.50 (d, J=8.8 Hz, 1H), 7.0 (d, J=9.2 Hz, 2H), 4.53 (d, J=5.6 Hz, 2H), 3.31 (brs, 4H), 2.26 (brs, 4H); [M+H]⁺ 447.

Example 120: 3-(4-Morpholinobenzamido)-N-(pyridin-4-ylmethyl)-1H-indazole-5-carboxamide

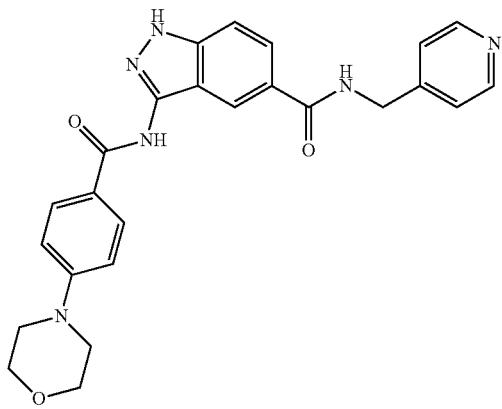 [SMILES: O=C(NCc1ccncc1)c1ccc2[nH]nc(NC(=O)c3ccc(N4CCOCC4)cc3)c2c1]

¹H NMR (400 MHz, DMSO-d$_6$) δ 12.98 (s, 1H), 10.58 (s, 1H), 9.10 (t, J=5.9 Hz, 1H), 8.52-8.46 (m, 2H), 8.36 (d, J=6.2 Hz, 1H), 8.00 (d, J=8.6 Hz, 2H), 7.97-7.88 (m, 1H), 7.55 (t, J=9.0 Hz, 1H), 7.29 (d, J=5.1 Hz, 2H), 7.04 (d, J=8.7 Hz, 2H), 4.49 (d, J=5.9 Hz, 2H), 3.75 (t, J=4.8 Hz, 4H), 3.27 (t, J=4.9 Hz, 4H); [M+H]$^+$ 457.

Example 121: 3-(4-(4-Methylpiperazin-1-yl)benzamido)-N-(pyridin-4-ylmethyl)-1H-indazole-5-carboxamide

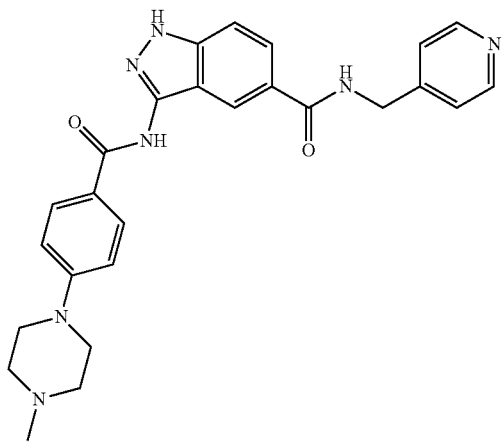 [SMILES: CN1CCN(c2ccc(C(=O)Nc3n[nH]c4ccc(C(=O)NCc5ccncc5)cc34)cc2)CC1]

¹H NMR (400 MHz, DMSO-d$_6$) δ 12.98 (s, 1H), 10.55 (s, 1H), 9.10 (t, J=6.0 Hz, 1H), 8.52-8.46 (m, 2H), 8.35 (d, J=1.5 Hz, 1H), 8.02-7.95 (m, 2H), 7.53 (d, J=8.9 Hz, 1H), 7.32-7.26 (m, 2H), 7.02 (d, J=8.9 Hz, 2H), 4.49 (d, J=5.8 Hz, 2H), 4.09 (t, J=5.3 Hz, 1H), 3.30 (t, J=5.1 Hz, 4H), 3.17 (d, J=4.7 Hz, 3H), 2.45 (t, J=5.1 Hz, 4H); [M+H]$^+$ 470.

Example 122: N-(Cyclopropyl(thiophen-2-yl)methyl)-3-(4-morpholinobenzamido)-1H-indazole-5-carboxamide

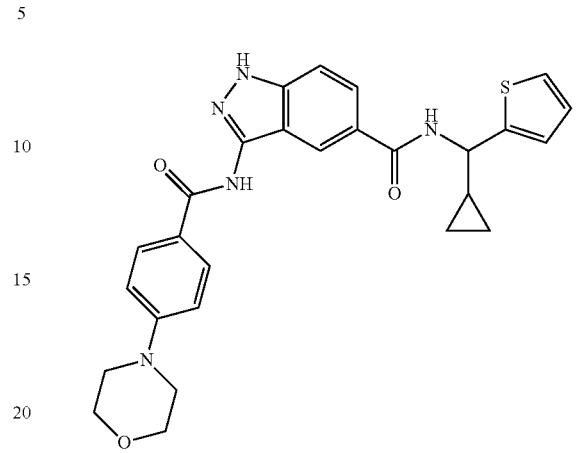

¹H NMR (400 MHz, DMSO-d$_6$) δ 12.96 (s, 1H), 10.55 (s, 1H), 9.08 (d, J=8.5 Hz, 1H), 8.34 (s, 1H), 8.04-7.96 (m, 2H), 7.93 (dd, J=8.8, 1.7 Hz, 1H), 7.52 (d, J=8.8 Hz, 1H), 7.37 (dd, J=5.1, 1.3 Hz, 1H), 7.10-7.01 (m, 3H), 6.97 (dd, J=5.1, 3.5 Hz, 1H), 4.65 (t, J=8.9 Hz, 1H), 3.79-3.72 (m, 4H), 3.27 (t, J=4.9 Hz, 4H), 1.45 (tt, J=8.0, 5.1 Hz, 1H), 0.67 (tt, J=7.3, 3.0 Hz, 1H), 0.53 (td, J=8.6, 8.1, 4.1 Hz, 1H), 0.51-0.36 (m, 2H); [M+H]$^+$ 502.

Example 123: 4-Morpholino-N-(5-((thiophen-2-ylmethyl)amino)methyl)-1H-indazol-3-yl)benzamide

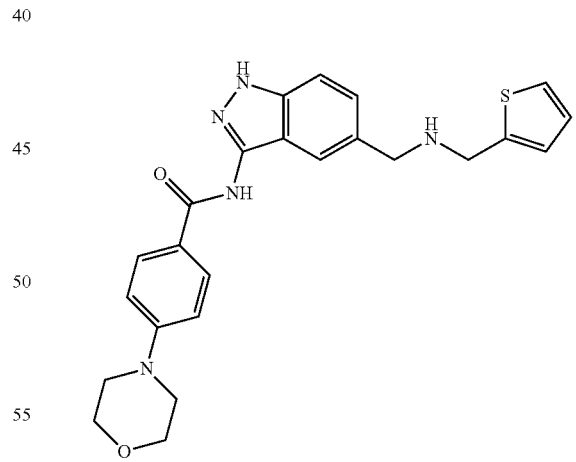

¹H NMR (400 MHz, DMSO-d$_6$) δ 12.66 (s, 1H), 10.42 (s, 1H), 8.03-7.95 (m, 2H), 7.58 (s, 1H), 7.42 (d, J=8.4 Hz, 1H), 7.36 (dt, J=6.8, 1.9 Hz, 2H), 7.03 (d, J=9.0 Hz, 2H), 6.98-6.90 (m, 2H), 3.86 (s, 2H), 3.79-3.72 (m, 6H), 3.27 (t, J=4.9 Hz, 4H); [M+H]$^+$ 448.

Example 124: 4-(4-Methylpiperazin-1-yl)-N-(5-((1-(thiophen-2-yl)propyl)amino)methyl)-1H-indazol-3-yl)benzamide

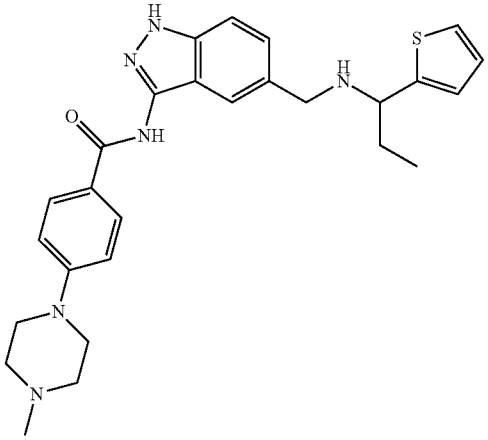 [SMILES: CCC(NCc1ccc2[nH]nc(NC(=O)c3ccc(N4CCN(C)CC4)cc3)c2c1)c1cccs1]

¹H NMR (400 MHz, DMSO-d₆) δ 7.96 (d, J=8.5 Hz, 2H), 7.50 (s, 1H), 7.44-7.34 (m, 2H), 7.32 (d, J=8.5 Hz, 1H), 7.02 (d, J=8.6 Hz, 2H), 6.94 (d, J=5.2 Hz, 2H), 3.74 (s, 1H), 3.67 (s, 1H), 3.56 (d, J=13.2 Hz, 1H), 3.30 (d, J=5.4 Hz, 4H), 2.45 (t, J=4.9 Hz, 4H), 2.23 (s, 3H), 1.79-1.69 (m, 1H), 1.54 (dt, J=13.9, 7.3 Hz, 1H), 0.76 (t, J=7.4 Hz, 3H); [M+H]⁺ 489.

Example 125: N-(Cyclopropyl(thiophen-2-yl)methyl)-3-(4-(4-methylpiperazin-1-yl)benzamido)-1H-indazole-5-carboxamide

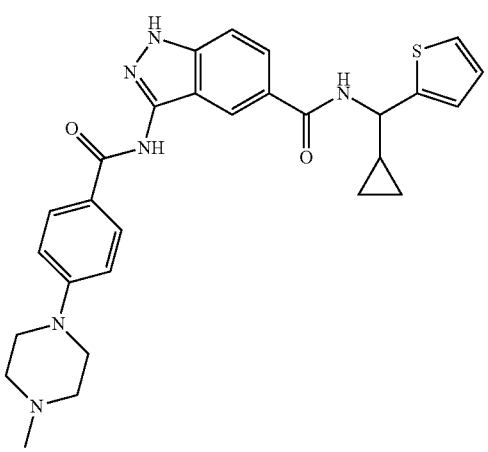 [SMILES: CN1CCN(c2ccc(C(=O)Nc3n[nH]c4ccc(C(=O)NC(c5cccs5)C5CC5)cc34)cc2)CC1]

¹H NMR (400 MHz, DMSO-d₆) δ 12.96 (s, 1H), 10.52 (s, 1H), 9.08 (d, J=8.4 Hz, 1H), 8.33 (s, 1H), 7.95 (dd, J=23.1, 8.9 Hz, 3H), 7.51 (d, J=8.8 Hz, 1H), 7.37 (d, J=5.3 Hz, 1H), 7.06 (d, J=3.3 Hz, 1H), 7.02 (d, J=8.9 Hz, 2H), 6.99-6.93 (m, 1H), 4.65 (t, J=9.0 Hz, 1H), 3.30 (s, 4H), 2.45 (t, J=5.0 Hz, 4H), 2.23 (s, MA 1.45 (s, 1H), 0.67 (s, 1H), 0.54 (s, 1H), 0.43 (s, 2H); [M+H]⁺ 515.

Example 126: N-(Cyclopropyl(thiophen-2-yl)methyl)-3-(4-(piperazin-1-yl)benzamido)-1H-indazole-5-carboxamide

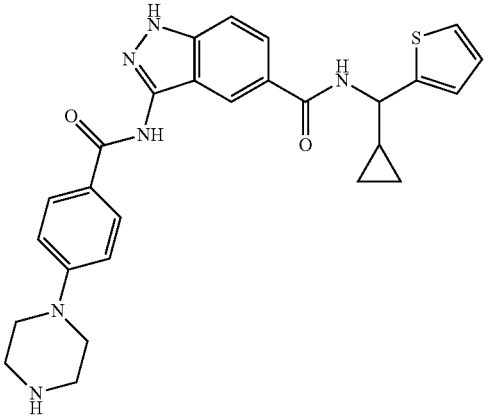 [SMILES: O=C(Nc1n[nH]c2ccc(C(=O)NC(c3cccs3)C3CC3)cc12)c1ccc(N2CCNCC2)cc1]

¹H NMR (400 MHz, DMSO-d₆) δ 12.96 (s, 1H), 10.51 (s, 1H), 9.08 (d, J=8.4 Hz, 1H), 8.33 (s, 1H), 7.97 (d, J=8.7 Hz, 2H), 7.95-7.80 (m, 1H), 7.55-7.48 (m, 1H), 7.37 (dd, J=5.1, 1.3 Hz, 1H), 7.06 (d, J=3.4 Hz, 1H), 7.05-6.93 (m, MA 4.65 (t, J=8.8 Hz, 1H), 3.22 (t, J=5.1 Hz, 4H), 2.83 (t, J=5.1 Hz, 4H), 1.45 (s, 1H), 0.49 (d, J=42.6 Hz, 4H); [M+H]⁺ 501.

Example 127: 3-(4-Morpholinobenzamido)-N-(1-(pyridin-2-yl)ethyl)-1H-indazole-5-carboxamide

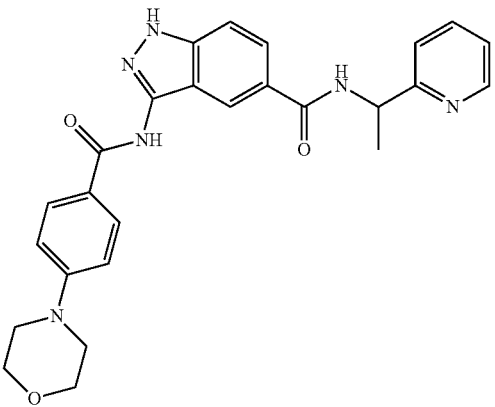 [SMILES: CC(NC(=O)c1ccc2[nH]nc(NC(=O)c3ccc(N4CCOCC4)cc3)c2c1)c1ccccn1]

¹H NMR (400 MHz, DMSO-d₆) δ 12.96 (s, 1H), 10.55 (s, 1H), 8.81 (d, J=7.8 Hz, 1H), 8.54-8.48 (m, 1H), 8.34 (s, 1H), 8.00 (d, J=8.9 Hz, 2H), 7.92 (dd, J=8.9, 1.7 Hz, 1H), 7.74 (td, J=7.7, 1.8 Hz, 1H), 7.51 (dd, J=8.8, 0.7 Hz, 1H), 7.39 (d, J=8.0 Hz, 1H), 7.24 (dd, J=6.8, 4.8 Hz, 1H), 7.04 (d, J=9.0 Hz, 2H), 5.25-5.17 (m, 1H), 3.78-3.71 (m, 4H), 3.27 (t, J=4.9 Hz, 4H), 1.50 (d, J=7.1 Hz, 3H); [M+H]⁺ 471.

Example 128: 3-(4-(4-Methylpiperazin-1-yl)benzamido)-N-(1-(pyridin-2-yl)ethyl)-1H-indazole-5-carboxamide

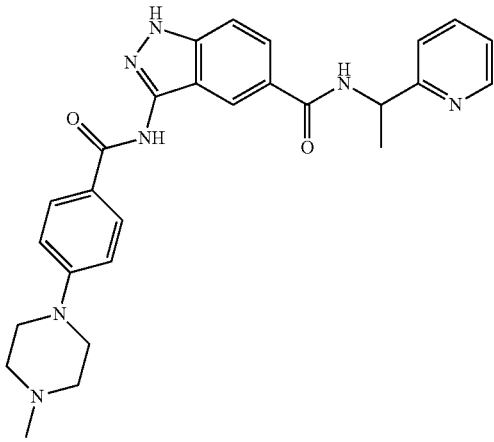 [SMILES: CC(NC(=O)c1ccc2[nH]nc(NC(=O)c3ccc(N4CCN(C)CC4)cc3)c2c1)c1ccccn1]

¹H NMR (400 MHz, DMSO-d₆) δ 12.95 (s, 1H), 10.53 (s, 1H), 8.81 (d, J=7.9 Hz, 1H), 8.51 (d, J=4.8 Hz, 1H), 8.33 (s, 1H), 7.95 (dd, J=24.8, 8.6 Hz, 3H), 7.74 (t, J=7.9 Hz, 1H), 7.51 (d, J=8.9 Hz, 1H), 7.39 (d, J=7.9 Hz, 1H), 7.03 (d, J=8.7 Hz, 2H), 5.25-5.17 (m, 1H), 3.30 (s, 4H), 2.45 (s, 4H), 2.23 (s, MA 1.50 (d, J=7.1 Hz, 3H); [M+H]⁺ 484.

Example 129: N-(3-Methyl-1-(thiophen-2-yl)butyl)-3-(4-(4-methylpiperazin-1-yl)benzamido)-1H-indazole-5-carboxamide

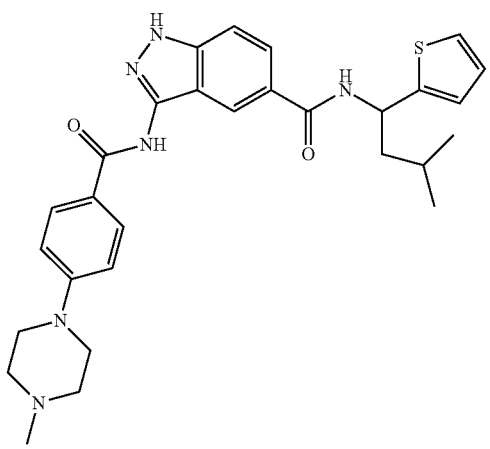 [SMILES: CC(C)CC(NC(=O)c1ccc2[nH]nc(NC(=O)c3ccc(N4CCN(C)CC4)cc3)c2c1)c1cccs1]

¹H NMR (400 MHz, DMSO-d₆) δ 8.80 (d, J=8.5 Hz, 1H), 8.29 (s, 1H), 7.98 (d, J=8.6 Hz, 2H), 7.87 (s, 1H), 7.51 (s, 1H), 7.35 (d, J=5.1 Hz, 1H), 7.02 (d, J=9.2 Hz, 3H), 6.96 (d, J=4.6 Hz, 1H), 5.42 (s, 1H), 2.45 (s, 2H), 2.23 (s, 3H), 1.96 (s, 1H), 0.92 (t, J=5.6 Hz, 6H); [M+H]⁺ 531.

Example 130: N-(3-Methyl-1-(thiophen-2-yl)butyl)-3-(4-morpholinobenzamido)-1H-indazole-5-carboxamide

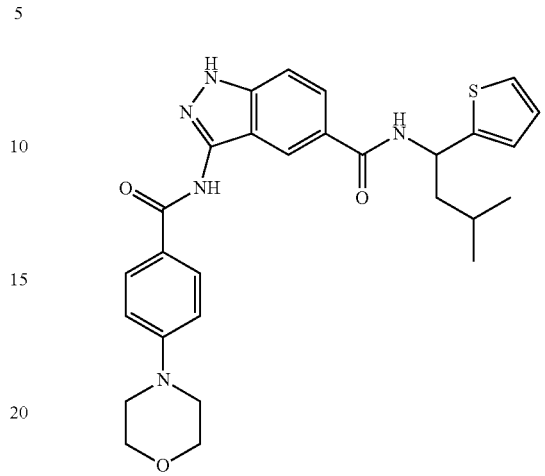

¹H NMR (400 MHz, DMSO-d₆) δ 12.96 (s, 1H), 10.55 (s, 1H), 8.81 (d, J=8.5 Hz, 1H), 8.29 (d, J=1.4 Hz, 1H), 8.04-7.96 (m, 2H), 7.89 (dd, J=8.8, 1.6 Hz, 1H), 7.51 (d, J=8.8 Hz, 1H), 7.35 (dd, J=5.0, 1.3 Hz, 1H), 7.04 (d, J=8.9 Hz, 2H), 7.02-6.99 (m, 1H), 6.95 (dd, J=5.0, 3.5 Hz, 1H), 5.62-5.16 (m, 1H), 3.75 (t, J=4.8 Hz, 4H), 3.27 (t, J=4.9 Hz, 4H), 2.02-1.85 (m, 1H), 1.68 (tq, J=13.2, 6.8, 6.2 Hz, 2H), 0.92 (dd, J=6.3, 4.5 Hz, 6H); [M+H]⁺ 518.

Example 131: 3-(4-(4-methylpiperazin-1-yl)benzamido)-N-(2-(thiophen-2-yl)butan-2-yl)-1H-indazole-5-carboxamide

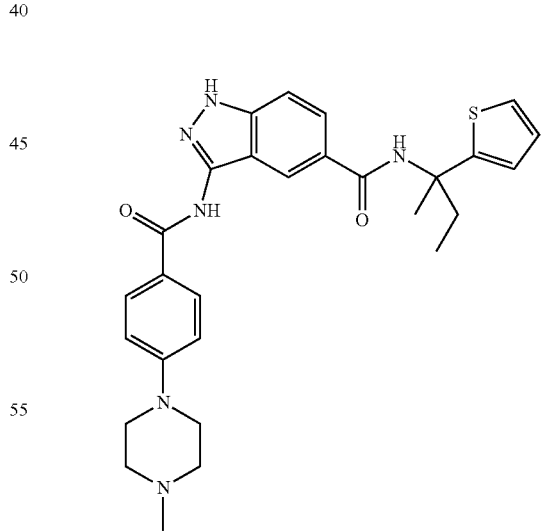

¹H NMR (400 MHz, DMSO-d₆) δ 10.55 (s, 1H), 8.25 (d, J=15.5 Hz, 2H), 7.98 (d, J=8.5 Hz, 2H), 7.78 (d, J=8.7 Hz, 1H), 7.48 (s, 1H), 7.30-7.23 (m, 1H), 7.01 (d, J=8.5 Hz, 2H), 6.90 (d, J=3.2 Hz, 2H), 3.28 (s, 4H), 2.45 (t, J=5.0 Hz, 4H), 2.43-2.31 (m, 1H), 2.23 (s, 3H), 1.86 (dt, J=14.8, 7.4 Hz, 1H), 1.69 (s, 3H), 0.84 (q, J=7.7 Hz, 3H); [M+H]⁺ 517.

Example 132: 3-(4-Morpholinobenzamido)-N-(1-(pyridin-4-yl)ethyl)-1H-indazole-5-carboxamide

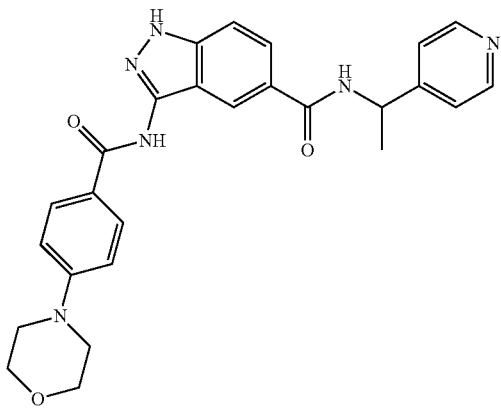 [SMILES: CC(NC(=O)c1ccc2[nH]nc(NC(=O)c3ccc(N4CCOCC4)cc3)c2c1)c1ccncc1]

$^1$H NMR (400 MHz, DMSO-d$_6$) δ 12.97 (s, 1H), 10.57 (s, 1H), 8.89 (d, J=7.7 Hz, 1H), 8.53-8.46 (m, 2H), 8.32 (s, 1H), 8.04-7.97 (m, 2H), 7.90 (dd, J=8.8, 1.6 Hz, 1H), 7.52 (d, J=8.8 Hz, 1H), 7.40-7.33 (m, 2H), 7.04 (d, J=9.0 Hz, 2H), 5.15 (p, J=7.2 Hz, 1H), 3.75 (t, J=4.9 Hz, 4H), 3.27 (t, J=4.9 Hz, 4H), 1.48 (d, J=7.1 Hz, 3H); [M+H]$^+$ 471.

Example 133: 3-(4-(4-Methylpiperazin-1-yl)benzamido)-N-(1-(pyridin-4-yl)ethyl)-1H-indazole-5-carboxamide

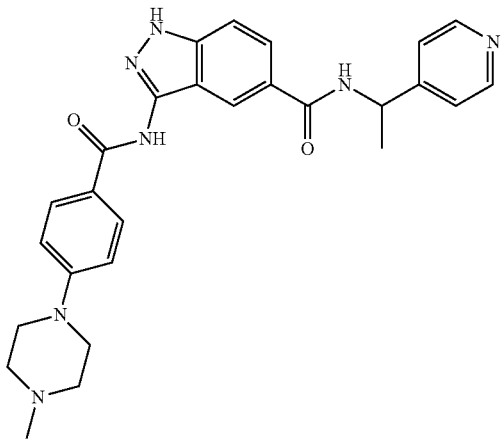 [SMILES: CC(NC(=O)c1ccc2[nH]nc(NC(=O)c3ccc(N4CCN(C)CC4)cc3)c2c1)c1ccncc1]

$^1$H NMR (400 MHz, DMSO-d$_6$) δ 12.97 (s, 1H), 10.54 (s, 1H), 8.89 (d, J=7.7 Hz, 1H), 8.53-8.46 (m, 2H), 8.32 (s, 1H), 8.02-7.94 (m, 2H), 7.90 (dd, J=8.8, 1.7 Hz, 1H), 7.52 (dd, J=8.9, 0.8 Hz, 1H), 7.40-7.33 (m, 2H), 7.06-6.99 (m, 2H), 5.15 (p, J=7.2 Hz, 1H), 3.30 (t, J=5.1 Hz, 4H), 2.45 (t, J=5.1 Hz, 4H), 2.23 (s, 3H), 1.48 (d, J=7.1 Hz, 3H); [M+H]$^+$ 484.

Example 134: 3-(4-Morpholinobenzamido)-N-(2-(thiophen-2-yl)propan-2-yl)-1H-indazole-5-carboxamide

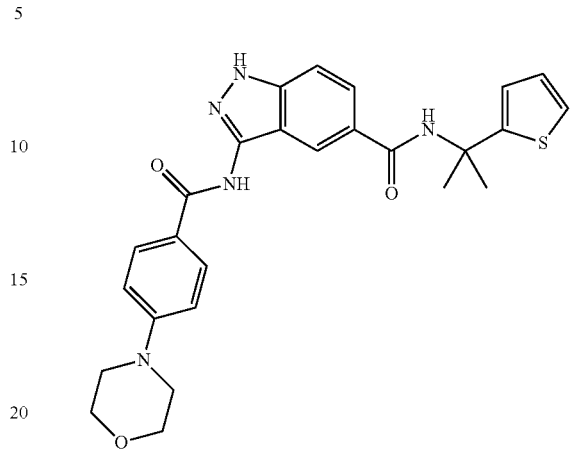

$^1$H NMR (400 MHz, DMSO-d$_6$) δ 12.93 (s, 1H), 10.56 (s, 1H), 8.48 (s, 1H), 8.22 (s, 1H), 8.04-7.97 (m, 2H), 7.81 (dd, J=8.8, 1.6 Hz, 1H), 7.48 (d, J=8.8 Hz, 1H), 7.26 (dd, J=5.0, 1.3 Hz, 1H), 7.08-7.01 (m, 2H), 6.95-6.85 (m, 2H), 3.83-3.56 (m, 4H), 3.27 (t, J=4.9 Hz, 4H), 1.76 (s, 6H); [M+H]$^+$ 490.

Example 135: 3-(4-(4-Methylpiperazin-1-yl)benzamido)-N-(2,2,2-trifluoro-1-(thiophen-2-yl)ethyl)-1H-indazole-5-carboxamide

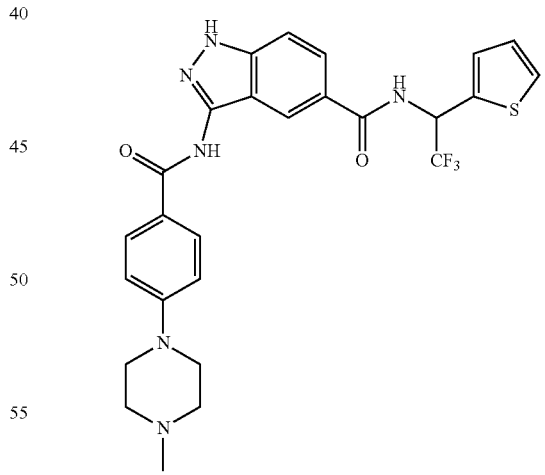

$^1$H NMR (400 MHz, DMSO-d$_6$) δ 10.59 (s, 1H), 9.61 (s, 1H), 8.39 (s, 1H), 7.99 (d, J=8.7 Hz, 2H), 7.98-7.86 (m, 1H), 7.61 (dd, J=5.1, 1.2 Hz, 1H), 7.53 (d, J=9.3 Hz, 1H), 7.38 (dd, J=11.8, 3.9 Hz, 1H), 7.09 (dd, J=5.1, 3.6 Hz, 1H), 7.03 (dd, J=8.8, 6.1 Hz, 2H), 6.35 (s, 1H), 3.30 (s, 4H), 2.45 (t, J=5.0 Hz, 4H), 2.23 (s, 3H); [M+H]$^+$ 543.

Example 136: 3-(4-(4-Methylpiperazin-1-yl)benzamido)-N-(2-(thiophen-2-yl)propan-2-yl)-1H-indazole-5-carboxamide

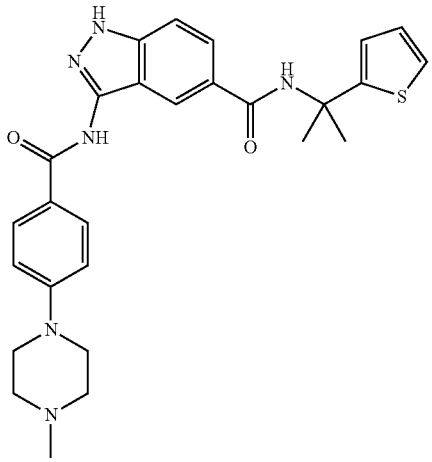 [SMILES: CN1CCN(c2ccc(C(=O)Nc3n[nH]c4ccc(C(=O)NC(C)(C)c5cccs5)cc34)cc2)CC1]

$^1$H NMR (400 MHz, DMSO-d$_6$) δ 12.92 (s, 1H), 10.53 (s, 1H), 8.48 (d, J=7.7 Hz, 1H), 8.21 (d, J=5.3 Hz, 1H), 7.98 (d, J=8.7 Hz, 2H), 7.87-7.74 (m, 1H), 7.48 (d, J=8.8 Hz, 1H), 7.26 (dd, J=5.0, 1.3 Hz, 1H), 7.03 (d, J=8.7 Hz, 2H), 6.95-6.85 (m, 2H), 3.31 (t, J=5.0 Hz, 4H), 2.45 (t, J=4.9 Hz, 4H), 2.23 (s, 3H), 1.75 (s, 6H); [M+H]$^+$ 503.

Example 137: (S)-3-(4-(3-Methylpiperazin-1-yl)benzamido)-N-(2-(thiophen-2-yl)propan-2-yl)-1H-indazole-5-carboxamide

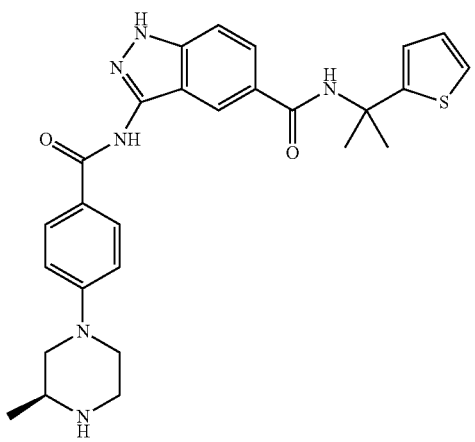 [SMILES: C[C@H]1CN(c2ccc(C(=O)Nc3n[nH]c4ccc(C(=O)NC(C)(C)c5cccs5)cc34)cc2)CCN1]

$^1$H NMR (400 MHz, DMSO-d$_6$) δ 12.92 (s, 1H), 10.51 (s, 1H), 8.47 (s, 1H), 8.22 (d, J=1.5 Hz, 1H), 7.97 (d, J=8.9 Hz, 2H), 7.81 (dd, J=8.8, 1.6 Hz, 1H), 7.48 (d, J=8.8 Hz, 1H), 7.26 (dd, J=4.9, 1.3 Hz, 1H), 7.04-6.97 (m, 2H), 6.92 (dd, J=3.6, 1.4 Hz, 1H), 6.89 (dd, J=5.0, 3.5 Hz, 1H), 3.73 (t, J=10.3 Hz, 2H), 3.00-2.92 (m, 1H), 2.76 (td, J=11.4, 10.7, 2.8 Hz, 2H), 2.66 (td, J=11.7, 3.0 Hz, 1H), 2.31 (dd, J=11.8, 10.1 Hz, 1H), 1.75 (s, 6H), 1.04 (d, J=6.3 Hz, 3H); [M+H]$^+$ 503.

Example 138: 3-(4-Morpholinobenzamido)-N-(2,2,2-trifluoro-1-(thiophen-2-yl)ethyl)-1H-indazole-5-carboxamide

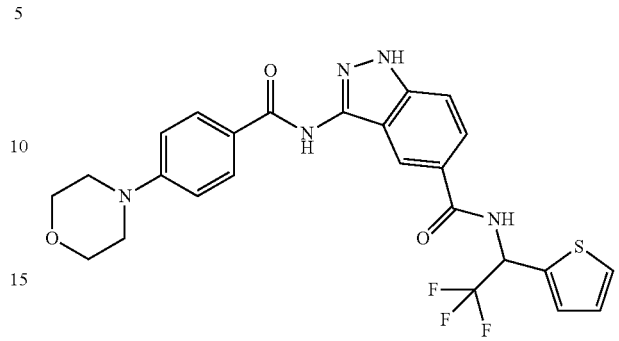

$^1$H NMR (400 MHz, DMSO-d$_6$) δ 9.60 (s, 1H), 8.40 (s, 1H), 8.05-7.96 (m, 2H), 7.88 (s, 1H), 7.61 (d, J=5.0 Hz, 1H), 7.53 (s, 1H), 7.40 (d, J=3.5 Hz, 1H), 7.13-7.00 (m, 3H), 6.36 (s, 1H), 3.75 (t, J=4.8 Hz, 4H), 3.27 (t, J=4.8 Hz, 4H); [M+H]$^+$ 530.

Example 139: N-(Cyclopropyl(pyridin-2-yl)methyl)-3-(4-morpholinobenzamido)-1H-indazole-5-carboxamide

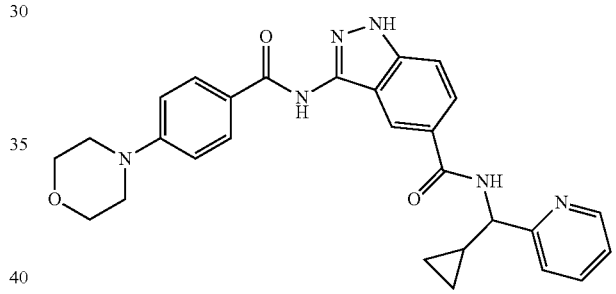

$^1$H NMR (400 MHz, DMSO-d$_6$) δ 12.95 (s, 1H), 10.56 (s, 1H), 8.94 (d, J=8.2 Hz, 1H), 8.54-8.47 (m, 1H), 8.33 (s, 1H), 8.04-7.98 (m, 2H), 7.92 (dd, J=8.8, 1.7 Hz, 1H), 7.86-7.71 (m, 1H), 7.50 (dd, J=8.3, 6.1 Hz, 2H), 7.29-7.21 (m, 1H), 7.04 (d, J=8.7 Hz, 2H), 4.47 (t, J=8.6 Hz, 1H), 3.75 (t, J=4.8 Hz, 4H), 3.27 (t, J=4.8 Hz, 4H), 1.39 (tt, J=9.3, 3.9 Hz, 1H), 0.56-0.39 (m, 4H); [M+H]$^+$ 497.

Example 140: N-(Cyclopropyl(pyridin-2-yl)methyl)-3-(4-(4-methylpiperazin-1-yl)benzamido)-1H-indazole-5-carboxamide

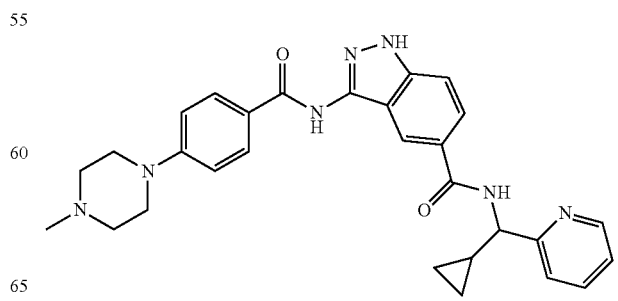

¹H NMR (400 MHz, DMSO-d₆) δ 12.95 (s, 1H), 10.53 (s, 1H), 8.95 (t, J=8.1 Hz, 1H), 8.51 (t, J=2.8 Hz, 1H), 8.32 (s, 1H), 7.98 (d, J=8.6 Hz, 2H), 7.98-7.87 (m, 1H), 7.75 (td, J=7.7, 1.9 Hz, 1H), 7.50 (dd, J=8.3, 5.0 Hz, 2H), 7.25 (dd, J=7.4, 4.9 Hz, 1H), 7.03 (d, J=8.7 Hz, 2H), 4.46 (t, J=8.6 Hz, 1H), 3.31 (d, J=5.5 Hz, 5H), 2.46 (d, J=4.9 Hz, 4H), 2.24 (s, 3H), 1.45-1.23 (m, 1H), 0.56-0.39 (m, 4H); [M+H]⁺ 510.

Example 141: 4-(4-Methylpiperazin-1-yl)-N-(5-(2-(thiophen-2-yl)acetamido)-1H-indazol-3-yl)benzamide

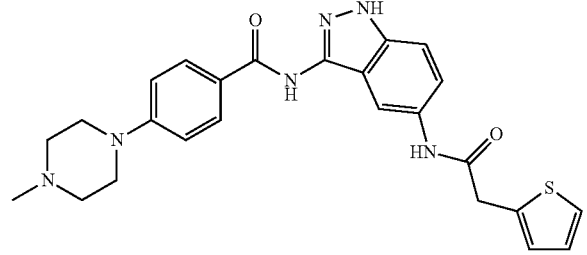 [SMILES: CN1CCN(c2ccc(C(=O)Nc3n[nH]c4ccc(NC(=O)Cc5cccs5)cc34)cc2)CC1]

¹H NMR (400 MHz, DMSO-d₆) δ 12.70 (s, 1H), 10.41 (s, 1H), 10.21 (s, 1H), 7.96 (d, J=8.7 Hz, 2H), 7.90 (d, J=1.9 Hz, 1H), 7.55 (dd, J=8.9, 1.9 Hz, 1H), 7.42 (d, J=9.0 Hz, 1H), 7.37 (dd, J=4.7, 1.8 Hz, 1H), 7.01 (d, J=8.8 Hz, 2H), 6.97 (d, J=4.9 Hz, 2H), 3.84 (s, 2H), 3.30 (t, J=5.1 Hz, 4H), 2.45 (t, J=5.0 Hz, 4H), 2.23 (s, 3H); [M+H]⁺ 475.

Example 142: N-(Cyclopropyl(pyridin-3-yl)methyl)-3-(4-morpholinobenzamido)-1H-indazole-5-carboxamide

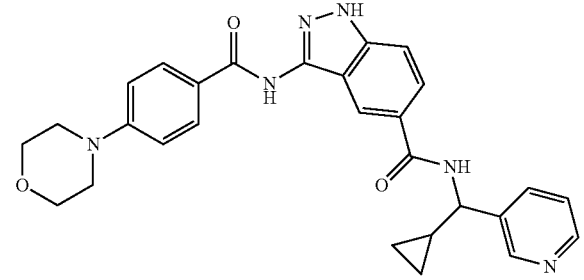 [SMILES: O=C(Nc1n[nH]c2ccc(C(=O)NC(c3cccnc3)C3CC3)cc12)c1ccc(N2CCOCC2)cc1]

¹H NMR (400 MHz, DMSO-d₆) δ 12.97 (s, 1H), 10.57 (s, 1H), 9.07 (d, J=8.1 Hz, 1H), 8.66 (d, J=2.2 Hz, 1H), 8.44 (dd, J=4.7, 1.7 Hz, 1H), 8.31 (s, 1H), 8.04-7.96 (m, 2H), 7.90 (dd, J=8.8, 1.7 Hz, 1H), 7.85 (dt, J=8.0, 2.0 Hz, 1H), 7.51 (d, J=8.9 Hz, 1H), 7.36 (dd, J=7.9, 4.8 Hz, 1H), 7.04 (d, J=9.0 Hz, 2H), 4.39 (t, J=8.9 Hz, 1H), 3.75 (t, J=4.8 Hz, 4H), 3.27 (t, J=4.9 Hz, 4H), 1.45-1.29 (m, 1H), 0.61-0.52 (m, 2H), 0.43 (d, J=4.3 Hz, 2H); [M+H]⁺ 497.

Example 143: N-(Cyclopropyl(pyridin-3-yl)methyl)-3-(4-(4-methylpiperazin-1-yl)benzamido)-1H-indazole-5-carboxamide

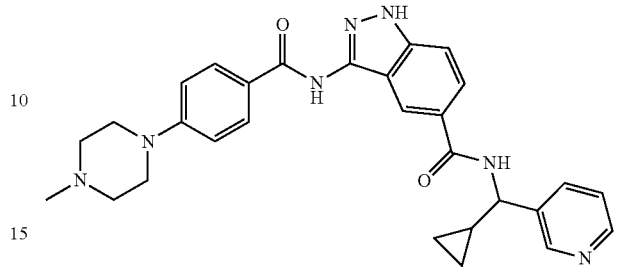

¹H NMR (400 MHz, DMSO-d₆) δ 12.96 (s, 1H), 10.54 (s, 1H), 9.07 (d, J=8.0 Hz, 1H), 8.66 (d, J=2.3 Hz, 1H), 8.44 (d, J=4.7 Hz, 1H), 8.30 (s, 1H), 7.98 (d, J=8.6 Hz, 2H), 7.90 (dd, J=8.8, 1.7 Hz, 1H), 7.85 (dt, J=8.2, 2.1 Hz, 1H), 7.51 (d, J=8.8 Hz, 1H), 7.36 (dd, J=7.8, 4.8 Hz, 1H), 7.03 (d, J=8.7 Hz, 2H), 4.39 (t, J=9.0 Hz, 1H), 3.31 (s, 4H), 2.50 (s, 4H), 2.26 (s, 3H), 1.47-1.26 (m, 1H), 0.61-0.52 (m, 2H), 0.43 (s, 2H); [M+H]⁺ 510.

Example 144: 4-Morpholino-N-(5-(2-(thiophen-2-yl)acetamido)-1H-indazol-3-yl)benzamide

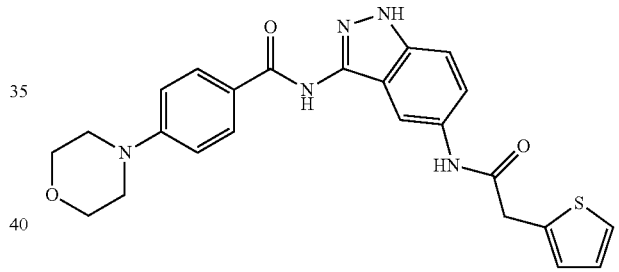

¹H NMR (400 MHz, DMSO-d₆) δ 12.68 (s, 1H), 10.43 (s, 1H), 10.20 (s, 1H), 8.02-7.92 (m, 2H), 7.90 (d, J=1.9 Hz, 1H), 7.56 (dd, J=9.0, 2.0 Hz, 1H), 7.42 (d, J=9.2 Hz, 1H), 7.37 (dd, J=4.6, 1.8 Hz, 1H), 7.03 (d, J=9.0 Hz, 2H), 7.00-6.91 (m, 2H), 3.84 (s, 2H), 3.75 (t, J=4.9 Hz, 4H), 3.27 (t, J=5.0 Hz, 4H); [M+H]⁺ 462.

Example 145: 3-(4-(4-methylpiperazin-1-yl)benzamido)-N-(2-(thiophen-3-yl)propan-2-yl)-1H-indazole-5-carboxamide

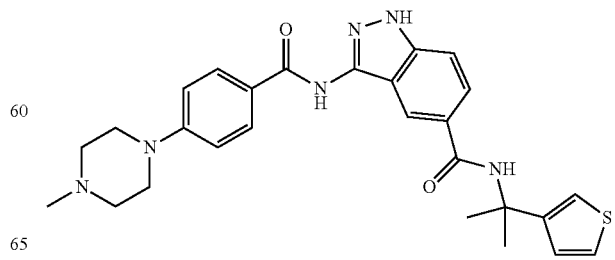

¹H NMR (400 MHz, DMSO-d₆) δ 12.92 (d, J=8.9 Hz, 1H), 10.52 (s, 1H), 8.29 (d, J=7.6 Hz, 1H), 8.22 (d, J=1.3 Hz, 1H), 7.98 (d, J=8.9 Hz, 2H), 7.89-7.73 (m, 1H), 7.52-7.43 (m, 1H), 7.37 (dd, J=5.0, 2.9 Hz, 1H), 7.23-7.13 (m, 1H), 7.08 (dd, J=5.0, 1.4 Hz, 1H), 7.02 (d, J=8.8 Hz, 2H), 3.31 (d, J=4.7 Hz, 4H), 2.45 (t, J=5.0 Hz, 4H), 2.23 (d, J=1.2 Hz, 3H), 1.68 (s, 6H); [M+H]⁺ 503.

Example 146: N-((5-chlorothiophen-2-yl)methyl)-3-(4-(4-methylpiperazin-1-yl)benzamido)-1H-indazole-5-carboxamide

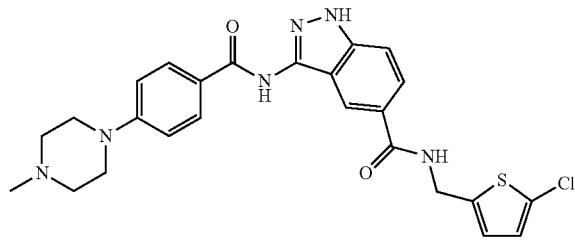 [SMILES: CN1CCN(c2ccc(C(=O)Nc3n[nH]c4ccc(C(=O)NCc5ccc(Cl)s5)cc34)cc2)CC1]

¹H NMR (400 MHz, DMSO-d₆) δ 12.97 (s, 1H), 10.55 (s, 1H), 9.15 (t, J=6.2 Hz, 1H), 8.30 (s, 1H), 7.98 (d, J=8.9 Hz, 2H), 7.87 (dd, J=8.8, 1.7 Hz, 1H), 7.51 (dd, J=8.8, 0.8 Hz, 1H), 7.03 (d, J=9.0 Hz, 2H), 6.93 (dd, J=3.7, 0.9 Hz, 1H), 6.87 (dd, J=3.8, 0.9 Hz, 1H), 4.52 (d, J=5.7 Hz, 2H), 3.31 (t, J=5.1 Hz, 4H), 2.45 (t, J=5.1 Hz, 4H), 2.23 (s, 3H); [M+H]⁺ 510.

Example 147: 3-(4-(4-Methylpiperazin-1-yl)benzamido)-N-(1-(thiophen-2-yl)cyclohexyl)-1H-indazole-5-carboxamide

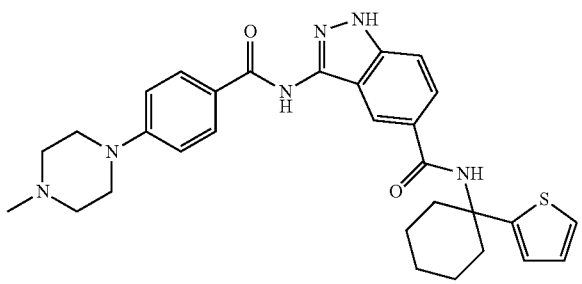 [SMILES: CN1CCN(c2ccc(C(=O)Nc3n[nH]c4ccc(C(=O)NC5(c6cccs6)CCCCC5)cc34)cc2)CC1]

¹H NMR (400 MHz, DMSO-d₆) δ 12.92 (s, 1H), 10.53 (s, 1H), 8.27-8.16 (m, 2H), 7.97 (d, J=8.9 Hz, 2H), 7.89-7.75 (m, 1H), 7.49 (dd, J=8.8, 0.8 Hz, 1H), 7.27 (dd, J=5.1, 1.2 Hz, 1H), 7.02 (d, J=8.9 Hz, 2H), 6.95 (dd, J=3.6, 1.3 Hz, 1H), 6.91 (dd, J=5.0, 3.6 Hz, 1H), 3.30 (t, J=5.1 Hz, 4H), 2.72 (d, J=12.7 Hz, 2H), 2.45 (t, J=5.1 Hz, 4H), 2.23 (s, 3H), 1.70 (d, J=14.0 Hz, 3H), 1.60 (dd, J=23.9, 10.0 Hz, 6H), 1.27 (d, J=28.0 Hz, 1H); [M+H]⁺ 543.

Example 148: 3-(4-Morpholinobenzamido)-N-(thiophen-2-ylmethyl)-1H-indazole-5-carboxamide

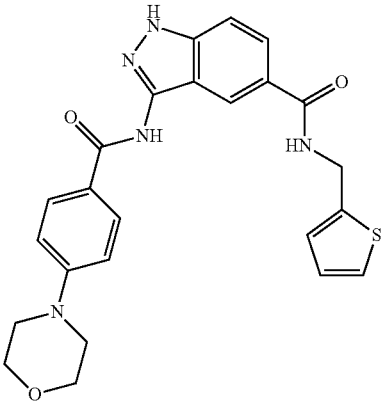 [SMILES: O=C(NCc1cccs1)c1ccc2[nH]nc(NC(=O)c3ccc(N4CCOCC4)cc3)c2c1]

¹H NMR (400 MHz, DMSO-d₆) δ 12.96 (s, 1H), 10.56 (s, 1H), 9.10 (t, J=5.7 Hz, 1H), 8.30 (s, 1H), 8.00 (d, J=8.8 Hz, 2H), 7.88 (d, J=8.8 Hz, 1H), 7.51 (d, J=8.8 Hz, 1H), 7.36 (dd, J=5.1, 1.2 Hz, 1H), 7.04 (d, J=8.9 Hz, 2H), 7.00 (d, J=2.4 Hz, 1H), 6.94 (dd, J=5.0, 3.5 Hz, 1H), 4.62 (d, J=5.6 Hz, 2H), 3.76 (t, J=4.7 Hz, 4H), 3.27 (t, J=4.8 Hz, 4H); [M+H]⁺ 462.

Example 149: 3-(4-(4-methylpiperazin-1-yl)benzamido)-N-(thiophen-2-ylmethyl)-1H-indazole-5-carboxamide

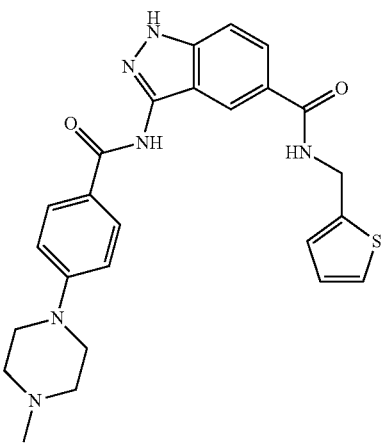 [SMILES: CN1CCN(c2ccc(C(=O)Nc3n[nH]c4ccc(C(=O)NCc5cccs5)cc34)cc2)CC1]

¹H NMR (400 MHz, DMSO-d₆) δ 12.95 (s, 1H), 10.53 (s, 1H), 9.10 (t, J=5.8 Hz, 1H), 7.98 (d, J=8.9 Hz, 2H), 7.88 (dd, J=8.7, 1.5 Hz, 1H), 7.51 (d, J=8.9 Hz, 1H), 7.36 (dd, J=5.1, 1.2 Hz, 1H), 7.04 (s, 1H), 6.99 (dd, J=13.3, 10.0 Hz, 2H), 6.94 (t, J=2.5 Hz, 1H), 4.62 (d, J=5.7 Hz, 2H), 3.31 (t, J=8.2 Hz, 4H), 2.45 (t, J=4.9 Hz, 4H), 2.23 (s, 3H); [M+H]⁺ 475.

Example 150: 3-(4-((2-methoxyethyl)amino)benzamido)-N-(thiophen-2-ylmethyl)-1H-indazole-5-carboxamide

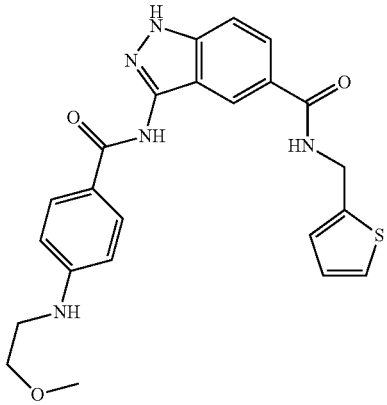 [SMILES: COCCNc1ccc(C(=O)Nc2n[nH]c3ccc(C(=O)NCc4cccs4)cc23)cc1]

$^1$H NMR (400 MHz, DMSO-$d_6$) δ 12.91 (s, 1H), 10.36 (s, 1H), 9.10 (t, J=5.9 Hz, 1H), 8.29 (s, 1H), 7.87 (d, J=11.2 Hz, 3H), 7.50 (d, J=8.8 Hz, 1H), 7.36 (dd, J=5.1, 1.2 Hz, 1H), 7.00 (d, J=2.8 Hz, 1H), 6.94 (dd, J=5.0, 3.5 Hz, 1H), 6.66 (d, J=8.8 Hz, 2H), 6.36 (t, J=5.6 Hz, 1H), 4.61 (d, J=5.7 Hz, 2H), 3.51 (t, J=5.6 Hz, 2H), 3.32-3.30 (m, 5H); [M+H]$^+$ 450.

Example 151: 3-(4-((3-Methoxypropyl)amino)benzamido)-N-(thiophen-2-ylmethyl)-1H-indazole-5-carboxamide

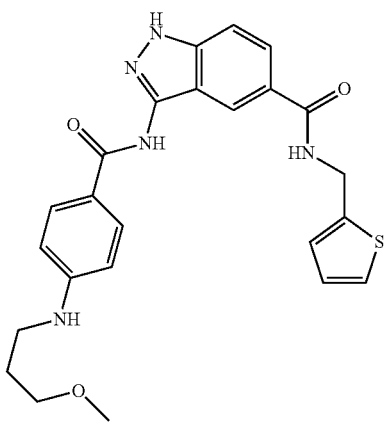 [SMILES: COCCCNc1ccc(C(=O)Nc2n[nH]c3ccc(C(=O)NCc4cccs4)cc23)cc1]

$^1$H NMR (400 MHz, Methanol-$d_4$) δ 8.33 (s, 1H), 7.87 (t, J=9.5 Hz, 3H), 7.50 (d, J=8.8 Hz, 1H), 7.25 (dd, J=5.2, 1.3 Hz, 1H), 7.03 (d, J=3.4 Hz, 1H), 6.92 (dd, J=5.1, 3.4 Hz, 1H), 6.66 (d, J=8.7 Hz, 2H), 4.73 (s, 2H), 3.51 (t, J=6.1 Hz, 2H), 3.35 (s, 3H), 3.25 (t, J=6.8 Hz, 2H), 1.92-1.84 (m, 2H); [M+H]$^+$ 464.

Example 152: 3-(4-((2-(Pyrrolidin-1-yl)ethyl)amino)benzamido)-N-(thiophen-2-ylmethyl)-1H-indazole-5-carboxamide

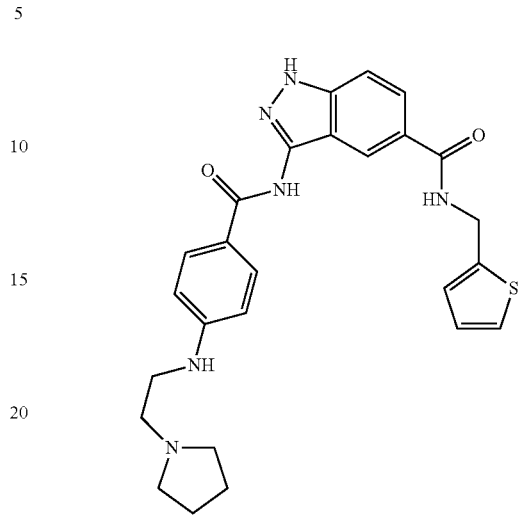

$^1$H NMR (400 MHz, Methanol-$d_4$) δ 8.33 (s, 1H), 7.93-7.85 (m, 3H), 7.53 (dd, J=8.9, 0.9 Hz, 1H), 7.27 (dd, J=5.1, 1.3 Hz, 1H), 7.04 (dd, J=3.5, 1.2 Hz, 1H), 6.94 (dd, J=5.2, 3.5 Hz, 1H), 6.70 (d, J=8.8 Hz, 2H), 4.74 (s, 2H), 3.37 (t, J=7.0 Hz, 2H), 2.77 (t, J=6.9 Hz, 2H), 2.64 (tt, J=10.0, 5.5 Hz, 4H), 1.85 (dq, J=7.7, 4.4, 3.9 Hz, 4H); [M+H]$^+$ 489.

Example 153: 3-(4-((2-morpholinoethyl)amino)benzamido)-N-(thiophen-2-ylmethyl)-1H-indazole-5-carboxamide

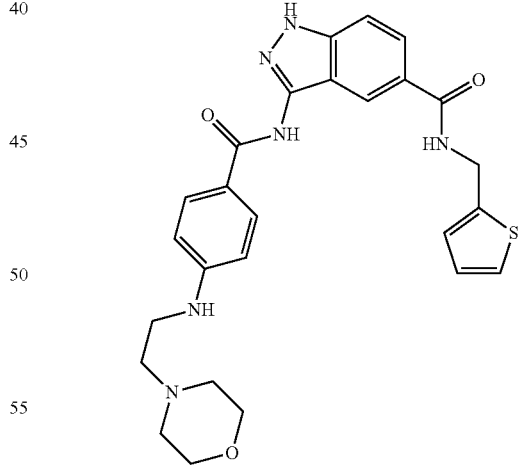

$^1$H NMR (400 MHz, DMSO-$d_6$) δ 12.92 (br s, 1H), 10.37 (s, 1H), 9.10 (t, J=6.0 Hz, 1H), 8.29 (d, J=1.5 Hz, 1H), 7.92-7.83 (m, 3H), 7.50 (d, J=8.8 Hz, 1H), 7.36 (dd, J=5.1, 1.3 Hz, 1H), 7.00 (dd, J=3.5, 1.2 Hz, 1H), 6.94 (dd, J=5.1, 3.4 Hz, 1H), 6.65 (d, J=8.8 Hz, 2H), 6.19 (t, J=5.5 Hz, 1H), 4.62 (d, J=5.8 Hz, 2H), 3.58 (dt, J=17.5, 4.5 Hz, 5H), 3.23 (q, J=6.4 Hz, 2H), 2.53 (d, J=6.7 Hz, 1H), 2.43 (t, J=4.7 Hz, 4H); [M+H]$^+$ 505.

Example 154: 3-(4-((3-(Dimethylamino)propyl)amino)benzamido)-N-(thiophen-2-ylmethyl)-1H-indazole-5-carboxamide

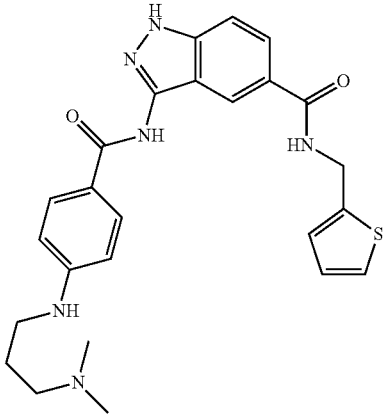 [SMILES: CN(C)CCCNc1ccc(C(=O)Nc2n[nH]c3ccc(C(=O)NCc4cccs4)cc23)cc1]

¹H NMR (400 MHz, DMSO-d₆) δ 10.36 (br s, 1H), 9.10 (t, J=5.9 Hz, 1H), 8.29 (d, J=1.6 Hz, 1H), 7.87 (dq, J=8.7, 2.3, 1.5 Hz, 3H), 7.50 (d, J=8.8 Hz, 1H), 7.36 (dd, J=5.1, 1.3 Hz, 1H), 7.03-6.91 (m, 2H), 6.61 (d, J=8.8 Hz, 2H), 6.35 (t, J=5.5 Hz, 1H), 4.62 (d, J=6.8 Hz, 2H), 3.12 (q, J=6.6 Hz, 2H), 2.30 (t, J=7.0 Hz, 2H), 2.14-2.06 (m, 7H), 1.69 (p, J=6.9 Hz, 2H); [M+H]⁺ 477.

Example 155: 3-(4-(Methyl(2-(methylamino)ethyl)amino)benzamido)-N-(thiophen-2-ylmethyl)-1H-indazole-5-carboxamide

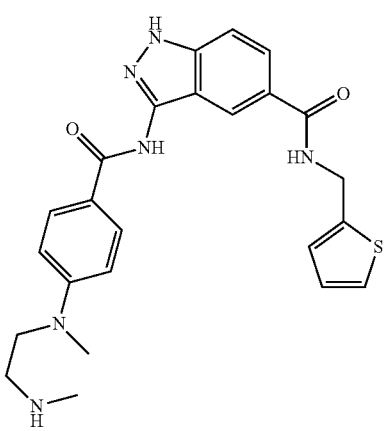 [SMILES: CNCCN(C)c1ccc(C(=O)Nc2n[nH]c3ccc(C(=O)NCc4cccs4)cc23)cc1]

¹H NMR (400 MHz, DMSO-d₆) δ 12.94 (br s, 1H), 10.44 (s, 1H), 9.10 (s, 1H), 8.30 (s, 1H), 7.96 (d, J=8.5 Hz, 2H), 7.87 (d, J=8.9 Hz, 1H), 7.50 (d, J=8.8 Hz, 1H), 7.36 (d, J=5.1 Hz, 1H), 7.00 (s, 1H), 6.95 (d, J=3.6 Hz, 1H), 6.78 (d, J=8.6 Hz, 2H), 4.62 (d, J=5.3 Hz, 2H), 3.01 (s, 3H), 2.72 (s, 2H), 2.08 (s, 2H), 1.90 (s, 3H); [M+H]⁺ 463.

Example 156: 3-(3-Morpholinobenzamido)-N-(thiophen-2-ylmethyl)-1H-indazole-5-carboxamide

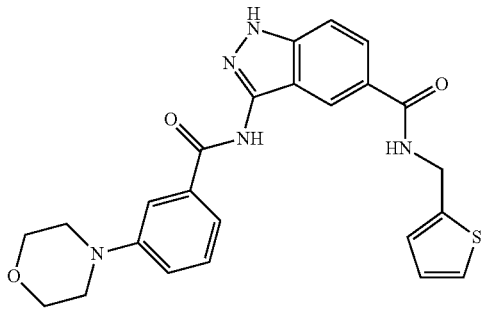 [SMILES: O=C(NCc1cccs1)c1ccc2[nH]nc(NC(=O)c3cccc(N4CCOCC4)c3)c2c1]

¹H NMR (400 MHz, Methanol-d₄) δ 8.37 (d, J=1.5 Hz, 1H), 7.91 (dd, J=8.9, 1.7 Hz, 1H), 7.62 (s, 1H), 7.58-7.50 (m, 1H), 7.48-7.39 (m, 1H), 7.36-7.21 (m, 4H), 7.14 (dd, J=7.8, 2.5 Hz, 1H), 4.74 (d, J=9.7 Hz, 2H), 3.91-3.80 (m, 4H), 3.29-3.15 (m, 4H); [M+H]⁺ 462.

Example 157: 3-(4-(((Tetrahydrofuran-2-yl)methyl)amino)benzamido)-N-(thiophen-2-ylmethyl)-1H-indazole-5-carboxamide

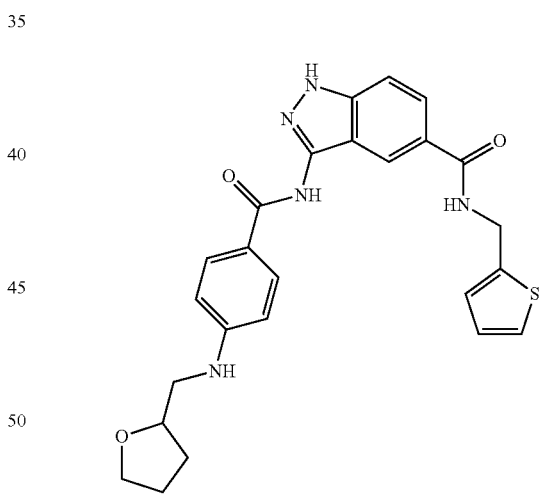

¹H NMR (400 MHz, Methanol-d₄) δ 8.33 (dd, J=1.7, 0.8 Hz, 1H), 7.93-7.83 (m, 3H), 7.53 (dd, J=8.8, 0.8 Hz, 1H), 7.27 (dd, J=5.1, 1.2 Hz, 1H), 7.04 (dd, J=3.4, 1.2 Hz, 1H), 6.94 (dd, J=5.1, 3.5 Hz, 1H), 6.76-6.69 (m, 2H), 4.74 (s, 2H), 4.13 (qd, J=6.9, 4.7 Hz, 1H), 3.90 (dt, J=8.3, 6.7 Hz, 1H), 3.78 (td, J=7.8, 6.4 Hz, 1H), 3.35 (s, 1H), 3.31-3.19 (m, 1H), 2.13-1.99 (m, 1H), 1.99-1.87 (m, 2H), 1.71 (ddt, J=11.9, 8.4, 7.0 Hz, 1H); [M+H]⁺ 476.

Example 158: 3-(4-((2-(Dimethylamino)ethyl)amino)benzamido)-N-(thiophen-2-ylmethyl)-1H-indazole-5-carboxamide

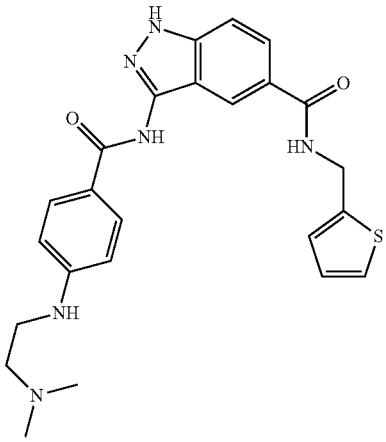

¹H NMR (400 MHz, DMSO-d₆) δ 12.92 (s, 1H), 10.36 (s, 1H), 9.10 (t, J=5.9 Hz, 1H), 8.31 (dd, J=12.5, 1.5 Hz, 1H), 7.88 (dq, J=8.8, 2.2, 1.6 Hz, 3H), 7.50 (d, J=8.8 Hz, 1H), 7.37 (td, J=4.8, 1.3 Hz, 1H), 7.05-6.91 (m, 2H), 6.65 (d, J=8.8 Hz, 2H), 4.62 (t, J=5.7 Hz, 2H), 3.18 (q, J=6.3 Hz, 1H), 2.50-2.32 (m, 2H), 2.22-2.08 (m, 8H); [M+H]⁺ 463.

Example 159: 3-(4-(Isopentylamino)benzamido)-N-(thiophen-2-ylmethyl)-1H-indazole-5-carboxamide

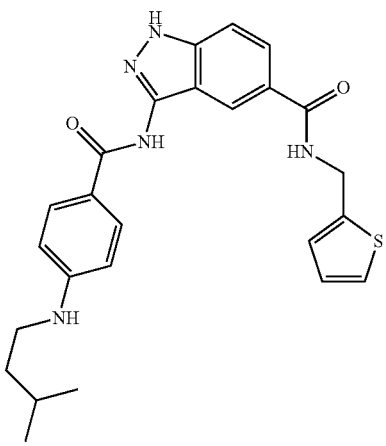 [SMILES: CC(C)CCNc1ccc(C(=O)Nc2n[nH]c3ccc(C(=O)NCc4cccs4)cc23)cc1]

¹H NMR (400 MHz, Methanol-d₄) δ 8.33 (t, J=1.2 Hz, 1H), 7.93-7.82 (m, 3H), 7.52 (dd, J=8.9, 0.9 Hz, 1H), 7.27 (dd, J=5.1, 1.2 Hz, 1H), 7.04 (dd, J=3.5, 1.1 Hz, 1H), 6.94 (dd, J=5.1, 3.5 Hz, 1H), 6.71-6.62 (m, 2H), 4.74 (s, 2H), 3.35 (s, 1H), 3.23-3.15 (m, 2H), 1.75 (dq, J=13.3, 6.7 Hz, 1H), 1.55 (q, J=7.1 Hz, 2H), 0.99 (d, J=6.6 Hz, 6H); [M+H]⁺ 462.

Example 160: 3-(4-((2-(Tetrahydro-2H-pyran-4-yl)ethyl)amino)benzamido)-N-(thiophen-2-ylmethyl)-1H-indazole-5-carboxamide

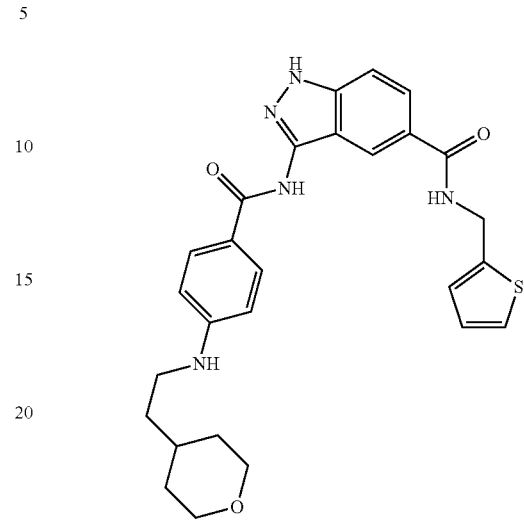

¹H NMR (400 MHz, Methanol-d₄) δ 8.33 (dd, J=1.7, 0.8 Hz, 1H), 7.92-7.81 (m, 3H), 7.50 (dd, J=8.8, 0.8 Hz, 1H), 7.25 (dd, J=5.1, 1.2 Hz, 1H), 7.02 (dd, J=3.5, 1.1 Hz, 1H), 6.92 (dd, J=5.1, 3.5 Hz, 1H), 6.65 (d, J=8.9 Hz, 2H), 4.72 (s, 2H), 3.96-3.87 (m, 2H), 3.40 (td, J=11.9, 1.9 Hz, 2H), 3.18 (t, J=7.2 Hz, 2H), 1.74-1.61 (m, 3H), 1.61-1.52 (m, 2H), 1.37-1.22 (m, 2H); [M+H]⁺ 504.

Example 161: 3-(4-(Hexylamino)benzamido)-N-(thiophen-2-ylmethyl)-1H-indazole-5-carboxamide

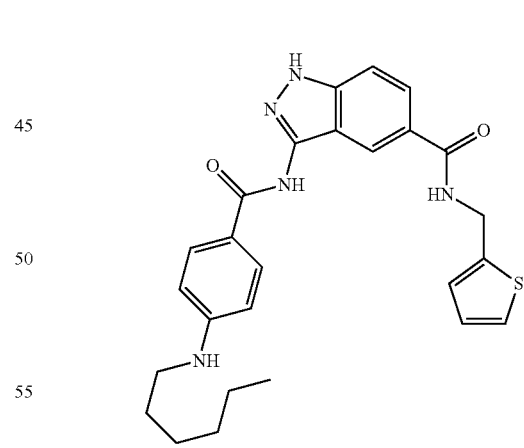

¹H NMR (400 MHz, Methanol-d₄) δ 8.36 (s, 1H), 7.89 (s, 3H), 7.53 (s, 1H), 7.27 (s, 1H), 7.05 (s, 1H), 6.95 (s, 1H), 6.69 (d, J=8.0 Hz, 2H), 5.49 (s, 1H), 4.75 (s, 2H), 3.18 (t, J=7.1 Hz, 2H), 1.65 (s, 2H), 1.44 (s, 2H), 1.44-1.30 (m, 5H), 0.92 (d, J=7.3 Hz, 3H); [M+H]⁺ 476.

Example 162: 3-(4-(Cyclohexylamino)benzamido)-N-(thiophen-2-ylmethyl)-1H-indazole-5-carboxamide

Example 164: 3-(4-(Cycloheptylamino)benzamido)-N-(thiophen-2-ylmethyl)-1H-indazole-5-carboxamide

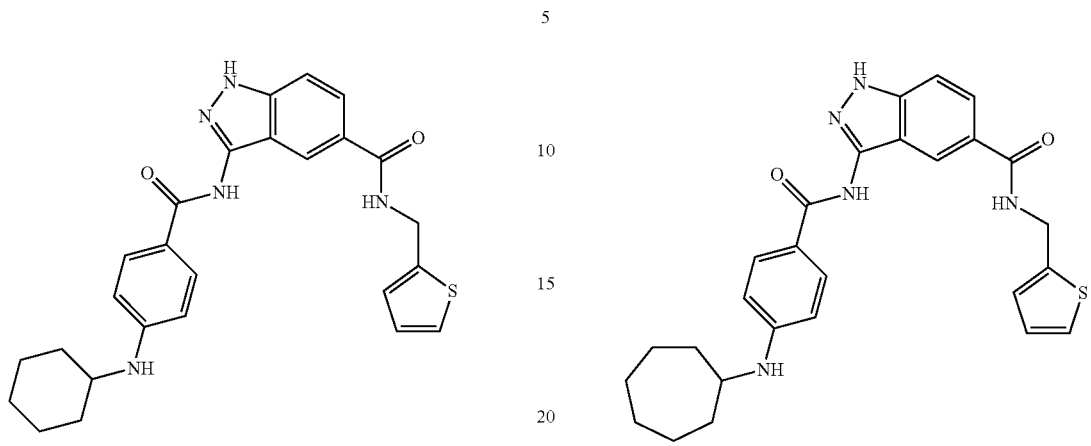

$^1$H NMR (400 MHz, Methanol-d$_4$) δ 8.33 (t, J=1.2 Hz, 1H), 7.90 (dd, J=8.8, 1.6 Hz, 1H), 7.85 (d, J=8.8 Hz, 2H), 7.53 (dd, J=8.9, 0.8 Hz, 1H), 7.27 (dd, J=5.1, 1.3 Hz, 1H), 7.04 (dd, J=3.4, 1.2 Hz, 1H), 6.94 (dd, J=5.1, 3.5 Hz, 1H), 6.67 (d, J=8.8 Hz, 2H), 4.74 (s, 2H), 2.05 (d, J=12.7 Hz, 2H), 1.84-1.80 (m, 2H), 1.69 (d, J=13.4 Hz, 1H), 1.44 (q, J=12.5 Hz, 2H), 1.35-1.19 (m, 4H); [M+H]$^+$ 474.

$^1$H NMR (400 MHz, Methanol-d$_4$) δ 8.25 (s, 1H), 7.90-7.82 (m, 3H), 7.51 (dd, J=8.9, 0.9 Hz, 1H), 6.63 (d, J=8.9 Hz, 2H), 4.08-4.04 (m, 1H), 3.55 (s, 2H), 2.08-1.95 (m, 4H), 1.77-1.53 (m, 8H); [M+H]$^+$ 488.

Example 163: 3-(4-(Cyclopentylamino)benzamido)-N-(thiophen-2-ylmethyl)-1H-indazole-5-carboxamide

Example 165: 3-(4-(Cyclooctylamino)benzamido)-N-(thiophen-2-ylmethyl)-1H-indazole-5-carboxamide

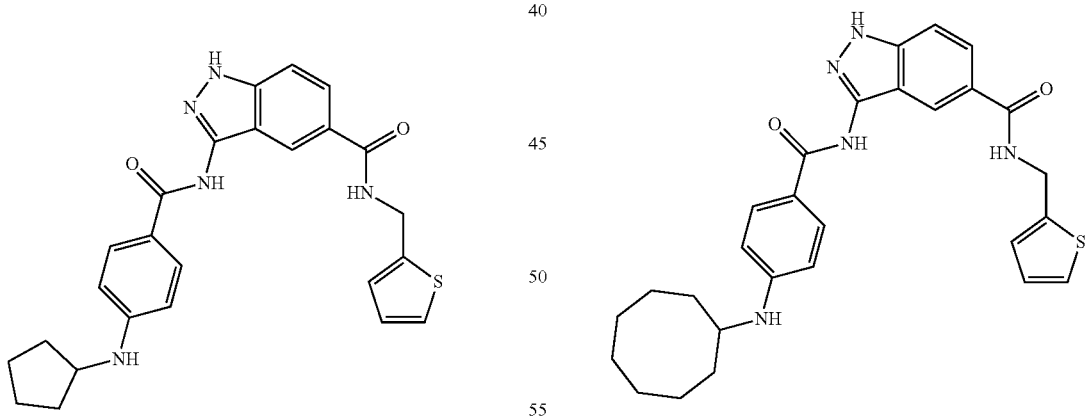

$^1$H NMR (400 MHz, Methanol-d$_4$) δ 8.33 (dd, J=1.7, 0.8 Hz, 1H), 7.89 (dd, J=8.8, 1.7 Hz, 1H), 7.88-7.82 (m, 2H), 7.52 (dd, J=8.9, 0.8 Hz, 1H), 7.27 (dd, J=5.1, 1.2 Hz, 1H), 7.04 (dd, J=3.5, 1.1 Hz, 1H), 6.94 (dd, J=5.1, 3.5 Hz, 1H), 6.72-6.63 (m, 2H), 4.74 (s, 2H), 3.87 (p, J=5.8 Hz, 1H), 2.11-1.98 (m, 2H), 1.84-1.73 (m, 2H), 1.73-1.65 (m, 2H), 1.65-1.49 (m, 2H); [M+H]$^+$ 460.

$^1$H NMR (400 MHz, Methanol-d$_4$) δ 8.33 (s, 1H), 7.89 (dd, J=8.9, 1.7 Hz, 1H), 7.87-7.83 (m, 2H), 7.52 (dd, J=8.9, 0.8 Hz, 1H), 7.27 (dd, J=5.1, 1.2 Hz, 1H), 7.04 (dt, J=3.3, 1.0 Hz, 1H), 6.94 (dd, J=5.1, 3.5 Hz, 1H), 6.67-6.58 (m, 2H), 4.74 (d, J=0.9 Hz, 2H), 3.58 (tt, J=8.5, 3.6 Hz, 1H), 1.96-1.85 (m, 2H), 1.83-1.72 (m, 2H), 1.72-1.57 (m, 10H); [M+H]$^+$ 502.

Example 166: 3-(4-((Cyclohexylmethyl)amino)benzamido)-N-(thiophen-2-ylmethyl)-1H-indazole-5-carboxamide

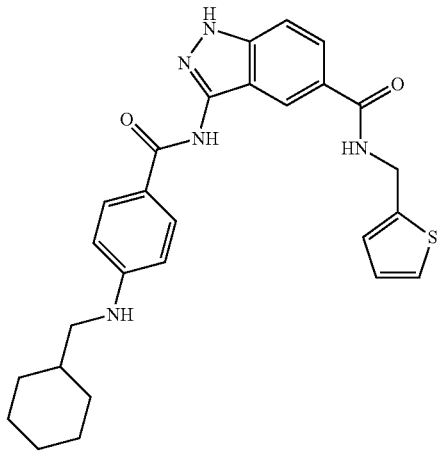 [SMILES: O=C(NCc1cccs1)c1ccc2[nH]nc(NC(=O)c3ccc(NCC4CCCCC4)cc3)c2c1]

¹H NMR (400 MHz, Methanol-d₄) δ 8.33 (dd, J=1.7, 0.8 Hz, 1H), 7.89 (dd, J=8.9, 1.7 Hz, 1H), 7.88-7.83 (m, 2H), 7.52 (dd, J=8.8, 0.8 Hz, 1H), 7.27 (dd, J=5.1, 1.2 Hz, 1H), 7.04 (dd, J=3.5, 1.2 Hz, 1H), 6.94 (dd, J=5.1, 3.5 Hz, 1H), 6.70-6.61 (m, 2H), 4.74 (d, J=0.9 Hz, 2H), 3.01 (d, J=6.8 Hz, 2H), 1.87 (d, J=13.0 Hz, 2H), 1.78 (d, J=12.8 Hz, 2H), 1.74-1.57 (m, 3H), 1.26 (dq, J=21.1, 10.9, 9.3 Hz, 4H), 1.05 (d, J=11.9 Hz, 1H); [M+H]⁺ 488.

Example 167: 3-(4-((2-(Cyclohex-1-en-1-yl)ethyl)amino)benzamido)-N-(thiophen-2-ylmethyl)-1H-indazole-5-carboxamide

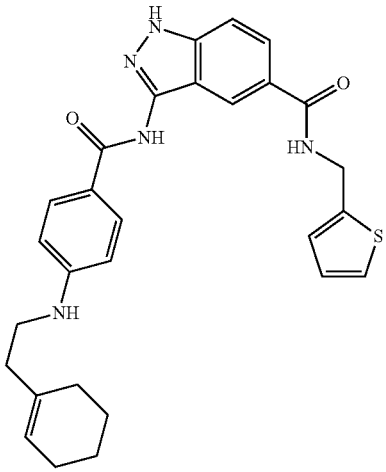 [SMILES: O=C(NCc1cccs1)c1ccc2[nH]nc(NC(=O)c3ccc(NCCC4=CCCCC4)cc3)c2c1]

¹H NMR (400 MHz, DMSO-d₆) δ 12.91 (br s, 1H), 10.36 (s, 1H), 9.10 (t, J=6.0 Hz, 1H), 8.29 (d, J=1.5 Hz, 1H), 7.91-7.83 (m, 3H), 7.50 (d, J=8.8 Hz, 1H), 7.36 (dd, J=5.0, 1.3 Hz, 1H), 7.00 (dd, J=3.5, 1.2 Hz, 1H), 6.94 (dd, J=5.1, 3.4 Hz, 1H), 6.66-6.59 (m, 2H), 6.25 (t, J=5.5 Hz, 1H), 4.61 (d, J=5.8 Hz, 2H), 3.17 (td, J=7.6, 5.5 Hz, 2H), 2.20 (t, J=7.4 Hz, 2H), 1.88 (t, J=5.9 Hz, 4H), 1.63-1.45 (m, 2H); [M+H]⁺ 500.

Example 168: 3-(2,4-Dimorpholinobenzamido)-N-(thiophen-2-ylmethyl)-1H-indazole-5-carboxamide

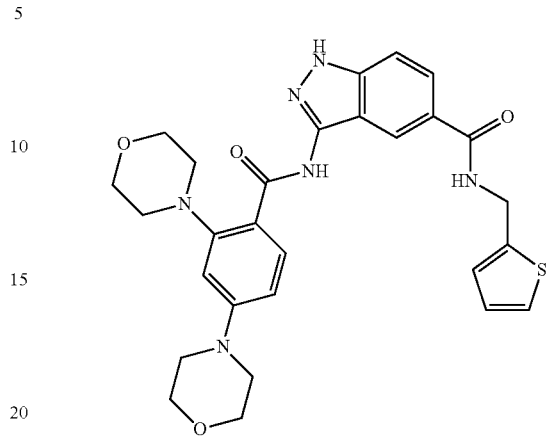

¹H NMR (400 MHz, Methanol-d₄) δ 8.64 (dd, J=1.7, 0.8 Hz, 1H), 8.10 (d, J=8.7 Hz, 1H), 7.89 (dd, J=8.9, 1.7 Hz, 1H), 7.51 (dd, J=8.9, 0.8 Hz, 1H), 7.28 (dd, J=5.1, 1.2 Hz, 1H), 7.06 (dt, J=3.2, 1.1 Hz, 1H), 6.99-6.85 (m, 3H), 4.76 (d, J=0.9 Hz, 2H), 4.01-3.94 (m, 4H), 3.88-3.81 (m, 4H), 3.34-3.30 (m, 4H), 3.15-3.08 (m, 4H); [M+H]⁺ 547.

Example 169: 3-(4-((2-(1H-Pyrrol-1-yl)ethyl)amino)benzamido)-N-(thiophen-2-ylmethyl)-1H-indazole-5-carboxamide

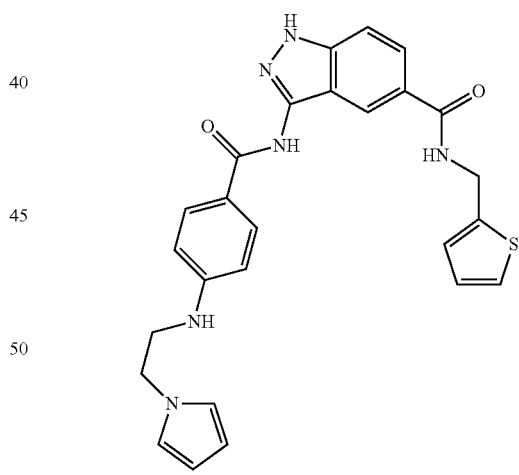

¹H NMR (400 MHz, Methanol-d₄) δ 8.33 (dd, J=1.7, 0.8 Hz, 1H), 7.93-7.82 (m, 3H), 7.60-7.55 (m, 1H), 7.52 (dd, J=8.8, 0.8 Hz, 1H), 7.26 (dd, J=5.1, 1.2 Hz, 1H), 7.04 (dd, J=3.4, 1.2 Hz, 1H), 6.93 (dd, J=5.1, 3.4 Hz, 1H), 6.74-6.60 (m, 6H), 6.60-6.51 (m, 1H), 6.09-6.01 (m, 4H), 4.74 (s, 2H), 4.09 (dt, J=15.5, 6.3 Hz, 4H), 3.60 (t, J=6.3 Hz, 1H), 3.53 (t, J=6.1 Hz, 2H), 3.48 (t, J=6.1 Hz, 1H); [M+H]⁺ 485.

Example 170: 3-(2-Fluoro-4-(4-methylpiperazin-1-yl)benzamido)-N-(thiophen-2-ylmethyl)-1H-indazole-5-carboxamide

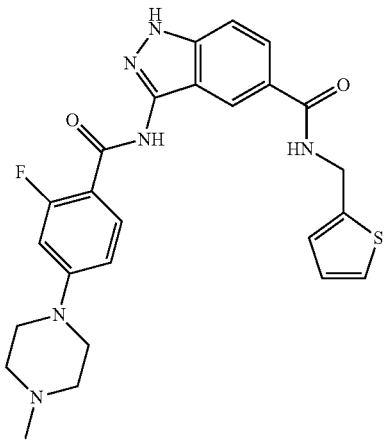 [SMILES: CN1CCN(c2ccc(C(=O)Nc3n[nH]c4ccc(C(=O)NCc5cccs5)cc34)c(F)c2)CC1]

¹H NMR (400 MHz, Methanol-d₄) δ 8.56 (s, 1H), 7.95-7.85 (m, 2H), 7.53 (d, J=8.8 Hz, 1H), 7.27 (dd, J=5.1, 1.1 Hz, 1H), 7.13-6.98 (m, 3H), 6.94 (dd, J=5.1, 3.5 Hz, 1H), 4.76 (s, 2H), 3.60 (br s, 1H), 3.51 (br s, 4H), 3.25 (br s, 1H), 2.96 (s, 2H); [M+H]⁺ 493.

Example 171: 3-(4-(Piperazin-1-yl)benzamido)-N-(thiophen-2-ylmethyl)-1H-indazole-5-carboxamide

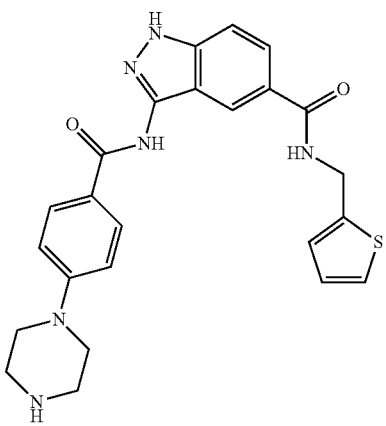 [SMILES: O=C(NCc1cccs1)c1ccc2[nH]nc(NC(=O)c3ccc(N4CCNCC4)cc3)c2c1]

¹H NMR (400 MHz, DMSO-d₆) δ 12.95 (s, 1H), 10.53 (s, 1H), 9.10 (t, J=6.0 Hz, 1H), 8.30 (d, J=1.3 Hz, 1H), 7.98 (d, J=8.8 Hz, 2H), 7.88 (dd, J=8.8, 1.7 Hz, 1H), 7.51 (d, J=8.8 Hz, 1H), 7.36 (dd, J=5.1, 1.3 Hz, 1H), 7.04-6.98 (m, 3H), 6.94 (dd, J=5.1, 3.4 Hz, 1H), 4.62 (d, J=5.9 Hz, 2H), 3.25 (t, J=5.1 Hz, 4H), 2.88 (t, J=5.0 Hz, 4H); [M+H]⁺ 461.

Example 172: 3-(4-(4-Methylpiperazin-1-yl)benzamido)-N-(oxazol-5-ylmethyl)-1H-indazole-5-carboxamide

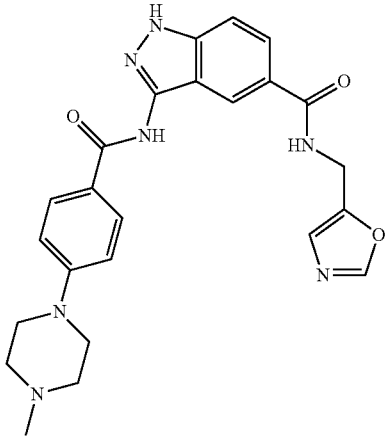 [SMILES: CN1CCN(c2ccc(C(=O)Nc3n[nH]c4ccc(C(=O)NCc5cnco5)cc34)cc2)CC1]

¹H NMR (400 MHz, DMSO-d₆) δ 12.97 (s, 1H), 10.55 (s, 1H), 8.99 (t, J=5.7 Hz, 1H), 8.28 (d, J=11.1 Hz, 2H), 7.98 (d, J=8.6 Hz, 2H), 7.87 (d, J=8.5 Hz, 1H), 7.51 (d, J=8.9 Hz, 1H), 7.06-6.99 (m, 3H), 4.53 (d, J=5.5 Hz, 2H), 3.30 (d, J=5.6 Hz, 4H), 2.45 (t, J=4.9 Hz, 4H), 2.23 (s, 3H), 1.23 (s, 1H); [M+H]⁺ 460.

Example 173: N-(Isoxazol-3-ylmethyl)-3-(4-(4-methylpiperazin-1-yl)benzamido)-1H-indazole-5-carboxamide

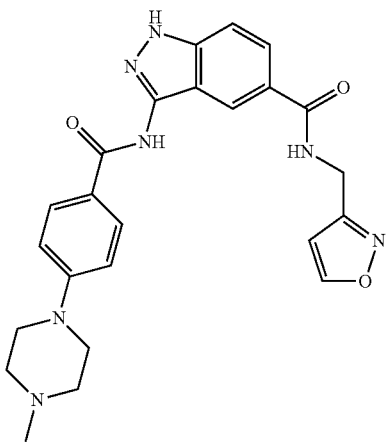 [SMILES: CN1CCN(c2ccc(C(=O)Nc3n[nH]c4ccc(C(=O)NCc5ccon5)cc34)cc2)CC1]

¹H NMR (400 MHz, DMSO-d₆) δ 13.00 (s, 1H), 10.56 (s, 1H), 9.08 (t, J=5.9 Hz, 1H), 8.82 (d, J=1.5 Hz, 1H), 8.32 (s, 1H), 7.98 (d, J=8.6 Hz, 2H), 7.89 (dd, J=8.8, 1.5 Hz, 1H), 7.52 (d, J=8.8 Hz, 1H), 7.03 (d, J=8.6 Hz, 2H), 6.49 (d, J=1.6 Hz, 1H), 4.54 (d, J=5.8 Hz, 2H), 3.30 (m, 4H), 2.45 (t, J=5.0 Hz, 4H), 2.23 (s, 3H); [M+1-1]⁺ 460.

Example 174: 3-(4-(4-Methylpiperazin-1-yl)benzamido)-N-(thiazol-4-ylmethyl)-1H-indazole-5-carboxamide

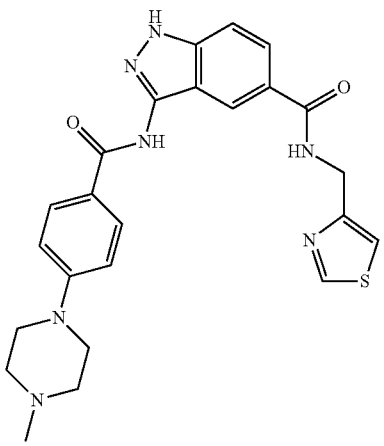 [SMILES: CN1CCN(c2ccc(C(=O)Nc3n[nH]c4ccc(C(=O)NCc5cscn5)cc34)cc2)CC1]

$^1$H NMR (400 MHz, DMSO-d$_6$) δ 12.96 (s, 1H), 10.54 (s, 1H), 9.05 (dd, J=6.9, 3.8 Hz, 2H), 8.33 (s, 1H), 7.98 (d, J=8.7 Hz, 2H), 7.91 (dd, J=8.8, 1.6 Hz, 1H), 7.51 (d, J=8.8 Hz, 1H), 7.42 (d, J=1.9 Hz, 1H), 7.02 (d, J=8.7 Hz, 2H), 4.60 (d, J=5.7 Hz, 2H), 3.30 (t, J=4.9 Hz, 4H), 2.45 (t, J=5.0 Hz, 4H), 2.23 (s, 3H); [M+H]$^+$ 476.

Example 175: (R)-3-(4-(4-Methylpiperazin-1-yl)benzamido)-N-(1-phenylethyl)-1H-indazole-5-carboxamide

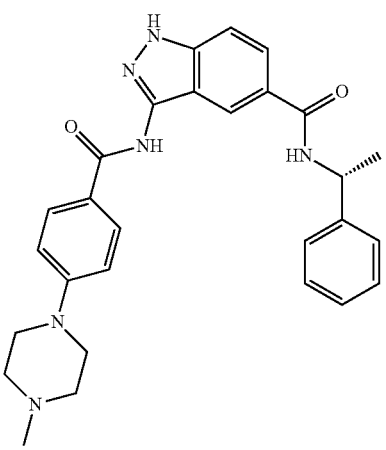

$^1$H NMR (400 MHz, DMSO-d$_6$) δ 12.94 (s, 1H), 10.53 (s, 1H), 8.80 (d, J=8.1 Hz, 1H), 8.29 (s, 1H), 7.98 (d, J=8.6 Hz, 2H), 7.89 (dd, J=8.8, 1.6 Hz, 1H), 7.50 (d, J=8.8 Hz, 1H), 7.39 (d, J=7.3 Hz, 2H), 7.31 (t, J=7.5 Hz, 2H), 7.21 (t, J=7.3 Hz, 1H), 7.03 (d, J=8.7 Hz, 2H), 5.19 (p, J=7.2 Hz, 1H), 3.30 (t, J=5.0 Hz, 4H), 2.45 (t, J=5.0 Hz, 4H), 2.23 (s, 3H), 1.47 (d, J=7.0 Hz, 3H); [M+H]$^+$ 483.

Example 176: (S)-3-(4-(4-Methylpiperazin-1-yl)benzamido)-N-(1-phenylethyl)-1H-indazole-5-carboxamide

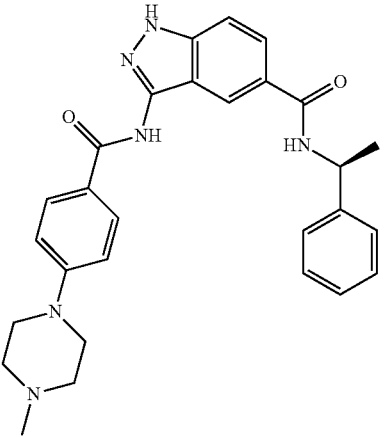 [SMILES: C[C@H](NC(=O)c1ccc2[nH]nc(NC(=O)c3ccc(N4CCN(C)CC4)cc3)c2c1)c1ccccc1]

$^1$H NMR (400 MHz, DMSO-d$_6$) δ 12.94 (s, 1H), 10.53 (s, 1H), 8.80 (d, J=8.1 Hz, 1H), 8.30 (d, J=1.5 Hz, 1H), 7.98 (d, J=8.9 Hz, 2H), 7.89 (dd, J=8.8, 1.6 Hz, 1H), 7.50 (d, J=8.8 Hz, 1H), 7.39 (d, J=7.2 Hz, 2H), 7.31 (dd, J=8.4, 6.8 Hz, 2H), 7.21 (t, J=7.2 Hz, 1H), 7.03 (d, J=9.0 Hz, 2H), 5.19 (p, J=7.2 Hz, 1H), 3.31 (t, J=4.9 Hz, 4H), 2.45 (t, J=5.0 Hz, 4H), 2.23 (s, 3H), 1.47 (d, J=7.1 Hz, 3H); [M+H]$^+$ 483.

Example 177: N-Benzyl-3-(4-morpholinobenzamido)-1H-indazole-5-carboxamide

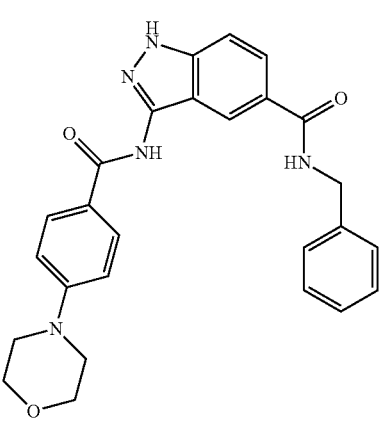 [SMILES: O=C(NCc1ccccc1)c1ccc2[nH]nc(NC(=O)c3ccc(N4CCOCC4)cc3)c2c1]

$^1$H NMR (400 MHz, DMSO-d$_6$) δ 12.97 (s, 1H), 10.57 (s, 1H), 9.02 (t, J=6.1 Hz, 1H), 8.33 (s, 1H), 8.00 (d, J=8.6 Hz, 2H), 7.90 (dd, J=8.8, 1.7 Hz, 1H), 7.52 (d, J=8.8 Hz, 1H), 7.31 (d, J=4.4 Hz, 4H), 7.23 (h, J=4.0 Hz, 1H), 7.04 (d, J=8.7 Hz, 2H), 4.48 (d, J=6.0 Hz, 2H), 3.75 (t, J=4.8 Hz, 4H), 3.27 (t, J=4.9 Hz, 4H); [M+H]$^+$ 456.

Example 178: N-(Isoxazol-5-ylmethyl)-3-(4-(4-methylpiperazin-1-yl)benzamido)-1H-indazole-5-carboxamide

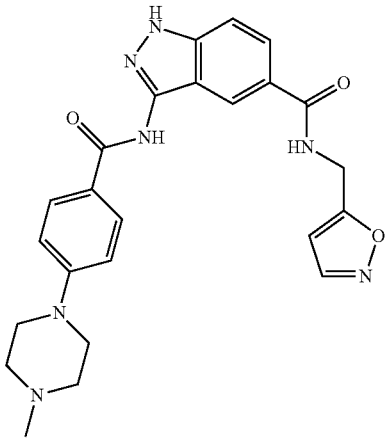 [SMILES: CN1CCN(c2ccc(C(=O)Nc3n[nH]c4ccc(C(=O)NCc5ccno5)cc34)cc2)CC1]

$^1$H NMR (400 MHz, Methanol-d$_4$) δ 8.39 (dd, J=1.7, 0.8 Hz, 1H), 8.31 (d, J=1.9 Hz, 1H), 7.98 (dd, J=8.8, 3.6 Hz, 2H), 7.91 (dd, J=8.8, 1.7 Hz, 1H), 7.54 (dd, J=8.9, 0.6 Hz, 1H), 7.05 (d, J=9.0 Hz, 2H), 6.34 (t, J=0.9 Hz, 1H), 4.72 (s, 2H), 3.39 (t, J=5.1 Hz, 4H), 2.62 (t, J=5.1 Hz, 4H), 2.36 (s, 3H); [M+H]$^+$ 460.

Example 179: 3-(4-(4-Methylpiperazin-1-yl)benzamido)-N-(1-phenylethyl)-1H-indazole-5-carboxamide

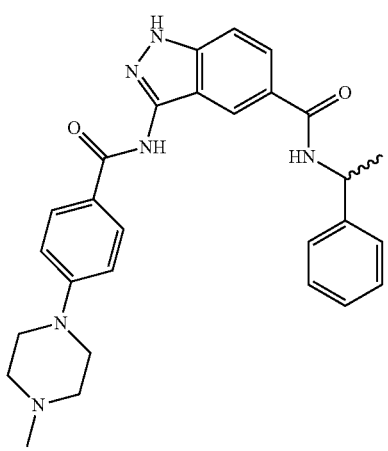 [SMILES: CC(NC(=O)c1ccc2[nH]nc(NC(=O)c3ccc(N4CCN(C)CC4)cc3)c2c1)c1ccccc1]

$^1$H NMR (400 MHz, DMSO-d$_6$) δ 12.94 (s, 1H), 10.53 (s, 1H), 8.80 (d, J=8.1 Hz, 1H), 8.29 (s, 1H), 7.98 (d, J=9.0 Hz, 2H), 7.89 (dd, J=8.8, 1.6 Hz, 1H), 7.50 (dd, J=8.8, 0.8 Hz, 1H), 7.41-7.36 (m, 2H), 7.31 (dd, J=8.4, 6.8 Hz, 2H), 7.25-7.16 (m, 1H), 7.03 (d, J=9.0 Hz, 2H), 5.18 (q, J=7.4 Hz, 1H), 3.30 (t, J=5.1 Hz, 4H), 2.45 (t, J=5.1 Hz, 4H), 2.23 (s, 3H), 1.47 (d, J=7.1 Hz, 3H); [M+H]$^+$ 483.

Example 180: 3-(4-Morpholinobenzamido)-N-(1-phenylethyl)-1H-indazole-5-carboxamide

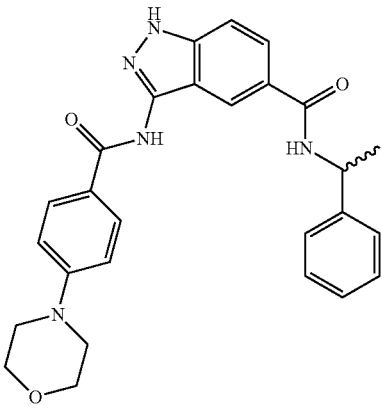 [SMILES: CC(NC(=O)c1ccc2[nH]nc(NC(=O)c3ccc(N4CCOCC4)cc3)c2c1)c1ccccc1]

$^1$H NMR (400 MHz, DMSO-d$_6$) δ 12.95 (s, 1H), 10.56 (s, 1H), 8.80 (d, J=8.1 Hz, 1H), 8.30 (t, J=1.2 Hz, 1H), 8.05-7.96 (m, 2H), 7.90 (dd, J=8.8, 1.6 Hz, 1H), 7.50 (dd, J=8.8, 0.8 Hz, 1H), 7.42-7.35 (m, 2H), 7.31 (dd, J=8.4, 6.8 Hz, 2H), 7.25-7.16 (m, 1H), 7.08-7.01 (m, 2H), 5.23-5.15 (m, 1H), 3.75 (t, J=4.9 Hz, 4H), 3.30-3.25 (m, 4H), 1.47 (d, J=7.1 Hz, 3H); [M+H]$^+$ 470.

Example 181: N-(1-Phenylethyl)-3-(4-(piperazin-1-yl)benzamido)-1H-indazole-5-carboxamide 2,2,2-trifluoroacetate

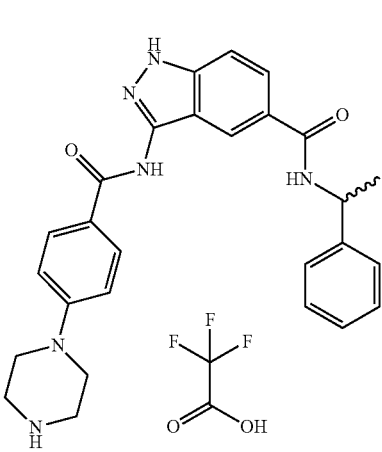 [SMILES: CC(NC(=O)c1ccc2[nH]nc(NC(=O)c3ccc(N4CCNCC4)cc3)c2c1)c1ccccc1 ; O=C(O)C(F)(F)F]

$^1$H NMR (400 MHz, Methanol-d$_4$) δ 8.63 (s, 1H), 8.37 (s, 1H), 8.03 (t, J=5.4 Hz, 2H), 7.90 (dd, J=4.3, 1.2 Hz, 2H), 7.69 (d, J=4.4 Hz, 1H), 7.53 (d, J=9.0 Hz, 1H), 7.41 (d, J=6.7 Hz, 2H), 7.32 (t, J=8.0 Hz, 2H), 7.22 (s, 1H), 7.14 (d, J=8.4 Hz, 2H), 5.46 (s, 1H), 5.26 (d, J=6.9 Hz, 1H), 3.60 (t, J=5.3 Hz, 4H), 3.38 (t, J=5.3 Hz, 4H), 1.62-1.53 (m, 3H); [M+H]$^+$ 469.

Example 182: 3-(4-(3,5-Dimethylpiperazin-1-yl)benzamido)-N-(1-phenylethyl)-1H-indazole-5-carboxamide

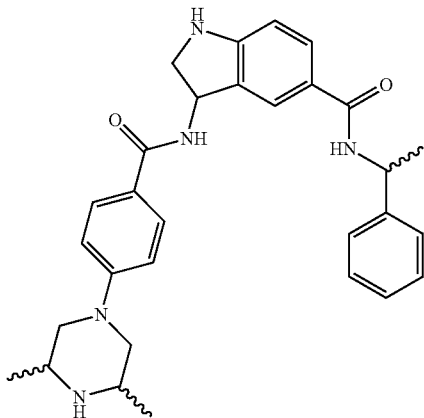

¹H NMR (400 MHz, Methanol-d₄) δ 8.36 (d, J=1.5 Hz, 1H), 7.97 (dd, J=9.0, 1.7 Hz, 2H), 7.88 (dd, J=8.9, 1.6 Hz, 1H), 7.56-7.49 (m, 1H), 7.44-7.37 (m, 2H), 7.31 (t, J=7.7 Hz, 2H), 7.26-7.17 (m, 1H), 7.05 (dd, J=9.1, 3.3 Hz, 2H), 5.25 (q, J=7.1 Hz, 1H), 3.81 (d, J=12.2 Hz, 2H), 2.96 (m, 2H), 2.40 (t, J=11.5 Hz, 2H), 1.56 (dd, J=7.2, 1.3 Hz, 3H), 1.18 (dd, J=6.4, 1.3 Hz, 6H); [M+H]⁺ 497.

Example 183: 3-(4-(2,6-Dimethylmorpholino)benzamido)-N-(1-phenylethyl)-1H-indazole-5-carboxamide

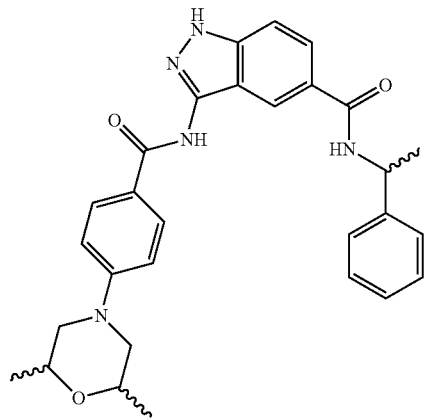

¹H NMR (400 MHz, Methanol-d₄) δ 8.35 (dd, J=1.7, 0.8 Hz, 1H), 8.02-7.94 (m, 2H), 7.88 (dd, J=8.8, 1.7 Hz, 1H), 7.52 (dd, J=8.8, 0.8 Hz, 1H), 7.44-7.37 (m, 2H), 7.31 (t, J=7.5 Hz, 2H), 7.26-7.17 (m, 1H), 7.08-7.03 (m, 2H), 5.25 (q, J=7.0 Hz, 1H), 3.84-3.71 (m, 4H), 2.52-2.41 (m, 2H), 1.56 (d, J=7.1 Hz, 3H), 1.28 (dd, J=15.4, 6.3 Hz, 6H); [M+H]⁺ 498.

Example 184: 3-(4-((S)-3-Methylpiperazin-1-yl)benzamido)-N-(1-phenylethyl)-1H-indazole-5-carboxamide 2,2,2-trifluoroacetate

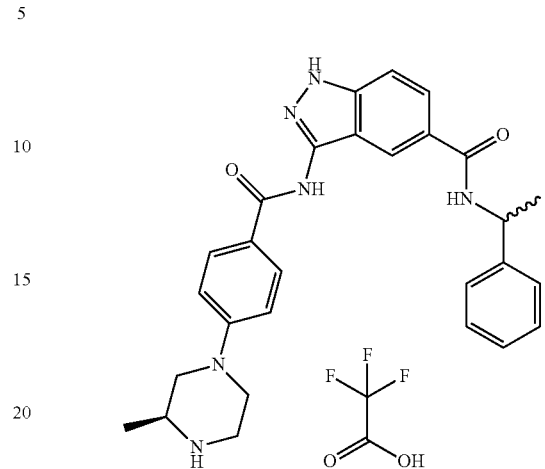

¹H NMR (400 MHz, Methanol-d₄) δ 8.39 (s, 1H), 7.99 (d, J=8.3 Hz, 2H), 7.89 (d, J=8.9 Hz, 1H), 7.52 (d, J=8.9 Hz, 1H), 7.40 (d, J=7.7 Hz, 2H), 7.30 (t, J=7.6 Hz, 2H), 7.25-7.16 (m, 1H), 7.09 (d, J=8.5 Hz, 2H), 5.25 (q, J=7.2 Hz, 1H), 4.05-3.91 (m, 2H), 3.47 (ddt, J=8.3, 5.9, 3.2 Hz, 2H), 3.26 (td, J=12.2, 3.3 Hz, 1H), 3.13 (ddd, J=13.4, 11.8, 3.0 Hz, 1H), 2.99-2.85 (m, 1H), 1.55 (d, J=7.1 Hz, 3H), 1.39 (d, J=6.5 Hz, 3H); [M+H]⁺ 483.

Example 185: 3-(4-((R)-3-Methylpiperazin-1-yl)benzamido)-N-(1-phenylethyl)-1H-indazole-5-carboxamide 2,2,2-trifluoroacetate

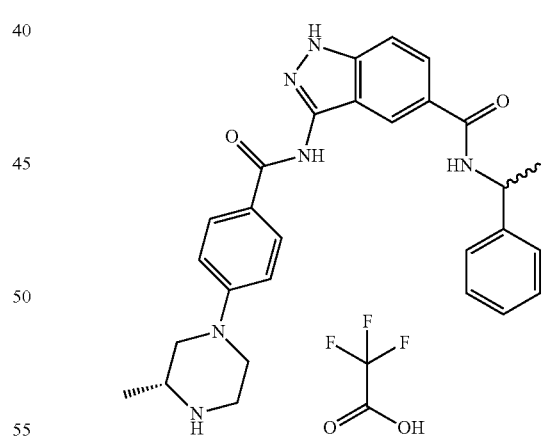

¹H NMR (400 MHz, Methanol-d₄) δ 8.39 (s, 1H), 7.98 (d, J=8.4 Hz, 2H), 7.89 (dd, J=8.9, 1.7 Hz, 1H), 7.51 (d, J=8.8 Hz, 1H), 7.39 (dd, J=7.5, 1.7 Hz, 2H), 7.29 (t, J=7.6 Hz, 2H), 7.24-7.15 (m, 1H), 7.10-7.03 (m, 2H), 5.24 (q, J=7.1 Hz, 1H), 4.03-3.89 (m, 2H), 3.51-3.40 (m, 2H), 3.25 (td, J=12.2, 3.3 Hz, 1H), 3.11 (ddd, J=13.4, 11.8, 3.0 Hz, 1H), 2.89 (dd, J=13.6, 10.6 Hz, 1H), 1.54 (d, J=7.1 Hz, 3H), 1.37 (d, J=6.6 Hz, 3H); [M+H]⁺ 483.

Example 186: 3-(4-((3R,5S)-3,5-Dimethylpiperazin-1-yl)benzamido)-N-(1-phenylethyl)-1H-indazole-5-carboxamide

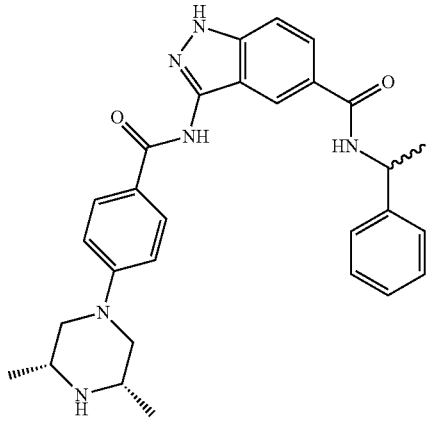 [SMILES: CC(NC(=O)c1ccc2[nH]nc(NC(=O)c3ccc(N4C[C@@H](C)N[C@@H](C)C4)cc3)c2c1)c1ccccc1]

$^1$H NMR (400 MHz, Methanol-d$_4$) δ 8.36 (dd, J=1.7, 0.8 Hz, 1H), 8.00-7.93 (m, 2H), 7.88 (dd, J=8.9, 1.7 Hz, 1H), 7.52 (dd, J=8.8, 0.8 Hz, 1H), 7.44-7.37 (m, 2H), 7.31 (t, J=7.6 Hz, 2H), 7.26-7.17 (m, 1H), 7.08-7.01 (m, 2H), 5.25 (q, J=7.0 Hz, 1H), 3.85-3.76 (m, 2H), 2.97 (ddd, J=10.7, 6.5, 3.0 Hz, 2H), 2.40 (dd, J=12.3, 10.7 Hz, 2H), 1.56 (d, J=7.1 Hz, 3H), 1.18 (d, J=6.4 Hz, 6H); [M+H]$^+$ 497.

Example 187: 3-(4-(4-Methylpiperazin-1-yl)benzamido)-N-(1-phenylpropyl)-1H-indazole-5-carboxamide

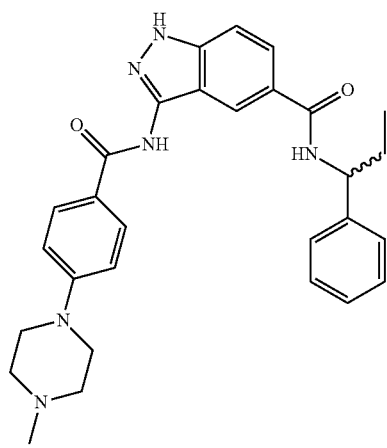 [SMILES: CCC(NC(=O)c1ccc2[nH]nc(NC(=O)c3ccc(N4CCN(C)CC4)cc3)c2c1)c1ccccc1]

$^1$H NMR (400 MHz, DMSO-d$_6$) δ 12.94 (s, 1H), 10.53 (s, 1H), 8.72 (d, J=8.3 Hz, 1H), 8.28 (s, 1H), 7.98 (d, J=8.5 Hz, 2H), 7.88 (d, J=8.8 Hz, 1H), 7.50 (d, J=8.8 Hz, 1H), 7.39 (d, J=7.7 Hz, 2H), 7.31 (t, J=7.5 Hz, 2H), 7.20 (t, J=7.2 Hz, 1H), 7.03 (d, J=8.6 Hz, 2H), 4.93 (q, J=8.1 Hz, 1H), 3.34 (s, 4H), 2.45 (t, J=4.9 Hz, 4H), 2.23 (s, 3H), 1.81 (ddt, J=27.3, 13.9, 6.9 Hz, 2H), 0.90 (t, J=7.2 Hz, 3H); [M+H]$^+$ 497.

Example 188: 3-(4-Morpholinobenzamido)-N-(1-phenylpropyl)-1H-indazole-5-carboxamide

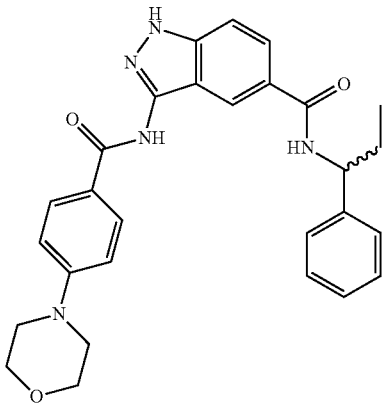 [SMILES: CCC(NC(=O)c1ccc2[nH]nc(NC(=O)c3ccc(N4CCOCC4)cc3)c2c1)c1ccccc1]

$^1$H NMR (400 MHz, DMSO-d$_6$) δ 12.95 (s, 1H), 10.56 (s, 1H), 8.72 (d, J=8.4 Hz, 1H), 8.29 (s, 1H), 8.04-7.97 (m, 2H), 7.89 (dd, J=8.9, 1.6 Hz, 1H), 7.50 (dd, J=8.8, 0.8 Hz, 1H), 7.43-7.35 (m, 2H), 7.30 (dd, J=8.3, 6.8 Hz, 2H), 7.26-7.16 (m, 1H), 7.04 (d, J=9.1 Hz, 2H), 4.93 (q, J=8.5 Hz, 1H), 3.75 (t, J=4.9 Hz, 4H), 3.27 (t, J=4.9 Hz, 4H), 1.93-1.72 (m, 2H), 0.90 (t, J=7.3 Hz, 3H); [M+H]$^+$ 484.

Example 189: N-(4-Fluorobenzyl)-3-(4-(4-methylpiperazin-1-yl)benzamido)-1H-indazole-5-carboxamide

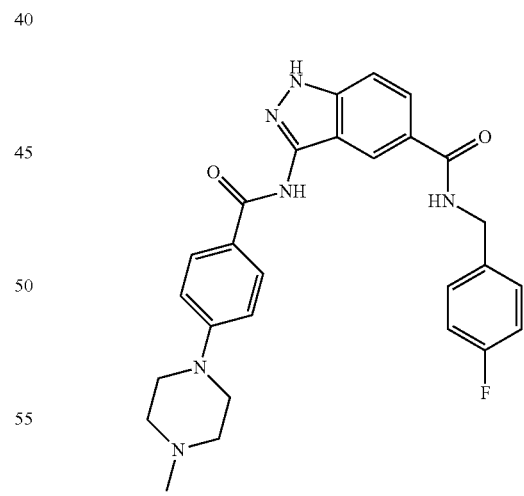

$^1$H NMR (400 MHz, Methanol-d$_4$) δ 8.36 (dd, J=1.7, 0.9 Hz, 1H), 8.01-7.95 (m, 2H), 7.91 (dd, J=8.8, 1.7 Hz, 1H), 7.53 (dd, J=8.8, 0.8 Hz, 1H), 7.43-7.34 (m, 2H), 7.10-6.98 (m, 4H), 4.55 (s, 2H), 3.39 (t, J=5.1 Hz, 4H), 2.62 (t, J=5.1 Hz, 4H), 2.37 (s, 3H); [M+H]$^+$ 487.

Example 190: (S)-3-(4-(4-Methylpiperazin-1-yl)benzamido)-N-(1-phenylpropyl)-1H-indazole-5-carboxamide

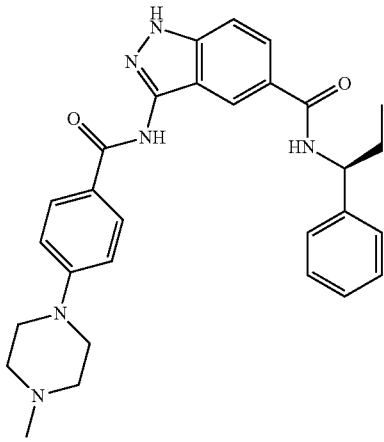 [SMILES: CC[C@H](NC(=O)c1ccc2[nH]nc(NC(=O)c3ccc(N4CCN(C)CC4)cc3)c2c1)c1ccccc1]

$^1$H NMR (400 MHz, DMSO-d$_6$) δ 12.94 (s, 1H), 10.53 (s, 1H), 8.72 (d, J=8.4 Hz, 1H), 8.28 (s, 1H), 7.98 (d, J=8.8 Hz, 2H), 7.89 (dd, J=8.8, 1.7 Hz, 1H), 7.50 (d, J=8.8 Hz, 1H), 7.43-7.34 (m, 2H), 7.31 (t, J=7.6 Hz, 2H), 7.26-7.16 (m, 1H), 7.03 (d, J=8.8 Hz, 2H), 4.93 (td, J=8.7, 6.1 Hz, 1H), 3.31 (t, J=4.9 Hz, 4H), 2.45 (t, J=5.1 Hz, 4H), 2.23 (s, 3H), 1.93-1.72 (m, 2H), 0.90 (t, J=7.2 Hz, 3H); [M+H]$^+$ 497.

Example 191: (R)-3-(4-(4-Methylpiperazin-1-yl)benzamido)-N-(1-phenylpropyl)-1H-indazole-5-carboxamide

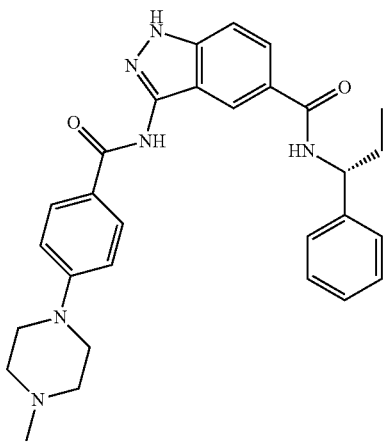 [SMILES: CC[C@@H](NC(=O)c1ccc2[nH]nc(NC(=O)c3ccc(N4CCN(C)CC4)cc3)c2c1)c1ccccc1]

$^1$H NMR (400 MHz, DMSO-d$_6$) δ 12.94 (s, 1H), 10.53 (s, 1H), 8.72 (d, J=8.4 Hz, 1H), 8.28 (s, 1H), 8.02-7.94 (m, 2H), 7.89 (dd, J=8.9, 1.6 Hz, 1H), 7.50 (dd, J=8.8, 0.8 Hz, 1H), 7.43-7.33 (m, 2H), 7.30 (dd, J=8.4, 6.8 Hz, 2H), 7.26-7.16 (m, 1H), 7.06-6.99 (m, 2H), 4.93 (td, J=8.7, 6.2 Hz, 1H), 3.31 (t, J=5.1 Hz, 4H), 2.44 (dt, J=12.4, 6.1 Hz, 4H), 2.23 (s, 3H), 1.93-1.72 (m, 2H), 0.90 (t, J=7.2 Hz, 3H); [M+H]$^+$ 497.

Example 192: (R)-3-(4-(4-Methylpiperazin-1-yl)benzamido)-N-(1-phenylpropyl)-1H-indazole-5-carboxamide Hydrochloride

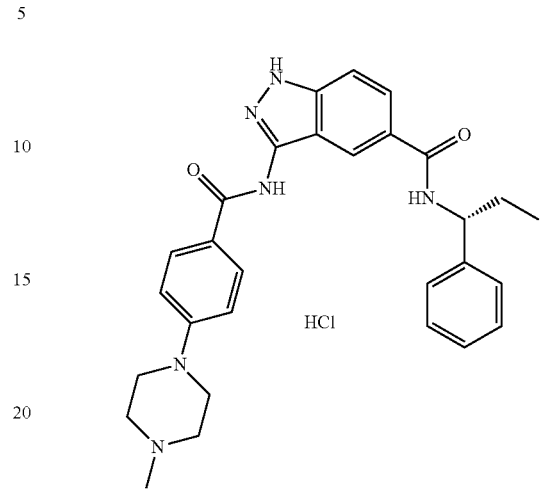

$^1$H NMR (400 MHz, DMSO-d$_6$) δ 10.62 (s, 1H), 8.73 (d, J=8.5 Hz, 1H), 8.27 (s, 1H), 8.03 (d, J=8.5 Hz, 2H), 7.90 (d, J=8.4 Hz, 1H), 7.51 (d, J=8.6 Hz, 1H), 7.39 (d, J=8.1 Hz, 3H), 7.31 (t, J=7.5 Hz, 3H), 7.22 (d, J=8.0 Hz, 1H), 7.12 (d, J=8.6 Hz, 2H), 4.92 (d, J=8.5 Hz, 1H), 4.06 (d, J=12.5 Hz, 2H), 3.59-3.47 (m, 4H), 3.21 (d, J=12.2 Hz, 1H), 3.17 (s, 2H), 3.12 (s, 2H), 2.82 (s, 3H), 1.83 (m, 2H), 1.26 (dd, J=15.7, 8.4 Hz, 4H), 0.90 (t, J=7.3 Hz, 4H); [M+H]$^+$ 497.

Example 193: (S)-3-(4-(4-Methylpiperazin-1-yl)benzamido)-N-(1-phenylbutyl)-1H-indazole-5-carboxamide

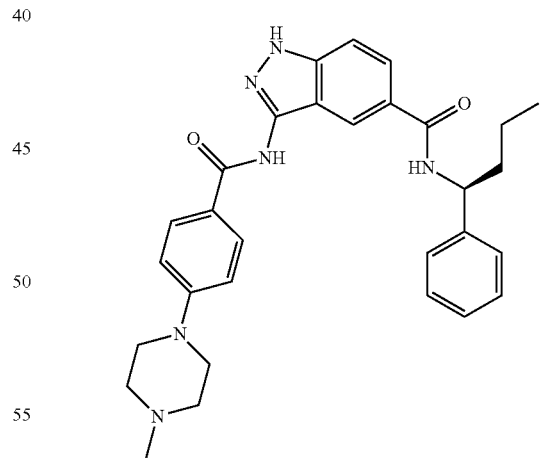

$^1$H NMR (400 MHz, DMSO-d$_6$) δ 12.94 (s, 1H), 10.53 (s, 1H), 8.73 (d, J=8.4 Hz, 1H), 8.28 (d, J=1.5 Hz, 1H), 8.02-7.94 (m, 2H), 7.88 (dd, J=8.8, 1.6 Hz, 1H), 7.50 (d, J=8.8 Hz, 1H), 7.44-7.34 (m, 2H), 7.34-7.27 (m, 2H), 7.26-7.16 (m, 1H), 7.03 (d, J=9.1 Hz, 2H), 5.09-4.98 (m, 1H), 3.31 (t, J=5.1 Hz, 4H), 2.45 (t, J=5.1 Hz, 4H), 2.23 (s, 3H), 1.86 (dtd, J=14.3, 9.3, 5.3 Hz, 1H), 1.71 (dq, J=15.3, 6.2 Hz, 1H), 1.45-1.21 (m, 2H), 0.90 (t, J=7.4 Hz, 3H); [M+H]$^+$ 511.

Example 194: (R)-3-(4-(4-Methylpiperazin-1-yl)benzamido)-N-(1-phenylbutyl)-1H-indazole-5-carboxamide

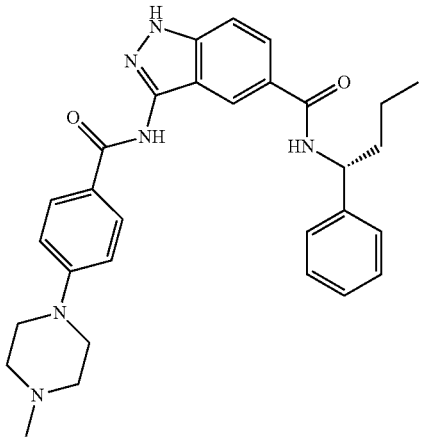 [SMILES: CCC[C@@H](NC(=O)c1ccc2[nH]nc(NC(=O)c3ccc(N4CCN(C)CC4)cc3)c2c1)c1ccccc1]

$^1$H NMR (400 MHz, DMSO-d$_6$) δ 12.94 (s, 1H), 10.53 (s, 1H), 8.73 (d, J=8.4 Hz, 1H), 8.28 (d, J=1.5 Hz, 1H), 8.02-7.94 (m, 2H), 7.88 (dd, J=8.8, 1.6 Hz, 1H), 7.50 (d, J=8.8 Hz, 1H), 7.43-7.35 (m, 2H), 7.34-7.27 (m, 2H), 7.26-7.16 (m, 1H), 7.03 (d, J=9.1 Hz, 2H), 5.09-4.98 (m, 1H), 3.31 (t, J=5.1 Hz, 4H), 2.45 (t, J=5.1 Hz, 4H), 2.23 (s, 3H), 1.86 (dtd, J=14.3, 9.3, 5.3 Hz, 1H), 1.71 (dq, J=15.3, 6.2 Hz, 1H), 1.45-1.21 (m, 2H), 0.90 (t, J=7.4 Hz, 3H); [M+H]$^+$ 511.

Example 195: N-(3-Fluorobenzyl)-3-(4-(4-methylpiperazin-1-yl)benzamido)-1H-indazole-5-carboxamide

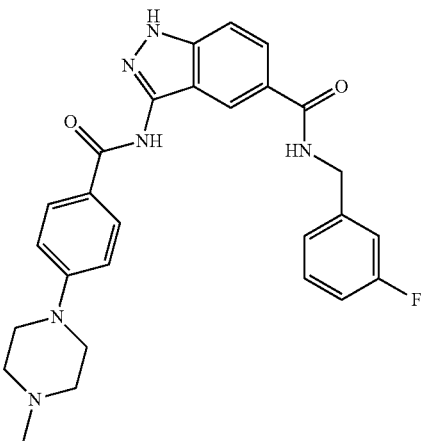 [SMILES: CN1CCN(c2ccc(C(=O)Nc3n[nH]c4ccc(C(=O)NCc5cccc(F)c5)cc34)cc2)CC1]

$^1$H NMR (400 MHz, DMSO-d$_6$) δ 12.97 (s, 1H), 10.55 (s, 1H), 9.07 (t, J=6.0 Hz, 1H), 8.33 (s, 1H), 7.98 (d, J=8.8 Hz, 2H), 7.90 (dd, J=8.8, 1.7 Hz, 1H), 7.52 (d, J=8.8 Hz, 1H), 7.36 (td, J=7.9, 6.1 Hz, 1H), 7.19-6.99 (m, 5H), 4.48 (d, J=5.9 Hz, 2H), 3.30 (t, J=5.0 Hz, 4H), 2.45 (t, J=5.1 Hz, 4H), 2.23 (s, 3H); [M+H]$^+$ 487.

Example 196: N-(2-Fluorobenzyl)-3-(4-(4-methylpiperazin-1-yl)benzamido)-1H-indazole-5-carboxamide

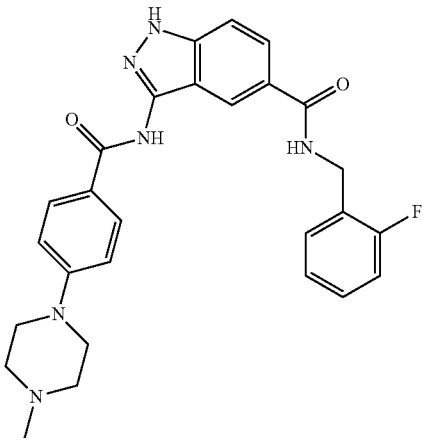 [SMILES: CN1CCN(c2ccc(C(=O)Nc3n[nH]c4ccc(C(=O)NCc5ccccc5F)cc34)cc2)CC1]

$^1$H NMR (400 MHz, DMSO-d$_6$) δ 12.97 (s, 1H), 10.55 (s, 1H), 9.01 (t, J=5.9 Hz, 1H), 8.33 (s, 1H), 7.98 (d, J=8.9 Hz, 2H), 7.90 (dd, J=8.8, 1.7 Hz, 1H), 7.52 (d, J=8.9 Hz, 1H), 7.32 (ddd, J=25.7, 8.1, 6.0 Hz, 2H), 7.22-7.11 (m, 2H), 7.02 (d, J=9.0 Hz, 2H), 4.51 (d, J=5.8 Hz, 2H), 3.30 (t, J=5.1 Hz, 4H), 2.45 (t, J=5.0 Hz, 4H), 2.23 (s, 3H); [M+H]$^+$ 487.

Example 197: N-(Cyclopropyl(phenyl)methyl)-3-(4-(4-methylpiperazin-1-yl)benzamido)-1H-indazole-5-carboxamide

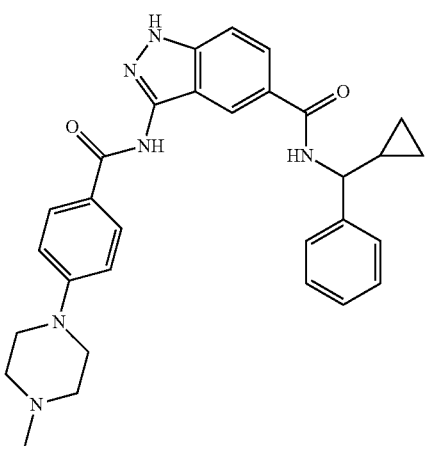 [SMILES: CN1CCN(c2ccc(C(=O)Nc3n[nH]c4ccc(C(=O)NC(c5ccccc5)C5CC5)cc34)cc2)CC1]

$^1$H NMR (400 MHz, DMSO-d$_6$) δ 12.94 (s, 1H), 10.53 (s, 1H), 8.99 (d, J=8.3 Hz, 1H), 8.30 (s, 1H), 7.98 (d, J=8.9 Hz, 2H), 7.91 (dd, J=8.8, 1.7 Hz, 1H), 7.50 (dd, J=8.7, 0.8 Hz, 1H), 7.48-7.44 (m, 2H), 7.31 (t, J=7.5 Hz, 2H), 7.22 (t, J=7.3 Hz, 1H), 7.03 (d, J=8.8 Hz, 2H), 4.39 (t, J=9.0 Hz, 1H), 3.30 (t, J=5.1 Hz, 4H), 2.45 (t, J=5.0 Hz, 4H), 2.23 (s, 3H), 1.35-1.33 (m, 1H), 0.54 (d, J=8.1 Hz, 2H), 0.39 (s, 2H); [M+H]$^+$ 509.

Example 198: tert-Butyl 4-(4-((5-(((thiophen-2-ylmethyl)carbamoyl)-1H-indazol-3-yl)carbamoyl)phenyl)-3,6-tetrahydropyridine-1(2H)-carboxylate

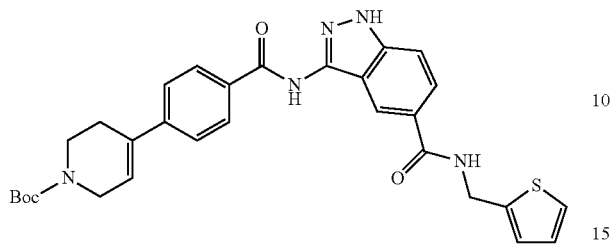

$^1$H NMR (400 MHz, Chloroform-d) δ 11.39 (s, 1H), 9.50 (s, 1H), 8.22 (s, 1H), 7.87 (s, 2H), 7.55 (s, 1H), 7.39 (s, 1H), 7.31 (s, 2H), 6.97 (s, 2H), 6.88 (s, 1H), 6.02 (s, 1H), 4.70 (s, 2H), 4.04 (s, 2H), 3.58 (s, 2H), 2.40 (s, 2H), 1.49 (s, 9H); [M+H]$^+$ 558.

Example 199: 3-(4-(1,2,3,6-Tetrahydropyridin-4-yl)benzamido)-N-(thiophen-2-ylmethyl)-1H-indazole-5-carboxamide

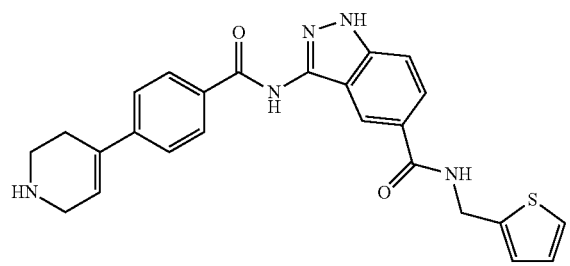 [SMILES: O=C(NCc1cccs1)c1ccc2[nH]nc(NC(=O)c3ccc(C4=CCNCC4)cc3)c2c1]

$^1$H NMR (400 MHz, DMSO-d$_6$) δ 13.09 (s, 1H), 10.90 (s, 1H), 9.22 (s, 2H), 9.13 (t, J=5.9 Hz, 1H), 8.32 (s, 1H), 8.12 (d, J=8.1 Hz, 2H), 7.94-7.86 (m, 1H), 7.67 (d, J=8.2 Hz, 2H), 7.54 (d, J=8.8 Hz, 1H), 7.36 (d, J=5.0 Hz, 1H), 7.00 (d, J=3.3 Hz, 1H), 6.97-6.92 (m, 1H), 6.40 (s, 1H), 4.62 (d, J=5.8 Hz, 2H), 3.79 (s, 2H), 3.69 (dd, J=14.2, 5.2 Hz, 2H), 2.75 (s, 2H); [M+H]$^+$ 458.

Example 200: 3-(4-Hydroxybenzamido)-N-(thiophen-2-ylmethyl)-1H-indazole-5-carboxamide

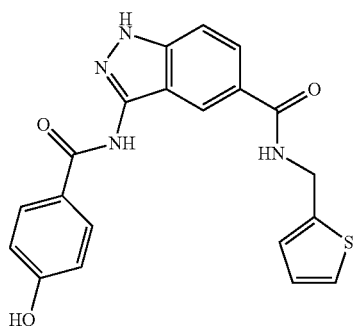

$^1$H NMR (400 MHz, Methanol-d$_4$) δ 8.35 (d, J=1.1 Hz, 1H), 7.98-7.93 (m, 2H), 7.90 (dd, J=8.9, 1.7 Hz, 1H), 7.54 (d, J=8.7 Hz, 1H), 7.27 (dd, J=5.1, 1.3 Hz, 1H), 7.04 (d, J=2.8 Hz, 1H), 6.98-6.87 (m, 3H), 4.74 (s, 2H); [M+H]$^+$ 393.

Example 201: 3-(4-(2-Morpholinoethoxy)benzamido)-N-(thiophen-2-ylmethyl)-1H-indazole-5-carboxamide

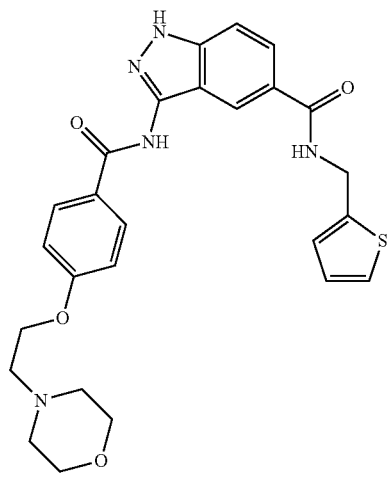 [SMILES: O=C(NCc1cccs1)c1ccc2[nH]nc(NC(=O)c3ccc(OCCN4CCOCC4)cc3)c2c1]

$^1$H NMR (400 MHz, Methanol-d$_4$) δ 8.38 (s, 1H), 8.02 (d, J=8.4 Hz, 2H), 7.89 (dd, J=8.8, 1.7 Hz, 1H), 7.52 (d, J=8.8 Hz, 1H), 7.25 (dd, J=5.1, 1.2 Hz, 1H), 7.13-7.06 (m, 2H), 7.02 (dd, J=3.5, 1.2 Hz, 1H), 6.92 (dd, J=5.1, 3.5 Hz, 1H), 4.73 (s, 2H), 4.45 (t, J=4.8 Hz, 2H), 4.02 (br s, 2H), 3.83 (br s, 2H), 3.65 (t, J=4.8 Hz, 2H), 3.58 (br s, 2H), 3.28 (br s, 2H); [M+H]$^+$ 506.

Example 202: tert-Butyl 3-(4-nitrobenzamido)-5-((thiophen-2-ylmethyl)carbamoyl)-1H-indazole-1-carboxylate

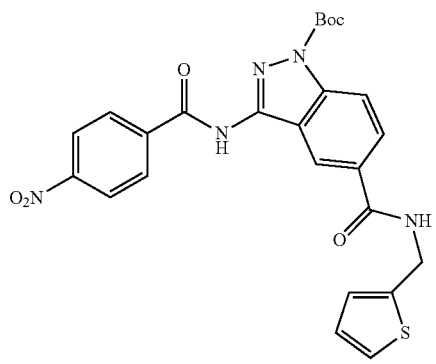 [SMILES: CC(C)(C)OC(=O)n1nc(NC(=O)c2ccc([N+](=O)[O-])cc2)c2cc(C(=O)NCc3cccs3)ccc21]

To a solution of SM (50 mg, 0.13 mmol) in DMF (1.00 mL) was added DMAP (35 mg, 0.26 mmol) and 4-nitrobenzoyl chloride (74 mg, 0.40 mmol) at room temperature. The resulting mixture was stirred at room temperature for overnight, separated by using EtOAc and water, and then extracted with EtOAc (50 mL×2). The combined organic layers were dried over MgSO$_4$, filtered and concentrated in vacuo to give the crude product (15 mg, 21%) as a brown oil.

¹H NMR (400 MHz, CDCl₃) δ 8.88 (s, 1H), 8.62 (s, 1H), 8.40 (dd, J=6.8, 2.0 Hz, 2H), 8.20 (d, J=8.4 Hz, 1H), 8.15-8.10 (m, 3H), 7.24 (d, J=1.2 Hz, 1H), 7.07 (d, J=2.4 Hz, 1H), 7.00-6.97 (m, 1H), 6.67-6.65 (m, 1H), 4.86 (d, J=5.6 Hz, 2H), 1.73 (s, 9H); [M+H]⁺ 520.

Example 203: 3-(4-Nitrobenzamido)-N-(thiophen-2-ylmethyl)-1H-indazole-5-carboxamide

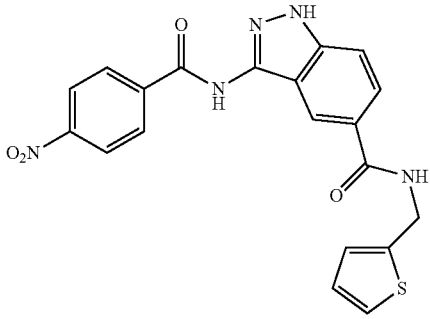 [SMILES: O=C(NCc1cccs1)c1ccc2[nH]nc(NC(=O)c3ccc([N+](=O)[O-])cc3)c2c1]

¹H NMR (400 MHz, CDCl₃) δ 13.11 (s, 1H), 11.25 (s, 1H), 9.11-9.10 (m, 1H), 8.41-8.30 (m, 5H), 7.91 (d, J=7.2 Hz, 1H), 7.55 (d, J=8.4 Hz, 1H), 7.37 (d, J=6.4 Hz, 1H), 7.00 (s, 1H), 6.96-6.94 (m, 1H), 4.63 (d, J=6.0 Hz, 2H); [M+H]⁺ 422.

Example 204: 3-(3-Nitrobenzamido)-N-(thiophen-2-ylmethyl)-1H-indazole-5-carboxamide

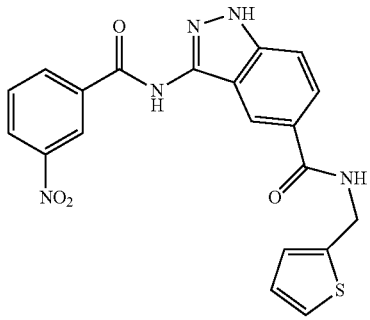 [SMILES: O=C(NCc1cccs1)c1ccc2[nH]nc(NC(=O)c3cccc([N+](=O)[O-])c3)c2c1]

¹H NMR (400 MHz, CDCl₃) δ 13.11 (s, 1H), 11.30 (s, 1H), 9.10 (t, J=5.6 Hz, 1H), 8.93 (s, 1H), 8.54-8.48 (m, 2H), 8.36 (s, 1H), 7.92-7.86 (m, 2H), 7.56 (d, J=8.4 Hz, 1H), 7.37 (d, J=4.8 Hz, 1H), 7.00 (s, 1H), 6.96-6.94 (m, 1H), 4.63 (d, J=6.0 Hz, 2H); [M+1]⁺ 422.

Example 205: 3-(4-Aminobenzamido)-N-(thiophen-2-ylmethyl)-1H-indazole-5-carboxamide

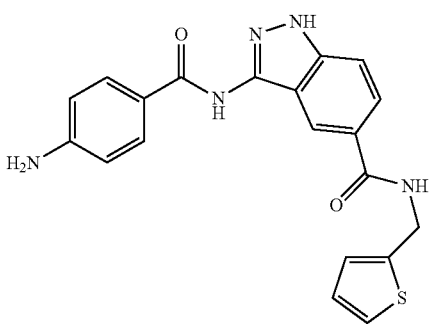

To a solution of SM (400 mg, 0.76 mmol) in MeOH (5.0 mL) was added ammonium formate (968 mg, 15.3 mmol) at room temperature. The resulting mixture was stirred under reflux for overnight. The mixture was filtered through a Celite pad and then evaporated to remove the solvent. The residue thus obtained was precipitated with water, filtered and concentrated in vacuo to give the product (350 mg, 99%) as a yellow solid.

¹H NMR (400 MHz, DMSO-d₆) δ 9.11 (s, 1H), 8.29 (s, 1H), 7.82 (d, J=8.8 Hz, 1H), 7.50 (d, J=8.0 Hz, 1H), 7.37 (d, J=5.2 Hz, 1H), 7.00-6.93 (m, 2H), 6.60 (d, J=8.4 Hz, 1H), 5.80 (s, 1H), 4.60 (d, J=5.6 Hz, 2H); [M+H]⁺ 392.

Example 206: 3-(4-(Cyclobutanecarboxamido)benzamido)-N-(thiophen-2-ylmethyl)-1H-indazole-5-carboxamide

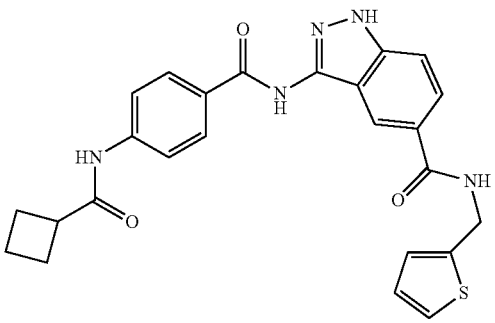 [SMILES: O=C(NCc1cccs1)c1ccc2[nH]nc(NC(=O)c3ccc(NC(=O)C4CCC4)cc3)c2c1]

A mixture of SM (50 mg, 0.12 mmol), cyclobutanecarboxylic acid (19 mg, 0.19 mmol), DIPEA (47 mg, 0.36 mmol) and HBTU (72 mg, 0.19 mmol) in DMF (1.00 mL) was stirred at room temperature for overnight. The resulting mixture was purified with prep. HPLC to give the title product (10.1 mg, 17%).

¹H NMR (400 MHz, DMSO-d₆) δ 10.79 (s, 1H), 9.28 (s, 1H), 8.40-8.38 (m, 2H), 8.12 (dd, J=9.0, 1.4 Hz, 1H), 7.84 (d, J=8.6 Hz, 2H), 7.38 (dd, J=5.0, 1.4 Hz, 1H), 7.02 (d, J=2.4 Hz, 1H), 6.96-6.94 (m, 1H), 6.62 (d, J=8.6 Hz, 2H), 5.92 (s, 2H), 4.64 (d, J=6.0 Hz, 2H), 4.23 (m, 1H), 2.41-2.28 (m, 4H), 2.10-2.02 (m, 1H), 1.93-1.90 (m, 1H); [M+1-1]⁺ 474.

Example 207: N-(Thiophen-2-ylmethyl)-3-(4-(1-(trifluoromethyl)cyclopropanecarboxamido)benzamido)-1H-indazole-5-carboxamide

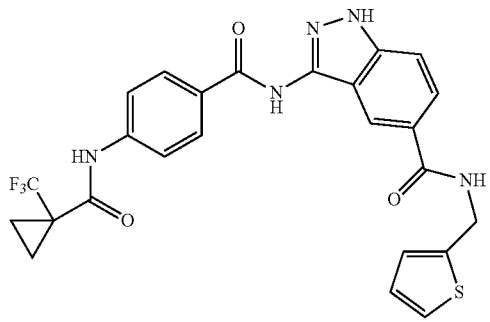

-continued

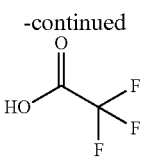

¹H NMR (400 MHz, DMSO-d₆) δ 10.84 (s, 1H), 9.30 (t, J=5.8 Hz, 1H), 9.11 (s, 1H), 8.45 (s, 1H), 8.37 (d, J=8.8 Hz 1H), 8.15 (d, J=8.8 Hz, 1H), 7.84 (d, J=8.8 Hz, 1H), 7.37 (d, J=4.8 Hz, 1H), 7.02 (d, J=3.2 Hz, 1H), 6.97-6.95 (m, 1H), 6.64 (d, J=8.4 Hz, 2H), 4.64 (d, J=5.6 Hz, 2H), 2.05 (s, 2H), 1.56 (s, 1H); [M+H]⁺ 528.

Example 208: 3-(4-(3-Oxocyclobutanecarboxamido) benzamido)-N-(thiophen-2-ylmethyl)-1H-indazole-5-carboxamide

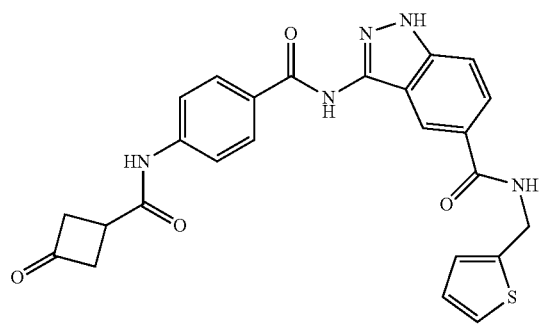 [SMILES: O=C1CC(C(=O)Nc2ccc(C(=O)Nc3n[nH]c4ccc(C(=O)NCc5cccs5)cc34)cc2)C1]

¹H NMR (400 MHz, DMSO-d₆) δ 10.89 (s, 1H), 9.30 (t, J=5.8 Hz, 1H), 8.43-8.41 (m, 2H), 8.15 (d, J=9.2 Hz, 1H), 7.86 (d, J=8.8 Hz, 2H), 7.32 (d, J=5.2 Hz, 1H), 7.02 (s, 1H), 6.97-6.95 (m, 2H), 6.65 (d, J=8.8 Hz, 2H), 4.64 (d, J=5.6 Hz, 2H), 4.39-4.36 (m, 1H), 3.54-5.46 (m, 4H); [M+H]⁺ 488.

Example 209: 3-(4-(4-Acetylpiperazin-1-yl)benzamido)-N-(1-(thiophen-3-yl)propyl)-1H-indazole-5-carboxamide

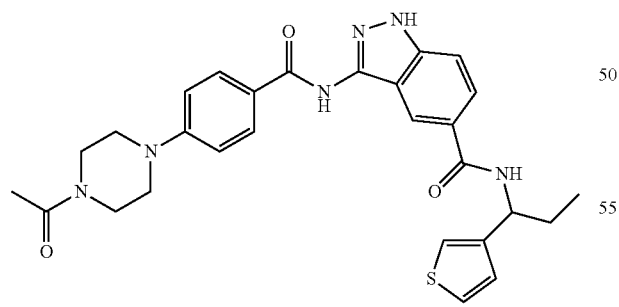

¹H NMR (400 MHz, DMSO-d₆) δ 12.96 (s, 1H), 10.55 (s, 1H), 8.80 (d, J=8.4 Hz, 1H), 8.30 (s, 1H), 8.00 (d, J=9.2 Hz, 2H), 7.90 (dd, J=10.4, 1.6 Hz, 1H), 7.51 (d, J=8.8 Hz, 1H), 7.36 (dd, J=4.8, 1.2 Hz, 1H), 7.05 (d, J=8.8 Hz, 2H), 7.01 (d, J=3.2 Hz, 1H), 6.97-6.95 (m, 1H), 5.25-5.21 (m, 1H), 3.60 (t, J=5.2 Hz, 4H), 2.51-2.49 (m, 7H), 1.97-1.92 (m, 2H), 0.93 (t, J=7.4 Hz, 3H); [M+H]⁺ 531.

Example 210: tert-Butyl (S)-2-((4-((5-((thiophen-2-ylmethyl)carbamoyl)-1H-indazol-3-yl)carbamoyl) phenyl)carbamoyl)pyrrolidine-1-carboxylate

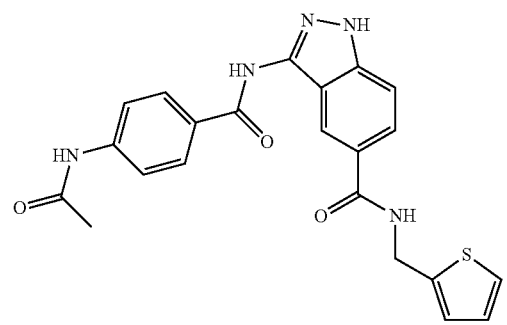

[M+H]⁺ 589.

Example 211: 3-(4-Acetamidobenzamido)-N-(thiophen-2-ylmethyl)-1H-indazole-5-carboxamide

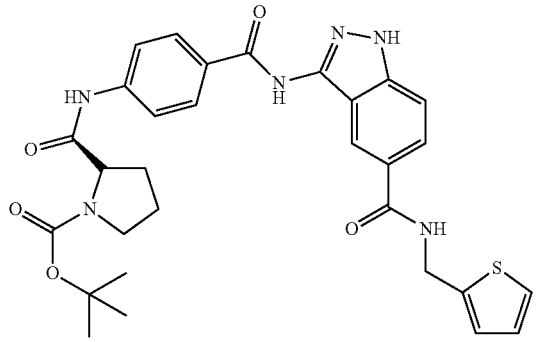

¹H NMR (400 MHz, DMSO-d₆) δ 13.00 (brs, 1H), 10.73 (s, 1H), 10.25 (brs, 1H), 9.12 (s, 1H), 8.37 (s, 1H), 8.05 (d, J=8.0 Hz, 2H), 7.89 (d, J=8.4 Hz, 1H), 7.13 (dd, J=8.4, 1.6 Hz, 1H), 7.36 (s, 1H), 6.99 (d, J=8.4 Hz, 2H), 4.63 (d, J=5.6, 2H), 2.26 (s, 3H); [M+H]⁺ 434.

Example 212: 3-(4-(1H-Imidazol-1-yl)benzamido)-N-(thiophen-2-ylmethyl)-1H-indazole-5-carboxamide

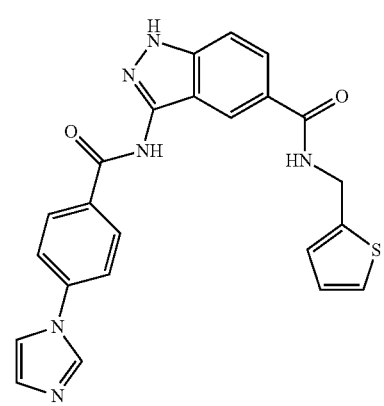 [SMILES: O=C(NCc1cccs1)c1ccc2[nH]nc(NC(=O)c3ccc(-n4ccnc4)cc3)c2c1]

¹H NMR (400 MHz, Methanol-d₄) δ 9.57 (s, 1H), 8.42 (s, 1H), 8.33 (d, J=8.1 Hz, 2H), 8.20 (s, 1H), 7.93 (dd, J=16.5, 8.5 Hz, 3H), 7.81 (s, 1H), 7.61-7.53 (m, 1H), 7.28 (d, J=5.2 Hz, 1H), 7.08-7.02 (m, 1H), 6.98-6.91 (m, 1H), 4.76 (s, 2H); [M+H]⁺ 443.

Example 213: 3-(4-(1-Methylpiperidin-4-yl)amino)benzamido)-N-(thiophen-2-ylmethyl)-1H-indazole-5-carboxamide

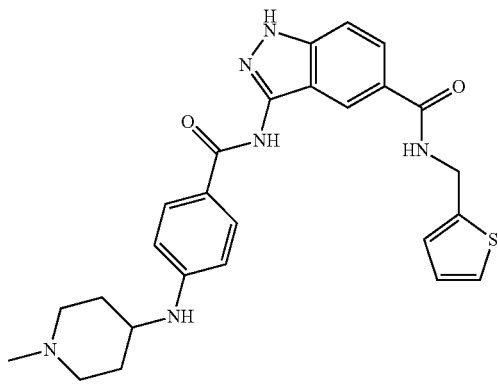 [SMILES: CN1CCC(Nc2ccc(C(=O)Nc3n[nH]c4ccc(C(=O)NCc5cccs5)cc34)cc2)CC1]

¹H NMR (400 MHz, DMSO-d₆) δ 12.91 (s, 1H), 10.36 (s, 1H), 9.10 (t, J=5.9 Hz, 1H), 8.29 (s, 1H), 7.93-7.83 (m, 3H), 7.50 (d, J=8.8 Hz, 1H), 7.36 (dd, J=5.1, 1.3 Hz, 1H), 7.03-6.91 (m, 2H), 6.64 (d, J=8.8 Hz, 2H), 6.24 (d, J=7.6 Hz, 1H), 4.61 (d, J=5.8 Hz, 2H), 2.81 (s, 2H), 2.50 (m, 1H), 2.24 (s, 4H), 1.92 (d, J=11.9 Hz, 2H), 1.45 (d, J=12.0 Hz, 2H), 1.23 (s, 1H); [M+H]⁺ 489.

Example 214: 3-(4-Fluorobenzamido)-N-(1-(pyridin-4-yl)ethyl)-1H-indazole-5-carboxamide

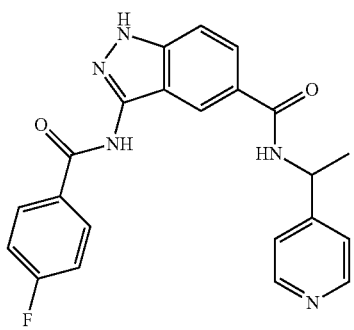 [SMILES: CC(NC(=O)c1ccc2[nH]nc(NC(=O)c3ccc(F)cc3)c2c1)c1ccncc1]

¹H NMR (400 MHz, DMSO-d₆) δ 8.90 (d, J=7.6 Hz, 1H), 8.50 (d, J=5.6 Hz, 2H), 8.35 (s, 1H), 8.18 (dd, J=8.0, 5.6 Hz, 2H), 7.93 (d, J=8.8 Hz, 1H), 7.55 (d, J=8.8 Hz, 1H), 7.42-7.32 (m, 4H), 5.15 (q, J=7.2 Hz, 1H), 1.48 (d, J=7.2 Hz, 3H); [M+H]⁺ 404.

Example 215: 3-(4-Fluorobenzamido)-N-(2-(thiophen-2-yl)propan-2-yl)-1H-indazole-5-carboxamide

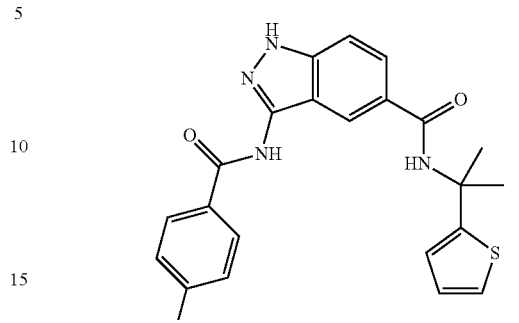

¹H NMR (400 MHz, DMSO-d₆) δ 13.63 (1H, s), 13.10 (1H, s), 8.48 (s, 1H), 8.24 (s, 1H), 8.17 (dd, J=8.68, 5.52 Hz, 2H), 7.83 (dd J=8.8, 1.48 Hz, 1H), 7.50 (d, J=8.8 Hz, 1H), 7.39 (t, J=8.8 Hz, 2H), 7.26 (dd, J=5.0, 1.2 Hz, 1H), 6.93-6.88 (m, 2H), 1.76 (s, 6H); [M+H]⁺ 423.

Example 216: 3-(4-Fluorobenzamido)-N-(1-(pyridin-2-yl)cyclopropyl)-1H-indazole-5-carboxamide

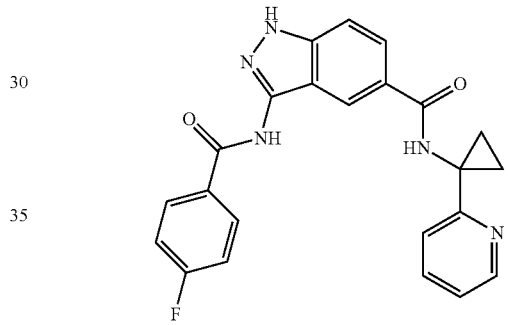

¹H NMR (400 MHz, DMSO-d₆) δ 13.04 (s, 1H), 10.90 (s, 1H), 8.95 (d, J=7.9 Hz, 1H), 8.51 (d, J=4.2 Hz, 1H), 8.35 (s, 1H), 8.17 (dd, J=5.5, 8.8 Hz, 3H), 7.93 (dd, J=8.9, 1.4 Hz, 1H), 7.76 (td, J=7.7, 1.8 Hz, 1H), 7.51 (dd, J=14.8, 8.4 Hz, 2H), 7.40 (t, J=8.8 Hz, 2H), 7.25 (dd, J=6.5, 4.9 Hz, 1H), 4.46 (t, J=4.5 Hz, 1H), 2.97-2.89 (m, 1H), 2.73-2.67 (m, 1H), 1.39 (t, J=4.5 Hz, 1H), 0.94 (d, J=6.6 Hz, 3H), 0.54-0.41 (m, 4H); [M+H]⁺ 416.

Example 217: 3-(4-Fluorobenzamido)-N-(1-(pyridin-3-yl)cyclopropyl)-1H-indazole-5-carboxamide

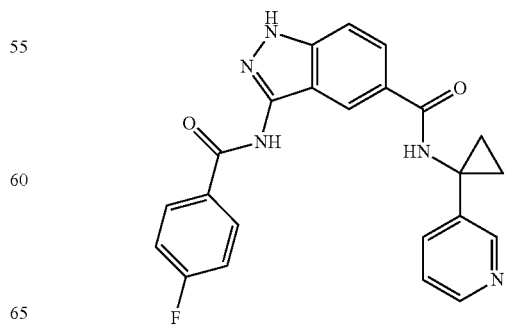

¹H NMR (400 MHz, DMSO-d₆) δ 13.06 (s, 1H), 10.92 (s, 1H), 9.08 (d, J=8.2 Hz, 1H), 8.66 (d, J=1.8 Hz, 1H), 8.44 (dd, J=4.7, 1.5 Hz, 1H), 8.33 (s, 1H), 8.17 (dd, J=8.7, 5.5 Hz, 2H), 7.92 (d, J=8.9 Hz, 1H), 7.85 (d, J=7.9 Hz, 1H), 7.54 (d, J=8.8 Hz, 1H), 7.40 (t, J=8.9 Hz, 2H), 7.36-7.34 (m, 1H), 4.39 (t, J=8.8 Hz, 1H), 1.40-1.36 (m, 1), 0.60-0.42 (m, 4H); [M+H]⁺ 416.

Preparation Example 2: Preparation of 5-bromo-1H-thieno[3,2-c]pyrazole-3-amine (23)

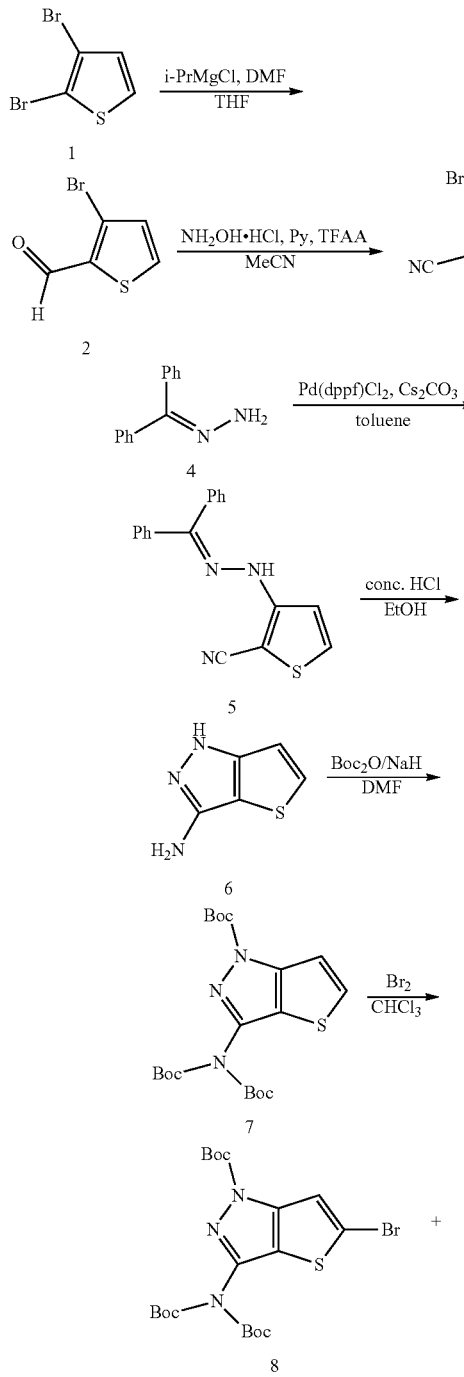

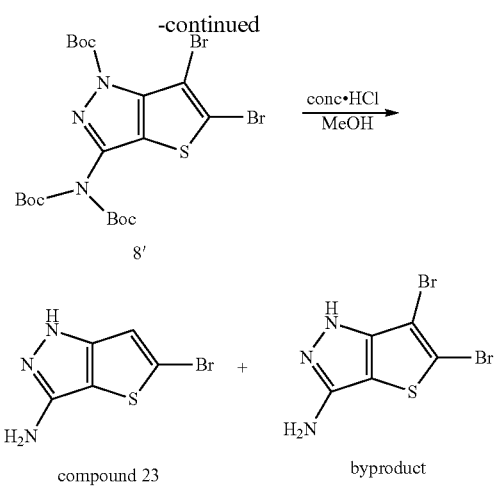

Step 1: Preparation of Intermediate 2

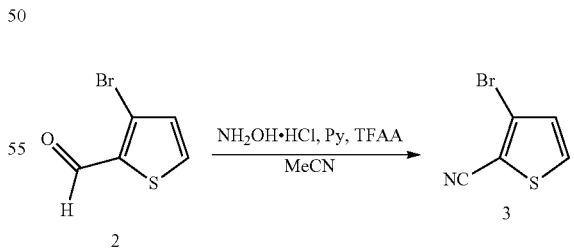

2,3-Dibromothiophene (250.0 g, 1.03 mol, 1.0 eq.) was dissolved in THF (1.8 L), cooled to −50° C., and i-PrMgCl (568 mL, 1.13 mol, 1.1 eq., 2 M in THF) was added dropwise to the mixture. The resulting mixture was stirred at −35° C. for 2 hours, followed by dropwise addition of DMF (226.5 g, 3.10 mol, 3.0 eq.). The mixture was heated to 35° C. and stirred for 0.5 hour. The reaction mixture was added with 1 M HCl (5 L), extracted with EtOAc (3 L×2), washed with water (3 L) and concentrated to give the pure intermediate 2 (197.4 g, 1.03 mol).

¹H NMR (400 MHz, DMSO-d⁶): δ 9.89-9.88 (d, J=1.2 Hz, 1H), 8.23-8.22 (d, J=5.1 Hz, 1H), 7.40-7.38 (d, J=5.1 Hz, 1H).

Step 2: Preparation of Intermediate 3

The intermediate 2 (197.4 g, 1.03 mol, 1.0 eq.) was dissolved in MeCN (2 L), and added with NH₂OH.HCl (86.2 g, 1.24 mol, 1.2 eq.) and pyridine (490.3 g, 6.19 mol, 6.0 eq.). The resulting mixture was heated to 20° C., followed by stirring for 3 hours. The mixture was cooled to 0° C., and then TFAA (650.9 g, 3.10 mol, 3.0 eq.) was added dropwise thereto while the temperature of the mixture was maintained in a range of 0 to 20° C. The reaction mixture thus obtained was stirred at room temperature for 15 hours. Subsequently, the reaction mixture was added with 1 M HCl (6.2 L), extracted with EtOAc (3 L×2), washed with water (3 L) and concentrated to give the crude product as an oil, which was then recrystallized from EtOAc (50 mL) and hexane (300 mL) to give the pure intermediate 3 (142.7 g, 0.76 mol, 73.9%).

¹H NMR (400 MHz, DMSO-d₆) δ 8.14-8.13 (d, J=5.3 Hz, 1H), 7.42-7.41 (d, J=5.2 Hz, 1H).

Step 3: Preparation of Intermediate 5

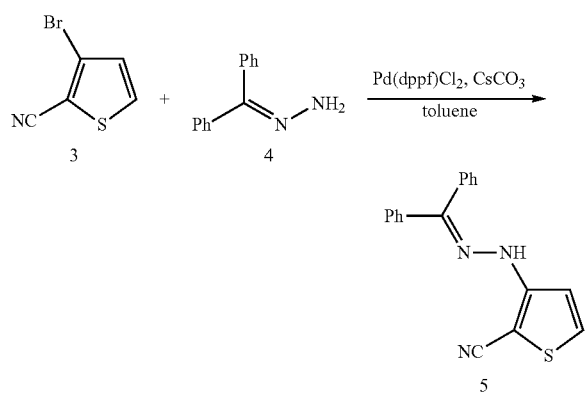

The intermediate 3 (142.7 g, 0.76 mol, 1.0 eq.) was dissolved in toluene (2.5 L) and added with a mixture of the compound 4 (178.8 g, 0.91 mol, 1.2 eq.), Cs₂CO₃ (395.5 g, 1.24 mol, 1.6 eq.) and Pd(dppf)Cl₂ (44.7 g, 0.06 mol, 0.08 eq.). The resulting mixture was stirred under N₂ at 80° C. for 16 hours. After cooled to room temperature, the reaction mixture was filtered through a Celite pad, and the filtrate thus obtained was washed with water (2 L×2) and concentrated to give the crude product. The crude product was dissolved in EtOAc (300 mL), filtered and dried to give the pure intermediate 5 (100.0 g, 0.32 mol, 43.4%).

¹H NMR (400 MHz, DMSO-d₆) δ 9.92 (s, 1H), 7.73-7.72 (d, J=5.3 Hz, 1H), 7.657.55 (m, 5H), 7.35-7.32 (m, 5H), 6.94-6.92 (d, J=5.5 Hz, 1H).

Step 4: Preparation of Intermediate 6

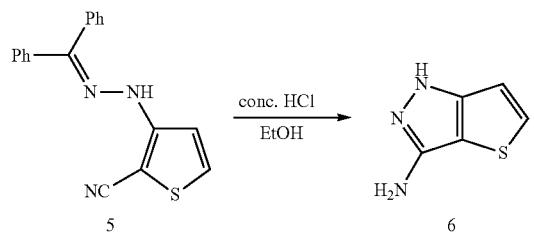 [SMILES: "EtOH" ; N#Cc1sccc1NN=C(c1ccccc1)c1ccccc1 ; Nc1n[nH]c2ccsc12]

A mixture of the intermediate 5 (100.0 g, 0.32 mol, 1.0 eq.) and concentrated HCl (1.25 L) in EtOH (2.8 L) was stirred for 2 hours at 80° C. The reaction mixture was concentrated, and the resulting concentrate was added with water (3 L) and EtOAc (2 L). Solid NaHCO₃ was added to the mixture, adjusted to the pH of about 8, and then filtered. The filtrate was extracted with EtOAc (2 L×2), washed with a saturated NaCl solution (3 L) and concentrated to give the crude product. The crude product was purified by using flash column chromatography to give the intermediate 6 (11.4 g, 0.08 mol, 25.0%).

¹H NMR (400 MHz, DMSO-d₆) δ 11.43 (s, 1H), 7.45-7.44 (d, J=5.2 Hz, 1H), 6.86-6.85 (d, J=5.2 Hz, 1H), 5.01 (s, 2H).

Step 5: Preparation of Intermediate 7

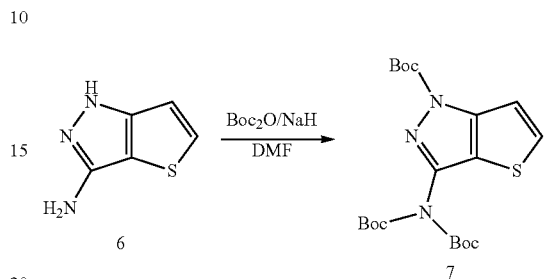

A solution of the intermediate 6 (9.5 g, 68.2 mmol, 1.0 eq.) in DMF (900 mL) was added with 60% NaH (10.9 g, 273.0 mmol, 4.0 eq.) at 0° C., stirred for 30 minutes and added with Boc₂O (59.6 g, 273.0 mmol, 4.0 eq.). The resulting mixture was stirred under N₂ at 50° C. for 16 hours. After cooled to room temperature, the mixture was poured into water (3 L) and extracted with EtOAc (1.5 L×2). The organic layer was washed with water and brine, dried and concentrated to give the crude product. The crude product was purified by using flash column chromatography to give the intermediate 7 (24.1 g, 54.8 mmol, 80.3%).

¹H NMR (400 MHz, DMSO-d₆) δ 7.96-7.94 (d, J=5.2 Hz, 1H), 7.29-7.28 (t, J=5.2 Hz, 1H), 1.61 (s, 9H), 1.46 (m, 18H).

Step 6: Preparation of Compound 23

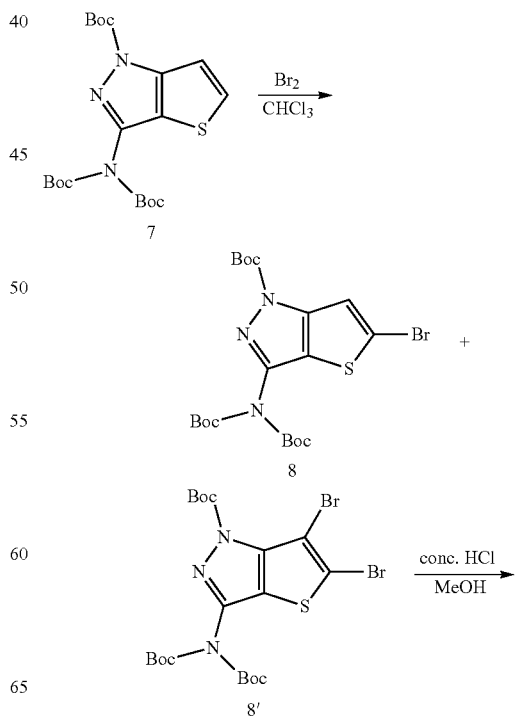

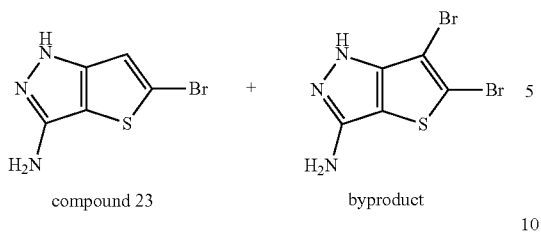

compound 23    byproduct

Bromine (9.56 g, 57.8 mmol, 1.2 eq.) was added dropwise to a solution of the intermediate 7 (21.9 g, 49.8 mmol, 1.0 eq.) in CHCl₃ (300 mL) The mixture was stirred for 6 hours at 20° C. Subsequently, the reaction mixture was concentrated. The residue was dissolved in DCM (300 mL), adjusted to the pH of about 8 by adding an aqueous solution of Na₂CO₃, extracted with DCM (300 mL×2), washed with brine and concentrated to give a mixture of 8 and 8' (21 g). The mixture was dissolved in MeOH (300 mL), added with concentrated HCl (60 mL) and stirred for 1 hour at 60° C. Subsequently, the reaction mixture was cooled to room temperature and concentrated to give the crude residue. The residue was dissolved in EtOAc (200 mL) and water (200 mL), and then adjusted to the pH of about 8 by adding NaHCO₃. The organic phase was washed with brine and concentrated to give the crude product, which was then purified by using chromatography to give the compound 23 (1.6 g, 7.3 mmol) and the byproduct (400 mg, 1.3 mmol).

¹H NMR (400 MHz, DMSO-d₆) δ 11.68 (s, 1H), 7.17 (s, 1H), 5.20 (s, 2H).

Byproduct

¹H NMR (400 MHz, DMSO-d₆) δ 12.30 (s, 1H), 12.13 (s, 1H), 5.70 (s, 2H), 5.31 (s, 4H).

Preparation Example 3: Preparation of methyl 3-amino-1H-thieno[3,2-c]pyrazole-5-carboxylate (112A-014)

Scheme 3. Reaction scheme for compound 112A-014

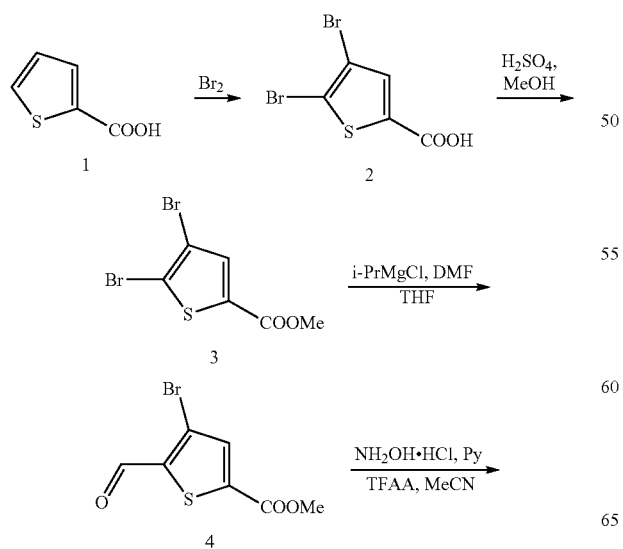

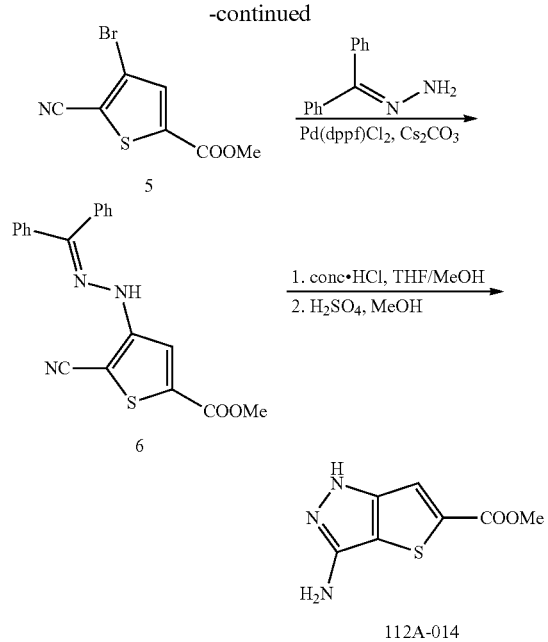

Step 1: Preparation of Compound 2

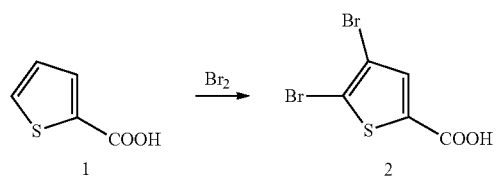 [SMILES: O=C(O)c1cccs1 ; "Br2" ; O=C(O)c1cc(Br)c(Br)s1]

The compound 1 (100.00 g, 0.78 mol) was added to Br₂ (240 mL, 4.69 mol) at room temperature. The resulting mixture was stirred at room temperature for 3 hours, added with EtOAc (500 mL), stirred for 10 minutes and filtered. The filtrate thus obtained was washed with EtOAc (2×200 mL) and H₂O (2×400 mL) The cake was dried to give the compound 2 (175.00 g, 78%) as an off-white solid.

¹H NMR (400 MHz, DMSO-d₆) δ 13.76 (s, 1H), 7.70 (s, 1H).

Step 2: Preparation of Compound 3

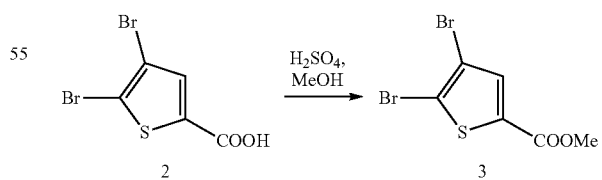

98% H₂SO₄ (120 mL) was added dropwise to a suspension of the compound 2 (205 g, 0.72 mol) in MeOH (1.5 L). The resulting mixture was heated to 70° C. and stirred at the same temperature for 16 hours. Subsequently, the reaction mixture was cooled to room temperature and concentrated. The residue was separated by using 10% aqueous solution of NaOH (1.3 L) and DCM (1.5 L), and the water phase was adjusted to the pH of 8 to 9. The DCM phase was washed with H₂O (1.5 L), dried over anhydrous Na₂SO₄ and concentrated to give the intermediate 3 (227.00 g, >100%) as an off-white solid.

¹H NMR (400 MHz, DMSO-d₆) δ 7.80-7.79 (d, d, J=0.92 HZ, 1H), 3.84 (s, 3H).

Step 3: Preparation of Compound 4

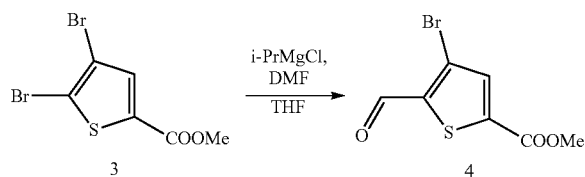 [SMILES: COC(=O)c1cc(Br)c(Br)s1 ; COC(=O)c1cc(Br)c(C=O)s1 ; "THF"]

i-PrMgCl (2 M in THF, 289 mL, 0.58 mol) was added dropwise to a solution of the intermediate 3 (157.00 g, 0.52 mol) in an anhydrous THF (1.1 L) at −35° C. The resulting mixture was stirred at −35° C. for 2 hours. Subsequently, DMF (114.76 g, 1.57 mol) was added to the mixture at the same temperature, and the system was slowly heated to room temperature, followed by stirring for 2 hours. Then, 1 M HCl (2.0 L) was added dropwise to the reaction mixture, which was then extracted with MTBE (1.5 L). The organic phase was washed with water (1.5 L), dried over anhydrous Na₂SO₄ and concentrated to give the crude compound 4 (250.0 g) as an off-yellow solid. The crude compound 4 was titrated with N-hexane (900 mL) and filtered to give the intermediate 4. The filtrate was purified by using chromatography to give the intermediate 4 (96.20 g, 73%) as an off-white solid.

¹H NMR (400 MHz, CDCl₃) δ 10.02 (s, 1H), 7.76 (s, 1H), 3.95 (s, 3H).

Step 4: Preparation of Compound 5

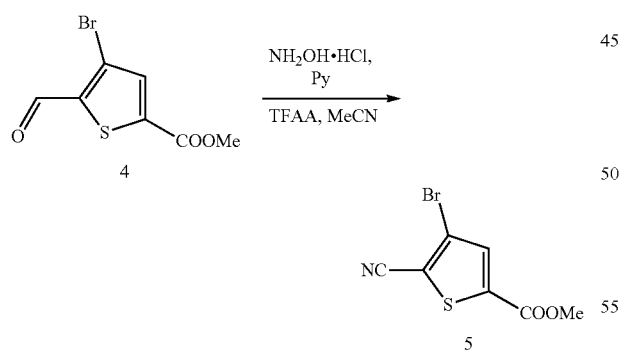

A solution of the intermediate 4 (101.00 g, 0.41 mol) in MeCN (1000 mL) was added with NH₂OH·HCl (33.81 g, 0.49 mol) and then pyridine (192.45 g, 2.43 mol). The resulting mixture was stirred at room temperature for 1 hour and added with TFAA (255.48 g, 1.22 mol) at 10 to 15° C. Then, the mixture was heated to room temperature and stirred for 3 hours. Subsequently, the mixture was slowly added dropwise to 1 M HCl (1.2 L), added with H₂O (1.0 L), and the aqueous phase was extracted with EtOAc (1.5 L), washed with H₂O (1.5 L), dried and concentrated to give the crude product. The crude product was purified by using column chromatography (PE:EtOAC=50:1 to 20:1) to give the intermediate 5 (89.00 g, 89%) as a yellow solid.

¹H NMR (400 MHz, DMSO-d₆) δ 8.03 (s, 1H), 3.90 (s, 3H).

Step 5: Preparation of Compound 6

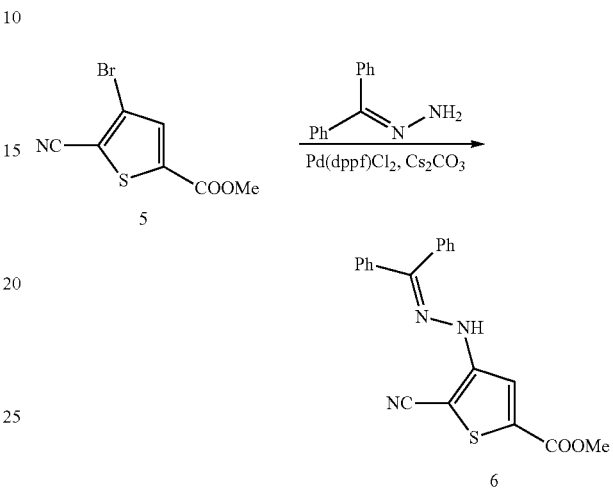

(Diphenyl-methylene)hydrazine (92.27 g, 0.47 mol), Cs₂CO₃ (188.54 g, 0.58 mol) and Pd(dppf)Cl₂·CH₂Cl₂ (21.18 g, 29.0 mmol) were added to a solution of the intermediate 5 (89.00 g, 0.36 mol) in toluene (1.7 L). The mixture was flashed, refilled with N₂ three times, heated to 100° C. and stirred at the same temperature for 16 hours. The resulting mixture was separated by using EtOAc (3.0 L) and H₂O (2.0 L). The EtOAc phase was dried and purified by using column chromatography (PE:EtOAc=10:1 to 1:1) to give the intermediate 6 (92.00 g, 70%) as a yellow solid.

¹H NMR (400 MHz, DMSO-d₆) δ 10.07 (s, 1H), 7.65-7.55 (m, 6H), 7.36-7.34 (m, 5H), 3.83 (s, 3H).

Step 6: Preparation of Compound 112A-014

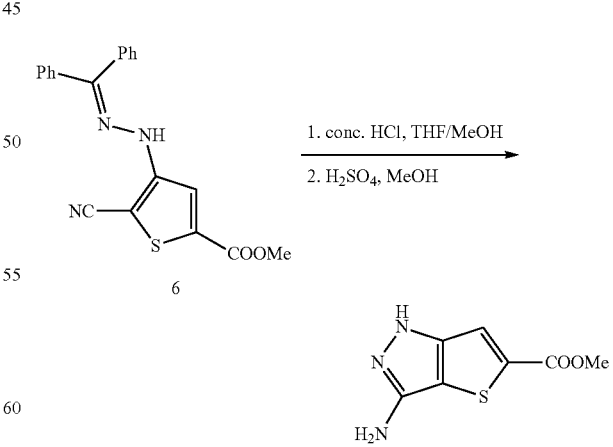

Concentrated HCl (240 mL) was added dropwise to a solution of the intermediate 6 (45.0 g, 124 mmol) in THF (700 mL)/MeOH (240 mL) at room temperature. Subsequently, the resulting mixture was heated under reflux for 16 hours. The organic solvent was removed in vacuo, and then the mixture was maintained at 4° C. for 24 hours and filtered to yield a brown solid (21.5 g) which contains a mixture of methyl ester and an acid. The solid was dissolved in MeOH (300 mL), treated with 98% $H_2SO_4$ (7.0 mL) and heated under reflux for 24 hours. The solvent was removed in vacuo, and the residue was diluted with $H_2O$ (350 mL) and adjusted to the pH of 8 to 9 by adding $NaHCO_3$. The filtered cake was washed with $H_2O$ (50 mL), titrated with DCM (350 mL), stirred for 1 hour and filtered to give the compound 112A-014 (14.6 g, 60%) as a yellow solid.

$^1$H NMR (400 MHz, DMSO-$d_6$) δ 11.83 (s, 1H), 7.57 (s, 1H), 5.27 (s, 2H), 3.84 (s, 3H); [M+H]$^+$ 198.

Preparation Example 4: Preparation of 4-(2-(piperidin-1-yl)ethylamino)-N-(5-(5-methylthiazol-2-yl)-1H-thieno[3,2-c]pyrazol-3-yl)benzamide (12)

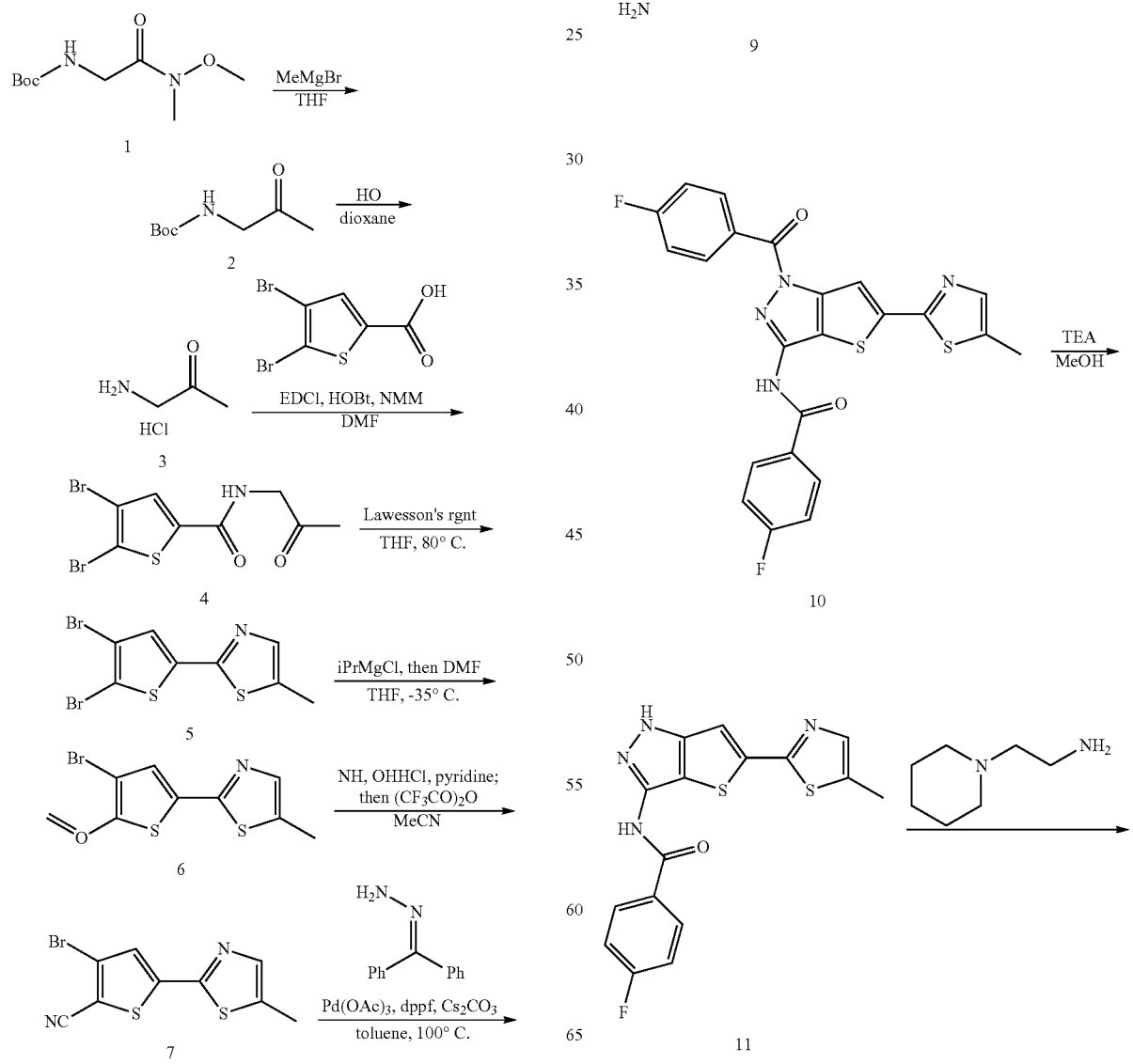

127

-continued

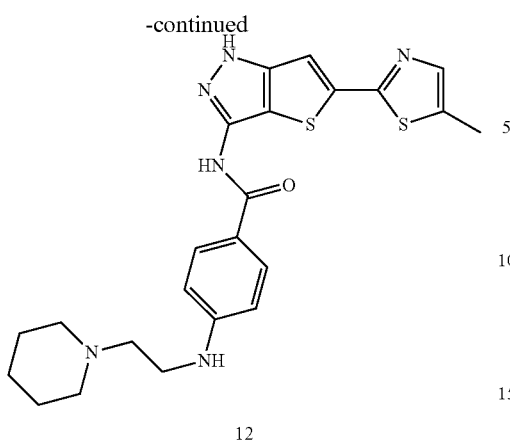

12

Step 1: Preparation of Intermediate 3

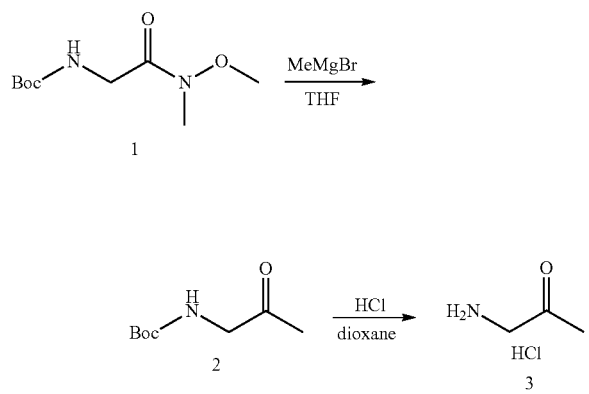

A solution of methyl magnesium bromide in diethyl ether (3.0 M, 46 mL, 137.4 mmol, 3.0 eq.) was added dropwise to a solution of tert-butyl (2-(methoxy(methyl)amino)-2-oxoethyl)carbamate 1 (10.0 g, 45.8 mmol, 1.0 eq.) in dry THF (230 mL) under nitrogen conditions at 0° C. The resulting mixture was heated to room temperature and stirred for 10 hours. Volatile materials contained in the mixture were evaporated under reduced pressure. The residual mixture was diluted with EtOAc and cooled to 0° C. The resulting solution was slowly added with a saturated aqueous ammonium chloride solution. The organic layer was separated, dried over anhydrous magnesium sulfate, filtered and concentrated to give the intermediate 2 (7.0 g, 40.4 mmol, 88%) as a brown liquid.

$^1$H NMR (400 MHz, DMSO-$d_6$) δ 7.05 (t, J=5.5 Hz, 1H), 3.72 (d, J=5.9 Hz, 2H), 2.04 (s, 3H), 1.38 (s, 9H).

A solution of hydrochloride in dioxane (4.0 M, 20.2 mL, 80.6 mmol, 2.0 eq.) was added with the intermediate 2 (7.0 g, 40.4 mmol, 1.0 eq.) while stirring at 0° C. The resulting mixture was stirred at room temperature for 13 hours. The mixture was added with EtOAc (80 mL) while stirring vigorously. The resulting mixture was filtered to give the intermediate 3 (4.1 g, 37.2 mmol, 92%) as a white solid.

$^1$H NMR (400 MHz, DMSO-$d_6$) δ 8.19 (br s, 3H), 3.91 (q, J=5.5 Hz, 2H), 2.20 (s, 3H).

128

Step 2: Preparation of Intermediate 4

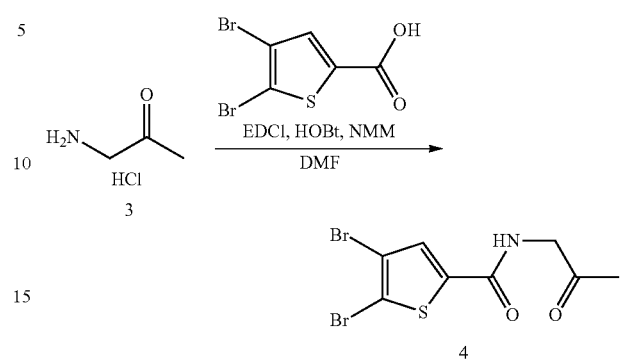

A mixture of 4,5-dibromothiophene-2-carboxylic acid (9.7 g, 33.8 mmol, 1 eq.), EDCI (9.7 g, 50.7 mmol, 1.5 eq.), HOBt (9.1 g, 67.5 mmol, 2.0 eq.) and the intermediate 3 (4.1 g, 37.2 mmol, 1.1 eq.) was suspended in DMF (190 mL, 0.18 M) and stirred for 18 hours at room temperature. The resulting mixture was diluted with EtOAc (500 mL) and then washed with a diluted aqueous hydrochloride solution (500 mL), water (500 mL) and a saturated aqueous sodium bicarbonate solution (500 mL) The organic layer was dried over anhydrous magnesium sulfate, filtered and concentrated. The residual mixture was titrated with IPA and filtered to give the intermediate 4 (6.9 g) as a yellow precipitate. The filtrate was concentrated and purified by flash chromatography using MeOH/DCM to give an additional intermediate 4 (1.4 g, total 8.2 g, 24.2 mmol, 72%).

$^1$H NMR (400 MHz, DMSO-$d_6$) δ 8.96 (t, J=5.6 Hz, 1H), 7.83 (s, 1H), 4.09 (d, J=5.8 Hz, 2H), 2.12 (s, 3H); [M+H]$^+$ 340.

Step 3: Preparation of Intermediate 5

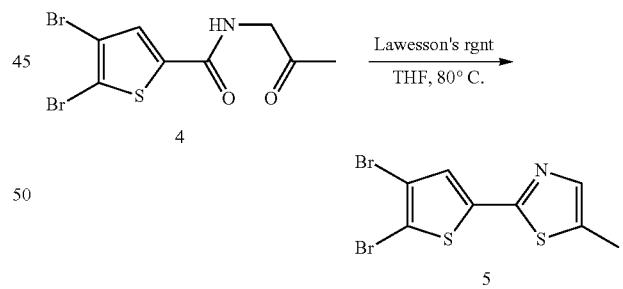

A mixture of Lawesson's reagent (4.1 g, 10.2 mmol, 2.5 eq.) and the intermediate 4 (1.4 g, 4.1 mmol, 1.0 eq.) was suspended in dry THF (45 mL, 0.1 M).

The mixture was stirred at 80° C. for 17 hours, cooled to room temperature and added with EtOAc (100 mL) The resulting solution was washed three times with a saturated aqueous sodium bicarbonate solution (100 mL) and brine (100 mL) The organic layer was dried over anhydrous magnesium sulfate, filtered and concentrated. The residue was purified by flash chromatography using EtOAc/N-hexane to give the intermediate 5 (0.94 g, 2.8 mmol, 68%) as a yellow solid.

$^1$H NMR (400 MHz, DMSO-d$_6$) δ 7.67 (s, 1H), 7.54 (d, J=1.1 Hz, 1H), 2.48 (d, J=0.9 Hz, 3H); [M+H]$^+$ 338.

Step 4: Preparation of Intermediate 6

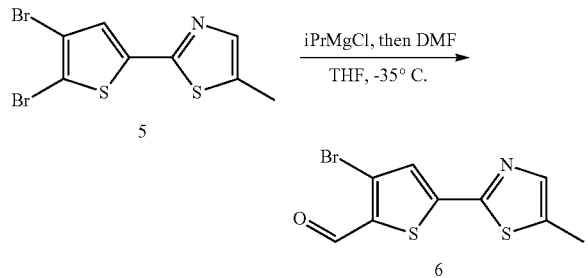

A solution of the intermediate 5 (0.94 g, 2.8 mmol, 1.0 eq.) in dry THF (14 mL, 0.1 M) was cooled to −35° C. Under nitrogen conditions, isopropyl magnesium chloride (2.0 M, 1.5 mL, 3.1 mmol, 1.1 eq.) in THF was added dropwise to the solution at the same temperature. The resulting mixture was stirred for 2 hours, and dry DMF (0.64 mL, 8.3 mmol, 3.0 eq.) was added thereto at the same temperature. The mixture thus obtained was cooled to room temperature and then concentrated. The residual mixture was added with 1N hydrogen chloride solution (50 mL) and stirred for 30 minutes. The suspended mixture was filtered to collect the precipitate. The cake was washed with N-hexane (50 mL) to give the intermediate 6 (0.72 g, 2.5 mmol, 90%) as a yellow solid.

$^1$H NMR (400 MHz, DMSO-d$_6$) δ 9.88 (s, 1H), 7.94 (s, 1H), 7.69 (d, J=1.1 Hz, 1H), 2.53 (d, J=0.9 Hz, 3H); [M+H]$^+$ 288.

Step 5: Preparation of Intermediate 7

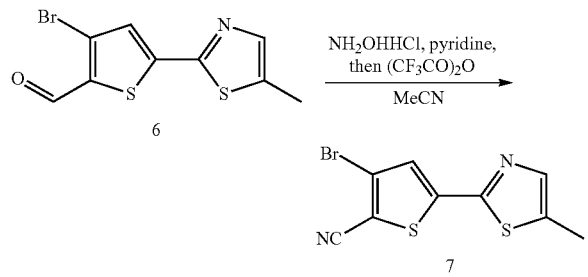

A mixture of hydroxylamine hydrochloride (1.1 g, 15.1 mmol, 1.1 eq.) and the intermediate 6 (3.9 g, 13.7 mmol, 1.0 eq.) was suspended in acetonitrile (68 mL, 0.2 M) and added with pyridine (4.4 mL, 54.8 mmol, 4.0 eq.). The resulting mixture was stirred for 1.5 hours and slowly added with trifluoroacetic anhydride (4.8 mL, 34.3 mmol, 2.5 eq.). The reaction mixture was stirred for 17 hours and quenched in 0.5N aqueous hydrochloride solution (100 mL) The resulting mixture was stirred for 10 minutes and filtered to give the intermediate 7 (3.7 g, 13.7 mmol, 99%) as a red solid.

$^1$H NMR (400 MHz, DMSO-d$_6$) δ 7.81 (s, 1H), 7.73 (s, 1H), 2.52 (s, 3H); [M+H]$^+$ 285.

Step 6: Preparation of Intermediate 8

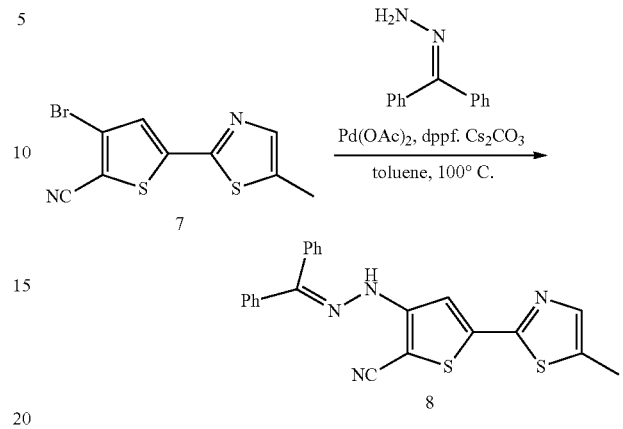

A mixture of the intermediate 7 (3.7 g, 13.7 mmol, 1.0 eq.), benzophenone hydrazone (3.2 g, 16.4 mmol, 1.2 eq.), palladium acetate (0.15 g, 0.69 mmol, 5 mol %), 1,1'-bis (diphenylphosphino)ferrocene (0.76 g, 1.37 mmol, 10 mol %) and cesium carbonate (6.7 g, 20.6 mmol, 1.5 eq.) was suspended in toluene (140 mL, 0.1 M), stirred at 100° C. for 18 hours and then cooled to room temperature. The resulting reaction mixture was diluted with EtOAc (150 mL) and filtered through a Celite plug. The resulting filtrate was concentrated and purified by flash chromatography using EtOAc/N-hexane to give the intermediate 8 (0.89 g, 2.2 mmol, 16%) as a yellow solid.

$^1$H NMR (400 MHz, DMSO-d$_6$) δ 9.99 (s, 1H), 7.64-7.56 (m, 6H), 7.37-7.34 (m, 6H), 2.48 (s, 3H); [M+H]$^+$ 401.

Step 7: Preparation of Intermediate 9

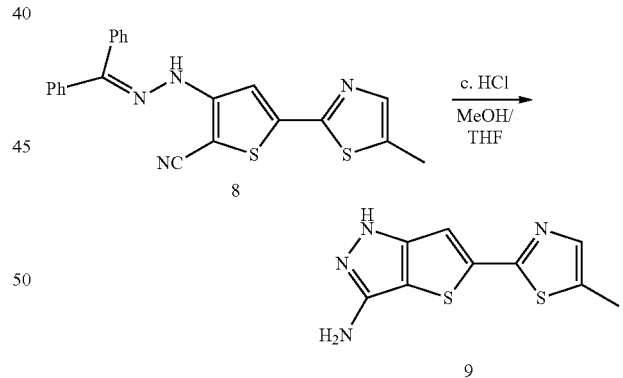

A solution of the intermediate 8 (0.52 g, 1.3 mmol, 1.0 eq.) in MeOH/THF (5:4, 18 mL) was added with concentrated hydrochloric acid and then stirred at 85° C. for 17 hours. The resulting mixture was cooled to room temperature, concentrated and added with water (25 mL) Sodium bicarbonate was added portionwise to the suspension solution for neutralization. The resulting mixture was extracted with EtOAc (25 mL) twice. The organic layer was dried over anhydrous sodium sulfate, filtered and concentrated. The residue was purified by flash chromatography using MeOH/DCM to give the intermediate 9 (0.18 g, 0.78 mmol, 60%) as a yellow solid.

¹H NMR (400 MHz, DMSO-d₆) δ 11.67 (s, 1H), 7.51 (d, J=1.1 Hz, 1H), 7.35 (s, 1H), 5.17 (br s, 2H), 2.47 (s, 3H); [M+H]⁺ 237.

Step 8: Preparation of Intermediate 11

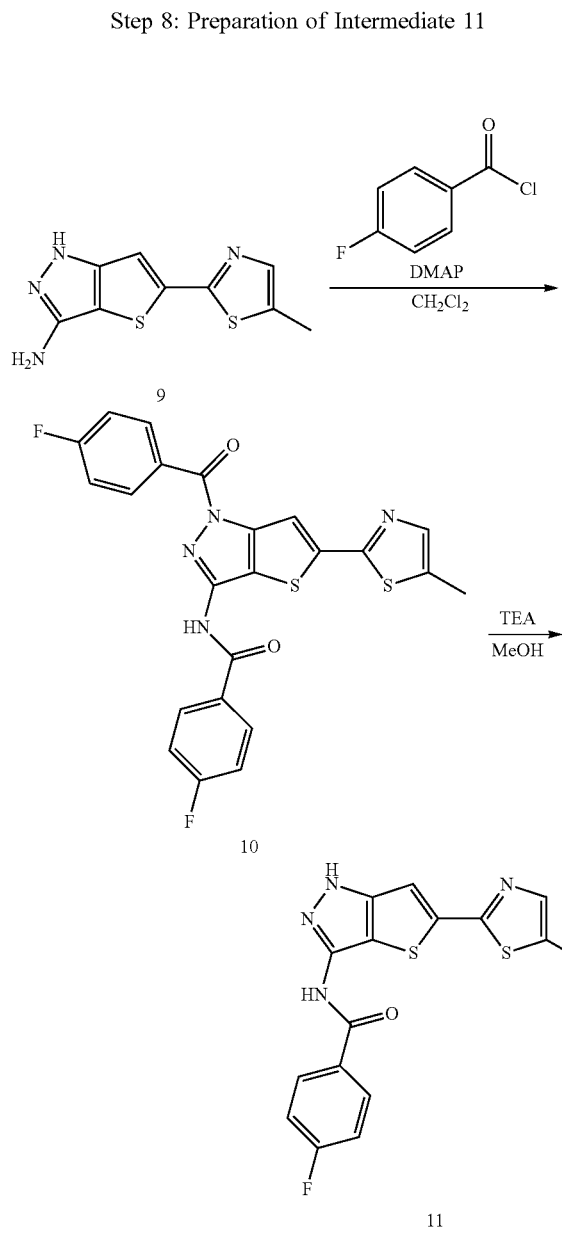

Step 9: Preparation of Intermediate 12

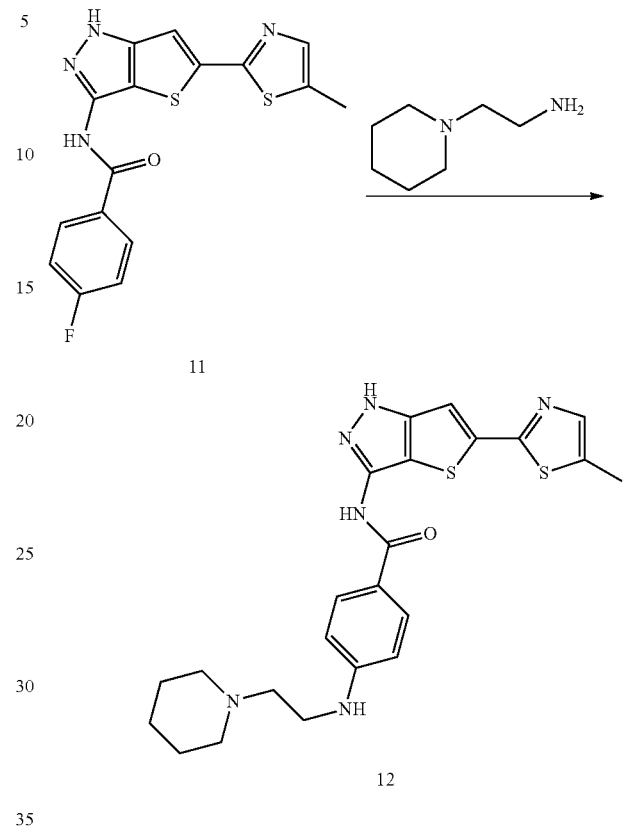

A mixture of the intermediate 9 (0.19 g, 0.80 mmol, 1.0 eq.), 4-fluorobenzoyl chloride (0.46 g, 2.9 mmol, 3.6 eq.) and DMAP (0.39 g, 3.2 mmol, 4.0 eq.) was suspended in DCM (2.0 mL) The reaction mixture was stirred for 2 days and concentrated. The residue was titrated with MeOH (10 mL) and filtered to give the intermediate 10 (0.31 g, 0.65 mmol, 81%) as a yellow liquid. The intermediate 10 was suspended in TEA/MeOH (1:10, 7 mL) The reaction mixture was stirred at 85° C. for 16 hours and cooled to room temperature. The suspension was filtered to give the intermediate 11 (0.2 g, 0.56 mmol, 87%) as a white solid.

¹H NMR (400 MHz, DMSO-d₆) δ 12.79 (s, 1H), 11.39 (s, 1H), 8.15 (dd, J=8.8, 5.5 Hz, 2H), 7.56 (d, J=1.2 Hz, 1H), 7.48 (s, 1H), 7.36 (d, J=8.8 Hz, 2H), 2.49 (s, 3H); [M+H]⁺ 359.

A mixture of the intermediate 11 (0.1 g, 0.28 mmol, 1.0 eq.) and 1-(2-aminoethyl)piperidine (0.14 g, 1.12 mmol, 4.0 eq.) was stirred at 165° C. for 19 hours and cooled to room temperature. The resulting mixture was titrated with MeOH/H₂O (4:1, 5 mL) and filtered to give the intermediate 12 (96 mg, 0.22 mmol, 80%) as a yellow solid.

¹H NMR (400 MHz, DMSO-d₆) δ 12.64 (br s, 1H), 10.80 (s, 1H), 7.87 (d, J=8.8 Hz, 2H), 7.55 (d, J=1.2 Hz, 1H), 7.44 (s, 1H), 6.61 (d, J=8.8 Hz, 2H), 6.19 (t, J=5.3 Hz, 1H), 6.19 (q, J=6.6 Hz, 2H), 2.46-2.44 (m, 2H), 2.39 (br s, 4H), 1.51 (quint, J=5.5 Hz, 4H), 1.40-1.39 (m, 2H); [M+H]⁺ 467.

Preparation Example 5: Preparation of Methyl 1-acetyl-1H-thieno[3,2-c]pyrazole-5-carboxylate (25)

Scheme 5. Total scheme for compound 25

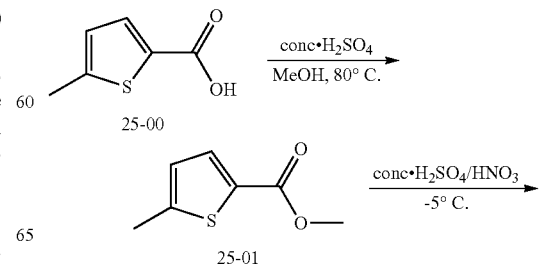

133

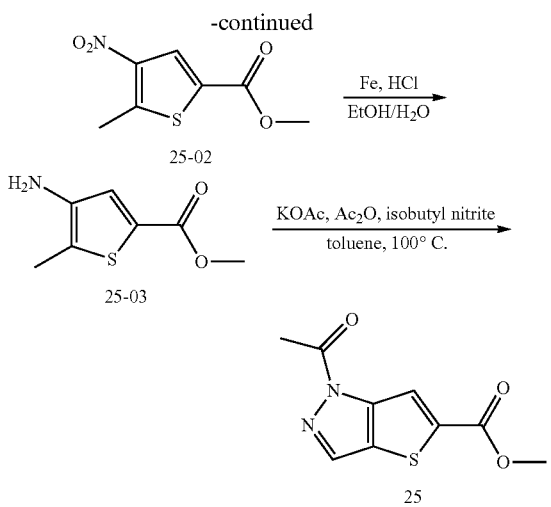

Step 1: Preparation of Compound 25-01

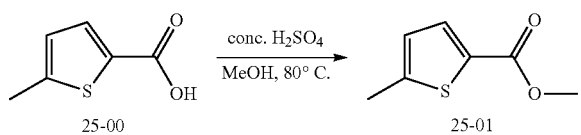

Concentrated H₂SO₄ (5 mL) was added dropwise to 5-methylthiophene-2-carboxylic acid 25-00 (50 g, 0.352 mol) in MeOH (500 mL), and the resulting mixture was stirred under reflux (70° C.) for 2 days. The reaction mixture was cooled to room temperature and concentrated to give the crude product, which was then diluted with EtOAc (400 mL) followed by washing with water (100 mL×5) and brine. Subsequently, the organic phase was washed with 5% aqueous NaOH solution and dried to give the title compound 25-01 (52.4 g).

$^1$H NMR (400 MHz, DMSO-d$_6$) δ 7.63-7.62 (d, J=3.7 Hz, 1H), 6.94-6.93 (d, J=3.6 Hz, 1H), 3.79 (s, 3H), 2.51 (s, 3H).

Step 2: Preparation of Compound 25-02

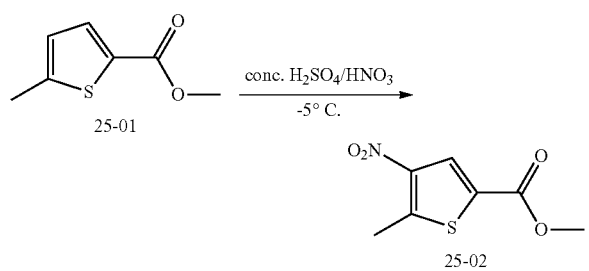

A solution of fuming HNO₃ (19.2 mL, 0.461 mol) in concentrated H₂SO₄ (125 mL) at 0° C. was added dropwise to a solution of methyl 5-methylthiophene 25-01 (48 g, 0.307 mol) in concentrated H₂SO₄ (480 mL) The resulting solution was stirred for 1 hour and added with ice (2.5 L). The resulting precipitate was washed with water and purified by column chromatography to give the title compound 25-02 (34.6 g).

134

$^1$H NMR (400 MHz, CDCl$_3$) δ 8.20 (s, 1H), 3.91 (s, 3H), 2.84 (s, 3H).

Step 3: Preparation of Compound 25-03

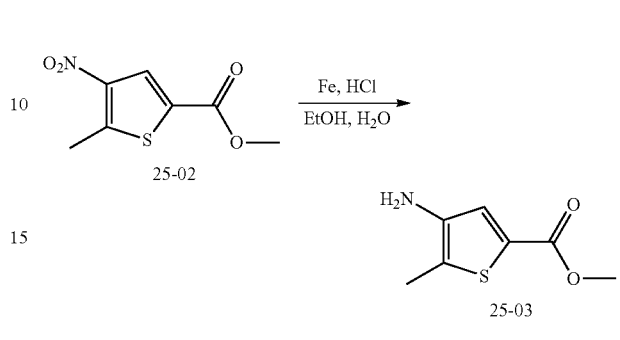

A suspension of Fe (41.7 g, 0.745 mol) in EtOH (450 mL) was added with H₂O (300 mL) and HCl (3 mL) The resulting mixture was heated to 70° C., added with methyl 5-methyl-4-nitrothiophene-2-carboxylate 25-02 (30 g, 0.149 mol), and then stirred for 15 minutes. The mixture was filtered through a Celite pad while it was still hot. The filtrate thus obtained was concentrated to remove EtOH, and then filtered to give the title compound. The Celite pad was washed with EtOAc (500 mL×2), and the EtOAc phase was concentrated to give the title compound 25-03 (23.3 g).

$^1$H NMR (400 MHz, DMSO) δ 7.19 (s, 1H), 4.77 (s, 2H), 3.74 (s, 3H), 2.17 (s, 3H).

Step 4: Preparation of Compound 25

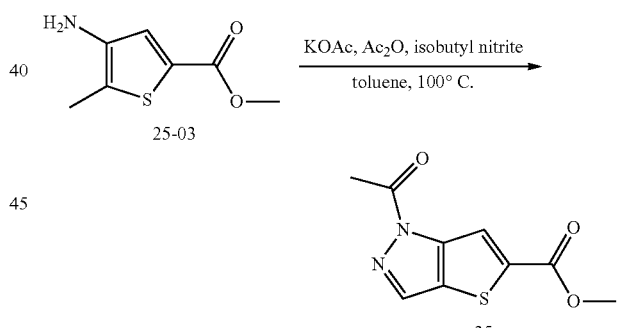

A solution of methyl 4-amino-5-methylthiophene-2-carboxylate 25-03 (8 g, 47 mmol) in toluene (190 mL) was added with acetic anhydrous (25.1 g, 246 mmol) and potassium acetate (2.4 g, 24 mmol). The reaction mixture was stirred at 100° C. for 3 hours. After cooled to room temperature, the reaction mixture was treated with isobutyl nitrate (16.5 g, 160 mmol) and stirred overnight at 100° C. The resulting mixture was concentrated, and the residue was diluted with 600 mL of EtOAc. The organic phase was washed with water (200 mL×3) and brine (400 mL×2), concentrated to remove most of the solvent, filtered, and the resulting crude product was recrystallized using EtOAc to give the title product 25 (5 g).

$^1$H NMR (400 MHz, DMSO-d$_6$) δ 8.32 (s, 1H), 8.00 (s, 1H), 3.90 (s, MA 2.69 (s, 3H).

Preparation Example 6: Preparation of 2-(3-(4-methoxyphenyl)-1H-thieno[3,2-c]pyrazol-5-yl)-5-methyloxazole (38)

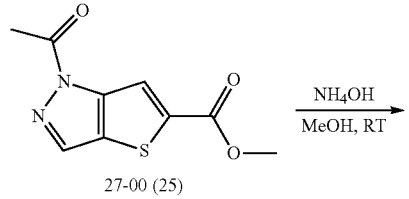

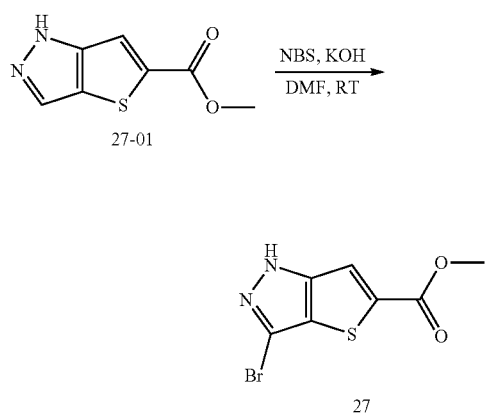

Step 1: Preparation of Methyl 1H-thieno[3,2-c]pyrazole-5-carboxylate (27-01)

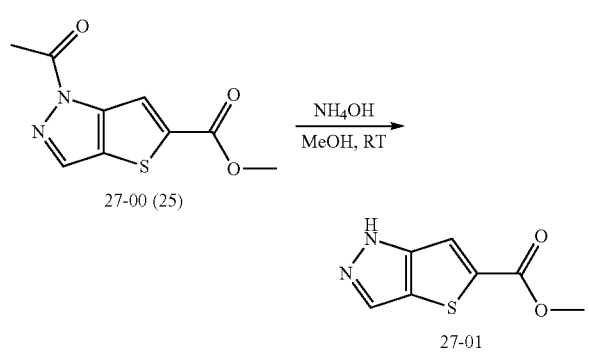

A solution of methyl 1-acetyl-1H-thieno[3,2-c]pyrazole-5-carboxylate 27-00 (5 g, 22.30 mmol) in MeOH (150 mL) was added with NH$_4$OH (4.56 g, 66.89 mmol), and the resulting mixture was stirred at room temperature for 20 minutes. The mixture was added with 100 mL of water, concentrated to remove MeOH, and the resulting residue was extracted with EtOAc (200 mL) The EtOAc phase was washed with water and brine, dried and concentrated to title intermediate 27-01 (4 g).

$^1$H NMR (400 MHz, DMSO-d$_6$) δ 13.51 (s, 1H), 7.99 (s, 1H), 7.87 (s, 1H), 3.86 (s, 3H).

Step 2: Preparation of Methyl 3-bromo-1H-thieno[3,2-c]pyrazole-5-carboxylate (27)

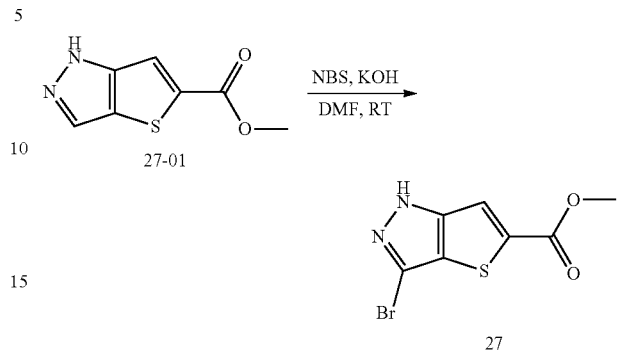

A solution of methyl 1H-thieno[3,2-c]pyrazole-5-carboxylate 27-01 (4 g, 21.954 mmol) in DMF (120 mL) was added with NBS (4.7 g, 26.345 mmol) and KOH (3.7 g, 65.862 mmol), and the resulting mixture was stirred at room temperature for 3 hours. The mixture was added with water (200 mL) and extracted with EtOAc (300 mL×6). The EtOAc phase was washed with water (300 mL×2) and brine (400 mL), concentrated and purified by chromatography to give the title compound (5 g).

$^1$H NMR (400 MHz, DMSO-d$_6$) δ 13.82 (s, 1H), 7.92 (s, 1H), 3.88 (s, 3H).

Step 3: Preparation of 1-tert-butyl 5-methyl 3-iodo-1H-thieno[3,2-c]pyrazole-1,5-dicarboxylate (28)

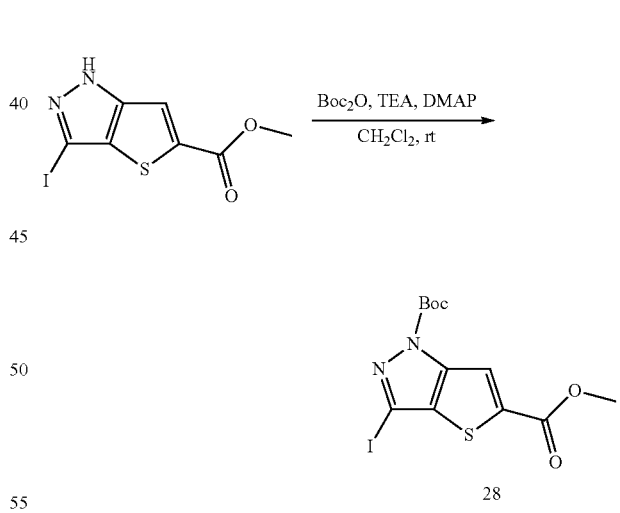

A mixture of methyl 3-iodo-1H-thieno[3,2-c]pyrazole-5-carboxylate (800 mg, 2.60 mmol), DMAP (63 mg, 0.52 mmol) and Boc$_2$O (680 mg, 3.12 mmol) in CH$_2$Cl$_2$ (25 mL) was slowly added with TEA (0.4 mL, 2.86 mmol) at room temperature. The reaction mixture was stirred for 12 hours. The resulting mixture was diluted with H$_2$O and then extracted with CH$_2$Cl$_2$. The organic layer was dried over MgSO$_4$, filtered and concentrated in vacuo. The solid thus obtained was washed with H$_2$O to give the title compound (670 mg, 63%) as a white solid.

Step 4: Preparation of Methyl 3-phenyl-1H-thieno[3,2-c]pyrazole-5-carboxylate (30)

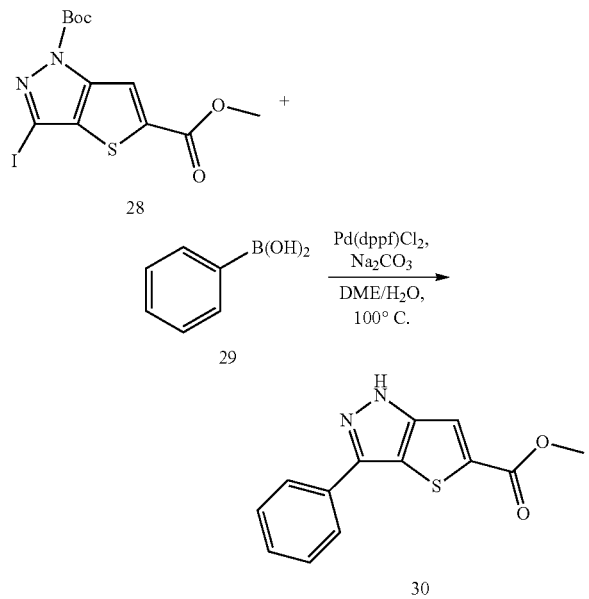

A mixture of 1-tert-butyl 5-methyl 3-iodo-1H-thieno[3,2-c]pyrazole-1,5-dicarboxylate (330 mg, 0.81 mmol), phenylboronic acid (246 mg, 2.02 mmol), Pd(dppf)Cl$_2$ (89 mg, 0.12 mmol) and Na$_2$CO$_3$ (257 mg, 2.43 mmol) in DME/H$_2$O (8/2 mL) was stirred at 100° C. for 12 hours. The resulting mixture was diluted with H$_2$O and then extracted with CH$_2$Cl$_2$. The organic layer was dried over MgSO$_4$, filtered and concentrated in vacuo. The crude product thus obtained was concentrated and purified by prep. HPLC system (Gilson, ACN/H$_2$O) to give the title compound (125 mg, 60%) as a white solid.

Step 5: Preparation of 3-phenyl-1H-thieno[3,2-c]pyrazole-5-carboxylic Acid (31)

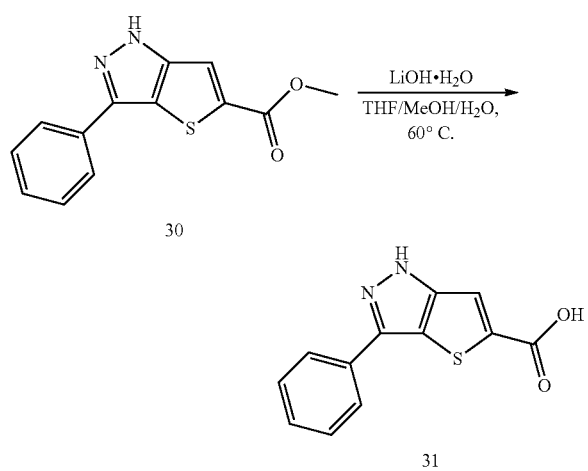

A mixture of methyl 3-phenyl-1H-thieno[3,2-c]pyrazole-5-carboxylate (110 mg, 0.43 mmol) and lithium hydroxide monohydrate (54 mg, 1.28 mmol) in THF/MeOH/H$_2$O (3/1/1 mL) was stirred at 60° C. for 12 hours. The resulting mixture was diluted with H$_2$O and then extracted with EtOAc. The organic layer was dried with MgSO$_4$, filtered and concentrated in vacuo. The crude product thus obtained was used without further purification.

Step 6: Preparation of N-ethyl-3-phenyl-1H-thieno[3,2-c]pyrazole-5-carboxamide (34)

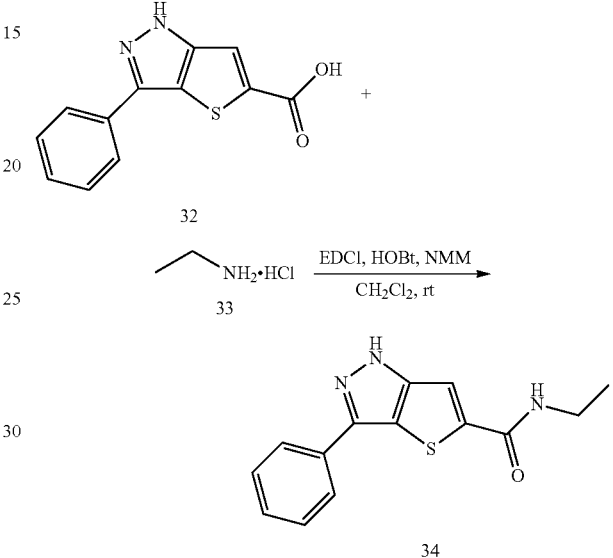

A mixture of methyl 3-phenyl-1H-thieno[3,2-c]pyrazole-5-carboxylic acid (50 mg, 0.20 mmol), ethylamine hydrochloride (25 mg, 0.31 mmol), EDCI (59 mg, 0.31 mmol), HOBt (55 mg, 0.41 mmol) in CH$_2$Cl$_2$ (1 mL) was added with NMM (68 µL, 0.61 mmol) at room temperature. The reaction mixture was stirred at room temperature for 12 hours, concentrated in vacuo and purified by silica gel column chromatography (Biotage flash purification system, EtOAc/Hex, KP-Sil) to give the title compound (44 mg, 81%) as a white solid.

Step 7: Preparation of 3-iodo-N-(2-oxopropyl)-1H-thieno[3,2-c]pyrazole-5-carboxamide (35)

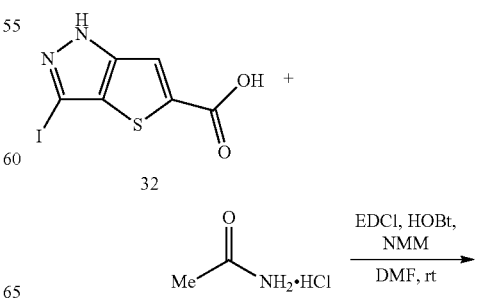

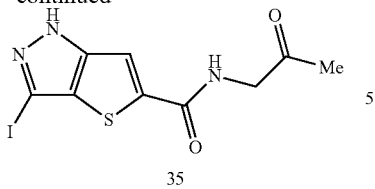

35

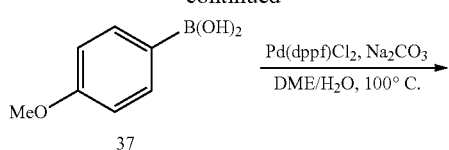

37

A mixture of methyl 3-phenyl-1H-thieno[3,2-c]pyrazole-5-carboxylic acid (1.15 g, 3.91 mmol), acetamido hydrochloride (0.65 g, 5.87 mmol), EDCI (1.2 g, 5.87 mmol) and HOBt (1.1 g, 7.82 mmol) in DMF (20 mL) was added with NMM (1.3 mL, 11.73 mmol) at room temperature. The reaction mixture was stirred at room temperature for 12 hours, diluted with H$_2$O and then extracted with EtOAc. The organic layer was dried over MgSO$_4$, filtered and concentrated in vacuo. The resulting crude product was purified by silica gel column chromatography (Biotage flash purification system, EtOAc/Hex, KP-Sil) to give the title compound (0.74 g, 54%) as a yellowish brown solid.

Step 8: Preparation of 2-(3-iodo-1H-thieno[3,2-c]pyrazol-5-yl)-5-methyloxazole (36)

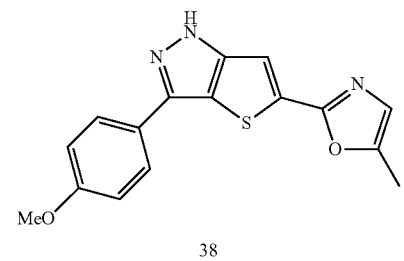

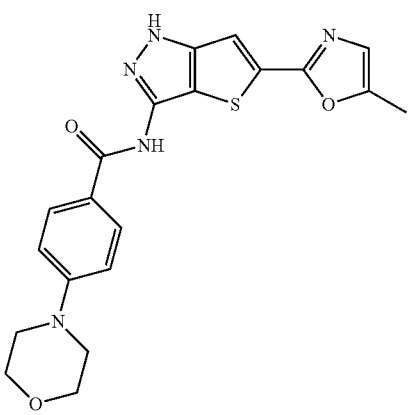 [SMILES: Cc1cnc(-c2cc3[nH]nc(NC(=O)c4ccc(N5CCOCC5)cc4)c3s2)o1]

38

A mixture of 2-(3-iodo-1H-thieno[3,2-c]pyrazol-5-yl)-5-methyloxazole (75 mg, 0.23 mmol), 4-methoxyphenylboronic acid (86 mg, 0.57 mmol), Pd(dppf)Cl$_2$ (25 mg, 0.03 mmol) and Na$_2$CO$_3$ (72 mg, 0.68 mmol) in DME/H$_2$O (2/0.5 mL) was stirred at 100° C. for 12 hours. The resulting mixture was diluted with H$_2$O and then extracted with EtOAc. The organic layer was dried over MgSO$_4$, filtered and concentrated in vacuo. The crude product thus obtained was purified with prep. HPLC (Waters, ACN/H$_2$O) to give the title compound (8 mg, 11%) as a white solid.

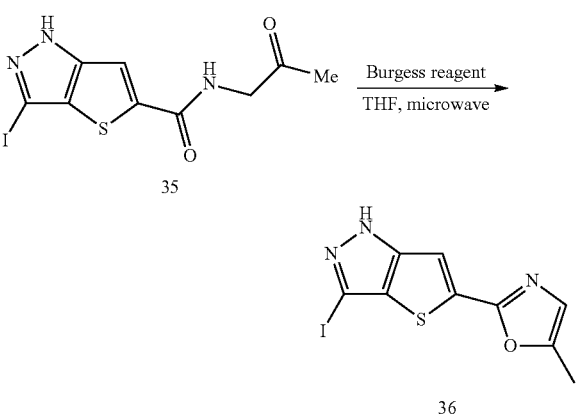

A mixture of 3-iodo-N-(2-oxopropyl)-1H-thieno[3,2-c]pyrazole-5-carboxamide (740 mg, 2.11 mmol) and Burgess reagent (1.51 g, 6.33 mmol) in THF (21 mL) was stirred at 150° C. under electromagnetic irradiation for 40 minutes. The resulting mixture was diluted with H$_2$O and then extracted with EtOAc. The organic layer was dried over MgSO$_4$, filtered and concentrated in vacuo. The crude product thus obtained was purified by silica gel column chromatography (Biotage flash purification system, EtOAc/Hex, KP-Sil) to give the title compound (150 mg, 21%) as a pale yellow solid.

Step 9: Preparation of 2-(3-(4-methoxyphenyl)-1H-thieno[3,2-c]pyrazol-5-yl)-5-methyloxazole (38)

Example 218: N-(5-(5-methyloxazol-2-yl)-1H-thieno[3,2-c]pyrazol-3-yl)-4-morpholinobenzamide

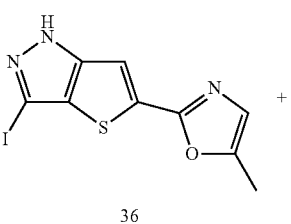

36

$^1$H NMR (400 MHz, DMSO-d$_6$) δ 11.05 (s, 1H), 8.00 (d, J=8.9 Hz, 2H), 7.46 (s, 1H), 7.01 (d, J=8.9 Hz, 2H), 3.75 (t, J=4.7 Hz, 4H), 3.27 (t, J=4.8 Hz, 4H), 2.39 (s, 3H); MS (ESI) m/z 410 (M+H)$^+$.

Example 219: N-(5-(5-methylthiazol-2-yl)-1H-thieno[3,2-c]pyrazol-3-yl)-4-morpholinobenzamide

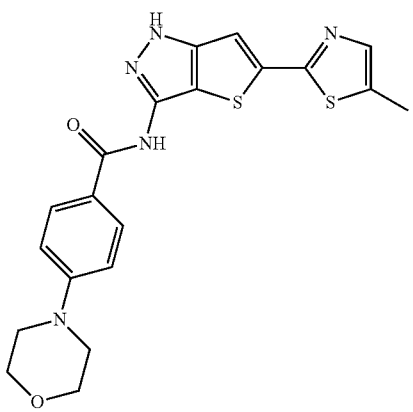

¹H NMR (400 MHz, DMSO-d₆) δ 12.66 (s, 1H), 11.00 (s, 1H), 7.95 (d, J=8.8 Hz, 2H), 7.54 (s, 1H), 7.44 (s, 1H), 7.00 (d, J=8.9 Hz, 2H), 3.73 (t, J=4.7 Hz, 4H), 3.26 (t, J=4.8 Hz, 4H), 2.48 (s, 3H); MS (ESI) m/z 426 (M+H)⁺.

Example 220: N-(5-(5-Methyloxazol-2-yl)-1H-thieno[3,2-c]pyrazol-3-yl)benzamide

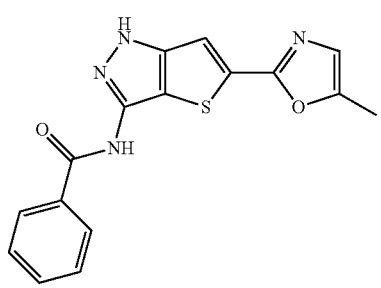 [SMILES: Cc1cnc(-c2cc3[nH]nc(NC(=O)c4ccccc4)c3s2)o1]

¹H NMR (400 MHz, DMSO-d₆) δ 12.81 (s, 1H), 11.37 (s, 1H), 8.07 (d, J=8.8 Hz, 2H), 7.65-7.43 (m, 4H), 7.00 (s, 1H), 2.39 (s, 3H); MS (ESI) m/z 325 (M+H)⁺.

Example 221: 4-Fluoro-N-(5-(5-methyloxazol-2-yl)-1H-thieno[3,2-c]pyrazol-3-yl)benzamide

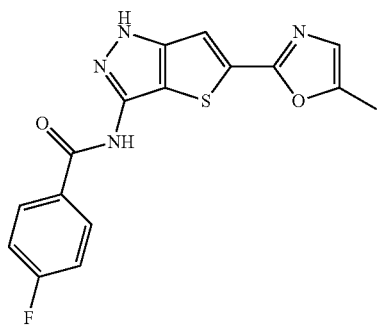 [SMILES: Cc1cnc(-c2cc3[nH]nc(NC(=O)c4ccc(F)cc4)c3s2)o1]

¹H NMR (400 MHz, DMSO-d₆) δ 12.82 (s, 1H), 11.42 (s, 1H), 8.19-8.11 (m, 2H), 7.49 (s, 1H), 7.36 (t, J=8.8 Hz, 2H), 7.00 (s, 1H), 2.39 (s, 3H); MS (ESI) m/z 343 (M+H)⁺.

Example 222: 4-Methoxy-N-(5-(5-methyloxazol-2-yl)-1H-thieno[3,2-c]pyrazol-3-yl)benzamide

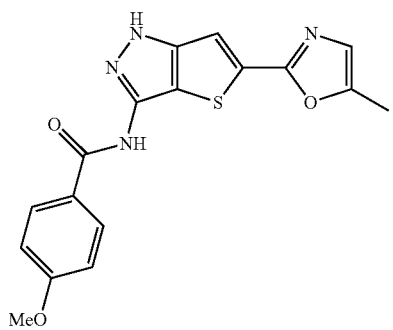 [SMILES: COc1ccc(C(=O)Nc2n[nH]c3cc(-c4ncc(C)o4)sc23)cc1]

¹H NMR (400 MHz, DMSO-d₆) δ 12.76 (s, 1H), 11.22 (s, 1H), 8.08 (d, J=8.8 Hz, 2H), 7.47 (s, 1H), 7.05 (d, J=8.8 Hz, 2H), 7.00 (s, 1H), 2.39 (s, 3H); MS (ESI) m/z 355 (M+H)⁺.

Example 223: 4-(Dimethylamino)-N-(5-(5-methyloxazol-2-yl)-1H-thieno[3,2-c]pyrazol-3-yl)benzamide

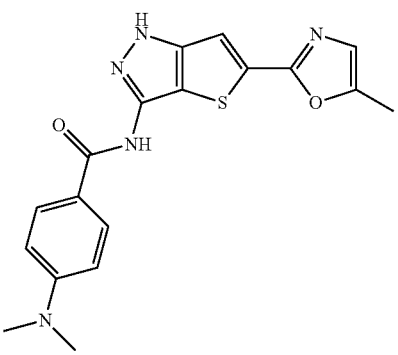

¹H NMR (400 MHz, DMSO-d₆) δ 12.69 (s, 1H), 10.92 (s, 1H), 7.96 (d, J=8.9 Hz, 2H), 7.45 (s, 1H), 7.00 (s, 1H), 6.75 (d, J=8.9 Hz, 2H), 3.01 (s, 6H), 2.39 (s, 3H); MS (ESI) m/z 368 (M+H)⁺.

Example 224: N-(5-(5-Methyloxazol-2-yl)-1H-thieno[3,2-c]pyrazol-3-yl)-4-((2-(piperidin-1-yl)ethyl)amino)benzamide

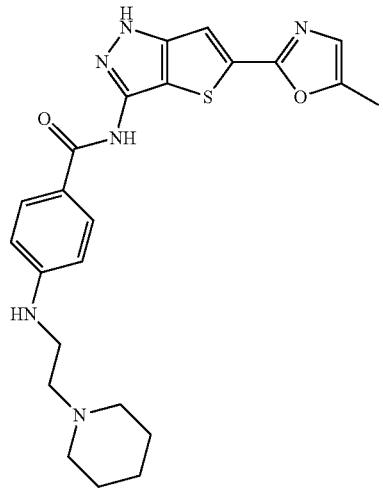

$^1$H NMR (400 MHz, DMSO-d$_6$) δ 12.68 (s, 1H), 10.84 (s, 1H), 7.87 (d, J=8.8 Hz, 2H), 7.45 (s, 1H), 7.00 (s, 1H), 6.62 (d, J=8.9 Hz, 2H), 6.20 (t, J=5.4 Hz, 1H), 3.19 (q, J=6.3 Hz, 2H), 2.54-2.25 (m, 9H), 1.55-1.35 (m, 6H); MS (ESI) m/z 451 (M+H)$^+$.

Example 225: N-(5-(5-Methyloxazol-2-yl)-1H-thieno[3,2-c]pyrazol-3-yl)-4-(4-methylpiperazin-1-yl)benzamide

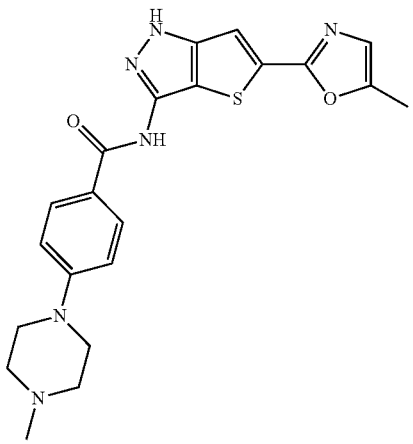 [SMILES: Cc1cnc(-c2cc3[nH]nc(NC(=O)c4ccc(N5CCN(C)CC5)cc4)c3s2)o1]

$^1$H NMR (400 MHz, DMSO-d$_6$) δ 12.62 (s, 1H), 10.80 (s, 1H), 7.96 (d, J=8.9 Hz, 2H), 7.45 (s, 1H), 7.00-6.95 (m, 3H), 3.36-3.29 (m, 4H), 2.45-2.38 (m, 4H), 2.37 (s, 3H), 2.21 (s, 3H); MS (ESI) m/z 423 (M+H)$^+$.

Example 226: N-(5-(5-methyloxazol-2-yl)-1H-thieno[3,2-c]pyrazol-3-yl)-4-((2-(pyrrolidin-1-yl)ethyl)amino)benzamide

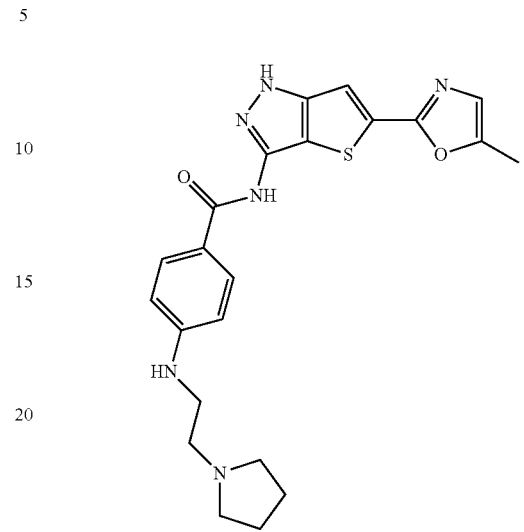

$^1$H NMR (400 MHz, DMSO-d$_6$) δ 12.65 (s, 1H), 10.83 (s, 1H), 7.86 (d, J=8.8 Hz, 2H), 7.44 (s, 1H), 6.98 (s, 1H), 6.61 (d, J=8.8 Hz, 2H), 6.27 (t, J=5.3 Hz, 1H), 3.19 (q, J=6.3 Hz, 2H), 2.65-2.51 (m, 6H), 2.45 (s, 3H), 1.75-1.1.63 (m, 4H); MS (ESI) m/z 437 (M+H)$^+$.

Example 227: N-(5-(5-Methyloxazol-2-yl)-1H-thieno[3,2-c]pyrazol-3-yl)-4-((2-morpholinoethyl)amino)benzamide

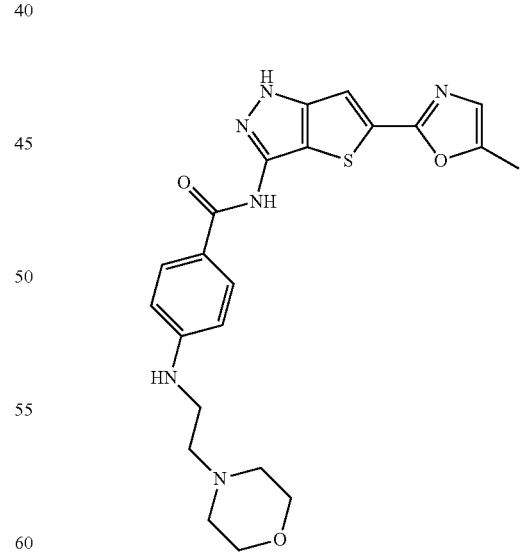

$^1$H NMR (400 MHz, DMSO-d$_6$) δ 12.66 (s, 1H), 10.85 (s, 1H), 7.86 (d, J=8.7 Hz, 2H), 7.44 (s, 1H), 6.98 (s, 1H), 6.61 (d, J=8.8 Hz, 2H), 6.24 (t, J=5.3 Hz, 1H), 3.61-3.54 (m, 4H), 3.31-3.18 (m, 2H), 2.45-2.21 (m, 7H); MS (ESI) m/z 453 (M+H)$^+$.

Example 228: 4-((2-hydroxyethyl)amino)-N-(5-(5-methyloxazol-2-yl)-1H-thieno[3,2-c]pyrazol-3-yl)benzamide

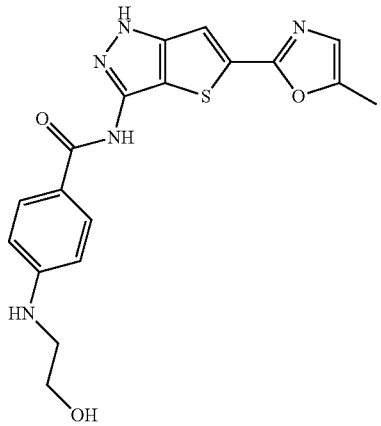 [SMILES: Cc1cnc(-c2cc3[nH]nc(NC(=O)c4ccc(NCCO)cc4)c3s2)o1]

¹H NMR (400 MHz, DMSO-d₆) δ 12.66 (s, 1H), 10.85 (s, 1H), 7.86 (d, J=8.7 Hz, 2H), 7.44 (s, 1H), 6.99 (s, 1H), 6.60 (d, J=8.8 Hz, 2H), 6.34 (t, J=5.3 Hz, 1H), 4.75 (t, J=5.3 Hz, 1H), 3.60-3.52 (m, 2H), 3.21-3.13 (m, 2H), 2.37 (s, 3H); MS (ESI) m/z 384 (M+H)⁺.

Example 229: 4-((2-Methoxyethyl)amino)-N-(5-(5-methyloxazol-2-yl)-1H-thieno[3,2-c]pyrazol-3-yl)benzamide

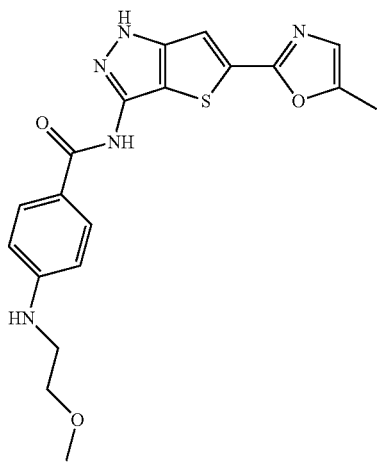 [SMILES: COCCNc1ccc(C(=O)Nc2n[nH]c3cc(-c4ncc(C)o4)sc23)cc1]

¹H NMR (400 MHz, DMSO-d₆) δ 12.66 (s, 1H), 10.83 (s, 1H), 7.86 (d, J=8.7 Hz, 2H), 7.44 (s, 1H), 6.98 (s, 1H), 6.62 (d, J=8.8 Hz, 2H), 6.39 (t, J=5.3 Hz, 1H), 3.49 (t, J=5.5 Hz, 1H), 3.33-3.21 (m, 5H), 2.37 (s, 3H); MS (ESI) m/z 398 (M+H)⁺.

Example 230: 3-Fluoro-N-(5-(5-methyloxazol-2-yl)-1H-thieno[3,2-c]pyrazol-3-yl)benzamide

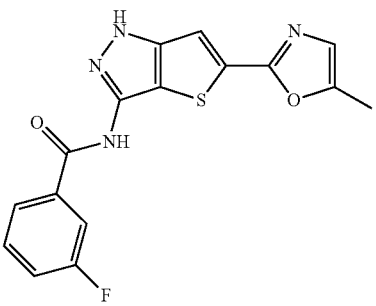 [SMILES: Cc1cnc(-c2cc3[nH]nc(NC(=O)c4cccc(F)c4)c3s2)o1]

¹H NMR (400 MHz, DMSO-d₆) δ 12.86 (s, 1H), 11.49 (s, 1H), 7.95-7.83 (m, 2H), 7.63-7.55 (m, 1H), 7.50-7.42 (m, 2H), 6.99 (s, 1H), 2.37 (s, 3H); MS (ESI) m/z 398 (M+H)⁺.

Example 231: Methyl 3-(4-methoxyphenyl)-1H-thieno[3,2-c]pyrazole-5-carboxylate

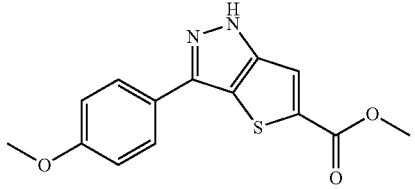

¹H NMR (400 MHz, DMSO-d₆) δ 7.91 (s, 1H), 7.75 (d, J=8.4 Hz, 2H), 7.10 (d, J=8.8 Hz, 2H), 3.89 (s, MA 3.82 (s, 3H); [M+11]⁺ 289.

Example 232: N-Ethyl-3-(4-methoxyphenyl)-1H-thieno[3,2-c]pyrazole-5-carboxamide

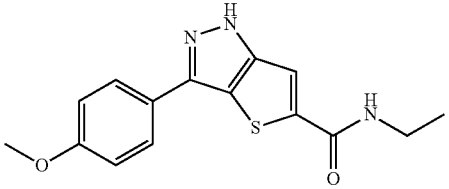 [SMILES: CCNC(=O)c1cc2[nH]nc(-c3ccc(OC)cc3)c2s1]

¹H NMR (400 MHz, DMSO-d₆) δ 13.32 (br s, 1H), 8.68 (t, J=5.2 Hz, 1H), 7.84 (s, 1H), 7.74 (d, J=8.8 Hz, 2H), 7.09 (d, J=8.4 Hz, 2H), 3.81 (s, 3H), 3.32-3.28 (m, 2H), 1.15 (t, J=7.2 Hz, 3H); [M+H]⁺ 302.

Example 233: N-Isopropyl-3-(4-methoxyphenyl)-
1H-thieno[3,2-c]pyrazole-5-carboxamide

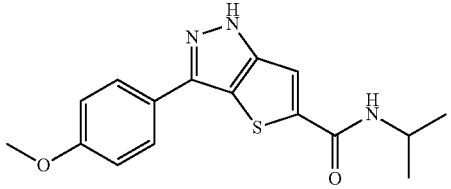 [SMILES: COc1ccc(-c2n[nH]c3cc(C(=O)NC(C)C)sc23)cc1]

$^1$H NMR (400 MHz, DMSO-d$_6$) δ 13.33 (br s, 1H), 8.43 (d, J=7.6 Hz, 1H), 7.90 (s, 1H), 7.75 (d, J=8.8 Hz, 2H), 7.08 (d, J=8.8 Hz, 2H), 4.12-4.03 (m, 1H), 3.81 (s, 3H), 1.19 (t, J=6.8 Hz, 3H); [M+H]$^+$ 316.

Example 234: Methyl 3-(4-(dimethylamino)phenyl)-
1H-thieno[3,2-c]pyrazole-5-carboxylate

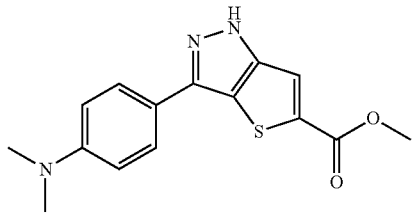

$^1$H NMR (400 MHz, DMSO-d$_6$) δ 13.30 (br s, 1H), 7.83 (s, 1H), 7.64-7.63 (m, 2H), 6.86 (d, J=8.0 Hz, 2H), 3.88 (s, 3H), 2.96 (s, 6H); [M+11]$^+$ 302.

Example 235: 2-(3-(4-methoxyphenyl)-1H-thieno[3,2-c]pyrazol-5-yl)-5-methyloxazole

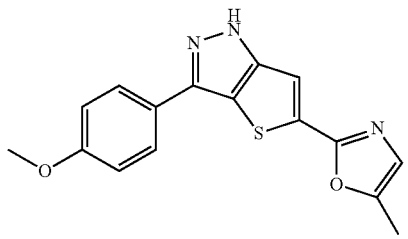 [SMILES: COc1ccc(-c2n[nH]c3cc(-c4ncc(C)o4)sc23)cc1]

$^1$H NMR (400 MHz, DMSO-d$_6$) δ 11.7); 13.35 (br s, 1H), 7.75 (d, J=8.4 Hz, 2H), 7.67 (s, 1H), 7.10 (d, J=8.0 Hz, 2H), 7.03 (s, 1H), 3.82 (s, MA 2.40 (s, 3H); [M+H]$^+$ 312.

Example 236: Methyl 3-phenyl-1H-thieno[3,2-c]
pyrazole-5-carboxylate

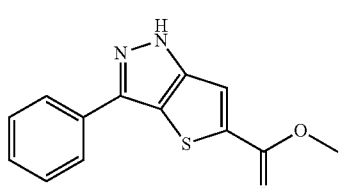

$^1$H NMR (400 MHz, DMSO-d$_6$) δ 13.67 (br s, 1H), 7.94 (s, 1H), 7.83 (d, J=7.6 Hz, 2H), 7.54 (t, J=7.6 Hz, 2H), 7.40 (t, J=7.4 Hz, 1H), 3.89 (s, 3H); [M+H]$^+$ 259.

Example 237: 3-(4-(Dimethylamino)phenyl)-N-
ethyl-1H-thieno[3,2-c]pyrazole-5-carboxamide

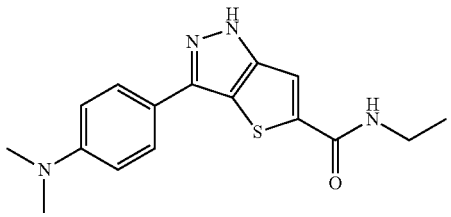 [SMILES: CCNC(=O)c1cc2[nH]nc(-c3ccc(N(C)C)cc3)c2s1]

$^1$H NMR (400 MHz, DMSO-d$_6$) δ 13.18 (br s, 1H), 8.68 (t, J=5.2 Hz, 1H), 7.82 (s, 1H), 7.63 (d, J=7.2 Hz, 2H), 6.85 (d, J=8.8 Hz, 2H), 3.32-3.28 (m, 1H), 2.96 (s, 6H), 1.14 (t, J=7.4 Hz, 3H); [M+H]$^+$ 315.

Example 238: N-Ethyl-3-phenyl-1H-thieno[3,2-c]
pyrazole-5-carboxamide

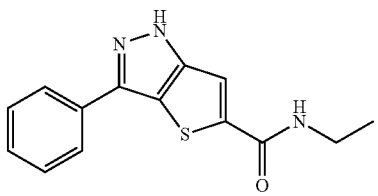 [SMILES: CCNC(=O)c1cc2[nH]nc(-c3ccccc3)c2s1]

$^1$H NMR (400 MHz, DMSO-d$_6$) δ 13.49 (br s, 1H), 8.72 (t, J=5.6 Hz, 1H), 7.87 (s, 1H), 7.82 (d, J=7.2 Hz, 2H), 7.52 (t, J=7.4 Hz, 2H), 7.38 (t, J=7.2 Hz, 1H), 3.32-3.27 (m, 2H), 1.15 (t, J=7.2 Hz, 3H); [M+H]$^+$ 272.

Example 239: Methyl 3-(4-fluorophenyl)-1H-thieno
[3,2-c]pyrazole-5-carboxylate

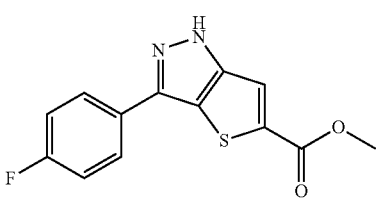 [SMILES: COC(=O)c1cc2[nH]nc(-c3ccc(F)cc3)c2s1]

$^1$H NMR (400 MHz, DMSO-d$_6$) δ 13.66 (br s, 1H), 7.92 (br s, 1H), 7.86 (t, J=6.6 Hz, 2H), 7.37 (t, J=8.2 Hz, 2H), 3.89 (s, 3H); [M+H]$^+$ 277.

Example 240: N-Ethyl-3-(4-fluorophenyl)-1H-thieno[3,2-c]pyrazole-5-carboxamide

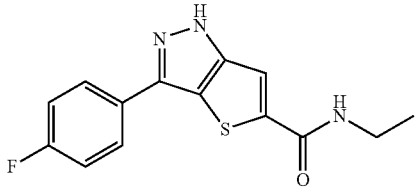 [SMILES: CCNC(=O)c1cc2[nH]nc(-c3ccc(F)cc3)c2s1]

¹H NMR (400 MHz, DMSO-d₆) δ 13.48 (br s, 1H), 8.69 (t, J=5.4 Hz, 1H), 7.89-7.86 (m, 3H), 7.36 (t, J=6.0 Hz, 2H), 3.29-3.24 (m, 2H), 1.15 (t, J=7.2 Hz, 3H); [M+H]⁺ 290.

Example 241: N-Ethyl-3-(4-morpholinophenyl)-1H-thieno[3,2-c]pyrazole-5-carboxamide

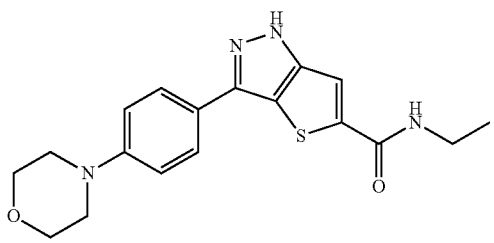 [SMILES: CCNC(=O)c1cc2[nH]nc(-c3ccc(N4CCOCC4)cc3)c2s1]

¹H NMR (400 MHz, DMSO-d₆) δ 13.24 (br s, 1H), 8.66 (t, J=5.0 Hz, 1H), 7.82 (s, 1H), 7.68 (d, J=8.8 Hz, 2H), 7.08 (d, J=8.4 Hz, 2H), 3.76 (t, J=4.6 Hz, 4H), 3.30-3.28 (m, 2H), 3.18 (br s, 4H), 1.15 (t, J=7.2 Hz, 3H); [M+H]⁺ 357.

Example 242: 3-(4-Fluorophenyl)-N-(2-morpholinoethyl)-1H-thieno[3,2-c]pyrazole-5-carboxamide

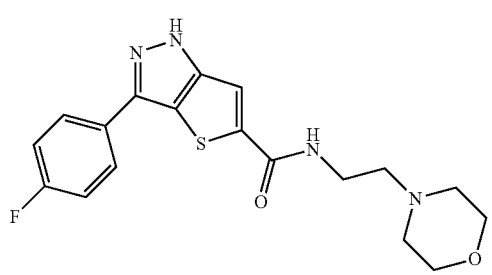 [SMILES: O=C(NCCN1CCOCC1)c1cc2[nH]nc(-c3ccc(F)cc3)c2s1]

¹H NMR (400 MHz, DMSO-d₆) δ 8.66 (t, J=5.8 Hz, 1H), 7.87 (s, 1H), 7.84 (dd, J=8.8, 5.6 Hz, 2H), 7.36 (t, J=8.8 Hz, 2H), 3.58 (t, J=4.4 Hz, 4H), 3.40 (q, J=6.8 Hz, 2H), 2.49-2.46 (m, 2H), 2.42 (br s, 4H); [M+H]⁺ 375.

Example 243: 4-(4-(5-(5-methyloxazol-2-yl)-1H-thieno[3,2-c]pyrazol-3-yl)phenyl)morpholine

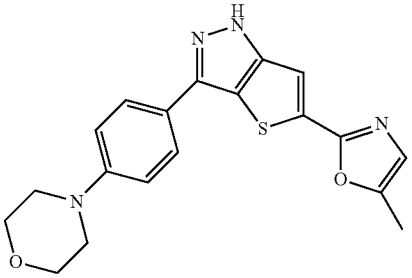 [SMILES: Cc1cnc(-c2cc3[nH]nc(-c4ccc(N5CCOCC5)cc4)c3s2)o1]

¹H NMR (400 MHz, DMSO-d₆) δ 13.27 (br s, 1H), 7.72-7.61 (m, 3H), 7.13-7.08 (m, 2H), 7.03 (s, 1H), 3.77-3.75 (m, 4H), 3.18-3.16 (m, 4H), 2.40 (s, 3H); [M+H]⁺ 367.

Example 244: 4-(4-(5-(5-ethyloxazol-2-yl)-1H-thieno[3,2-c]pyrazol-3-yl)phenyl)morpholine

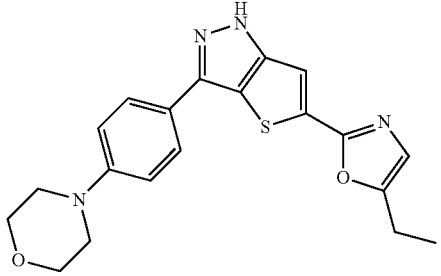 [SMILES: CCc1cnc(-c2cc3[nH]nc(-c4ccc(N5CCOCC5)cc4)c3s2)o1]

¹H NMR (400 MHz, DMSO-d₆) δ 13.29 (s, 1H), 7.73-7.26 (m, 3H), 7.10-7.08 (m, 2H), 7.05 (s, 1H), 3.76 (t, J=4.8 Hz, 4H), 3.17 (t, J=4.8 Hz, 4H), 2.76 (q, J=7.4 Hz, 2H), 1.25 (t, J=7.4 Hz, 3H); [M+H]⁺ 381.

Example 245: Methyl 3-(4-acetamidophenyl)-1H-thieno[3,2-c]pyrazole-5-carboxylate

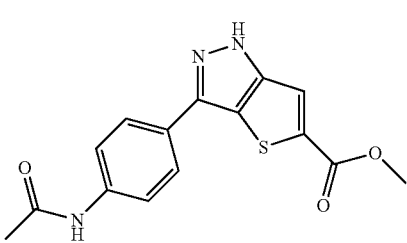 [SMILES: COC(=O)c1cc2[nH]nc(-c3ccc(NC(C)=O)cc3)c2s1]

¹H NMR (400 MHz, DMSO-d₆) δ 10.11 (s, 1H), 7.92 (s, 1H), 7.74 (br s, 4H), 3.88 (s, 3H), 2.07 (s, 3H); [M+11]⁺ 316.

Example 246: 2-(3-(4-Fluorophenyl)-1H-thieno[3,2-c]pyrazol-5-yl)-5-methyloxazole

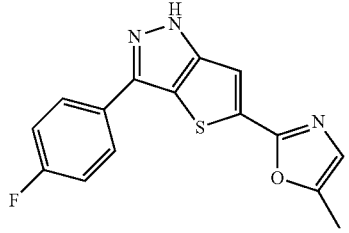 [SMILES: Cc1cnc(-c2cc3[nH]nc(-c4ccc(F)cc4)c3s2)o1]

¹H NMR (400 MHz, DMSO-d₆) δ 13.52 (br s, 1H), 7.84-7.83 (m, 2H), 7.70 (s, 1H), 7.39-7.35 (m, 2H), 7.04 (s, 1H), 2.40 (s, 3H); [M+11]⁺ 300.

Example 247: 3-(4-Fluorophenyl)-5-(5-methylthiazol-2-yl)-1H-thieno[3,2-c]pyrazole

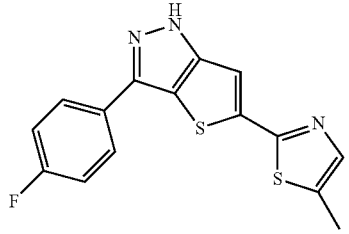 [SMILES: Cc1cnc(-c2cc3[nH]nc(-c4ccc(F)cc4)c3s2)s1]

¹H NMR (400 MHz, DMSO-d₆) δ 13.47 (s, 1H), 7.86-7.83 (m, 2H), 7.71 (s, 1H), 7.58 (s, 1H), 7.38-7.34 (m, 2H), 2.50 (s, 3H); [M+H]⁺ 316.

Example 248: (3-(4-morpholinophenyl)-1H-thieno[3,2-c]pyrazol-5-yl)(pyrrolidin-1-yl)methanone

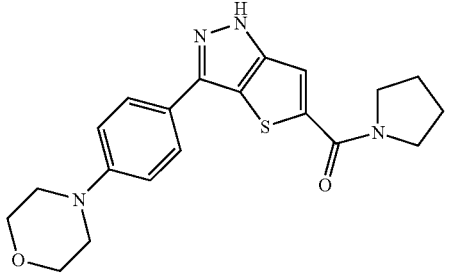 [SMILES: O=C(c1cc2[nH]nc(-c3ccc(N4CCOCC4)cc3)c2s1)N1CCCC1]

¹H NMR (400 MHz, DMSO-d₆) δ 13.46 (br s, 1H), 7.67-7.66 (m, 3H), 7.10-7.08 (m, 2H), 3.84-3.81 (m, 2H), 3.76-3.73 (m, 4H), 3.53-3.51 (m, 2H), 3.18-3.16 (m, 4H), 1.98-1.93 (m, 2H), 1.89-1.85 (m, 2H); [M+H]⁺ 383.

Example 249: Methyl 3-(4-(2-morpholinoethoxy)phenyl)-1H-thieno[3,2-c]pyrazole-5-carboxylate

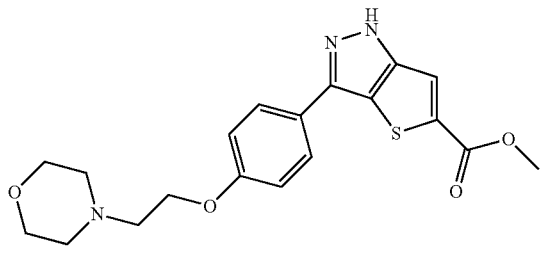 [SMILES: COC(=O)c1cc2[nH]nc(-c3ccc(OCCN4CCOCC4)cc3)c2s1]

¹H NMR (400 MHz, DMSO-d₆) δ 13.51 (s, 1H), 7.89 (s, 1H), 7.74 (d, J=8.4 Hz, 2H), 7.52 (d, J=8.8 Hz, 1H), 7.10 (d, J=8.0 Hz, 2H), 4.16-4.14 (m, 2H), 3.88 (s, 3H), 3.62-3.56 (m, 4H), 2.72-2.63 (m, 4H); [M+H]⁺ 388.

Example 250: 4-(2-(4-(5-(5-methyloxazol-2-yl)-1H-thieno[3,2-c]pyrazol-3-yl)phenoxy)ethyl)morpholine

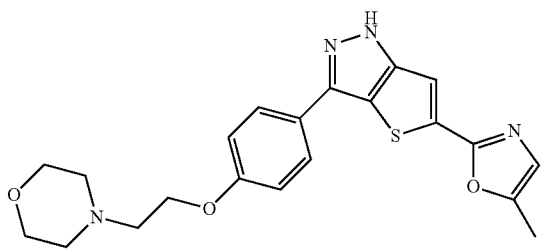 [SMILES: Cc1cnc(-c2cc3[nH]nc(-c4ccc(OCCN5CCOCC5)cc4)c3s2)o1]

¹H NMR (400 MHz, DMSO-d₆) δ 13.35 (s, 1H), 7.74-7.67 (m, 2H), 7.67 (s, 1H), 7.11-7.08 (m, 2H), 7.03 (s, 1H), 4.15 (t, J=5.6 Hz, 2H), 3.58 (t, J=4.8 Hz, 4H), 2.72 (t, J=5.6 Hz, 2H), 2.53-2.50 (m, 4H), 2.40 (s, 3H); [M+H]⁺ 411.

Example 251: 4-(Dimethylamino)-N-(5-(5-methylthiazol-2-yl)-1H-thieno[3,2-c]pyrazol-3-yl)benzamide

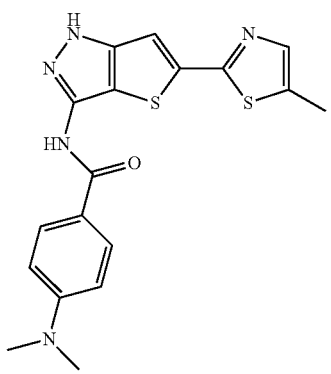

¹H NMR (400 MHz, DMSO-d₆) δ 12.65 (s, 1H), 10.90 (s, 1H), 7.97 (d, J=9.0 Hz, 2H), 7.55 (d, J=1.2 Hz, 1H), 7.44 (s, 1H), 6.74 (d, J=9.0 Hz, 2H), 3.01 (s, 6H); [M+H]⁺ 400.

Example 252: N-(5-(5-Ethylthiazol-2-yl)-1H-thieno[3,2-c]pyrazol-3-yl)-4-morpholinobenzamide

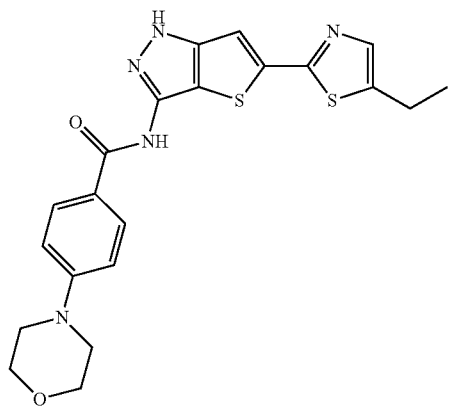 [SMILES: CCc1cnc(-c2cc3[nH]nc(NC(=O)c4ccc(N5CCOCC5)cc4)c3s2)s1]

$^1$H NMR (400 MHz, DMSO-d$_6$) δ 12.69 (s, 1H), 11.02 (s, 1H), 7.99 (d, J=8.9 Hz, 2H), 7.56 (s, 1H), 7.46 (s, 1H), 7.01 (d, J=9.0 Hz, 2H), 3.74 (t, J=4.8 Hz, 4H), 3.27 (t, J=4.7 Hz, 4H), 2.88 (q, J=7.1 Hz, 2H), 1.28 (t, J=7.5 Hz, 3H); [M+H]$^+$ 440.

Example 253: N-(5-(5-methylthiazol-2-yl)-1H-thieno[3,2-c]pyrazol-3-yl)-4-((2-(piperidin-1-yl)ethyl)amino)benzamide

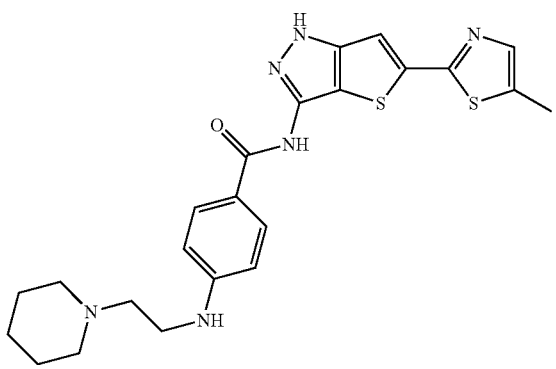 [SMILES: Cc1cnc(-c2cc3[nH]nc(NC(=O)c4ccc(NCCN5CCCCC5)cc4)c3s2)s1]

$^1$H NMR (400 MHz, DMSO-d$_6$) δ 12.64 (br s, 1H), 10.80 (s, 1H), 7.87 (d, J=8.8 Hz, 2H), 7.55 (d, J=1.2 Hz, 1H), 7.44 (s, 1H), 6.61 (d, J=8.8 Hz, 2H), 6.19 (t, J=5.3 Hz, 1H), 6.19 (q, J=6.6 Hz, 2H), 2.46-2.44 (m, 2H), 2.39 (br s, 4H), 1.51 (quint, J=5.5 Hz, 4H), 1.40-1.39 (m, 2H); [M+H]$^+$ 467.

Example 254: Methyl 3-(4-morpholinophenyl)-1H-thieno[3,2-c]pyrazole-5-carboxylate

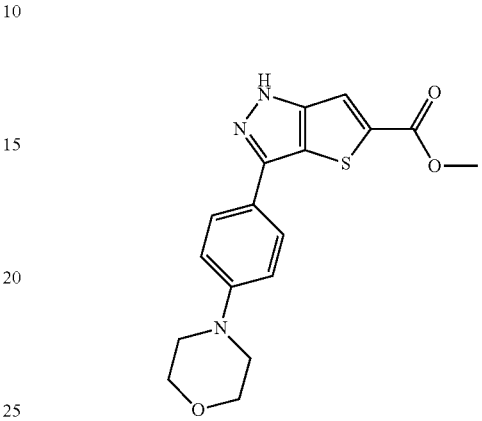

[M+H]$^+$ 344.

Inhibition activities on TNIK, IKKε and TBK1 were evaluated using the compounds of Examples 1 to 254.

The inhibition activities on TNIK, IKKε and TBK1 were measured by a luminometer, TNIK/IKKε/TBK1 Kinase Enzyme System (Promega, Ca# V4158; Invitrogen, PR8031B, Promega, Ca# V3991) and ADP-Glo Kinase Assay using ADP-Glo™ Kinase Analysis Kit (Promega, Ca# V9101) and a kinase reaction buffer [40 mM Tris(pH 7.5), 20 mM MgCl$_2$, 0.1 mg/mL BSA] in accordance with the manufacturer's protocol.

The results of the inhibition activities of the compounds of Examples 1 to 254 on TNIK, IKKε and TBK1 are shown in Table 1 below.

TABLE 1

| Example | Name | TNIK (μM) | TBK1 (μM) | IKKε (μM) |
|---|---|---|---|---|
| 1 | N-benzyl-3-(4-fluorobenzamido)-1H-indazole-5-carboxamide | | | |
| 2 | N-(furan-2-yl-methyl)-3-(4-methoxybenzamido)-1H-indazole-5-carboxamide | | 0.037 | 0.13 |
| 3 | 3-(4-methoxybenzamido)-N-(thiophen-2-ylmethyl)-1H-indazole-5-carboxamide | | 0.038 | 0.11 |
| 4 | 3-(4-methoxybenzamido)-N-methyl-N-(thiophen-2-ylmethyl)-1H-indazole-5-carboxamide | | 0.83 | |
| 5 | 4-methoxy-N-(5-(4,5,6,7-tetrahydrothieno[2,3-c]pyridine-6-carbonyl)-1H-indazol-3-yl)benzamide | | 8.40 | |
| 6 | 3-(4-(methylthio)benzamido)-N-(thiophen-2-ylmethyl)-1H-indazole-5-carboxamide | | 0.025 | |
| 7 | 3-(1-methyl-1H-pyrazole-4-carboxamido)-N-(thiophen-2-ylmethyl)-1H-indazole-5-carboxamide | | 0.16 | 0.25 |
| 8 | 3-(5-methoxypicolinamido)-N-(thiophen-2-ylmethyl)-1H-indazole-5-carboxamide hydrochloride | | 0.082 | 0.33 |

TABLE 1-continued

| Example | Name | TNIK (μM) | TBK1 (μM) | IKKε (μM) |
|---|---|---|---|---|
| 9 | 3-(2-methoxynicotinamido)-N-(thiophen-2-ylmethyl)-1H-indazole-5-carboxamide | | 0.11 | 0.033 |
| 10 | 3-(4-tert-butylbenzamido)-N-(thiophen-2-ylmethyl)-1H-indazole-5-carboxamide | | 0.030 | |
| 11 | 4-methoxy-N-(5-((thiophen-2-ylmethyl)amino)-1H-indazol-3-yl)benzamide | | 0.89 | |
| 12 | 4-methoxy-N-(5-(5-(morpholinomethyl)thiophen-2-yl)-1H-indazol-3-yl)benzamide | | 0.43 | |
| 13 | 3-benzamido-N-(thiophen-2-ylmethyl)-1H-indazole-5-carboxamide | | 0.036 | |
| 14 | 3-(4-fluorobenzamido)-N-(1-(thiophen-2-yl)ethyl)-1H-indazole-5-carboxamide | | 0.042 | |
| 15 | 3-(4-fluorobenzamido)-N-(1-(thiophen-2-yl)cyclopropyl)-1H-indazole-5-carboxamide | | 0.025 | 0.055 |
| 16 | N-(1-cyanocyclopropyl)-3-(4-fluorobenzamido)-1H-indazole-5-carboxamide | | 0.39 | 0.91 |
| 17 | 3-(4-fluorobenzamido)-N-(1-(thiophen-2-yl)propyl)-1H-indazole-5-carboxamide | | 0.013 | |
| 18 | 3-(4-fluorobenzamido)-N-(1-(thiophen-2-yl)butyl)-1H-indazole-5-carboxamide | | 0.21 | 1.23 |
| 19 | 3-(4-fluorobenzamido)-N-((5-methylthiophen-2-yl)methyl)-1H-indazole-5-carboxamide | | 0.49 | 2.91 |
| 20 | 3-(4-fluorobenzamido)-N-(2-phenylpropan-2-yl)-1H-indazole-5-carboxamide | | 0.31 | 0.35 |
| 21 | 3-(4-fluorobenzamido)-N-(4-(trifluoromethyl)benzyl)-1H-indazole-5-carboxamide | | >10 | >10 |
| 22 | N-(cyclohexylmethyl)-3-(4-fluorobenzamido)-1H-indazole-5-carboxamide | | | |
| 23 | N-(cyclopropylmethyl)-3-(4-fluorobenzamido)-1H-indazole-5-carboxamide | | 1.41 | 5.58 |
| 24 | N-butyl-3-(4-fluorobenzamido)-1H-indazole-5-carboxamide | | 0.66 | 2.46 |
| 25 | 3-(4-fluorobenzamido)-N-isopentyl-1H-indazole-5-carboxamide | | 0.42 | 5.87 |
| 26 | N-((1,2,4-oxadiazol-3-yl)methyl)-3-(4-fluorobenzamido)-1H-indazole-5-carboxamide | | | |
| 27 | 3-(4-fluorobenzamido)-N-(thiazol-5-ylmethyl)-1H-indazole-5-carboxamide 2,2,2-trifluoroacetate | | 0.20 | 0.36 |
| 28 | 3-(4-fluorobenzamido)-N-(pyridin-2-ylmethyl)-1H-indazole-5-carboxamide 2,2,2-trifluoroacetate | | 0.73 | 2.62 |
| 29 | 3-(4-fluorobenzamido)-N-(pyridin-4-ylmethyl)-1H-indazole-5-carboxamide | | 0.28 | |
| 30 | N-(cyclopropyl(thiophen-2-yl)methyl)-3-(4-fluorobenzamido)-1H-indazole-5-carboxamide | | 0.036 | |
| 31 | 4-fluoro-N-(5-(((thiophen-2-ylmethyl)amino)methyl)-1H-indazol-3-yl)benzamide hydrochloride | | >10 | |
| 32 | 4-fluoro-N-(5-(((1-(thiophen-2-yl)propyl)amino)methyl)-1H-indazol-3-yl)benzamide | | >10 | >10 |
| 33 | 3-(4-fluorobenzamido)-N-(3-methyl-1-(thiophen-2-yl)butyl)-1H-indazole-5-carboxamide | | 4.69 | 6.36 |
| 34 | 3-(4-fluorobenzamido)-N-(2-(thiophen-2-yl)butan-2-yl)-1H-indazole-5-carboxamide | | 0.58 | 1.74 |
| 35 | 3-(2,4-difluorobenzamido)-N-(thiophen-2-ylmethyl)-1H-indazole-5-carboxamide | | 0.28 | 0.93 |
| 36 | 3-(4-fluorobenzamido)-N-(thiophen-2-ylmethyl)-1H-indazole-5-carboxamide | | 0.089 | |
| 37 | 3-(4-fluorobenzamido)-N-(1-phenylethyl)-1H-indazole-5-carboxamide | | | |
| 38 | 3-(4-fluorobenzamido)-N-(1-phenylpropyl)-1H-indazole-5-carboxamide | | | |
| 39 | 3-(phenylsulfonamido)-N-(thiophen-2-ylmethyl)-1H-indazole-5-carboxamide | | >10 | |
| 40 | N-benzyl-3-(4-(4-methylpiperazin-1-yl)benzamido)-1H-indazole-5-carboxamide | | 0.00094 | 0.0089 |
| 41 | N-(1-phenylpropyl)-3-(4-(piperazin-1-yl)benzamido)-1H-indazole-5-carboxamide | | 0.0039 | 0.047 |
| 42 | N-methyl-3-(4-morpholinobenzamido)-N-(thiophen-2-ylmethyl)-1H-indazole-5-carboxamide | | 0.20 | |
| 43 | 3-(4-morpholinobenzamido)-N-(1-(thiophen-2-yl)ethyl)-1H-indazole-5-carboxamide | | 0.0021 | 0.0049 |
| 44 | 3-(4-(4-methylpiperazin-1-yl)benzamido)-N-(1-(thiophen-2-yl)ethyl)-1H-indazole-5-carboxamide | | 0.0035 | 0.0031 |
| 45 | N-(2-hydroxy-1-(thiophen-2-yl)ethyl)-3-(4-(4-methylpiperazin-1-yl)benzamido)-1H-indazole-5-carboxamide | | 0.0021 | 0.014 |
| 46 | 3-(4-morpholinobenzamido)-N-(thiophen-3-ylmethyl)-1H-indazole-5-carboxamide | | 0.0015 | 0.022 |
| 47 | 3-(4-(4-methylpiperazin-1-yl)benzamido)-N-(thiophen-3-ylmethyl)-1H-indazole-5-carboxamide | | 0.0014 | 0.014 |
| 48 | 3-(4-morpholinobenzamido)-N-(1-(thiophen-2-yl)cyclopropyl)-1H-indazole-5-carboxamide | | 0.0011 | 0.0032 |

TABLE 1-continued

| Example | Name | TNIK (µM) | TBK1 (µM) | IKKε (µM) |
|---|---|---|---|---|
| 49 | 3-(4-(4-methylpiperazin-1-yl)benzamido)-N-(1-(thiophen-2-yl)cyclopropyl)-1H-indazole-5-carboxamide | | 0.0025 | 0.0034 |
| 50 | N-(furan-2-ylmethyl)-3-(4-morpholinobenzamido)-1H-indazole-5-carboxamide | | 0.0058 | 0.037 |
| 51 | N-(furan-2-ylmethyl)-3-(4-(4-methylpiperazin-1-yl)benzamido)-1H-indazole-5-carboxamide | | 0.0081 | 0.064 |
| 52 | 3-(4-morpholinobenzamido)-N-(1-(pyridin-3-yl)ethyl)-1H-indazole-5-carboxamide | | 0.014 | >10 |
| 53 | 3-(4-(4-methylpiperazin-1-yl)benzamido)-N-(1-(pyridin-3-yl)ethyl)-1H-indazole-5-carboxamide | | 0.021 | >10 |
| 54 | 3-(4-morpholinobenzamido)-N-(1-(thiophen-2-yl)propyl)-1H-indazole-5-carboxamide | | 0.00036 | 0.0031 |
| 55 | 3-(4-(4-methylpiperazin-1-yl)benzamido)-N-(1-(thiophen-2-yl)propyl)-1H-indazole-5-carboxamide | | 0.00093 | 0.0027 |
| 56 | 3-(4-morpholinobenzamido)-N-(pyridin-3-ylmethyl)-1H-indazole-5-carboxamide 2,2,2-trifluoroacetate | | 0.0033 | 0.10 |
| 57 | 3-(4-(4-methylpiperazin-1-yl)benzamido)-N-(pyridin-3-ylmethyl)-1H-indazole-5-carboxamide bis(2,2,2-trifluoroacetate) | | 0.0012 | 0.14 |
| 58 | 3-(4-morpholinobenzamido)-N-(1-(thiophen-2-yl)butyl)-1H-indazole-5-carboxamide | | 0.039 | 0.13 |
| 59 | 3-(4-(4-methylpiperazin-1-yl)benzamido)-N-(1-(thiophen-2-yl)butyl)-1H-indazole-5-carboxamide | | 0.032 | 0.11 |
| 60 | N-((5-methylthiophen-2-yl)methyl)-3-(4-morpholinobenzamido)-1H-indazole-5-carboxamide | | 0.034 | 0.28 |
| 61 | 3-(4-(4-methylpiperazin-1-yl)benzamido)-N-((5-methylthiophen-2-yl)methyl)-1H-indazole-5-carboxamide | | 0.056 | 0.23 |
| 62 | 3-(4-morpholinobenzamido)-N-(2-phenylpropan-2-yl)-1H-indazole-5-carboxamide | | 0.011 | 0.032 |
| 63 | 3-(4-(4-methylpiperazin-1-yl)benzamido)-N-(2-phenylpropan-2-yl)-1H-indazole-5-carboxamide | | 0.0094 | 0.036 |
| 64 | 3-(4-(4-methylpiperazin-1-yl)benzamido)-N-(2-phenylpropan-2-yl)-1H-indazole-5-carboxamide hydrochloride | | | |
| 65 | 3-(4-morpholinobenzamido)-N-(4-(trifluoromethyl)benzyl)-1H-indazole-5-carboxamide | | 0.76 | 1.95 |
| 66 | 3-(4-(4-methylpiperazin-1-yl)benzamido)-N-(4-(trifluoromethyl)benzyl)-1H-indazole-5-carboxamide | | 0.98 | 3.19 |
| 67 | 3-(4-morpholinobenzamido)-N-(1-phenylcyclopropyl)-1H-indazole-5-carboxamide | | 0.0030 | 0.0050 |
| 68 | 3-(4-(4-methylpiperazin-1-yl)benzamido)-N-(1-phenylcyclopropyl)-1H-indazole-5-carboxamide | | 0.0006 | 0.0042 |
| 69 | N-((2-methylpyridin-4-yl)methyl)-3-(4-morpholinobenzamido)-1H-indazole-5-carboxamide | | 0.38 | 2.72 |
| 70 | 3-(4-(4-methylpiperazin-1-yl)benzamido)-N-((2-methylpyridin-4-yl)methyl)-1H-indazole-5-carboxamide | | 0.18 | 1.50 |
| 71 | 3-(4-morpholinobenzamido)-N-((6-(trifluoromethyl)pyridin-3-yl)methyl)-1H-indazole-5-carboxamide | | 0.44 | >10 |
| 72 | 3-(4-(4-methylpiperazin-1-yl)benzamido)-N-((6-(trifluoromethyl)pyridin-3-yl)methyl)-1H-indazole-5-carboxamide | | 0.35 | 1.83 |
| 73 | 3-(2-methyl-4-morpholinobenzamido)-N-(thiophen-2-ylmethyl)-1H-indazole-5-carboxamide | | 0.0040 | 0.044 |
| 74 | 3-(2-methyl-4-(4-methylpiperazin-1-yl)benzamido)-N-(thiophen-2-ylmethyl)-1H-indazole-5-carboxamide | | 0.0044 | 0.079 |
| 75 | 3-(3-(4-(4-methylpiperazin-1-yl)benzamido)-1H-indazol-5-yl)-3-oxo-2-(thiophen-2-yl)propanoic acid | | 0.18 | 0.67 |
| 76 | (S)-3-(4-(3-methylpiperazin-1-yl)benzamido)-N-(1-phenylcyclopropyl)-1H-indazole-5-carboxamide | | 0.0046 | 0.016 |
| 77 | (R)-3-(4-(3-methylpiperazin-1-yl)benzamido)-N-(1-phenylcyclopropyl)-1H-indazole-5-carboxamide | | 0.0048 | 0.018 |
| 78 | 3-(3-methyl-4-morpholinobenzamido)-N-(thiophen-2-ylmethyl)-1H-indazole-5-carboxamide | | 0.037 | 0.20 |
| 79 | 3-(3-methyl-4-(4-methylpiperazin-1-yl)benzamido)-N-(thiophen-2-ylmethyl)-1H-indazole-5-carboxamide | | 0.015 | 0.22 |
| 80 | 3-(4-(4-methylpiperazin-1-yl)benzamido)-N-(1-(thiophen-3-yl)ethyl)-1H-indazole-5-carboxamide | | 0.0025 | 0.0074 |
| 81 | N-(1-(furan-2-yl)ethyl)-3-(4-(4-methylpiperazin-1-yl)benzamido)-1H-indazole-5-carboxamide | | 0.0039 | 0.021 |
| 82 | 3-(4-(4-methylpiperazin-1-yl)benzamido)-N-(1-(thiazol-2-yl)ethyl)-1H-indazole-5-carboxamide | | 0.014 | 0.074 |
| 83 | 3-(4-(4-methylpiperazin-1-yl)benzamido)-N-(1-(thiazol-5-yl)ethyl)-1H-indazole-5-carboxamide | | 0.011 | 0.047 |
| 84 | 3-(4-(4-methylpiperazin-1-yl)benzamido)-N-(1-(thiazol-2-yl)propyl)-1H-indazole-5-carboxamide | | 0.016 | 0.069 |
| 85 | 3-(4-(4-methylpiperazin-1-yl)benzamido)-N-(pyridin-2-ylmethyl)-1H-indazole-5-carboxamide bis(2,2,2-trifluoroacetate) | | 0.16 | 1.63 |
| 86 | 3-(4-morpholinobenzamido)-N-(pyridin-2-ylmethyl)-1H-indazole-5-carboxamide | | 0.089 | 0.45 |

TABLE 1-continued

| Example | Name | TNIK (μM) | TBK1 (μM) | IKKε (μM) |
|---|---|---|---|---|
| 87 | N-(cyclohexylmethyl)-3-(4-(4-methylpiperazin-1-yl)benzamido)-1H-indazole-5-carboxamide | | 0.018 | 0.072 |
| 88 | N-(cyclohexylmethyl)-3-(4-morpholinobenzamido)-1H-indazole-5-carboxamide | | 0.020 | 0.11 |
| 89 | 3-(4-(3,5-dimethylpiperazin-1-yl)benzamido)-N-(thiophen-2-ylmethyl)-1H-indazole-5-carboxamide 2,2,2-trifluoroacetate | | 0.0056 | 0.079 |
| 90 | N-(cyclopentylmethyl)-3-(4-(4-methylpiperazin-1-yl)benzamido)-1H-indazole-5-carboxamide 2,2,2-trifluoroacetate | | 0.013 | 0.21 |
| 91 | N-(cyclopentylmethyl)-3-(4-morpholinobenzamido)-1H-indazole-5-carboxamide 2,2,2-trifluoroacetate | | 0.0053 | 0.093 |
| 92 | 3-(4-(2,6-dimethylmorpholino)benzamido)-N-(thiophen-2-ylmethyl)-1H-indazole-5-carboxamide 2,2,2-trifluoroacetate | | 0.0070 | 0.065 |
| 93 | N-(4-hydroxybutan-2-yl)-3-(4-(4-methylpiperazin-1-yl)benzamido)-1H-indazole-5-carboxamide | | 0.19 | 1.04 |
| 94 | N-((1H-1,2,3-triazol-4-yl)methyl)-3-(4-(4-methylpiperazin-1-yl)benzamido)-1H-indazole-5-carboxamide | | 0.24 | 1.59 |
| 95 | 3-(4-(3,5-dimethylpiperazin-1-yl)benzamido)-N-(1-(thiophen-2-yl)propyl)-1H-indazole-5-carboxamide 2,2,2-trifluoroacetate | | 0.0028 | 0.021 |
| 96 | 3-(4-(2,6-dimethylmorpholino)benzamido)-N-(1-(thiophen-2-yl)propyl)-1H-indazole-5-carboxamide 2,2,2-trifluoroacetate | | 0.0051 | 0.047 |
| 97 | 3-(4-((S)-3-methylpiperazin-1-yl)benzamido)-N-(1-(thiophen-2-yl)propyl)-1H-indazole-5-carboxamide 2,2,2-trifluoroacetate | | 0.0028 | 0.016 |
| 98 | 3-(4-((R)-3-methylpiperazin-1-yl)benzamido)-N-(1-(thiophen-2-yl)propyl)-1H-indazole-5-carboxamide 2,2,2-trifluoroacetate | | 0.0030 | 0.023 |
| 99 | 3-(4-((3R,5S)-3,5-dimethylpiperazin-1-yl)benzamido)-N-(1-(thiophen-2-yl)propyl)-1H-indazole-5-carboxamide 2,2,2-trifluoroacetate | | 0.0027 | 0.014 |
| 100 | N-((3-methyl-1,2,4-oxadiazol-5-yl)methyl)-3-(4-morpholinobenzamido)-1H-indazole-5-carboxamide 2,2,2-trifluoroacetate | | 0.22 | 0.95 |
| 101 | N-((3-methyl-1,2,4-oxadiazol-5-yl)methyl)-3-(4-(4-methylpiperazin-1-yl)benzamido)-1H-indazole-5-carboxamide 2,2,2-trifluoroacetate | | 0.15 | 0.96 |
| 102 | 3-(4-(piperazin-1-yl)benzamido)-N-(1-(thiophen-2-yl)propyl)-1H-indazole-5-carboxamide | | 0.0058 | 0.025 |
| 103 | 3-(4-(4-methylpiperazin-1-yl)benzamido)-N-(thiazol-2-ylmethyl)-1H-indazole-5-carboxamide 2,2,2-trifluoroacetate | | 0.020 | 0.44 |
| 104 | 3-(4-morpholinobenzamido)-N-(thiazol-2-ylmethyl)-1H-indazole-5-carboxamide 2,2,2-trifluoroacetate | | 0.026 | 0.37 |
| 105 | N-((1,2,4-oxadiazol-3-yl)methyl)-3-(4-morpholinobenzamido)-1H-indazole-5-carboxamide 2,2,2-trifluoroacetate | | 0.10 | 1.14 |
| 106 | N-cyclobutylmethyl)-3-(4-(4-methylpiperazin-1-yl)benzamido)-1H-indazole-5-carboxamide | | 0.023 | 0.15 |
| 107 | 3-(4-(3,3-dimethylpiperazin-1-yl)benzamido)-N-(thiophen-2-ylmethyl)-1H-indazole-5-carboxamide 2,2,2-trifluoroacetate | | 0.0025 | 0.014 |
| 108 | 3-(4-(4-hydroxypiperidin-1-yl)benzamido)-N-(1-(thiophen-2-yl)propyl)-1H-indazole-5-carboxamide | | 0.0028 | 0.015 |
| 109 | 3-(4-(4-ethylpiperazin-1-yl)benzamido)-N-(1-(thiophen-2-yl)propyl)-1H-indazole-5-carboxamide | | 0.0036 | 0.025 |
| 110 | 3-(4-(4-methoxypiperidin-1-yl)benzamido)-N-(1-(thiophen-2-yl)propyl)-1H-indazole-5-carboxamide | | 0.0072 | 0.036 |
| 111 | (S)-3-(4-(4-methylpiperazin-1-yl)benzamido)-N-(1-(thiophen-2-yl)propyl)-1H-indazole-5-carboxamide | | 0.014 | 0.074 |
| 112 | (R)-3-(4-(4-methylpiperazin-1-yl)benzamido)-N-(1-(thiophen-2-yl)propyl)-1H-indazole-5-carboxamide | | 0.0042 | 0.011 |
| 113 | N-butyl-3-(4-(4-methylpiperazin-1-yl)benzamido)-1H-indazole-5-carboxamide 2,2,2-trifluoroacetate | | 0.018 | 0.18 |
| 114 | N-isopentyl-3-(4-(4-methylpiperazin-1-yl)benzamido)-1H-indazole-5-carboxamide 2,2,2-trifluoroacetate | | 0.082 | 0.41 |
| 115 | N-butyl-3-(4-morpholinobenzamido)-1H-indazole-5-carboxamide 2,2,2-trifluoroacetate | | 0.071 | 0.97 |
| 116 | N-isopentyl-3-(4-morpholinobenzamido)-1H-indazole-5-carboxamide 2,2,2-trifluoroacetate | | 0.48 | 3.12 |
| 117 | (S)-3-(4-(3-methylpiperazin-1-yl)benzamido)-N-(thiophen-2-ylmethyl)-1H-indazole-5-carboxamide 2,2,2-trifluoroacetate | | 0.0033 | 0.071 |
| 118 | N-((1,2,4-oxadiazol-3-yl)methyl)-3-(4-(4-methylpiperazin-1-yl)benzamido)-1H-indazole-5-carboxamide 2,2,2-trifluoroacetate | | 0.30 | 1.96 |
| 119 | N-((1H-1,2,3-triazol-4-yl)methyl)-3-(4-morpholinobenzamido)-1H-indazole-5-carboxamide 2,2,2-trifluoroacetate | | 0.46 | 1.24 |
| 120 | 3-(4-morpholinobenzamido)-N-(pyridin-4-ylmethyl)-1H-indazole-5-carboxamide | | 0.019 | |
| 121 | 3-(4-(4-methylpiperazin-1-yl)benzamido)-N-(pyridin-4-ylmethyl)-1H-indazole-5-carboxamide | | 0.0063 | 0.11 |
| 122 | N-(cyclopropyl(thiophen-2-yl)methyl)-3-(4-morpholinobenzamido)-1H-indazole-5-carboxamide | | 0.0044 | 0.025 |
| 123 | 4-morpholino-N-(5-(((thiophen-2-ylmethyl)amino)methyl)-1H-indazol-3-yl)benzamide | | 0.66 | 4.47 |

TABLE 1-continued

| Example | Name | TNIK (µM) | TBK1 (µM) | IKKε (µM) |
|---|---|---|---|---|
| 124 | 4-(4-methylpiperazin-1-yl)-N-(5-(((1-(thiophen-2-yl)propyl)amino)methyl)-1H-indazol-3-yl)benzamide | | 2.44 | >10 |
| 125 | N-(cyclopropyl(thiophen-2-yl)methyl)-3-(4-(4-methylpiperazin-1-yl)benzamido)-1H-indazole-5-carboxamide | | 0.026 | 0.037 |
| 126 | N-(cyclopropyl(thiophen-2-yl)methyl)-3-(4-(piperazin-1-yl)benzamido)-1H-indazole-5-carboxamide | | 0.019 | 0.013 |
| 127 | 3-(4-morpholinobenzamido)-N-(1-(pyridin-2-yl)ethyl)-1H-indazole-5-carboxamide | | 0.027 | 0.14 |
| 128 | 3-(4-(4-methylpiperazin-1-yl)benzamido)-N-(1-(pyridin-2-yl)ethyl)-1H-indazole-5-carboxamide | | 0.028 | 0.11 |
| 129 | N-(3-methyl-1-(thiophen-2-yl)butyl)-3-(4-(4-methylpiperazin-1-yl)benzamido)-1H-indazole-5-carboxamide | | 0.022 | 0.054 |
| 130 | N-(3-methyl-1-(thiophen-2-yl)butyl)-3-(4-morpholinobenzamido)-1H-indazole-5-carboxamide | | 0.11 | 0.90 |
| 131 | 3-(4-(4-methylpiperazin-1-yl)benzamido)-N-(2-(thiophen-2-yl)butan-2-yl)-1H-indazole-5-carboxamide | | 0.030 | 0.14 |
| 132 | 3-(4-morpholinobenzamido)-N-(1-(pyridin-4-yl)ethyl)-1H-indazole-5-carboxamide | | 0.023 | 0.043 |
| 133 | 3-(4-(4-methylpiperazin-1-yl)benzamido)-N-(1-(pyridin-4-yl)ethyl)-1H-indazole-5-carboxamide | | 0.028 | 0.053 |
| 134 | 3-(4-morpholinobenzamido)-N-(2-(thiophen-2-yl)propan-2-yl)-1H-indazole-5-carboxamide | | 0.012 | 0.033 |
| 135 | 3-(4-(4-methylpiperazin-1-yl)benzamido)-N-(2,2,2-trifluoro-1-(thiophen-2-yl)ethyl)-1H-indazole-5-carboxamide | | 0.0085 | 0.038 |
| 136 | 3-(4-(4-methylpiperazin-1-yl)benzamido)-N-(2-(thiophen-2-yl)propan-2-yl)-1H-indazole-5-carboxamide | | 0.0057 | 0.024 |
| 137 | (S)-3-(4-(3-methylpiperazin-1-yl)benzamido)-N-(2-(thiophen-2-yl)propan-2-yl)-1H-indazole-5-carboxamide | | 0.0049 | 0.032 |
| 138 | 3-(4-morpholinobenzamido)-N-(2,2,2-trifluoro-1-(thiophen-2-yl)ethyl)-1H-indazole-5-carboxamide | | 0.039 | 0.12 |
| 139 | N-(cyclopropyl(pyridin-2-yl)methyl)-3-(4-morpholinobenzamido)-1H-indazole-5-carboxamide | | 0.10 | 0.34 |
| 140 | N-(cyclopropyl(pyridin-2-yl)methyl)-3-(4-(4-methylpiperazin-1-yl)benzamido)-1H-indazole-5-carboxamide | | 0.084 | 0.27 |
| 141 | 4-(4-methylpiperazin-1-yl)-N-(5-(2-(thiophen-2-yl)acetamido)-1H-indazol-3-yl)benzamide | | 0.024 | 0.38 |
| 142 | N-(cyclopropyl(pyridin-3-yl)methyl)-3-(4-morpholinobenzamido)-1H-indazole-5-carboxamide | | 0.067 | 0.096 |
| 143 | N-(cyclopropyl(pyridin-3-yl)methyl)-3-(4-(4-methylpiperazin-1-yl)benzamido)-1H-indazole-5-carboxamide | | 0.071 | 0.12 |
| 144 | 4-morpholino-N-(5-(2-(thiophen-2-yl)acetamido)-1H-indazol-3-yl)benzamide | | 0.069 | 0.25 |
| 145 | 3-(4-(4-methylpiperazin-1-yl)benzamido)-N-(2-(thiophen-3-yl)propan-2-yl)-1H-indazole-5-carboxamide | | 0.012 | 0.033 |
| 146 | N-((5-chlorothiophen-2-yl)methyl)-3-(4-(4-methylpiperazin-1-yl)benzamido)-1H-indazole-5-carboxamide | | 0.019 | 0.065 |
| 147 | 3-(4-(4-methylpiperazin-1-yl)benzamido)-N-(1-(thiophen-2-yl)cyclohexyl)-1H-indazole-5-carboxamide | | 0.11 | 0.34 |
| 148 | 3-(4-morpholinobenzamido)-N-(thiophen-2-ylmethyl)-1H-indazole-5-carboxamide | | 0.0040 | 0.031 |
| 149 | 3-(4-(4-methylpiperazin-1-yl)benzamido)-N-(thiophen-2-ylmethyl)-1H-indazole-5-carboxamide | | 0.0075 | 0.032 |
| 150 | 3-(4-((2-methoxyethyl)amino)benzamido)-N-(thiophen-2-ylmethyl)-1H-indazole-5-carboxamide | | 0.0072 | 0.049 |
| 151 | 3-(4-((3-methoxypropyl)amino)benzamido)-N-(thiophen-2-ylmethyl)-1H-indazole-5-carboxamide | | 0.0079 | 0.052 |
| 152 | 3-(4-((2-(pyrrolidin-1-yl)ethyl)amino)benzamido)-N-(thiophen-2-ylmethyl)-1H-indazole-5-carboxamide | | 0.0040 | 0.092 |
| 153 | 3-(4-((2-morpholinoethyl)amino)benzamido)-N-(thiophen-2-ylmethyl)-1H-indazole-5-carboxamide | | 0.0037 | 0.037 |
| 154 | 3-(4-((3-(dimethylamino)propyl)amino)benzamido)-N-(thiophen-2-ylmethyl)-1H-indazole-5-carboxamide | | 0.0086 | 0.13 |
| 155 | 3-(4-(methyl(2-(methylamino)ethyl)amino)benzamido)-N-(thiophen-2-ylmethyl)-1H-indazole-5-carboxamide | | 0.0064 | 0.094 |
| 156 | 3-(3-morpholinobenzamido)-N-(thiophen-2-ylmethyl)-1H-indazole-5-carboxamide | | 0.077 | 0.29 |
| 157 | 3-(4-(((tetrahydrofuran-2-yl)methyl)amno)benzamido)-N-(thiophen-2-ylmethyl)-1H-indazole-5-carboxamide | | 0.0080 | 0.050 |
| 158 | 3-(4-((2-(dimethylamino)ethyl)amino)benzamido)-N-(thiophen-2-ylmethyl)-1H-indazole-5-carboxamide | | 0.0087 | 0.096 |
| 159 | 3-(4-(isopentylamino)benzamido)-N-(thiophen-2-ylmethyl)-1H-indazole-5-carboxamide | | 0.033 | 0.31 |
| 160 | 3-(4-((2-(tetrahydro-2H-pyran-4-yl)ethyl)amino)benzamido)-N-(thiophen-2-ylmethyl)-1H-indazole-5-carboxamide | | 0.0054 | |
| 161 | 3-(4-(hexylamino)benzamido)-N-(thiophen-2-ylmethyl)-1H-indazole-5-carboxamide | | 0.76 | |

TABLE 1-continued

| Example | Name | TNIK (µM) | TBK1 (µM) | IKKε (µM) |
|---|---|---|---|---|
| 162 | 3-(4-(cyclohexylamino)benzamido)-N-(thiophen-2-ylmethyl)-1H-indazole-5-carboxamide | | 0.080 | |
| 163 | 3-(4-(cyclopentylamino)benzamido)-N-(thiophen-2-ylmethyl)-1H-indazole-5-carboxamide | | 0.036 | |
| 164 | 3-(4-(cycloheptylamino)benzamido)-N-(thiophen-2-ylmethyl)-1H-indazole-5-carboxamide | | 5.60 | |
| 165 | 3-(4-(cyclooctylamino)benzamido)-N-(thiophen-2-ylmethyl)-1H-indazole-5-carboxamide | | 0.43 | |
| 166 | 3-(4-((cyclohexylmethyl)amino)benzamido)-N-(thiophen-2-ylmethyl)-1H-indazole-5-carboxamide | | 0.26 | |
| 167 | 3-(4-((2-(cyclohex-1-en-1-yl)ethyl)amino)benzamido)-N-(thiophen-2-ylmethyl)-1H-indazole-5-carboxamide | | 1.10 | 3.90 |
| 168 | 3-(2,4-dimorpholinobenzamido)-N-(thiophen-2-ylmethyl)-1H-indazole-5-carboxamide | | 6.60 | |
| 169 | 3-(4-((2-(1H-pyrrol-1-yl)ethyl)amino)benzamido)-N-(thiophen-2-ylmethyl)-1H-indazole-5-carboxamide | | 0.030 | |
| 170 | 3-(2-fluoro-4-(4-methylpiperazin-1-yl)benzamido)-N-(thiophen-2-ylmethyl)-1H-indazole-5-carboxamide | | >10 | |
| 171 | 3-(4-(piperazin-1-yl)benzamido)-N-(thiophen-2-ylmethyl)-1H-indazole-5-carboxamide | | 0.0003 | 0.0038 |
| 172 | 3-(4-(4-methylpiperazin-1-yl)benzamido)-N-(oxazol-5-ylmethyl)-1H-indazole-5-carboxamide | | 0.035 | 0.31 |
| 173 | N-(isoxazol-3-ylmethyl)-3-(4-(4-methylpiperazin-1-yl)benzamido)-1H-indazole-5-carboxamide | | 0.033 | 0.26 |
| 174 | 3-(4-(4-methylpiperazin-1-yl)benzamido)-N-(thiazol-4-ylmethyl)-1H-indazole-5-carboxamide | | 0.045 | 0.54 |
| 175 | (R)-3-(4-(4-methylpiperazin-1-yl)benzamido)-N-(1-phenylethyl)-1H-indazole-5-carboxamide | | 0.0024 | 0.0076 |
| 176 | (S)-3-(4-(4-methylpiperazin-1-yl)benzamido)-N-(1-phenylethyl)-1H-indazole-5-carboxamide | | 0.058 | 0.34 |
| 177 | N-benzyl-3-(4-morpholinobenzamido)-1H-indazole-5-carboxamide | | 0.011 | 0.033 |
| 178 | N-(isoxazol-5-ylmethyl)-3-(4-(4-methylpiperazin-1-yl)benzamido)-1H-indazole-5-carboxamide | | 0.037 | 0.16 |
| 179 | 3-(4-(4-methylpiperazin-1-yl)benzamido)-N-(1-phenylethyl)-1H-indazole-5-carboxamide | | 0.0012 | 0.019 |
| 180 | 3-(4-morpholinobenzamido)-N-(1-phenylethyl)-1H-indazole-5-carboxamide | | 0.0023 | 0.12 |
| 181 | N-(1-phenylethyl)-3-(4-(piperazin-1-yl)benzamido)-1H-indazole-5-carboxamide 2,2,2-trifluoroacetate | | 0.0039 | 0.022 |
| 182 | 3-(4-(3,5-dimethylpiperazin-1-yl)benzamido)-N-(1-phenylethyl)-1H-indazole-5-carboxamide | | 0.0030 | 0.0081 |
| 183 | 3-(4-(2,6-dimethylmorpholino)benzamido)-N-(1-phenylethyl)-1H-indazole-5-carboxamide | | 0.0043 | 0.018 |
| 184 | 3-(4-((S)-3-methylpiperazin-1-yl)benzamido)-N-(1-phenylethyl)-1H-indazole-5-carboxamide 2,2,2-trifluoroacetate | | 0.0037 | 0.015 |
| 185 | 3-(4-((R)-3-methylpiperazin-1-yl)benzamido)-N-(1-phenylethyl)-1H-indazole-5-carboxamide 2,2,2-trifluoroacetate | | 0.0033 | 0.019 |
| 186 | 3-(4-((3R,5S)-3,5-dimethylpiperazin-1-yl)benzamido)-N-(1-phenylethyl)-1H-indazole-5-carboxamide | | 0.0027 | 0.012 |
| 187 | 3-(4-(4-methylpiperazin-1-yl)benzamido)-N-(1-phenylpropyl)-1H-indazole-5-carboxamide | | 0.0035 | 0.018 |
| 188 | 3-(4-morpholinobenzamido)-N-(1-phenylpropyl)-1H-indazole-5-carboxamide | | 0.0032 | 0.017 |
| 189 | N-(4-fluorobenzyl)-3-(4-(4-methylpiperazin-1-yl)benzamido)-1H-indazole-5-carboxamide | | 0.019 | 0.13 |
| 190 | (S)-3-(4-(4-methylpiperazin-1-yl)benzamido)-N-(1-phenylpropyl)-1H-indazole-5-carboxamide | | 0.34 | 1.23 |
| 191 | (R)-3-(4-(4-methylpiperazin-1-yl)benzamido)-N-(1-phenylpropyl)-1H-indazole-5-carboxamide | | 0.0013 | 0.014 |
| 192 | (R)-3-(4-(4-methylpiperazin-1-yl)benzamido)-N-(1-phenylpropyl)-1H-indazole-5-carboxamide hydrochloride | | | |
| 193 | (S)-3-(4-(4-methylpiperazin-1-yl)benzamido)-N-(1-phenylbutyl)-1H-indazole-5-carboxamide | | 0.80 | 4.47 |
| 194 | (R)-3-(4-(4-methylpiperazin-1-yl)benzamido)-N-(1-phenylbutyl)-1H-indazole-5-carboxamide | | 0.0075 | 0.038 |
| 195 | N-(3-fluorobenzyl)-3-(4-(4-methylpiperazin-1-yl)benzamido)-1H-indazole-5-carboxamide | | 0.0072 | 0.050 |
| 196 | N-(2-fluorobenzyl)-3-(4-(4-methylpiperazin-1-yl)benzamido)-1H-indazole-5-carboxamide | | 0.0070 | 0.032 |
| 197 | N-(cyclopropyl(phenyl)methyl)-3-(4-(4-methylpiperazin-1-yl)benzamido)-1H-indazole-5-carboxamide | | 0.027 | 0.042 |
| 198 | tert-butyl 4-(4-((5-((thiophen-2-ylmethyl)carbamoyl)-1H-indazol-3-yl)carbamoyl)phenyl)-3,6-tetrahydropyridine-1(2H)-carboxylate | | 0.15 | 1.28 |
| 199 | 3-(4-(1,2,3,6-tetrahydropyridin-4-yl)benzamido)-N-(thiophen-2-ylmethyl)-1H-indazole-5-carboxamide | | 0.0097 | 0.14 |
| 200 | 3-(4-hydroxybenzamido)-N-(thiophen-2-ylmethyl)-1H-indazole-5-carboxamide | | 0.093 | |

TABLE 1-continued

| Example | Name | TNIK (µM) | TBK1 (µM) | IKKε (µM) |
|---|---|---|---|---|
| 201 | 3-(4-(2-morpholinoethoxy)benzamido)-N-(thiophen-2-ylmethyl)-1H-indazole-5-carboxamide | | 0.0030 | 0.038 |
| 202 | tert-butyl 3-(4-nitrobenzamido)-5-((thiophen-2-ylmethyl)carbamoyl)-1H-indazole-1-carboxylate | | | |
| 203 | 3-(4-nitrobenzamido)-N-(thiophen-2-ylmethyl)-1H-indazole-5-carboxamide | | 0.075 | |
| 204 | 3-(3-nitrobenzamido)-N-(thiophen-2-ylmethyl)-1H-indazole-5-carboxamide | | 0.077 | |
| 205 | 3-(4-aminobenzamido)-N-(thiophen-2-ylmethyl)-1H-indazole-5-carboxamide | | 0.0030 | |
| 206 | 3-(4-(cyclobutanecarboxamido)benzamido)-N-(thiophen-2-ylmethyl)-1H-indazole-5-carboxamide | | 0.026 | |
| 207 | N-(thiophen-2-ylmethyl)-3-(4-(1-(trifluoromethyl)cyclopropanecarboxamido)benzamido)-1H-indazole-5-carboxamide | | 0.038 | |
| 208 | 3-(4-(3-oxocyclobutanecarboxamido)benzamido)-N-(thiophen-2-ylmethyl)-1H-indazole-5-carboxamide | | 0.027 | |
| 209 | 3-(4-(4-acetylpiperazin-1-yl)benzamido)-N-(1-(thiophen-3-yl)propyl)-1H-indazole-5-carboxamide | | 0.0029 | 0.015 |
| 210 | tert-butyl (S)-2-((4-((5-((thiophen-2-ylmethyl)carbamoyl)-1H-indazol-3-yl)carbamoyl)phenyl)carbamoyl)pyrrolidine-1-carboxylate | | 0.12 | |
| 211 | 3-(4-acetamidobenzamido)-N-(thiophen-2-ylmethyl)-1H-indazole-5-carboxamide | | 0.0013 | 0.079 |
| 212 | 3-(4-(1H-imidazol-1-yl)benzamido)-N-(thiophen-2-ylmethyl)-1H-indazole-5-carboxamide | | 0.078 | 0.36 |
| 213 | 3-(4-((1-methylpiperidin-4-yl)amino)benzamido)-N-(thiophen-2-ylmethyl)-1H-indazole-5-carboxamide | | 0.0044 | 0.069 |
| 214 | 3-(4-fluorobenzamido)-N-(1-(pyridin-4-yl)ethyl)-1H-indazole-5-carboxamide | | 0.27 | 0.59 |
| 215 | 3-(4-fluorobenzamido)-N-(2-(thiophen-2-yl)propan-2-yl)-1H-indazole-5-carboxamide | | 0.021 | 0.32 |
| 216 | 3-(4-fluorobenzamido)-N-(1-(pyridin-2-yl)cyclopropyl)-1H-indazole-5-carboxamide | | 3.70 | 5.25 |
| 217 | 3-(4-fluorobenzamido)-N-(1-(pyridin-3-yl)cyclopropyl)-1H-indazole-5-carboxamide | | 0.52 | 0.65 |
| 218 | N-(5-(5-methyloxazol-2-yl)-1H-thieno[3,2-c]pyrazol-3-yl)-4-morpholinobenzamide | 0.048 | | |
| 219 | N-(5-(5-methylthiazol-2-yl)-1H-thieno[3,2-c]pyrazol-3-yl)-4-morpholinobenzamide | 0.13 | 0.33 | |
| 220 | N-(5-(5-methyloxazol-2-yl)-1H-thieno[3,2-c]pyrazol-3-yl)benzamide | 0.36 | 1.2 | |
| 221 | 4-fluoro-N-(5-(5-methyloxazol-2-yl)-1H-thieno[3,2-c]pyrazol-3-yl)benzamide | 0.65 | 1.7 | |
| 222 | 4-methoxy-N-(5-(5-methyloxazol-2-yl)-1H-thieno[3,2-c]pyrazol-3-yl)benzamide | 0.31 | 0.35 | |
| 223 | 4-(dimethylamino)-N-(5-(5-methyloxazol-2-yl)-1H-thieno[3,2-c]pyrazol-3-yl)benzamide | 0.11 | 0.094 | |
| 224 | N-(5-(5-methyloxazol-2-yl)-1H-thieno[3,2-c]pyrazol-3-yl)-4-((2-(piperidin-1-yl)ethyl)amino)benzamide | 0.085 | 0.12 | 0.32 |
| 225 | N-(5-(5-methyloxazol-2-yl)-1H-thieno[3,2-c]pyrazol-3-yl)-4-(4-methylpiperazin-1-yl)benzamide | 0.049 | 0.13 | 0.35 |
| 226 | N-(5-(5-methyloxazol-2-yl)-1H-thieno[3,2-c]pyrazol-3-yl)-4-((2-(pyrrolidin-1-yl)ethyl)amino)benzamide | 0.15 | 0.12 | |
| 227 | N-(5-(5-methyloxazol-2-yl)-1H-thieno[3,2-c]pyrazol-3-yl)-4-((2-morpholinoethyl)amino)benzamide | 0.085 | 0.12 | |
| 228 | 4-((2-hydroxyethyl)amino)-N-(5-(5-methyloxazol-2-yl)-1H-thieno[3,2-c]pyrazol-3-yl)benzamide | 0.11 | 0.12 | |
| 229 | 4-((2-methoxyethyl)amino)-N-(5-(5-methyloxazol-2-yl)-1H-thieno[3,2-c]pyrazol-3-yl)benzamide | 0.15 | 0.14 | |
| 230 | 3-fluoro-N-(5-(5-methyloxazol-2-yl)-1H-thieno[3,2-c]pyrazol-3-yl)benzamide | 0.66 | 1.70 | |
| 231 | methyl 3-(4-methoxyphenyl)-1H-thieno[3,2-c]pyrazole-5-carboxylate | 0.54 | >10 | |
| 232 | N-ethyl-3-(4-methoxyphenyl)-1H-thieno[3,2-c]pyrazole-5-carboxamide | 1.95 | >10 | |
| 233 | N-isopropyl-3-(4-methoxyphenyl)-1H-thieno[3,2-c]pyrazole-5-carboxamide | 2.86 | >10 | |
| 234 | methyl 3-(4-(dimethylamino)phenyl)-1H-thieno[3,2-c]pyrazole-5-carboxylate | insoluble | | |
| 235 | 2-(3-(4-methoxyphenyl)-1H-thieno[3,2-c]pyrazol-5-yl)-5-methyloxazole | 0.34 | >10 | |
| 236 | methyl 3-phenyl-1H-thieno[3,2-c]pyrazole-5-carboxylate | 1.27 | >10 | |
| 237 | 3-(4-(dimethylamino)phenyl)-N-ethyl-1H-thieno[3,2-c]pyrazole-5-carboxamide | 1.79 | | |
| 238 | N-ethyl-3-phenyl-1H-thieno[3,2-c]pyrazole-5-carboxamide | 3.47 | | |
| 239 | methyl 3-(4-fluorophenyl)-1H-thieno[3,2-c]pyrazole-5-carboxylate | 0.86 | >10 | |

TABLE 1-continued

| Example | Name | TNIK (μM) | TBK1 (μM) | IKKε (μM) |
|---|---|---|---|---|
| 240 | N-ethyl-3-(4-fluorophenyl)-1H-thieno[3,2-c]pyrazole-5-carboxamide | 2.85 | >10 | |
| 241 | N-ethyl-3-(4-morpholinophenyl)-1H-thieno[3,2-c]pyrazole-5-carboxamide | 1.09 | >10 | |
| 242 | 3-(4-fluorophenyl)-N-(2-morpholinoethyl)-1H-thieno[3,2-c]pyrazole-5-carboxamide | >20 | >10 | |
| 243 | 4-(4-(5-(5-methyloxazol-2-yl)-1H-thieno[3,2-c]pyrazol-3-yl)phenyl)morpholine | 0.15 | >10 | |
| 244 | 4-(4-(5-(5-ethyloxazol-2-yl)-1H-thieno[3,2-c]pyrazol-3-yl)phenyl)morpholine | 1.01 | | |
| 245 | methyl 3-(4-acetamidophenyl)-1H-thieno[3,2-c]pyrazole-5-carboxylate | 0.16 | | |
| 246 | 2-(3-(4-fluorophenyl)-1H-thieno[3,2-c]pyrazol-5-yl)-5-methyloxazole | 0.50 | | |
| 247 | 3-(4-fluorophenyl)-5-(5-methylthiazol-2-yl)-1H-thieno[3,2-c]pyrazole | >20 | | |
| 248 | (3-(4-morpholinophenyl)-1H-thieno[3,2-c]pyrazol-5-yl)(pyrrolidin-1-yl)methanone | 8.09 | | |
| 249 | methyl 3-(4-(2-morpholinoethoxy)phenyl)-1H-thieno[3,2-c]pyrazole-5-carboxylate | 0.47 | | |
| 250 | 4-(2-(4-(5-(5-methyloxazol-2-yl)-1H-thieno[3,2-c]pyrazol-3-yl)phenoxy)ethyl)morpholine | 0.11 | | |
| 251 | 4-(dimethylamino)-N-(5-(5-methylthiazol-2-yl)-1H-thieno[3,2-c]pyrazol-3-yl)benzamide | 0.25 | 1.40 | |
| 252 | N-(5-(5-ethylthiazol-2-yl)-1H-thieno[3,2-c]pyrazol-3-yl)-4-morpholinobenzamide | 0.41 | 1.3 | |
| 253 | N-(5-(5-methylthiazol-2-yl)-1H-thieno [3,2-c]pyrazol-3-yl)-4-((2-(piperidin-1-yl)ethyl)amino)benzamide | 0.28 | 0.62 | |
| 254 | methyl 3-(4-morpholinophenyl)-1H-thieno[3,2-c]pyrazole-5-carboxylate | 0.3 | >10 | |

What is claimed is:
1. A compound selected from the group consisting of:
(1) N-benzyl-3-(4-fluorobenzamido)-1H-indazole-5-carboxamide;
(2) N-(furan-2-yl-methyl)-3-(4-methoxybenzamido)-1H-indazole-5-carboxamide;
(3) 3-(4-methoxybenzamido)-N-(thiophen-2-ylmethyl)-1H-indazole-5-carboxamide;
(4) 3-(4-methoxybenzamido)-N-methyl-N-(thiophen-2-ylmethyl)-1H-indazole-5-carboxamide;
(5) 4-methoxy-N-(5-(4,5,6,7-tetrahydrothieno[2,3-c]pyridine-6-carbonyl)-1H-indazol-3-yl)benzamide
(6) 3-(4-(methylthio)benzamido)-N-(thiophen-2-ylmethyl)-1H-indazole-5-carboxamide;
(7) 3-(1-methyl-1H-pyrazole-4-carboxamido)-N-(thiophen-2-ylmethyl)-1H-indazole-5-carboxamide;
(8) 3-(5-methoxypicolinamido)-N-(thiophen-2-ylmethyl)-1H-indazole-5-carboxamide hydrochloride;
(9) 3-(2-methoxynicotinamido)-N-(thiophen-2-ylmethyl)-1H-indazole-5-carboxamide;
(10) 3-(4-tert-butylbenzamido)-N-(thiophen-2-ylmethyl)-1H-indazole-5-carboxamide;
(11) 4-methoxy-N-(5-(((thiophen-2-ylmethyl)amino)-1H-indazol-3-yl)benzamide;
(13) 3-benzamido-N-(thiophen-2-ylmethyl)-1H-indazole-5-carboxamide;
(14) 3-(4-fluorobenzamido)-N-(1-(thiophen-2-yl)ethyl)-1H-indazole-5-carboxamide;
(15) 3-(4-fluorobenzamido)-N-(1-(thiophen-2-yl)cyclopropyl)-1H-indazole-5-carboxamide;
(16) N-(1-cyanocyclopropyl)-3-(4-fluorobenzamido)-1H-indazole-5-carboxamide;
(17) 3-(4-fluorobenzamido)-N-(1-(thiophen-2-yl)propyl)-1H-indazole-5-carboxamide;
(18) 3-(4-fluorobenzamido)-N-(1-(thiophen-2-yl)butyl)-1H-indazole-5-carboxamide;
(19) 3-(4-fluorobenzamido)-N-((5-methylthiophen-2-yl)methyl)-1H-indazole-5-carboxamide;
(20) 3-(4-fluorobenzamido)-N-(2-phenylpropan-2-yl)-1H-indazole-5-carboxamide;
(21) 3-(4-fluorobenzamido)-N-(4-(trifluoromethyl)benzyl)-1H-indazole-5-carboxamide;
(22) N-(cyclohexylmethyl)-3-(4-fluorobenzamido)-1H-indazole-5-carboxamide;
(23) N-(cyclopropylmethyl)-3-(4-fluorobenzamido)-1H-indazole-5-carboxamide;
(24) N-butyl-3-(4-fluorobenzamido)-1H-indazole-5-carboxamide;
(25) 3-(4-fluorobenzamido)-N-isopentyl-1H-indazole-5-carboxamide;
(26) N-((1,2,4-oxadiazol-3-yl)methyl)-3-(4-fluorobenzamido)-1H-indazole-5-carboxamide;
(27) 3-(4-fluorobenzamido)-N-(thiazol-5-ylmethyl)-1H-indazole-5-carboxamide 2,2,2-trifluoroacetate;
(28) 3-(4-fluorobenzamido)-N-(pyridin-2-ylmethyl)-1H-indazole-5-carboxamide 2,2,2-trifluoroacetate;
(29) 3-(4-fluorobenzamido)-N-(pyridin-4-ylmethyl)-1H-indazole-5-carboxamide;
(30) N-(cyclopropyl(thiophen-2-yl)methyl)-3-(4-fluorobenzamido)-1H-indazole-5-carboxamide;
(33) 3-(4-fluorobenzamido)-N-(3-methyl-1-(thiophen-2-yl)butyl)-1H-indazole-5-carboxamide;
(34) 3-(4-fluorobenzamido)-N-(2-(thiophen-2-yl)butan-2-yl)-1H-indazole-5-carboxamide;
(35) 3-(2,4-difluorobenzamido)-N-(thiophen-2-ylmethyl)-1H-indazole-5-carboxamide;
(36) 3-(4-fluorobenzamido)-N-(thiophen-2-ylmethyl)-1H-indazole-5-carboxamide;
(37) 3-(4-fluorobenzamido)-N-(1-phenylethyl)-1H-indazole-5-carboxamide;
(38) 3-(4-fluorobenzamido)-N-(1-phenylpropyl)-1H-indazole-5-carboxamide;

(39) 3-(phenylsulfonamido)-N-(thiophen-2-ylmethyl)-1H-indazole-5-carboxamide;
(40) N-benzyl-3-(4-(4-methylpiperazin-1-yl)benzamido)-1H-indazole-5-carboxamide;
(41) N-(1-phenylpropyl)-3-(4-(piperazin-1-yl)benzamido)-1H-indazole-5-carboxamide;
(42) N-methyl-3-(4-morpholinobenzamido)-N-(thiophen-2-ylmethyl)-1H-indazole-5-carboxamide;
(43) 3-(4-morpholinobenzamido)-N-(1-(thiophen-2-yl)ethyl)-1H-indazole-5-carboxamide;
(44) 3-(4-(4-methylpiperazin-1-yl)benzamido)-N-(1-(thiophen-2-yl)ethyl)-1H-indazole-5-carboxamide;
(45) N-(2-hydroxy-1-(thiophen-2-yl)ethyl)-3-(4-(4-methylpiperazin-1-yl)benzamido)-1H-indazole-5-carboxamide;
(46) 3-(4-morpholinobenzamido)-N-(thiophen-3-ylmethyl)-1H-indazole-5-carboxamide;
(47) 3-(4-(4-methylpiperazin-1-yl)benzamido)-N-(thiophen-3-ylmethyl)-1H-indazole-5-carboxamide;
(48) 3-(4-morpholinobenzamido)-N-(1-(thiophen-2-yl)cyclopropyl)-1H-indazole-5-carboxamide;
(49) 3-(4-(4-methylpiperazin-1-yl)benzamido)-N-(1-(thiophen-2-yl)cyclopropyl)-1H-indazole-5-carboxamide;
(50) N-(furan-2-ylmethyl)-3-(4-morpholinobenzamido)-1H-indazole-5-carboxamide;
(51) N-(furan-2-ylmethyl)-3-(4-(4-methylpiperazin-1-yl)benzamido)-1H-indazole-5-carboxamide;
(52) 3-(4-morpholinobenzamido)-N-(1-(pyridin-3-yl)ethyl)-1H-indazole-5-carboxamide;
(53) 3-(4-(4-methylpiperazin-1-yl)benzamido)-N-(1-(pyridin-3-yl)ethyl)-1H-indazole-5-carboxamide;
(54) 3-(4-morpholinobenzamido)-N-(1-(thiophen-2-yl)propyl)-1H-indazole-5-carboxamide;
(55) 3-(4-(4-methylpiperazin-1-yl)benzamido)-N-(1-(thiophen-2-yl)propyl)-1H-indazole-5-carboxamide;
(56) 3-(4-morpholinobenzamido)-N-(pyridin-3-ylmethyl)-1H-indazole-5-carboxamide 2,2,2-trifluoroacetate;
(57) 3-(4-(4-methylpiperazin-1-yl)benzamido)-N-(pyridin-3-ylmethyl)-1H-indazole-5-carboxamide bis(2,2,2-trifluoroacetate);
(58) 3-(4-morpholinobenzamido)-N-(1-(thiophen-2-yl)butyl)-1H-indazole-5-carboxamide;
(59) 3-(4-(4-methylpiperazin-1-yl)benzamido)-N-(1-(thiophen-2-yl)butyl)-1H-indazole-5-carboxamide;
(60) N-((5-methylthiophen-2-yl)methyl)-3-(4-morpholinobenzamido)-1H-indazole-5-carboxamide;
(61) 3-(4-(4-methylpiperazin-1-yl)benzamido)-N-((5-methylthiophen-2-yl)methyl)-1H-indazole-5-carboxamide;
(62) 3-(4-morpholinobenzamido)-N-(2-phenylpropan-2-yl)-1H-indazole-5-carboxamide;
(63) 3-(4-(4-methylpiperazin-1-yl)benzamido)-N-(2-phenylpropan-2-yl)-1H-indazole-5-carboxamide;
(64) 3-(4-(4-methylpiperazin-1-yl)benzamido)-N-(2-phenylpropan-2-yl)-1H-indazole-5-carboxamide hydrochloride;
(65) 3-(4-morpholinobenzamido)-N-(4-(trifluoromethyl)benzyl)-1H-indazole-5-carboxamide;
(66) 3-(4-(4-methylpiperazin-1-yl)benzamido)-N-(4-(trifluoromethyl)benzyl)-1H-indazole-5-carboxamide;
(67) 3-(4-morpholinobenzamido)-N-(1-phenylcyclopropyl)-1H-indazole-5-carboxamide;
(68) 3-(4-(4-methylpiperazin-1-yl)benzamido)-N-(1-phenylcyclopropyl)-1H-indazole-5-carboxamide;
(69) N-((2-methylpyridin-4-yl)methyl)-3-(4-morpholinobenzamido)-1H-indazole-5-carboxamide;
(70) 3-(4-(4-methylpiperazin-1-yl)benzamido)-N-((2-methylpyridin-4-yl)methyl)-1H-indazole-5-carboxamide;
(71) 3-(4-morpholinobenzamido)-N-((6-(trifluoromethyl)pyridin-3-yl)methyl)-1H-indazole-5-carboxamide;
(72) 3-(4-(4-methylpiperazin-1-yl)benzamido)-N-((6-(trifluoromethyl)pyridin-3-yl)methyl)-1H-indazole-5-carboxamide;
(73) 3-(2-methyl-4-morpholinobenzamido)-N-(thiophen-2-ylmethyl)-1H-indazole-5-carboxamide;
(74) 3-(2-methyl-4-(4-methylpiperazin-1-yl)benzamido)-N-(thiophen-2-ylmethyl)-1H-indazole-5-carboxamide;
(75) 3-(3-(4-(4-methylpiperazin-1-yl)benzamido)-1H-indazol-5-yl)-3-oxo-2-(thiophen-2-yl)propanoic acid;
(76) (S)-3-(4-(3-methylpiperazin-1-yl)benzamido)-N-(1-phenylcyclopropyl)-1H-indazole-5-carboxamide;
(77) (R)-3-(4-(3-methylpiperazin-1-yl)benzamido)-N-(1-phenylcyclopropyl)-1H-indazole-5-carboxamide;
(78) 3-(3-methyl-4-morpholinobenzamido)-N-(thiophen-2-ylmethyl)-1H-indazole-5-carboxamide;
(79) 3-(3-methyl-4-(4-methylpiperazin-1-yl)benzamido)-N-(thiophen-2-ylmethyl)-1H-indazole-5-carboxamide;
(80) 3-(4-(4-methylpiperazin-1-yl)benzamido)-N-(1-(thiophen-3-yl)ethyl)-1H-indazole-5-carboxamide;
(81) N-(1-(furan-2-yl)ethyl)-3-(4-(4-methylpiperazin-1-yl)benzamido)-1H-indazole-5-carboxamide;
(82) 3-(4-(4-methylpiperazin-1-yl)benzamido)-N-(1-(thiazol-2-yl)ethyl)-1H-indazole-5-carboxamide;
(83) 3-(4-(4-methylpiperazin-1-yl)benzamido)-N-(1-(thiazol-5-yl)ethyl)-1H-indazole-5-carboxamide;
(84) 3-(4-(4-methylpiperazin-1-yl)benzamido)-N-(1-(thiazol-2-yl)propyl)-1H-indazole-5-carboxamide;
(85) 3-(4-(4-methylpiperazin-1-yl)benzamido)-N-(pyridin-2-ylmethyl)-1H-indazole-5-carboxamide bis(2,2,2-trifluoroacetate);
(86) 3-(4-morpholinobenzamido)-N-(pyridin-2-ylmethyl)-1H-indazole-5-carboxamide;
(87) N-(cyclohexylmethyl)-3-(4-(4-methylpiperazin-1-yl)benzamido)-1H-indazole-5-carboxamide;
(88) N-(cyclohexylmethyl)-3-(4-morpholinobenzamido)-1H-indazole-5-carboxamide;
(89) 3-(4-(3,5-dimethylpiperazin-1-yl)benzamido)-N-(thiophen-2-ylmethyl)-1H-indazole-5-carboxamide 2,2,2-trifluoroacetate;
(90) N-(cyclopentylmethyl)-3-(4-(4-methylpiperazin-1-yl)benzamido)-1H-indazole-5-carboxamide 2,2,2-trifluoroacetate;
(91) N-(cyclopentylmethyl)-3-(4-morpholinobenzamido)-1H-indazole-5-carboxamide 2,2,2-trifluoroacetate;
(92) 3-(4-(2,6-dimethylmorpholino)benzamido)-N-(thiophen-2-ylmethyl)-1H-indazole-5-carboxamide 2,2,2-trifluoroacetate;
(93) N-(4-hydroxybutan-2-yl)-3-(4-(4-methylpiperazin-1-yl)benzamido)-1H-indazole-5-carboxamide;
(94) N-((1H-1,2,3-triazol-4-yl)methyl)-3-(4-(4-methylpiperazin-1-yl)benzamido)-1H-indazole-5-carboxamide;
(95) 3-(4-(3,5-dimethylpiperazin-1-yl)benzamido)-N-(1-(thiophen-2-yl)propyl)-1H-indazole-5-carboxamide 2,2,2-trifluoroacetate;
(96) 3-(4-(2,6-dimethylmorpholino)benzamido)-N-(1-(thiophen-2-yl)propyl)-1H-indazole-5-carboxamide 2,2,2-trifluoroacetate;

(97) 3-(4-((S)-3-methylpiperazin-1-yl)benzamido)-N-(1-(thiophen-2-yl)propyl)-1H-indazole-5-carboxamide 2,2,2-trifluoroacetate;
(98) 3-(4-((R)-3-methylpiperazin-1-yl)benzamido)-N-(1-(thiophen-2-yl)propyl)-1H-indazole-5-carboxamide 2,2,2-trifluoroacetate;
(99) 3-(4-((3R,5S)-3,5-dimethylpiperazin-1-yl)benzamido)-N-(1-(thiophen-2-yl)propyl)-1H-indazole-5-carboxamide 2,2,2-trifluoroacetate;
(100) N-((3-methyl-1,2,4-oxadiazol-5-yl)methyl)-3-(4-morpholinobenzamido)-1H-indazole-5-carboxamide 2,2,2-trifluoroacetate;
(101) N-((3-methyl-1,2,4-oxadiazol-5-yl)methyl)-3-(4-(4-methylpiperazin-1-yl)benzamido)-1H-indazole-5-carboxamide 2,2,2-trifluoroacetate;
(102) 3-(4-(piperazin-1-yl)benzamido)-N-(1-(thiophen-2-yl)propyl)-1H-indazole-5-carboxamide;
(103) 3-(4-(4-methylpiperazin-1-yl)benzamido)-N-(thiazol-2-ylmethyl)-1H-indazole-5-carboxamide 2,2,2-trifluoroacetate;
(104) 3-(4-morpholinobenzamido)-N-(thiazol-2-ylmethyl)-1H-indazole-5-carboxamide 2,2,2-trifluoroacetate;
(105) N-((1,2,4-oxadiazol-3-yl)methyl)-3-(4-morpholinobenzamido)-1H-indazole-5-carboxamide 2,2,2-trifluoroacetate;
(106) N-(cyclobutylmethyl)-3-(4-(4-methylpiperazin-1-yl)benzamido)-1H-indazole-5-carboxamide;
(107) 3-(4-(3,3-dimethylpiperazin-1-yl)benzamido)-N-(thiophen-2-ylmethyl)-1H-indazole-5-carboxamide 2,2,2-trifluoroacetate;
(108) 3-(4-(4-hydroxypiperidin-1-yl)benzamido)-N-(1-(thiophen-2-yl)propyl)-1H-indazole-5-carboxamide;
(109) 3-(4-(4-ethylpiperazin-1-yl)benzamido)-N-(1-(thiophen-2-yl)propyl)-1H-indazole-5-carboxamide;
(110) 3-(4-(4-methoxypiperidin-1-yl)benzamido)-N-(1-(thiophen-2-yl)propyl)-1H-indazole-5-carboxamide;
(111) (S)-3-(4-(4-methylpiperazin-1-yl)benzamido)-N-(1-(thiophen-2-yl)propyl)-1H-indazole-5-carboxamide;
(112) (R)-3-(4-(4-methylpiperazin-1-yl)benzamido)-N-(1-(thiophen-2-yl)propyl)-1H-indazole-5-carboxamide;
(113) N-butyl-3-(4-(4-methylpiperazin-1-yl)benzamido)-1H-indazole-5-carboxamide 2,2,2-trifluoroacetate;
(114) N-isopentyl-3-(4-(4-methylpiperazin-1-yl)benzamido)-1H-indazole-5-carboxamide 2,2,2-trifluoroacetate;
(115) N-butyl-3-(4-morpholinobenzamido)-1H-indazole-5-carboxamide 2,2,2-trifluoroacetate;
(116) N-isopentyl-3-(4-morpholinobenzamido)-1H-indazole-5-carboxamide 2,2,2-trifluoroacetate;
(117) (S)-3-(4-(3-methylpiperazin-1-yl)benzamido)-N-(thiophen-2-ylmethyl)-1H-indazole-5-carboxamide 2,2,2-trifluoroacetate;
(118) N-((1,2,4-oxadiazol-3-yl)methyl)-3-(4-(4-methylpiperazin-1-yl)benzamido)-1H-indazole-5-carboxamide 2,2,2-trifluoroacetate;
(119) N-((1H-1,2,3-triazol-4-yl)methyl)-3-(4-morpholinobenzamido)-1H-indazole-5-carboxamide 2,2,2-trifluoroacetate;
(120) 3-(4-morpholinobenzamido)-N-(pyridin-4-ylmethyl)-1H-indazole-5-carboxamide;
(121) 3-(4-(4-methylpiperazin-1-yl)benzamido)-N-(pyridin-4-ylmethyl)-1H-indazole-5-carboxamide;
(122) N-(cyclopropyl(thiophen-2-yl)methyl)-3-(4-morpholinobenzamido)-1H-indazole-5-carboxamide;
(125) N-(cyclopropyl(thiophen-2-yl)methyl)-3-(4-(4-methylpiperazin-1-yl)benzamido)-1H-indazole-5-carboxamide;
(126) N-(cyclopropyl(thiophen-2-yl)methyl)-3-(4-(piperazin-1-yl)benzamido)-1H-indazole-5-carboxamide;
(127) 3-(4-morpholinobenzamido)-N-(1-(pyridin-2-yl)ethyl)-1H-indazole-5-carboxamide;
(128) 3-(4-(4-methylpiperazin-1-yl)benzamido)-N-(1-(pyridin-2-yl)ethyl)-1H-indazole-5-carboxamide;
(129) N-(3-methyl-1-(thiophen-2-yl)butyl)-3-(4-(4-methylpiperazin-1-yl)benzamido)-1H-indazole-5-carboxamide;
(130) N-(3-methyl-1-(thiophen-2-yl)butyl)-3-(4-morpholinobenzamido)-1H-indazole-5-carboxamide;
(131) 3-(4-(4-methylpiperazin-1-yl)benzamido)-N-(2-(thiophen-2-yl)butan-2-yl)-1H-indazole-5-carboxamide;
(132) 3-(4-morpholinobenzamido)-N-(1-(pyridin-4-yl)ethyl)-1H-indazole-5-carboxamide;
(133) 3-(4-(4-methylpiperazin-1-yl)benzamido)-N-(1-(pyridin-4-yl)ethyl)-1H-indazole-5-carboxamide;
(134) 3-(4-morpholinobenzamido)-N-(2-(thiophen-2-yl)propan-2-yl)-1H-indazole-5-carboxamide;
(135) 3-(4-(4-methylpiperazin-1-yl)benzamido)-N-(2,2,2-trifluoro-1-(thiophen-2-yl)ethyl)-1H-indazole-5-carboxamide;
(136) 3-(4-(4-methylpiperazin-1-yl)benzamido)-N-(2-(thiophen-2-yl)propan-2-yl)-1H-indazole-5-carboxamide;
(137) (S)-3-(4-(3-methylpiperazin-1-yl)benzamido)-N-(2-(thiophen-2-yl)propan-2-yl)-1H-indazole-5-carboxamide;
(138) 3-(4-morpholinobenzamido)-N-(2,2,2-trifluoro-1-(thiophen-2-yl)ethyl)-1H-indazole-5-carboxamide;
(139) N-(cyclopropyl(pyridin-2-yl)methyl)-3-(4-morpholinobenzamido)-1H-indazole-5-carboxamide;
(140) N-(cyclopropyl(pyridin-2-yl)methyl)-3-(4-(4-methylpiperazin-1-yl)benzamido)-1H-indazole-5-carboxamide;
(141) 4-(4-methylpiperazin-1-yl)-N-(5-(2-(thiophen-2-yl)acetamido)-1H-indazol-3-yl)benzamide;
(142) N-(cyclopropyl(pyridin-3-yl)methyl)-3-(4-morpholinobenzamido)-1H-indazole-5-carboxamide;
(143) N-(cyclopropyl(pyridin-3-yl)methyl)-3-(4-(4-methylpiperazin-1-yl)benzamido)-1H-indazole-5-carboxamide;
(144) 4-morpholino-N-(5-(2-(thiophen-2-yl)acetamido)-1H-indazol-3-yl)benzamide;
(145) 3-(4-(4-methylpiperazin-1-yl)benzamido)-N-(2-(thiophen-3-yl)propan-2-yl)-1H-indazole-5-carboxamide;
(146) N-((5-chlorothiophen-2-yl)methyl)-3-(4-(4-methylpiperazin-1-yl)benzamido)-1H-indazole-5-carboxamide;
(147) 3-(4-(4-methylpiperazin-1-yl)benzamido)-N-(1-(thiophen-2-yl)cyclohexyl)-1H-indazole-5-carboxamide;
(148) 3-(4-morpholinobenzamido)-N-(thiophen-2-ylmethyl)-1H-indazole-5-carboxamide;
(149) 3-(4-(4-methylpiperazin-1-yl)benzamido)-N-(thiophen-2-ylmethyl)-1H-indazole-5-carboxamide;
(150) 3-(4-((2-methoxyethyl)amino)benzamido)-N-(thiophen-2-ylmethyl)-1H-indazole-5-carboxamide;
(151) 3-(4-((3-methoxypropyl)amino)benzamido)-N-(thiophen-2-ylmethyl)-1H-indazole-5-carboxamide;
(152) 3-(4-((2-(pyrrolidin-1-yl)ethyl)amino)benzamido)-N-(thiophen-2-ylmethyl)-1H-indazole-5-carboxamide;

(153) 3-(4-((2-morpholinoethyl)amino)benzamido)-N-(thiophen-2-ylmethyl)-1H-indazole-5-carboxamide;
(154) 3-(4-((3-(dimethylamino)propyl)amino)benzamido)-N-(thiophen-2-ylmethyl)-1H-indazole-5-carboxamide;
(155) 3-(4-(methyl(2-(methylamino)ethyl)amino)benzamido)-N-(thiophen-2-ylmethyl)-1H-indazole-5-carboxamide;
(156) 3-(3-morpholinobenzamido)-N-(thiophen-2-ylmethyl)-1H-indazole-5-carboxamide;
(157) 3-(4-(((tetrahydrofuran-2-yl)methyl)amino)benzamido)-N-(thiophen-2-ylmethyl)-1H-indazole-5-carboxamide;
(158) 3-(4-((2-(dimethylamino)ethyl)amino)benzamido)-N-(thiophen-2-ylmethyl)-1H-indazole-5-carboxamide;
(159) 3-(4-(isopentylamino)benzamido)-N-(thiophen-2-ylmethyl)-1H-indazole-5-carboxamide;
(160) 3-(4-((2-(tetrahydro-2H-pyran-4-yl)ethyl)amino)benzamido)-N-(thiophen-2-ylmethyl)-1H-indazole-5-carboxamide;
(161) 3-(4-(hexylamino)benzamido)-N-(thiophen-2-ylmethyl)-1H-indazole-5-carboxamide;
(162) 3-(4-(cyclohexylamino)benzamido)-N-(thiophen-2-ylmethyl)-1H-indazole-5-carboxamide;
(163) 3-(4-(cyclopentylamino)benzamido)-N-(thiophen-2-ylmethyl)-1H-indazole-5-carboxamide;
(164) 3-(4-(cycloheptylamino)benzamido)-N-(thiophen-2-ylmethyl)-1H-indazole-5-carboxamide;
(165) 3-(4-(cyclooctylamino)benzamido)-N-(thiophen-2-ylmethyl)-1H-indazole-5-carboxamide;
(166) 3-(4-((cyclohexylmethyl)amino)benzamido)-N-(thiophen-2-ylmethyl)-1H-indazole-5-carboxamide;
(167) 3-(4-((2-(cyclohex-1-en-1-yl)ethyl)amino)benzamido)-N-(thiophen-2-ylmethyl)-1H-indazole-5-carboxamide;
(168) 3-(2,4-dimorpholinobenzamido)-N-(thiophen-2-ylmethyl)-1H-indazole-5-carboxamide;
(169) 3-(4-((2-(1H-pyrrol-1-yl)ethyl)amino)benzamido)-N-(thiophen-2-ylmethyl)-1H-indazole-5-carboxamide;
(170) 3-(2-fluoro-4-(4-methylpiperazin-1-yl)benzamido)-N-(thiophen-2-ylmethyl)-1H-indazole-5-carboxamide;
(171) 3-(4-(piperazin-1-yl)benzamido)-N-(thiophen-2-ylmethyl)-1H-indazole-5-carboxamide;
(172) 3-(4-(4-methylpiperazin-1-yl)benzamido)-N-(oxazol-5-ylmethyl)-1H-indazole-5-carboxamide;
(173) N-(isoxazol-3-ylmethyl)-3-(4-(4-methylpiperazin-1-yl)benzamido)-1H-indazole-5-carboxamide;
(174) 3-(4-(4-methylpiperazin-1-yl)benzamido)-N-(thiazol-4-ylmethyl)-1H-indazole-5-carboxamide;
(175) (R)-3-(4-(4-methylpiperazin-1-yl)benzamido)-N-(1-phenylethyl)-1H-indazole-5-carboxamide;
(176) (S)-3-(4-(4-methylpiperazin-1-yl)benzamido)-N-(1-phenylethyl)-1H-indazole-5-carboxamide;
(177) N-benzyl-3-(4-morpholinobenzamido)-1H-indazole-5-carboxamide;
(178) N-(isoxazol-5-ylmethyl)-3-(4-(4-methylpiperazin-1-yl)benzamido)-1H-indazole-5-carboxamide;
(179) 3-(4-(4-methylpiperazin-1-yl)benzamido)-N-(1-phenylethyl)-1H-indazole-5-carboxamide;
(180) 3-(4-morpholinobenzamido)-N-(1-phenylethyl)-1H-indazole-5-carboxamide;
(181) N-(1-phenylethyl)-3-(4-(piperazin-1-yl)benzamido)-1H-indazole-5-carboxamide 2,2,2-trifluoroacetate;
(182) 3-(4-(3,5-dimethylpiperazin-1-yl)benzamido)-N-(1-phenylethyl)-1H-indazole-5-carboxamide;
(183) 3-(4-(2,6-dimethylmorpholino)benzamido)-N-(1-phenylethyl)-1H-indazole-5-carboxamide;
(184) 3-(4-((S)-3-methylpiperazin-1-yl)benzamido)-N-(1-phenylethyl)-1H-indazole-5-carboxamide 2,2,2-trifluoroacetate;
(185) 3-(4-((R)-3-methylpiperazin-1-yl)benzamido)-N-(1-phenylethyl)-1H-indazole-5-carboxamide 2,2,2-trifluoroacetate;
(186) 3-(4-((3R,5S)-3,5-dimethylpiperazin-1-yl)benzamido)-N-(1-phenylethyl)-1H-indazole-5-carboxamide;
(187) 3-(4-(4-methylpiperazin-1-yl)benzamido)-N-(1-phenylpropyl)-1H-indazole-5-carboxamide;
(188) 3-(4-morpholinobenzamido)-N-(1-phenylpropyl)-1H-indazole-5-carboxamide;
(189) N-(4-fluorobenzyl)-3-(4-(4-methylpiperazin-1-yl)benzamido)-1H-indazole-5-carboxamide;
(190) (S)-3-(4-(4-methylpiperazin-1-yl)benzamido)-N-(1-phenylpropyl)-1H-indazole-5-carboxamide;
(191) (R)-3-(4-(4-methylpiperazin-1-yl)benzamido)-N-(1-phenylpropyl)-1H-indazole-5-carboxamide;
(192) (R)-3-(4-(4-methylpiperazin-1-yl)benzamido)-N-(1-phenylpropyl)-1H-indazole-5-carboxamide hydrochloride;
(193) (S)-3-(4-(4-methylpiperazin-1-yl)benzamido)-N-(1-phenylbutyl)-1H-indazole-5-carboxamide;
(194) (R)-3-(4-(4-methylpiperazin-1-yl)benzamido)-N-(1-phenylbutyl)-1H-indazole-5-carboxamide;
(195) N-(3-fluorobenzyl)-3-(4-(4-methylpiperazin-1-yl)benzamido)-1H-indazole-5-carboxamide;
(196) N-(2-fluorobenzyl)-3-(4-(4-methylpiperazin-1-yl)benzamido)-1H-indazole-5-carboxamide;
(197) N-(cyclopropyl(phenyl)methyl)-3-(4-(4-methylpiperazin-1-yl)benzamido)-1H-indazole-5-carboxamide;
(198) tert-butyl 4-(4-((5-((thiophen-2-ylmethyl)carbamoyl)-1H-indazol-3-yl)carbamoyl)phenyl)-3,6-tetrahydropyridine-1(2H)-carboxylate;
(199) 3-(4-(1,2,3,6-tetrahydropyridin-4-yl)benzamido)-N-(thiophen-2-ylmethyl)-1H-indazole-5-carboxamide;
(200) 3-(4-hydroxybenzamido)-N-(thiophen-2-ylmethyl)-1H-indazole-5-carboxamide;
(201) 3-(4-(2-morpholinoethoxy)benzamido)-N-(thiophen-2-ylmethyl)-1H-indazole-5-carboxamide;
(202) tert-butyl 3-(4-nitrobenzamido)-5-((thiophen-2-ylmethyl)carbamoyl)-1H-indazole-1-carboxylate;
(203) 3-(4-nitrobenzamido)-N-(thiophen-2-ylmethyl)-1H-indazole-5-carboxamide;
(204) 3-(3-nitrobenzamido)-N-(thiophen-2-ylmethyl)-1H-indazole-5-carboxamide;
(205) 3-(4-aminobenzamido)-N-(thiophen-2-ylmethyl)-1H-indazole-5-carboxamide;
(206) 3-(4-(cyclobutanecarboxamido)benzamido)-N-(thiophen-2-ylmethyl)-1H-indazole-5-carboxamide;
(207) N-(thiophen-2-ylmethyl)-3-(4-(1-(trifluoromethyl)cyclopropanecarboxamido)benzamido)-1H-indazole-5-carboxamide;
(208) 3-(4-(3-oxocyclobutanecarboxamido)benzamido)-N-(thiophen-2-ylmethyl)-1H-indazole-5-carboxamide;
(209) 3-(4-(4-acetylpiperazin-1-yl)benzamido)-N-(1-(thiophen-3-yl)propyl)-1H-indazole-5-carboxamide;
(210) tert-butyl (S)-2-((4-((5-((thiophen-2-ylmethyl)carbamoyl)-1H-indazol-3-yl)carbamoyl)phenyl)carbamoyl)pyrrolidine-1-carboxylate;
(211) 3-(4-acetamidobenzamido)-N-(thiophen-2-ylmethyl)-1H-indazole-5-carboxamide;
(212) 3-(4-(1H-imidazol-1-yl)benzamido)-N-(thiophen-2-ylmethyl)-1H-indazole-5-carboxamide;

(213) 3-(4-((1-methylpiperidin-4-yl)amino)benzamido)-N-(thiophen-2-ylmethyl)-1H-indazole-5-carboxamide;
(214) 3-(4-fluorobenzamido)-N-(1-(pyridin-4-yl)ethyl)-1H-indazole-5-carboxamide;
(215) 3-(4-fluorobenzamido)-N-(2-(thiophen-2-yl)propan-2-yl)-1H-indazole-5-carboxamide;
(216) 3-(4-fluorobenzamido)-N-(1-(pyridin-2-yl)cyclopropyl)-1H-indazole-5-carboxamide;
(217) 3-(4-fluorobenzamido)-N-(1-(pyridin-3-yl)cyclopropyl)-1H-indazole-5-carboxamide;
(218) N-(5-(5-methyloxazol-2-yl)-1H-thieno[3,2-c]pyrazol-3-yl)-4-morpholinobenzamide;
(219) N-(5-(5-methylthiazol-2-yl)-1H-thieno[3,2-c]pyrazol-3-yl)-4-morpholinobenzamide;
(220) N-(5-(5-methyloxazol-2-yl)-1H-thieno[3,2-c]pyrazol-3-yl)benzamide;
(221) 4-fluoro-N-(5-(5-methyloxazol-2-yl)-1H-thieno[3,2-c]pyrazol-3-yl)benzamide;
(222) 4-methoxy-N-(5-(5-methyloxazol-2-yl)-1H-thieno[3,2-c]pyrazol-3-yl)benzamide;
(223) 4-(dimethylamino)-N-(5-(5-methyloxazol-2-yl)-1H-thieno[3,2-c]pyrazol-3-yl)benzamide;
(224) N-(5-(5-methyloxazol-2-yl)-1H-thieno[3,2-c]pyrazol-3-yl)-4-((2-(piperidin-1-yl)ethyl)amino)benzamide;
(225) N-(5-(5-methyloxazol-2-yl)-1H-thieno[3,2-c]pyrazol-3-yl)-4-(4-methylpiperazin-1-yl)benzamide;
(226) N-(5-(5-methyloxazol-2-yl)-1H-thieno[3,2-c]pyrazol-3-yl)-4-((2-(pyrrolidin-1-yl)ethyl)amino)benzamide;
(227) N-(5-(5-methyloxazol-2-yl)-1H-thieno[3,2-c]pyrazol-3-yl)-4-((2-morpholinoethyl)amino)benzamide;
(228) 4-((2-hydroxyethyl)amino)-N-(5-(5-methyloxazol-2-yl)-1H-thieno[3,2-c]pyrazol-3-yl)benzamide;
(229) 4-((2-methoxyethyl)amino)-N-(5-(5-methyloxazol-2-yl)-1H-thieno[3,2-c]pyrazol-3-yl)benzamide;
(230) 3-fluoro-N-(5-(5-methyloxazol-2-yl)-1H-thieno[3,2-c]pyrazol-3-yl)benzamide;
(231) methyl 3-(4-methoxyphenyl)-1H-thieno[3,2-c]pyrazole-5-carboxylate;
(232) N-ethyl-3-(4-methoxyphenyl)-1H-thieno[3,2-c]pyrazole-5-carboxamide;
(233) N-isopropyl-3-(4-methoxyphenyl)-1H-thieno[3,2-c]pyrazole-5-carboxamide;
(234) methyl 3-(4-(dimethylamino)phenyl)-1H-thieno[3,2-c]pyrazole-5-carboxylate;
(235) 2-(3-(4-methoxyphenyl)-1H-thieno[3,2-c]pyrazol-5-yl)-5-methyloxazole;
(236) methyl 3-phenyl-1H-thieno[3,2-c]pyrazole-5-carboxylate;
(237) 3-(4-(dimethylamino)phenyl)-N-ethyl-1H-thieno[3,2-c]pyrazole-5-carboxamide;
(238) N-ethyl-3-phenyl-1H-thieno[3,2-c]pyrazole-5-carboxamide;
(239) methyl 3-(4-fluorophenyl)-1H-thieno[3,2-c]pyrazole-5-carboxylate;
(240) N-ethyl-3-(4-fluorophenyl)-1H-thieno[3,2-c]pyrazole-5-carboxamide;
(241) N-ethyl-3-(4-morpholinophenyl)-1H-thieno[3,2-c]pyrazole-5-carboxamide;
(242) 3-(4-fluorophenyl)-N-(2-morpholinoethyl)-1H-thieno[3,2-c]pyrazole-5-carboxamide;
(243) 4-(4-(5-(5-methyloxazol-2-yl)-1H-thieno[3,2-c]pyrazol-3-yl)phenyl)morpholine;
(244) 4-(4-(5-(5-ethyloxazol-2-yl)-1H-thieno[3,2-c]pyrazol-3-yl)phenyl)morpholine;
(245) methyl 3-(4-acetamidophenyl)-1H-thieno[3,2-c]pyrazole-5-carboxylate;
(246) 2-(3-(4-fluorophenyl)-1H-thieno[3,2-c]pyrazol-5-yl)-5-methyloxazole;
(247) 3-(4-fluorophenyl)-5-(5-methylthiazol-2-yl)-1H-thieno[3,2-c]pyrazole;
(248) (3-(4-morpholinophenyl)-1H-thieno[3,2-c]pyrazol-5-yl)(pyrrolidin-1-yl)methanone;
(249) methyl 3-(4-(2-morpholinoethoxy)phenyl)-1H-thieno[3,2-c]pyrazole-5-carboxylate;
(250) 4-(2-(4-(5-(5-methyloxazol-2-yl)-1H-thieno[3,2-c]pyrazol-3-yl)phenoxy)ethyl)morpholine;
(251) 4-(dimethylamino)-N-(5-(5-methylthiazol-2-yl)-1H-thieno[3,2-c]pyrazol-3-yl)benzamide;
(252) N-(5-(5-ethylthiazol-2-yl)-1H-thieno[3,2-c]pyrazol-3-yl)-4-morpholinobenzamide;
(253) N-(5-(5-methylthiazol-2-yl)-1H-thieno[3,2-c]pyrazol-3-yl)-4-((2-(piperidin-1-yl)ethyl)amino)benzamide; and
(254) methyl 3-(4-morpholinophenyl)-1H-thieno[3,2-c]pyrazole-5-carboxylate, or pharmaceutically acceptable salt, a hydrate, or a solvate thereof.

\* \* \* \* \*